(12) United States Patent
Siegel

(10) Patent No.: US 6,255,455 B1
(45) Date of Patent: Jul. 3, 2001

(54) RH(D)-BINDING PROTEINS AND MAGNETICALLY ACTIVATED CELL SORTING METHOD FOR PRODUCTION THEREOF

(75) Inventor: Donald L. Siegel, Hatboro, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/240,274

(22) Filed: Jan. 29, 1999

Related U.S. Application Data

(63) Continuation-in-part of application No. 08/884,045, filed on Jun. 27, 1997, now Pat. No. 5,876,925.
(60) Provisional application No. 60/081,380, filed on Apr. 10, 1998, and provisional application No. 60/028,550, filed on Oct. 11, 1996.

(51) Int. Cl.[7] ............................ C07K 14/00; C07K 16/00
(52) U.S. Cl. ........................ 530/350; 530/380; 530/386; 530/387.1; 435/5; 435/6; 435/7.1; 435/7.21; 435/7.25
(58) Field of Search ........................... 435/5.6, 7.1, 7.21, 435/7.25; 530/350, 380, 386, 387.1

(56) References Cited

U.S. PATENT DOCUMENTS 5,876,925 * 3/1999 Siegel ....................................... 435/5

FOREIGN PATENT DOCUMENTS

94/07922 * 4/1994 (WO) .

OTHER PUBLICATIONS

MP Search Result 2, Abstract and query match, Abstract of WO 94/07922, Apr. 1994.*
Barbas et al., 1991, Proc. Natl. Acad. Sci. USA 88:7978–7982.
Barbas and Lerner, 1991, Methods: A Companion to Meth. Enzymol. 2:119–124.
Barbas, 1995, Nature Medicine 1:837–839.
Boucher et al., 1997, Blood 89:3277–33286.
Burton and Barbas et al., 1994, Adv. Immunol. 57:191–280.
Bye et al., 1992, J. Clin. Invest. 90:2481–2490.
Chothia et al., 1992, J. Mol. Biol. 227:799–817.
Chown et al., 1963, Vox Sang. 8:420–429.
Coia et al., 1996, J. Immunol. Methods 192:13–23.
Cook 1971, Br. J. Haemaol. 20:369–375.
de Kruif et al. 1995, J. Mol. Biol.248:97–105.
de Kruif et al., 1995, Proc. Natl. Acad. Sci. USA 92:3938–3942.
Dörner et al, 1997, J. Immunol. 158:2779–2789.
Dziegiel et al., 1995, J. Immunol. Methods 182:7–19.
Frame et al., 1969, Immunology 16:277–283.
Gorick et al., 1988, Vox Sang. 55:165–170.
Hughes–Jones et al., 1994, Brit. J. of Haematology 88:180–186.
Kang et al., 1991, Methods: A Companion to Methods in Enzymology 2:111–118.
Kretzschmar et al., 1995, Anal. Biochem. 224:413–419.
Lapierre et al., 1990, Transfusion 30:109–1130.
Lomas et al., 1989, Vox Sang. 57:261–264.
Marks et al., 1991, J. Mol. Biol. 222:581–597.
Marks et al., 1993, Bio/Technology 11:1145–1149.
Mo et al., 1996, Immunol. 157:2440–2448.
Mollison et al., 1993, In: *Blood Transfusion in Clinical Medicine*, Oxford, Blackwell Scientific Publications (too voluminous to submit).
Mukherjee et al., 1995, J. Exp. Med. 181:405–409.
Pascual et al., 1991, J. Immunol. 146:4385–4391.
Pereira et al., 1997, J. Immunol. Methods 203:11–24.
Portolano et al., 1993, 151:2839–2851.
Roben et al., 1995, J. Immunol. 154:6437–6445.
Russell et al., 1993, Nucl. Acids Res. 21:1081–1085.
Russo et al., "The Use of Resealed Erythrocytes as Carriers and Bioreactors", ed. Magnani and DeLoach, Plenum Press, New York and London.
Siegel, 1995, ann. NY Acad. Sci. 547–558.
Siegel and Silberstein, 1994, Structural analysis of red cell autoantibodies, Garratty (ed.) Immunobiology of Transfusion Medicine, Dekker, New York, New York; pp. 387–399.
Siegel et al., 1997, J. Immunol. Meth. 206:73–85.
Siegel and Silberstein, 1994, Blood 83:2334–2344.
Silberstein et al., 1991, Blood 78:2372–2386.
Silverman et al., 1988, J. Exp. Med. 168:2361–2366.
Silverman et al., 1995, J. Clin. Invest. 96:417–426.
Sternberg and Hoess, 1995, Proc. Natl. Acad. Sci. USA 92:1609–1613.
Stevenson et al., 1989, Br. J. Haematol. 72:9–15.
Stollar, 1995, Ann. NY Acad. Sci. 265–274.
Thompson et al., 1991, Scand. J. Immunol. 34:509–518.
Tippett et al., 1996, Vox Sang. 70:123–131.
Walker, ed. 1993, In: *Technical Manual*, 11th Ed., Bethesda, MD, American Association of Blood Banks (too voluminous to submit).
Winter et al., 1994, Annu. Rev. Immunol. 12:433–455.

* cited by examiner

*Primary Examiner*—Bennett Celsa
(74) *Attorney, Agent, or Firm*—Morgan, Lewis & Bockius, L.L.P.

(57) ABSTRACT

The invention includes Rh(D) binding proteins, including antibodies, and DNA encoding such proteins. Methods of generating such proteins and DNAs are also included.

21 Claims, 42 Drawing Sheets

1. couple magnetic beads (·) to antigen-positive cells (⊘)

2. add excess antigen-negative cells (O)

3. add phage library containing specific ▬ and non-specfic ⊂⊃ binders 4. incubate 5. load on column without magnetic field 6. place column in magnetic field and wash away antigen-negative cells and non-specific phage 7. flush antigen-positive cells and bound phage from column, elute bound phage, infect bacterial culture

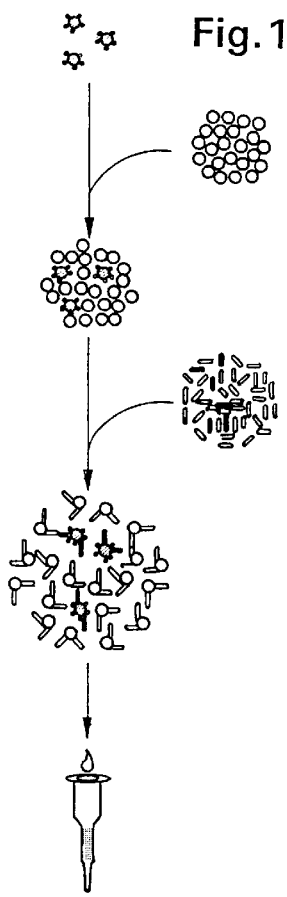

Fig. 1

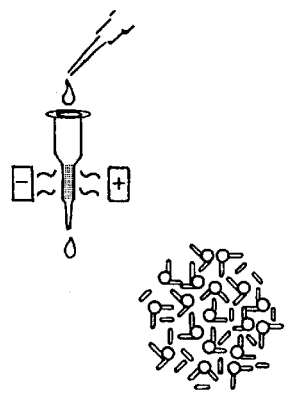

```
CAR  DSRYSNFLRWVR-SDGMDV   WGQG  E01
CAR  DSRYSNFLRWVR-SDGMDV   WGQG  E03
CAN  LRGEVTRRASVP----LDI   WGQG  C05
CAN  LRGEVTRRASVP----LDI   WGQG  C08
CAN  LRGEVTRRASVP----FDI   WGPG  C01
CAN  LRGEVTRRASVP----FDI   WGPG  C10
CAN  LRGEVTRRASVP----FDI   WGPG  C03
CAN  LRGEVTRRASIP----FDI   WGQG  C04
CAR  DWR-VRAFS-SGWLSAFDI   WGQG  D04
CAR  DWR-VRAFS-SGWLSAFDI   WGQG  D05
CAR  EEV-VR--GVILWSRKFDY   WGQG  D03
CAR  EEV-VR--GVILWSRKFDY   WGQG  D20
CAR  ENV-ARGGGGVRYKYYFDY   WGQG  D13
CAR  ENV-ARGGGGIRYKYYFDY   WGQG  D14
CAR  DQ---RAAAGIFYYSRMDV   WGQG  D08
CAR  ERN-FR-SGYSRYYYGMDV   WGPG  D30
CAR  ERN-FR-SGYSRYYYGMDV   WGPG  D31
CAR  EAS-ML-RGISRYYYAMDV   WGPG  D12
CAR  ENQ-IK-L-WSRYLYYFDY   WGQG  D01
CAR  ENQ-IK-L-WSRYLYYFDY   WGQG  D15
CAR  ENQ-IK-L-WSRYLYYFDY   WGQG  D16
CAR  ENQ-IK-L-WSRYLYYFDY   WGQG  D17
CAR  ENQ-IK-L-WSRYLYYFDY   WGQG  D18
CAR  EGS-KK-VALSRYYYMDV   WGQG  D09
CAR  EVS-KK-VALSRYYYMDV   WGQG  D10
CAR  EVS-KK-LALSRYYYMDV   WGQG  D11
CAR  ERR-EK--VYILFYSWLDR   WGQG  D07
CAR  GGFYYDSSGYYGLRHYFDS   WGQG  B01
```

| FIG. 8A-1 | FIG. 8A-2 |
|---|---|
| FIG. 8A-3 | FIG. 8A-4 |

```
                                 H1                                                              H2
                      ----------------                                                 ----------------
               FR1           CDR1              FR2                                   CDR2
          ....1.........2.........3      .....4.........5      .....6........
          1234567890123456789012345678901234567890  1AB2345  67890123456789  012ABC345678901 2345
3-21 DA4  JH6B  EVQLVESGGGLVKPGGSLRLSCAASGFTFS     S--YSMN  WVRQAPGKGLEWVS  SISS--SSSYIYYADSVKG
VDJ1 E01        >>>>>>>>>>>>>>>>>>>>>>>>>>>>>>     ....H..  ..............  ....N-...NT.....A..
     E03        >>>>>>>>>>                         ....H..  .....G........  ....N-...NT.....A..

3-30 DN4  JH3B  QVQLVESGGGVVQPGRSLRLSCAASGFTFS     S--YGMH  WVRQAPGKGLEWVA  VISY--DGSNKYYADSVKG
VDJ2 CA         >>>>>>>>>>>>>>>>>>>>>>>>>>>>>>     .......  ..............  ...................
     C05        >>>>>>>>>>                         .*.....  ..............  ....*....T....F....
     C08        >>>>>>>>>>                         .*.....  ..............  ....*....T....F....
     CB         >>>>>>>>>>                    S    .......  ..............  ....-....H..N......
     C01        >>>>>>>>>>                    S    .......  ..............  ....-...HH..N......
     C10        >>>>>>>>>>                    S    .......  ..............  ....-...HH..N......
     C03        >>>>>>.*..H...*                    .......  ..............  ....-...HH..N......

3-33 DN1  JH3B  QVQLVESGGGVVQPGRSLRLSCAASGFTFS     S--YGMH  WVRQAPGKGLEWVA  VIWY--DGSNKYYADSVKG
VDJ3 D04        >>>>>>>>>>..A.........V...SLR      .......  .........*....  D.F-..........D....
     D05        >>>>>>>>>>..A.........V...SLR      .......  .........*....  D.F-..........D....

3-33 DXP'1 JH4B QVQLVESGGGVVQPGRSLRLSCAASGFTFS     S--YGMH  WVRQAPGKGLEWVA  VIWY--DGSNKYYADSVKG
VDJ4 D20        >>>>>>>>>>                         T......  .........*....  ..F-..........*E...
     D03        >>>>>>>>>>                         T......  .........*....  ..F-..........*E...

3-33 ?D   JH4B  QVQLVESGGGVVQPGRSLRLSCAASGFTFS     S--YGMH  WVRQAPGKGLEWVA  VIWY--DGSNKYYADSVKG
VDJ5 DA         >>>>>>>>>>                         T......  ..............  ..F-.........RD.E..
     D13        >>>>>>>>>>.L*....G..               T......  ..............  ..F-........*RD.E..
     D14        >>>>>>>>>>                         T......  ..............  ..F-........KRD.E..
```

FIG. 8A-1

```
3-33   DN1    JH6B   QVQLVESGGGVVQPGRSLRLSCAASGFTFS S--YGMH WVRQAPGKGLEWVA VIWY--DGSNKYYADSVKG
  VDJ6   D08   >>>>>>>>>........................ *....  ......  R....*L.*-..G*.E....*

3-33   DXP4   JH6B   QVQLVESGGGVVQPGRSLRLSCAASGFTFS S--YGMH WVRQAPGKGLEWVA VIWY--DGSNKYYADSVKG
  VDJ7   D31        >>>>>>>>>........................ .-..  .*....  ............... .VY.-..*.H.S....
         D30                                                                    .VY.-..*.H.S....

3-33   DXP'1  JH6B   QVQLVESGGGVVQPGRSLRLSCAASGFTFS S--YGMH WVRQAPGKGLEWVA VIWY--DGSNKYYADSVKG
  VDJ8   D12        >>>>>>>>>........................ A....S.R .-....  R....FT.F-..*..*.V....

3-33   DK4    JH4B   QVQLVESGGGVVQPGRSLRLSCAASGFTFS S--YGMH WVRQAPGKGLEWVA VIWY--DGSNKYYADSVKG
  VDJ9   D15        >>>>>>>>>........................ VV....N N-....  ........*.F-.........
         D16                                       VV.*..N N-....  ........*.F-.........
         D01                                       VV.*..N N-....  ........*.F-.........
         DB                                        VV.*..N N-....  ........*.F-.........
         D17                                       VV.*..N N-....  ........*.F-.........
         D18                                       VV.*..N N-....  ....S..*...*.F-......

3-33   DN1    JH6B   QVQLVESGGGVVQPGRSLRLSCAASGFTFS S--YGMH WVRQAPGKGLEWVA VIWY--DGSNKYYADSVKG
  VDJ10  DC         >>>>>>>>>........................ E..K..LY N-....  ........F..F-...........E....
         D10                                       E..K..LY N-....  ........F..F-...........E....
         D09                                       E..K..LY N-....  ........F..F-................
         D11                                       E..K..LY N-....E... ....F..F-....................

3-33   ?D     JH5B   QVQLVESGGGVVQPGRSLRLSCAASGFTFS S--YGMH WVRQAPGKGLEWVA VIWY--DGSNKYYADSVKG
  VDJ11  D07        >>>>>>>>>........................ V...LT N-....  HV.--..KTE....*....

3-30.3 ?D     JH4B   QVQLVESGGGVVQPGRSLRLSCAASGFTFS S--YAMH WVRQAPGKGLEWVA VISY--DGSNKYYADSVKG
  VDJ12  B01        >>>>>>>>>........................ .R.-....  ........  ATA.--...K.....
```

FIG. 8A-2

| FR3 | CDR3 | FR4 | # NUCLEOTIDE DIFFERENCES FROM GERMLINE VH |
|---|---|---|---|
| ........7.........8.........9.......... | ........10........11 | | |
| 6789012345678901 2abc3456789012 34 | 567890abcdefghijk12 | 3456 7890123 | |
| RFTISRDNAKNSLYLQMNSLRAEDTAVYYCAR | ++DYSNY+++YYYYYGMDV | WGQGTTVTVSS | |
| ..........................*....... | DSRYSNFLR-WVRSD..... | .......I... | 6 |
| ..........................H..*.... | DSRYSNFLR-WVRSD..... | .......I... | 8 |
| RFTISRDNSKNTLYLQMNSLRAEDTAVYYCAK..N | +++SIAAR+++++DAFDI | WGQGTMVTVSS | |
| .K...........P.................... | LRGEVTRRAS-----VP.. | ........... | 3 |
| .K.....T.....P....F............... | LRGEVTRRAS-----VPL. | ........... | 10 |
| .K.....T.....P....F............... | LRGEVTRRAS-----VPL. | ........... | 10 |
| .K...........P....*............... | LRGEVTRRAS-----VP.. | ........... | 9 |
| .K...........P....*............... | LRGEVTRRAS-----IP.. | ........... | 10 |
| .K...........P....*............... | LRGEVTRRAS-----VP.. | ...P....... | 11 |
| .K...........P....*............... | LRGEVTRRAS-----VP.. | ...P.L..... | 11 |
| .K...........P....*............... | LRGEVTRRAS-----VP..* | ...P....*.. | 14 |
| RFTISRDNSKNTLYLQMNSLRAEDTAVYYCAR..* | +++++GYSSSWY++DAFDI | WGQGTMVTVSS | |
| ............................*..... | DWRVRAFSSGWL--S..... | ........... | 13 |
| ............................*..... | DWRVRAFSSGWL--S..... | ....T.S.*.. | 13 |
| RFTISRDNSKNTLYLQMNSLRAEDTAVYYCAR..* | ITMVRGVII+++++YFDY | WGQGTLVTVSS | |
| ...V........................*..... | EEVVRGVILWSR---K... | ........... | 7 |
| ............................*..... | EEVVRGVILWSR---K... | ........... | 8 |
| RFTISRDNSKNTLYLQMNSLRAEDTAVYYCAR..S | +++++++++++++YFDY | WGQGTLVTVSS | |
| .............................S.... | ENVARGGGG?RYKY-.... | ........... | 8 |
| .....K.......................S.... | ENVARGGGGVRYKY-.... | ........... | 11 |
| .........*...................S.... | ENVARGGGGIRYKY-.... | ........... | 13 |

FIG. 8A-3

```
RFTISRDNSKNTLYLQMNSLRAEDTAVYYCAR  +GIAAAG+++YYYYYGMDV  WGQGTTVTVSS
..S........*....V.....D....*....  DQRAAAG---IF**SR...  ...........  15

RFTISRDNSKNTLYLQMNSLRAEDTAVYYCAR  YYDFWSGYYTYYYYGMDV  WGQGTTVTVSS
........*....D..................  ERNFRSGY--SR......  ..P........  11
........*....D..................  ERNFRSGY--SR......  ..P........  12

RFTISRDNSKNTLYLQMNSLRAEDTAVYYCAR  +ITMVRGVIIYYYYGMDV  WGQGTTVTVSS
.......E.....VD....*............  EASMLRGI--SR...A..  ..P........  14

RFTISRDNSKNTLYLQMNSLRAEDTAVYYCAR  ++WIQLWL+++++++YFDY  WGQGTLVTVSS
.......*........................  ENQIKLWSRYLY-------  ...........   9
.......*...*....................  ENQIKLWSRYLY-------  ...........  10
.......*...*....................  ENQIKLWSRYLY----*--  ...........  10
.......*...*....................  ENQIKLWSRYLY-------  ...........  10
.......*...*....................  ENQIKLWSRYLY-------  ...........  10
.......*...*....................  ENQIKLWSRYLY-------  ..........*  12

RFTISRDNSKNTLYLQMNSLRAEDTAVYYCAR  +++GYSSSWYYYYYGMDV  WGQGTTVTVSS
...V............................  EVSKK?AL--SR...Y..  ...*.......  12
...V............................  EVSKKVAL--SR*..Y..  ...*.......  13
...V............................  EGSKKVAL--SR*..*Y.  ...*..*....  13
...V............................  EVSKKLAL--SR...Y..  ...*.......  14

RFTISRDNSKNTLYLQMNSLRAEDTAVYYCAR  ++++++++++++++NWFDP  WGQGTLVTVSS
...AV...K...*.F......I..........  ERREKVYILFY---S.L.R  ...........  23

RFTISRDNSKNTLYLQMNSLRAEDTAVYYCAR  ++++++++++++++++YFDY  WGQGTLVTVSS
.....................F..........  GGFYDSSGYYGLRH...S   ...........   8
```

| FIG. 8B-1 | FIG. 8B-2 |

| VH | HOMOLOGY TO CON. | ........1.........2.........3......... | ....4......... |
|---|---|---|---|
| | | 1234567890123456789012345678901AB2345 | 6789012345678 9 |
| 3-21 | 85% | E........L.K..G................-.S.N | ..........S |
| 3-30 | 98 | ..............................-..G.. | |
| 3-33 | 98 | ..............................-..G.. | |
| 3-30.3 | 99 | ..............................-..A.. | |
| CONSENSUS | | QVQLVESGGGVVQPGRSLRLSCAASGFTFS S--YGMH | WVRQAPGKGLEWVA |

FIG. 8B-1

```
5.........6.........7.........8.........9....             CHOTHIA
012ABC3456789012345 67890123456789012ABC345678901234       CLASS
S...S--SS.YI......  .........A..S.................K       1-3
........................................................  1-3
...W.-.................................................   1-3
...-...-...............................................   1-3
VISY--DGSNKYYADSVKG RFTISRDNSKNTLYLQMNSLRAEDTAVYYCAR       1-3
```

| FIG. 10A-1 | FIG. 10A-2 |
|---|---|
| FIG. 10A-3 | FIG. 10A-4 |

FIG 10A-1

```
                          FR1                            CDR1           FR2                 CDR2
                                                          L1                                 L2
                                                         ---                                 ---
                    ....1....2....3       .....3......        ....4....         5....
              ...1234567890123456789012345678901234567890123  45678901abcdef234  567890123456789  0123456
    Vκ   Jκ   DIQMTQSPSSLSASVGDRVTITC                         RASQSISS------YLN  WYQQKPGKAPKLLIY  AASSLQS
DPK9
     I05 JK1  >>>>>>>>>>>>>>>>>>>>>>>                         .....RR-------...  .........H.....  .......
     I04      >>>>>>>>>>>>>>>>>>>>>>>                         ..N.RR-------..S  .....*.........  .......
     I15      >>>>>>>>>>>>>>>>>>>>>>>                         ..N.N.RR-----...  ...............  .......
     I02      >>>>>>>>>>>>>>>>>>>>>>>                         ..N.N.RR-----..S  .........N.....  ...T.G.
     I16      >>>>>>>>>>>>>>>>>>>>>*.P.*                      .......T.GF----.N..  *TS.*P.*.*..   .GV.K..N DPK9
     I12 JK2  DIQMTQSPSSLSASVGDRVTITC                         RASQSISS------YLN  WYQQKPGKAPKLLIY  AASSLQS
     I10      >>>>>>>>>>>>>>>>>>>>>>>                         .....N.-------...  ...............  .......
     I13      >>>>>>>>>>>>>>>>>>>>>>*                         .....R.-------...  .........H.....  .......
     I08      >>>>>>>>>>>>>>>>>>>>>>*F                        .......T.R----..S  .........E.....  .......
     I09      >>>>>>>>>>>>>>>>>>>>>>>                         .......T.R----..*  ............T..N  ...**R.
     I11      >>>>>>>>>>>>>>>>>>>>>>>                         ...............   ...............  .......

DPK9
     I01 JK3  DIQMTQSPSSLSASVGDRVTITC                         RASQSISS------YLN  WYQQKPGKAPKLLIY  AASSLQS
     I03      >>>>>>>>>>>>>>>>>>>>A>>                         ..*...*-------...  .....*.........  .......
              >>>>>>>>>>>>>>>>>>>>>>>                         ..T.RN.NR-----...  ...............  .......

DPK9
     I07 JK4  DIQMTQSPSSLSASVGDRVTITC                         RASQSISS------YLN  WYQQKPGKAPKLLIY  AASSLQS
              >>>>>>>>>>>>>>>>>>>>>>>                         ...............   ...............  .......
```

| | | | | |
|---|---|---|---|---|
| DPK9 I06 | JK5 | DIQMTQSPSSLSASVGDRVTITC >>>>>>>> | RASQSISS------YLN ------ | WYQQKPGKAPKLLIY . . * . | AASSLQS . . . . . . . |
| DPK8 H01 | JK3 | DIQLTQSPSFLSASVGDRVTITC >>>>>>>> | RASQGISS------YLA . . T . . . ------ | WYQQKPGKAPKLLIY . . . . * . | AASTLQS . . . . . . . |
| A30 F01 | JK1 | DIQMTQSPSSLSASVGDRVTITC >>>>>>>> | RASQGIRN------DLG . . F . . . ------ | WYQQKPGKAPKRLIY . . . . . . | AASSLQS . T . . . . . |
| DPK15 G01 | JK4 | DIVMTQSPLSLPVTPGEPASISC >>>>>>>> | RSSQSLLHSNGYN-YLD . S . F . - F . | WYLQKPGQSPQLLIY . . . . . . . | LGSNRAS M . . . . . . |

FIG. 10A-2

```
                                                                                   # nucleotide
                                                                                   differences from
              FR3                                    L3                            germline Vκ
                                            |---------------|
                                                   CDR3
   ..6.......7.......8........  9.......  .10.....
   7890123456789012345678901234567890123456789012345678901234567890123456789012345678
   GVPSRFSGSGSGTDFTLTISSLQPEDFATYYC  QQSYSTP+WT  FGQGTKVEIK
   ....T.........................   ..*....-Q.  ..........                          6
   ...................LA.........   ..SN.*-..   ..........                         11
   .................*..*..*.**...   .TSA.*-..   ..........                         20
   .....*..*E.*.*................   ...L-..-.   ..........                          4
   .....**..**.*..*..**..*..*.**.   .TNDAL-..   .....*..VR                         49

GVPSRFSGSGSGTDFTLTISSLQPEDFATYC   QQSYSTP+YT  FGQGTKLEIK
   ...L..........................   ...P..S.    ..........                          1
   ..........................*...   ..P*S...    .....R....                          2
   ...P..........................   ..G.-HS.    ..........                          4
   ...........................*..   .VRI*-.S    ..........                         23
   ..................S........*..   .LN.Y*-.    ..........                         11
   ..............*...........*.I.   ..RE----    ..........                          5

GVPSRFSGSGSGTDFTLTISSLQPEDFATYYC  QQSYSTP+FT  FGPGTKVDIK
   ...T..........................   ...P-..     ......EM.                           4
   .........T....................   ...I-..     ........L.                         13

GVPSRFSGSGSGTDFTLTISSLQPEDFATYYC  QQSYSTP+LT  FGGGTKVEIK
   ..............................   ...R-..     ..........                          1
```

FIG. 10A-3

```
GVPSRFSGSGSGTDFTLTISSLQPEDFATYYC QQSYSTP+IT FGQGTRLEIK
..............................  ........*- ..........   4

GVPSRFSGSGSGTEFTLTISSLQPEDFATYYC QQLNSYP+FT FGPGTKVDIK
.....A...D....................  .....N.*P. ..........   8

GVPSRFSGSGSGTEFTLTISSLQPEDFATYYC LQHNSYP+WT FGQGTKVEIK
.....N........................  .......F*- ..........   8
........S.....................

GVPDRFSGSGSGTDFTLKISRVEAEDVGVYYC MQALQTP+LT FGGGTKVEIK
.....N........................  .......F.- ..........   8
```

| FIG. 10B-1 | FIG. 10B-2 |

| Vκ GENE | FAM. | | | | |
|---|---|---|---|---|---|
| DPK9 | I | DIQMTQSPSSLSASVGDRVTITC | RASQSISS------ | -----YLN |
| DPK8 | I | ..L......F............ | .....G...----- | -----..A |
| A30 | I | ..............L..PVTP.EPAS.S. | ....G.RN------ | -----D.G |
| DPK15 | II | ..V................... | .S....LLHSNGYN- | -..D |

FIG. 10B-1

```
WYQQKPGKAPKLLIY AASSLQS GVPSRFSGSGSGTDFTLTISSLQPEDFATYYC QQSYSTP
..............  .......  .............E................  ..LN.Y.
......R.......  ...T...  .............E................  L.HN.Y.
..L...QS.Q....  LG.NRA.  .....D........K..RVEA..VGV....  M.ALQ..
```

| FIG. 11A-1 | FIG. 11A-2 |
|---|---|
| FIG. 11A-3 | FIG. 11A-4 |

```
                                  FR1                              CDR1                    FR2
                          .....1.........2.........         .....3..........         ....4.........
                          12345678912345678901234567890123   45678901abc234           567890123456789
   Vλ           Jλ        QTVVTQEPSLTVSPGGTVTLTC ASSTGAVTSGYYPN WFQQKPGQAPRALIY
7a.2.3/DPL18  JL2Vasicek
   K01                    >>>>>>>>>>>>>>>>>>>>>>>>>>>>>>>>>. .............R.F..       ........P....
   K02                    >>>>>>>>>>>>>>>>>>>>>>>>>>>>>>>>>. .............R.F..       ........P....
   K03                    >>>>>>>>>>>>>>>>>>>>>>>>>>>>>>>>>. .............R.F..       .............**

2c.118D9+     JL2Vasicek  QSALTQPPSASGSPGQSVTISC TGTSSDVGGYNYVS WYQQHPGKAPKLMIY
   R01                    >>>>>>>>>>>>>>>>>>>>>>>>>>>>>>>>>. ...A.....A...KH..        ........*....LTH DPL10/1v2066  JL2Vasicek  QSALTQPASVSGSPGQSITISC TGTSSDVGSYNLVS WYQQHPGKAPKLMIY
   S01                    >>>>>>>>>>>>>>>>>>>>>>>>>>>>>>>>>. .............N....       .....Y..*.....I..
DPL7/VL1.2    JL2Vasicek  QSVVTQPPSVSGAPGQRVTISC TGSSSNIGAGYDVH WYQQLPGTAPKLLIY
   O03                    >>>>>>>>>>>>>>>>>>>>>>>>>>>>..*..T. ..............           ...*H..........
   O02                    >>>>>>>>>>>>>>>>>>>>>>>>>>>>>....T. ......S...R...           .......F.......
   O01                    >>>>>>>>>>>>>>>>>>>>>>>>>>>>>>>>>. ..........P.G.           .........V..*..

1b.366F5/DPL5 JL2Vasicek  QSVLTQPPSVSAAPGQKVTISC SGSSSNIGNNY-VS WYQQLPGTAPKLLIY
   N02                    >>>>>>>>>>>>>>>>>>>>>>>>>>>>>>>>>. ...........*..           ........*......
   N01                    >>>>>>>>>>>>>>>>>>>>>>>>>>>>>>>>>. ........DS*.-.           ...............F
```

FIG. 11A-1

```
1g.400B5/DPL3  JL2Vasicek    QSVLTQPPSASGTPGQRVTISC  SGSSSNIGSNY-VY  WYQQLPGTAPKLLIY
  M02                        >>>>>>>>>                ........*.    ...............
  M03                        >>>>>>>>>                ...*......    ......-..HV....
  M01                        >>>>>>>>>                *.NF.....-.F  ...........*...

1c.10.2/DPL2   JL2Vasicek    QSVLTQPPSASGTPGQRVTISC  SGSSSNIGSNT-VN  WYQQLPGTAPKLLIY
  L05                        >>>>>>>>>...*..L.......  ..........I-..  ..............F
  L03                        >>>>>>>>>..............  .**.....N.H-.S  ...*......M....
  L04                        >>>>>>>>>..........S...  ..............  .........*.....
  L01                        >>>>>>>>>..............  ..G.....A..-..  ......*........

DPL16/VL3.1    JL2Vasicek    SSELTQDPAVSVALGQTVRITC  QGDSLR---SYYAS  WYQQKPGQAPVLVIY
  J02                        >>>>>>>>>............*  ..G.---...-*..  .........*K..M*
  J01                        >>>>>>>>>............*  ..G.---...-*..  .........*K..M*
  J05                        >>>>>>>>>..........K..  .*....---..K..  ..........*..F.
  J04                        >>>>>>>>>..............  ......---.....  ...............

3p.81A4+       JL2Vasicek    SYELTQPPSVSVSPGQTARITC  SGDALP--KKYAY  WYQQKSGQAPVLVIY
  P01                        >>>>>>>>>.....A.R*...*.*  G**KIG---SNTVH  ..R.M.......*..

4b.68B6        JL2Vasicek    QLVLTQSPSASASLGASVKLTC  TLSSG--HSSYAIA  WHQQPEKGPRYLMK
  Q01                        >>>>>>>>>*..T....G.*....  .I.Q.*--.RN..V*  ..H*EAG...**F..T
```

FIG. 11A-2

```
                                                                                                           # nucleotide
                                                                                                         differences from
                                                                                                            germline Vλ
       CDR2              FR3                                   CDR3                 FR4
 ----------  -------------------------------------  -------------------------  --------------
       5...      ...6.......7.......8.......             ...9.......               ...10...
 01abcd23456  7890123456789012345678901234567890    9012345abcdef67            8901234567
 ST----SNKHS  WTPARFSGSLLG--GKAALTLSGVQPEDEAEYYC    LLYYGGAQ+++++VV            FGGGTKLTVL          7
 .A--------   ............................         ...S..W----*..             .....*..                7
 .A--------   ............................         ...S..W----*..             ..........            12
 GS----N---   .................*..........         ...F.A.W----A.             ..........            17
 EV----SKRPS  GVPDRFSGSKSG--NTASLTVSGLQAEDEADYYC    SSYAGSNNF++++VV            FGGGTKLTVL
 ..G----T--   ............................         ..F.*NS-----VI             ..........            10
 EG----SKRPS  GVSNRFSGSKSG--NTASLTISGLQAEDEADYYC    CSYAGSSTF++++VV            FGGGTKLTVL             3
 ......S...   ...........R................H.       .....I..---RI              ..........            10
 GN----SNRPS  GVPDRFSGSKSG--TSASLAITGLQAEDEADYYC    QSYDSSLSG++++VV            FGGGTKLTVL            13
 ...H------   ............................         .....P--y..                ..........
 ND----N---   ............................         ...N....S--S*F             ..........             2
 ...*......   ............................    E.*  .........*R---*            ..........            15
 DN----NKRPS  GIPDRFSGSKSG--TSATLGITGLQTGDEADYYC    GTWDSSLSA+++VV             FGGGTKLTVL
 ...---YR..   .............*..............*        ..A...D..NG----R*          .....*..
```

FIG. 11A-3

```
RN-----NQRPS GVPDRFSGSKSG--TSASLAISGLRSEDEADYYC AAWDDSLSG++++VV FGGGTKLTVL        3
..............................................-------W*..........        6
....................A.........*.....A......................        23
..N....**.*...........L.......-A......N....D.....TG..R..*....LI...P*V..

SN-----NQRPS GVPDRFSGSKSG--TSASLAISGLQSEDEADYYC AAWDDSLNG++++VV FGGGTKLTVL        8
....K.............................*T....R*..........*           18
.*....G.............................**..........H..*Y.....P*...*           14
T......G...*....................S....R*.A.D........T.........*           18

GK-----NNRPS GIPDRFSGSSSG--NTASLTITGAQAEDEADYYC NSRDSSGNH++++VV FGGGTKLTVL       25
.R-----......*..-Q..A....*.T..*.........Q.*AT*..P-.....*        26
.R-----...G..*..-Q..A....*.T..*.........Q.*AT*..P-.....*        18
AR-----*S......-N....-T......A.R..........H..*.N.H.-----R*        21

ED-----SKRPS GIPERFSGSSSG--TMATLTISGAQVEDEADYYC YSTDSSGNH++++VV FGGGTKLTVL       41
*.-----K...P.......*.T.....-T...S.....*.........*..R.N..DQ----RR*..A......

LNSDGSHSKGD GIPDRFSGSSSG--AERYLTISSLQSEDEADYYC QTWGTGI+++++VV FGGGTKLTVL       38
VTN..R.I.......A..-...*....S..G........G..*..........M-----H*......
```

FIG. 11A-4

| GENE | Vλ FAM. | | | |
|---|---|---|---|---|
| 7a.2.3/DPL18 | VII | QTVVTQEPSLTVSPGGTVTLTC | ASSTGAVTSGYYPN | |
| 2c.118D9+ | II | QSALTQPPSASGSPGQSVTISC | TGTSSDVGGYNYVS | |
| DPL10/1v2066 | II | QSALTQPASVSGSPGQSITISC | TGTSSDVGSYNLVS | |
| DPL7/VL1.2 | I | QSVVTQPPSVSGAPGQRVTISC | TGSSSNIGAGYDVH | |
| 1b.366F5/DPL5 | I | QSVLTQPPSVSAAPGQKVTISC | SGSSSNIGNNY-VS | |
| 1g.400B5/DPL3 | I | QSVLTQPPSASGTPGQRVTISC | SGSSSNIGSNY-VY | |
| 1c.10.2/DPL2 | I | QSVLTQPPSASGTPGQRVTISC | SGSSSNIGSNT-VN | |
| DPL16/VL3.1 | III | SSELTQDPAVSVALGQTVRITC | QGDSLR---SYYAS | |
| 3p.81A4+ | III | SYELTQPPSVSVSPGQTARITC | SGDALP---KKYAY | |
| 4b.68B6 | IV | QLVLTQSPSASASLGASVKLTC | TLSSG--HSSYAIA | |

FIG. 11B-1

```
WFQQKPGQAPRALIY ST-----SNKHS WTPARFSGSLLG--GKAALTLSGVQPEDEAEYYC LLYYGGAQ
WYQQHPGKAPKLMIY EV-----SKRPS GVPDRFSGSKSG--NTASLTVSGLQAEDEADYYC SSYAGSNNF
WYQQHPGKAPKLMIY EG-----SKRPS GVSNRFSGSKSG--NTASLTISGLQAEDEADYYC CSYAGSSTF
WYQQLPGTAPKLLIY GN-----SNRPS GVPDRFSGSKSG--TSASLAITGLQAEDEADYYC QSYDSSLSG
WYQQLPGTAPKLLIY DN-----NKRPS GIPDRFSGSKSG--TSATLGITGLQTGDEADYYC GTWDSSLSA
WYQQLPGTAPKLLIY RN-----NQRPS GVPDRFSGSKSG--TSASLAISGLRSEDEADYYC AAWDDSLSG
WYQQLPGTAPKLLIY SN-----NQRPS GVPDRFSGSKSG--TSASLAISGLQSEDEADYYC AAWDDSLNG
WYQQKPGQAPVLVIY GK-----NNRPS GIPDRFSGSSSG--NTASLTITGAQAEDEADYYC NSRDSSGNH
WYQQKSGQAPVLVIY ED-----SKRPS GIPERFSGSSSG--TMATLTISGAQVEDEADYYC YSTDSSGNH
WHQQPEKGPRYLMK LNS-DGSHSKGD GIPDRFSGSSSG--AERYLTISSLQSEDEADYYC QTWGTGI
```

FIG. 11B-2

| CLONE (HC/LC) | Rh(D) VARIANT CATEGORY | | | | | | ASSIGNED EPITOPE |
|---|---|---|---|---|---|---|---|
| | IIIc | IVa | IVb | Va | VI | VII | |
| E1/L4 | ● | ● | ● | ● | ● | ● | epD1 |
| E1/M2 | ● | ● | ● | ● | ● | ● | epD2 |
| E1/M3 | ● | ● | ● | ● | ● | ● | epD3 |
| D20/K3 | ● | ● | ● | ● | ● | ● | epD6/7 |
| D7/J4 | ● | ● | ● | ● | ● | ● | "epDX" |

FIG. 13

SEQUENCE LISTING

<160> NUMBER OF SEQ ID NOS: 224

<210> SEQ ID NO 1
<211> LENGTH: 128
<212> TYPE: PRT
<213> ORGANISM: Homo sapiens
<220> FEATURE:
<223> OTHER INFORMATION: anti-Rh(D) chain B01

<400> SEQUENCE: 1

Glu Val Gln Leu Leu Glu Ser Gly Gly Val Val Gln Pro Gly Arg
 1               5                  10                  15

Ser Leu Arg Leu Ser Cys Ala Ala Ser Gly Phe Thr Phe Arg Ser Tyr
                20                  25                  30

Ala Met His Trp Val Arg Gln Ala Pro Gly Lys Gly Leu Glu Trp Val
            35                  40                  45

Ala Ala Thr Ala Tyr Asp Gly Lys Asn Lys Tyr Tyr Ala Asp Ser Val
        50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Phe Tyr Cys
                85                  90                  95

Ala Arg Gly Gly Phe Tyr Tyr Asp Ser Ser Gly Tyr Tyr Gly Leu Arg
            100                 105                 110

His Tyr Phe Asp Ser Trp Gly Gln Gly Thr Leu Val Thr Val Ser Ser
        115                 120                 125

<210> SEQ ID NO 2
<211> LENGTH: 124
<212> TYPE: PRT
<213> ORGANISM: Homo sapiens
<220> FEATURE:
<223> OTHER INFORMATION: anti-Rh(D) chain C01

<400> SEQUENCE: 2

Glu Val Gln Leu Leu Glu Ser Gly Gly Val Val Gln Pro Gly Arg
 1               5                  10                  15

Ser Leu Arg Leu Ser Cys Ala Ala Ser Gly Phe Ser Phe Ser Ser Tyr
                20                  25                  30

Gly Met His Trp Val Arg Gln Ala Pro Gly Lys Gly Leu Glu Trp Val
            35                  40                  45

Ser Val Ile Ser Tyr Asp Gly His His Lys Asn Tyr Ala Asp Ser Val
        50                  55                  60

Lys Gly Arg Phe Thr Ile Ser Arg Asp Asn Ser Lys Lys Thr Leu Tyr
 65                  70                  75                  80

Leu Gln Met Asn Ser Leu Arg Pro Glu Asp Thr Ala Val Tyr Tyr Cys
                85                  90                  95

Ala Asn Leu Arg Gly Glu Val Thr Arg Arg Ala Ser Val Pro Phe Asp
            100                 105                 110

Ile Trp Gly Pro Gly Thr Met Val Thr Val Ser Ser
        115                 120

<210> SEQ ID NO 3
<211> LENGTH: 124
<212> TYPE: PRT
<213> ORGANISM: Homo sapiens
<220> FEATURE:
<223> OTHER INFORMATION: anti-Rh(D) chain C03

-continued

<400> SEQUENCE: 3

```
Glu Val Gln Leu Leu Glu Ser Gly Gly Gly Val Val Gln His Gly Arg
 1               5                  10                  15
Ser Leu Arg Leu Ser Cys Ala Ala Ser Gly Phe Ser Phe Ser Ser Tyr
             20                  25                  30
Gly Met His Trp Val Arg Gln Ala Pro Gly Lys Gly Leu Glu Trp Val
         35                  40                  45
Ser Val Ile Ser Tyr Asp Gly His His Lys Asn Tyr Ala Asp Ser Val
     50                  55                  60
Lys Gly Arg Phe Thr Ile Ser Arg Asp Asn Ser Lys Lys Thr Leu Tyr
 65                  70                  75                  80
Leu Gln Met Asn Ser Leu Arg Pro Glu Asp Thr Ala Val Tyr Tyr Cys
                 85                  90                  95
Ala Asn Leu Arg Gly Glu Val Thr Arg Arg Ala Ser Val Pro Phe Asp
             100                 105                 110
Ile Trp Gly Pro Gly Thr Met Val Thr Val Ser Ser
         115                 120
```

<210> SEQ ID NO 4
<211> LENGTH: 124
<212> TYPE: PRT
<213> ORGANISM: Homo sapiens
<220> FEATURE:
<223> OTHER INFORMATION: anti-Rh(D) chain C04

<400> SEQUENCE: 4

```
Glu Val Gln Leu Leu Glu Ser Gly Gly Gly Val Val Gln Pro Gly Arg
 1               5                  10                  15
Ser Leu Arg Leu Ser Cys Ala Ala Ser Gly Phe Ser Phe Ser Thr Tyr
             20                  25                  30
Gly Met His Trp Val Arg Gln Ala Pro Gly Lys Gly Leu Glu Trp Val
         35                  40                  45
Ser Val Ile Ser Tyr Asp Gly His Asn Lys Asn Tyr Ala Asp Ser Val
     50                  55                  60
Lys Gly Arg Phe Thr Ile Ser Arg Asp Asn Ser Lys Lys Thr Leu Tyr
 65                  70                  75                  80
Leu Gln Met Asn Ser Leu Arg Pro Glu Asp Thr Ala Val Tyr Tyr Cys
                 85                  90                  95
Ala Asn Leu Arg Gly Glu Val Thr Arg Arg Ala Ser Ile Pro Phe Asp
             100                 105                 110
Ile Trp Gly Gln Gly Thr Met Val Thr Val Ser Ser
         115                 120
```

<210> SEQ ID NO 5
<211> LENGTH: 124
<212> TYPE: PRT
<213> ORGANISM: Homo sapiens
<220> FEATURE:
<223> OTHER INFORMATION: anti-Rh(D) chain C04

<400> SEQUENCE: 5

```
Glu Val Gln Leu Leu Glu Ser Gly Gly Gly Val Val Gln Pro Gly Arg
 1               5                  10                  15
Ser Leu Arg Leu Ser Cys Ala Ala Ser Gly Phe Ser Phe Ser Ser Tyr
             20                  25                  30
Gly Met His Trp Val Arg Gln Ala Pro Gly Lys Gly Leu Glu Trp Val
         35                  40                  45
```

-continued

```
Ala Val Ile Ser Tyr Asp Gly Thr Asn Lys Tyr Phe Ala Asp Ser Val
         50                  55                  60

Lys Gly Arg Phe Thr Ile Ser Arg Asp Asn Ser Lys Lys Thr Leu Tyr
 65                  70                  75                  80

Leu Gln Met Thr Ser Leu Arg Pro Glu Asp Thr Ala Val Tyr Phe Cys
                 85                  90                  95

Ala Asn Leu Arg Gly Glu Val Thr Arg Arg Ala Ser Val Pro Leu Asp
            100                 105                 110

Ile Trp Gly Gln Gly Thr Met Val Thr Val Ser Ser
        115                 120
```

<210> SEQ ID NO 6
<211> LENGTH: 124
<212> TYPE: PRT
<213> ORGANISM: Homo sapiens
<220> FEATURE:
<223> OTHER INFORMATION: anti-Rh(D) chain C08

<400> SEQUENCE: 6

```
Glu Val Gln Leu Leu Glu Ser Gly Gly Val Val Gln Pro Gly Arg
 1               5                  10                  15

Ser Leu Arg Leu Ser Cys Ala Ala Ser Gly Phe Ser Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Thr Asn Lys Tyr Phe Ala Asp Ser Val
         50                  55                  60

Lys Gly Arg Phe Thr Ile Ser Arg Asp Asn Ser Lys Lys Thr Leu Tyr
 65                  70                  75                  80

Leu Gln Met Thr Ser Leu Arg Pro Glu Asp Thr Ala Val Tyr Phe Cys
                 85                  90                  95

Ala Asn Leu Arg Gly Glu Val Thr Arg Arg Ala Ser Val Pro Leu Asp
            100                 105                 110

Ile Trp Gly Gln Gly Thr Met Val Thr Val Ser Ser
        115                 120
```

<210> SEQ ID NO 7
<211> LENGTH: 124
<212> TYPE: PRT
<213> ORGANISM: Homo sapiens
<220> FEATURE:
<223> OTHER INFORMATION: anti-Rh(D) chain C10

<400> SEQUENCE: 7

```
Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Ser Phe Ser Ser Tyr
                 20                  25                  30

Gly Met His Trp Val Arg Gln Ala Pro Gly Lys Gly Leu Glu Trp Val
             35                  40                  45

Ser Val Ile Ser Tyr Asp Gly His His Lys Asn Tyr Ala Asp Ser Val
         50                  55                  60

Lys Gly Arg Phe Thr Ile Ser Arg Asp Asn Ser Lys Lys Thr Leu Tyr
 65                  70                  75                  80

Leu Gln Met Asn Ser Leu Arg Pro Glu Asp Thr Ala Val Tyr Tyr Cys
                 85                  90                  95

Ala Asn Leu Arg Gly Glu Val Thr Arg Arg Ala Ser Val Pro Phe Asp
```

```
                100              105              110
Ile Trp Gly Pro Gly Thr Leu Val Thr Val Ser Ser
            115              120
```

<210> SEQ ID NO 8
<211> LENGTH: 125
<212> TYPE: PRT
<213> ORGANISM: Homo sapiens
<220> FEATURE:
<223> OTHER INFORMATION: anti-Rh(D) chain D01

<400> SEQUENCE: 8

```
Glu Val Gln Leu Leu Glu Ser Gly Gly Val Val Gln Pro Gly Arg
 1               5                  10                  15

Ser Leu Arg Leu Ser Cys Val Val Gly Phe Thr Phe Asn Asn Tyr
            20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Asn Gln Ile Lys Leu Trp Ser Arg Tyr Leu Tyr Tyr Phe
            100                 105                 110

Asp Tyr Trp Gly Gln Gly Thr Leu Val Thr Val Ser Ser
            115                 120                 125
```

<210> SEQ ID NO 9
<211> LENGTH: 125
<212> TYPE: PRT
<213> ORGANISM: Homo sapiens
<220> FEATURE:
<223> OTHER INFORMATION: anti-Rh(D) chain D03

<400> SEQUENCE: 9

```
Glu Val Gln Leu Leu Glu Ser Gly Gly Val Val Gln Pro Gly Arg
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Glu Tyr Ala Asp Ser Val
        50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Glu Val Val Arg Gly Val Ile Leu Trp Ser Arg Lys Phe
            100                 105                 110

Asp Tyr Trp Gly Gln Gly Thr Leu Val Thr Val Ser Ser
            115                 120                 125
```

<210> SEQ ID NO 10
<211> LENGTH: 126
<212> TYPE: PRT
<213> ORGANISM: Homo sapiens
<220> FEATURE:

<223> OTHER INFORMATION: anti-Rh(D) chain D04

<400> SEQUENCE: 10

```
Glu Val Gln Leu Leu Glu Ser Gly Gly Val Ala Gln Pro Gly Arg
 1               5                  10                  15

Ser Leu Arg Leu Ser Cys Val Ala Ser Gly Phe Ser Leu Arg Ser Tyr
             20                  25                  30

Gly Met His Trp Val Arg Gln Ala Pro Gly Lys Gly Leu Glu Trp Val
             35                  40                  45

Ala Asp Ile Trp Phe Asp Gly Ser Asn Lys Asp Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Arg Val Arg Ala Phe Ser Ser Gly Trp Leu Ser Ala
                100                 105                 110

Phe Asp Ile Trp Gly Gln Gly Thr Met Val Thr Val Ser Ser
            115                 120                 125
```

<210> SEQ ID NO 11
<211> LENGTH: 127
<212> TYPE: PRT
<213> ORGANISM: Homo sapiens
<220> FEATURE:
<223> OTHER INFORMATION: anti-Rh(D) chain D05

<400> SEQUENCE: 11

```
Glu Val Gln Leu Leu Glu Ser Gly Gly Gly Val Ala Gln Pro Gly
 1               5                  10                  15

Arg Ser Leu Arg Leu Ser Cys Val Ala Ser Gly Phe Ser Leu Arg Ser
             20                  25                  30

Tyr Gly Met His Trp Val Arg Gln Ala Pro Gly Lys Gly Leu Glu Trp
             35                  40                  45

Val Ala Asp Ile Trp Phe Asp Gly Ser Asn Lys Asp Tyr Ala Asp Ser
 50                      55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                 85                  90                  95

Cys Ala Arg Asp Trp Arg Val Arg Ala Phe Ser Ser Gly Trp Leu Ser
                100                 105                 110

Ala Phe Asp Ile Trp Gly Gln Gly Thr Thr Val Ser Val Ser Ser
            115                 120                 125
```

<210> SEQ ID NO 12
<211> LENGTH: 125
<212> TYPE: PRT
<213> ORGANISM: Homo sapiens
<220> FEATURE:
<223> OTHER INFORMATION: anti-Rh(D) chain D07

<400> SEQUENCE: 12

```
Glu Val Gln Leu Leu Glu Ser Gly Gly Gly Val Val Gln Pro Gly Arg
 1               5                  10                  15

Ser Leu Arg Leu Ser Cys Ala Val Ser Gly Phe Thr Leu Thr Asn Tyr
             20                  25                  30

Gly Met His Trp Val Arg Gln Ala Pro Gly Lys Gly Leu Glu Trp Val
```

-continued

```
                35                  40                  45
Ala His Val Trp Tyr Asp Gly Ser Lys Thr Glu Tyr Ala Asp Ser Val
            50                  55                  60

Lys Gly Arg Phe Ala Val Ser Arg Asp Lys Ser Lys Asn Thr Leu Phe
 65                  70                  75                  80

Leu Gln Met Asn Ser Leu Thr Ala Glu Asp Thr Ala Ile Tyr Tyr Cys
                85                  90                  95

Ala Arg Glu Arg Arg Glu Lys Val Tyr Ile Leu Phe Tyr Ser Trp Leu
            100                 105                 110

Asp Arg Trp Gly Gln Gly Thr Leu Val Thr Val Ser Ser
            115                 120                 125
```

<210> SEQ ID NO 13
<211> LENGTH: 126
<212> TYPE: PRT
<213> ORGANISM: Homo sapiens
<220> FEATURE:
<223> OTHER INFORMATION: anti-Rh(D) chain D08

<400> SEQUENCE: 13

```
Glu Val Gln Leu Leu Glu Ser Gly Gly Gly Val Val Gln Pro Gly
 1               5                  10                  15

Arg Ser Leu Arg Leu Ser Cys Ala Ala Ser Gly Phe Thr Phe Ser Ser
                20                  25                  30

Tyr Gly Met His Trp Val Arg Gln Ala Pro Gly Arg Gly Leu Glu Trp
                35                  40                  45

Val Ala Leu Ile Trp Tyr Asp Gly Gly Asn Lys Glu Tyr Ala Asp Ser
            50                  55                  60

Val Lys Gly Arg Phe Ser Ile Ser Arg Asp Asn Ser Lys Asn Thr Leu
 65                  70                  75                  80

Tyr Leu Gln Val Asn Ser Leu Arg Ala Asp Asp Thr Ala Val Tyr Tyr
                85                  90                  95

Cys Ala Arg Asp Gln Arg Ala Ala Ala Gly Ile Phe Tyr Tyr Ser Arg
            100                 105                 110

Met Asp Val Trp Gly Gln Gly Thr Thr Val Thr Val Ser Ser
            115                 120                 125
```

<210> SEQ ID NO 14
<211> LENGTH: 126
<212> TYPE: PRT
<213> ORGANISM: Homo sapiens
<220> FEATURE:
<223> OTHER INFORMATION: anti-Rh(D) chain D09

<400> SEQUENCE: 14

```
Glu Val Gln Leu Leu Glu Ser Gly Gly Gly Val Val Gln Pro Gly Arg
 1               5                  10                  15

Ser Leu Arg Leu Ser Cys Glu Ala Ser Lys Phe Thr Leu Tyr Asn Tyr
                20                  25                  30

Gly Met His Trp Val Arg Gln Ala Pro Gly Lys Gly Leu Glu Trp Val
                35                  40                  45

Ala Phe Ile Trp Phe Asp Gly Ser Asn Lys Tyr Tyr Glu Asp Ser Val
            50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

```
Ala Arg Glu Gly Ser Lys Lys Val Ala Leu Ser Arg Tyr Tyr Tyr Tyr
            100                 105                 110

Met Asp Val Trp Gly Gln Gly Thr Thr Val Thr Val Ser Ser
            115                 120                 125

<210> SEQ ID NO 15
<211> LENGTH: 126
<212> TYPE: PRT
<213> ORGANISM: Homo sapiens
<220> FEATURE:
<223> OTHER INFORMATION: anti-Rh(D) chain D10

<400> SEQUENCE: 15

Glu Val Gln Leu Leu Glu Ser Gly Gly Val Val Gln Pro Gly Arg
  1               5                  10                  15

Ser Leu Arg Leu Ser Cys Glu Ala Ser Lys Phe Thr Leu Tyr Asn Tyr
                20                  25                  30

Gly Met His Trp Val Arg Gln Ala Pro Gly Lys Gly Leu Glu Trp Val
            35                  40                  45

Ala Phe Ile Trp Phe Asp Gly Ser Asn Lys Tyr Tyr Glu Asp Ser Val
        50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Ser Lys Lys Val Ala Leu Ser Arg Tyr Tyr Tyr Tyr
            100                 105                 110

Met Asp Val Trp Gly Gln Gly Thr Thr Val Thr Val Ser Ser
            115                 120                 125

<210> SEQ ID NO 16
<211> LENGTH: 126
<212> TYPE: PRT
<213> ORGANISM: Homo sapiens
<220> FEATURE:
<223> OTHER INFORMATION: anti-Rh(D) chain D11

<400> SEQUENCE: 16

Glu Val Gln Leu Leu Glu Ser Gly Gly Val Val Gln Pro Gly Arg
  1               5                  10                  15

Ser Leu Arg Leu Ser Cys Glu Ala Ser Lys Phe Thr Leu Tyr Asn Tyr
                20                  25                  30

Gly Met His Trp Val Arg Gln Ala Pro Gly Glu Gly Leu Glu Trp Val
            35                  40                  45

Ala Phe Ile Trp Phe Asp Gly Ser Asn Lys Tyr Tyr Ala Asp Ser Val
        50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Val Ser Lys Lys Leu Ala Leu Ser Arg Tyr Tyr Tyr Tyr
            100                 105                 110

Met Asp Val Trp Gly Gln Gly Thr Thr Val Thr Val Ser Ser
            115                 120                 125

<210> SEQ ID NO 17
<211> LENGTH: 126
<212> TYPE: PRT
<213> ORGANISM: Homo sapiens
```

```
<220> FEATURE:
<223> OTHER INFORMATION: anti-Rh(D) chain D12

<400> SEQUENCE: 17
```

Glu Val Gln Leu Leu Glu Ser Gly Gly Gly Val Val Gln Pro Gly Arg
 1               5                  10                  15

Ser Leu Arg Leu Ala Cys Ala Ala Ser Gly Phe Ser Phe Arg Ser Tyr
            20                  25                  30

Gly Met His Trp Val Arg Gln Ala Pro Gly Arg Gly Leu Glu Trp Val
        35                  40                  45

Ala Phe Thr Trp Phe Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Val Asp Asp Thr Ala Val Tyr Tyr Cys
                85                  90                  95

Ala Arg Glu Ala Ser Met Leu Arg Gly Ile Ser Arg Tyr Tyr Tyr Ala
            100                 105                 110

Met Asp Val Trp Gly Pro Gly Thr Thr Val Thr Val Ser Ser
        115                 120                 125

```
<210> SEQ ID NO 18
<211> LENGTH: 127
<212> TYPE: PRT
<213> ORGANISM: Homo sapiens
<220> FEATURE:
<223> OTHER INFORMATION: anti-Rh(D) chain D13

<400> SEQUENCE: 18
```

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Arg Asp Tyr Ala Glu Ser Val
    50                  55                  60

Lys Gly Arg Phe Thr Ile Ser Arg Asp Lys Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Glu Asn Val Ala Arg Gly Gly Gly Val Arg Tyr Lys Tyr
            100                 105                 110

Tyr Phe Asp Tyr Trp Gly Gln Gly Thr Leu Val Thr Val Ser Ser
        115                 120                 125

```
<210> SEQ ID NO 19
<211> LENGTH: 127
<212> TYPE: PRT
<213> ORGANISM: Homo sapiens
<220> FEATURE:
<223> OTHER INFORMATION: anti-Rh(D) chain D14

<400> SEQUENCE: 19
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

```
Gly Met His Trp Val Arg Gln Ala Pro Gly Lys Gly Leu Glu Trp Val
            35                  40                  45

Ala Val Ile Trp Phe Asp Gly Ser Lys Arg Asp Tyr Ala Glu Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Glu Asn Val Ala Arg Gly Gly Gly Ile Arg Tyr Lys Tyr
                100                 105                 110

Tyr Phe Asp Tyr Trp Gly Gln Gly Thr Leu Val Thr Val Ser Ser
            115                 120                 125

<210> SEQ ID NO 20
<211> LENGTH: 125
<212> TYPE: PRT
<213> ORGANISM: Homo sapiens
<220> FEATURE:
<223> OTHER INFORMATION: anti-Rh(D) chain D15

<400> SEQUENCE: 20

Glu Val Gln Leu Leu Glu Ser Gly Gly Val Val Gln Pro Gly Arg
1               5                   10                  15

Ser Leu Arg Leu Ser Cys Val Val Ser Gly Phe Thr Phe Asn Asn Tyr
                20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Gln Ile Lys Leu Trp Ser Arg Tyr Leu Tyr Tyr Phe
                100                 105                 110

Asp Tyr Trp Gly Gln Gly Thr Leu Val Thr Val Ser Ser
            115                 120                 125

<210> SEQ ID NO 21
<211> LENGTH: 125
<212> TYPE: PRT
<213> ORGANISM: Homo sapiens
<220> FEATURE:
<223> OTHER INFORMATION: anti-Rh(D) chain D16

<400> SEQUENCE: 21

Glu Val Gln Leu Leu Glu Ser Gly Gly Val Val Gln Pro Gly Arg
1               5                   10                  15

Ser Leu Arg Leu Ser Cys Val Val Ser Gly Phe Thr Phe Asn Asn Tyr
                20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Glu Asn Gln Ile Lys Leu Trp Ser Arg Tyr Leu Tyr Tyr Phe
            100                 105                 110

Asp Tyr Trp Gly Gln Gly Thr Leu Val Thr Val Ser Ser
        115                 120                 125

<210> SEQ ID NO 22
<211> LENGTH: 125
<212> TYPE: PRT
<213> ORGANISM: Homo sapiens
<220> FEATURE:
<223> OTHER INFORMATION: anti-Rh(D) chain D17

<400> SEQUENCE: 22

Glu Val Gln Leu Leu Glu Ser Gly Gly Val Val Gln Pro Gly Arg
 1               5                  10                  15

Ser Leu Arg Leu Ser Cys Val Val Ser Gly Phe Thr Phe Asn Asn Tyr
                20                  25                  30

Gly Met His Trp Val Arg Gln Ala Pro Gly Lys Gly Leu Glu Trp Val
             35                  40                  45

Ala Val Ile Trp Phe Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asn Gln Ile Lys Leu Trp Ser Arg Tyr Leu Tyr Tyr Phe
            100                 105                 110

Asp Tyr Trp Gly Gln Gly Thr Leu Val Thr Val Ser Ser
        115                 120                 125

<210> SEQ ID NO 23
<211> LENGTH: 125
<212> TYPE: PRT
<213> ORGANISM: Homo sapiens
<220> FEATURE:
<223> OTHER INFORMATION: anti-Rh(D) chain D18

<400> SEQUENCE: 23

Glu Val Gln Leu Leu Glu Ser Gly Gly Val Val Gln Pro Gly Arg
 1               5                  10                  15

Ser Leu Arg Leu Ser Cys Val Val Ser Gly Phe Thr Phe Asn Asn Tyr
                20                  25                  30

Gly Met His Trp Val Arg Gln Ala Ser Gly Lys Gly Leu Glu Trp Val
             35                  40                  45

Ala Val Ile Trp Phe Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Asn Gln Ile Lys Leu Trp Ser Arg Tyr Leu Tyr Tyr Phe
            100                 105                 110

Asp Tyr Trp Gly Gln Gly Thr Leu Val Thr Val Ser Ser
        115                 120                 125

<210> SEQ ID NO 24
<211> LENGTH: 125
<212> TYPE: PRT
```

```
<213> ORGANISM: Homo sapiens
<220> FEATURE:
<223> OTHER INFORMATION: anti-Rh(D) chain D20

<400> SEQUENCE: 24

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Asn Lys Glu Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Val Val Arg Gly Val Ile Leu Trp Ser Arg Lys Phe
            100                 105                 110

Asp Tyr Trp Gly Gln Gly Thr Leu Val Thr Val Ser Ser
        115                 120                 125

<210> SEQ ID NO 25
<211> LENGTH: 126
<212> TYPE: PRT
<213> ORGANISM: Homo sapiens
<220> FEATURE:
<223> OTHER INFORMATION: anti-Rh(D) chain D30

<400> SEQUENCE: 25

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met Arg Trp Val Arg Gln Ala Pro Gly Lys Gly Leu Glu Trp Val
        35                  40                  45

Ala Val Val Tyr Tyr Asp Gly Ser Asn Lys His Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Glu Arg Asn Phe Arg Ser Gly Tyr Ser Arg Tyr Tyr Tyr Gly
            100                 105                 110

Met Asp Val Trp Gly Pro Gly Thr Thr Val Thr Val Ser Ser
        115                 120                 125

<210> SEQ ID NO 26
<211> LENGTH: 126
<212> TYPE: PRT
<213> ORGANISM: Homo sapiens
<220> FEATURE:
<223> OTHER INFORMATION: anti-Rh(D) chain D31

<400> SEQUENCE: 26

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
        35                  40                  45

Ala Val Val Tyr Tyr Asp Gly Ser Asn Lys His Tyr Ser Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                 85                  90                  95

Ala Arg Glu Arg Asn Phe Arg Ser Gly Tyr Ser Arg Tyr Tyr Tyr Gly
            100                 105                 110

Met Asp Val Trp Gly Pro Gly Thr Thr Val Thr Val Ser Ser
        115                 120                 125

<210> SEQ ID NO 27
<211> LENGTH: 127
<212> TYPE: PRT
<213> ORGANISM: Homo sapiens
<220> FEATURE:
<223> OTHER INFORMATION: anti-Rh(D) chain E01is

<400> SEQUENCE: 27

Glu Val Gln Leu Leu Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
             20                  25                  30

Ser Met His Trp Val Arg Gln Ala Pro Gly Lys Gly Leu Glu Trp Val
        35                  40                  45

Ser Ser Ile Ser Asn Ser Asn Thr Tyr Ile Tyr Tyr Ala Asp Ala Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ser Arg Tyr Ser Asn Phe Leu Arg Trp Val Arg Ser Asp
            100                 105                 110

Gly Met Asp Val Trp Gly Gln Gly Thr Thr Val Ile Val Ser Ser
        115                 120                 125

<210> SEQ ID NO 28
<211> LENGTH: 131
<212> TYPE: PRT
<213> ORGANISM: Homo sapiens
<220> FEATURE:
<223> OTHER INFORMATION: anti-Rh(D) chain E03

<400> SEQUENCE: 28

Glu Val Gln Leu Leu Glu Ser Gly Val Glu Ser Gly Gly Gly Leu Val
 1               5                  10                  15

Lys Pro Gly Gly Ser Leu Arg Leu Ser Cys Ala Ala Ser Gly Phe Thr
             20                  25                  30

Phe Ser Ser Tyr Ser Met His Trp Val Arg Gln Gly Pro Gly Lys Gly
        35                  40                  45

Leu Glu Trp Val Ser Ser Ile Ser Asn Ser Asn Thr Tyr Ile Tyr Tyr
 50                  55                  60

Ala Asp Ala Val Lys Gly Arg Phe Thr Ile Ser Arg Asp Asn Ala Lys
 65                  70                  75                  80

Asn Ser Leu Tyr Leu Gln Met Asn Ser Leu Arg Ala Glu His Thr Ala
```

```
                        85                  90                  95
Val Tyr Tyr Cys Ala Arg Asp Ser Arg Tyr Ser Asn Phe Leu Arg Trp
                100                 105                 110

Val Arg Ser Asp Gly Met Asp Val Trp Gly Gln Gly Thr Thr Val Ile
            115                 120                 125

Val Ser Ser
        130

<210> SEQ ID NO 29
<211> LENGTH: 107
<212> TYPE: PRT
<213> ORGANISM: Homo sapiens
<220> FEATURE:
<223> OTHER INFORMATION: anti-Rh(D) chain F01

<400> SEQUENCE: 29

Ala Glu Leu Thr Gln Ser Pro Ser Ser Leu Ser Ala Ser Val Gly Asp
  1               5                  10                  15

Arg Val Thr Ile Thr Cys Arg Ala Ser Gln Gly Phe Arg Asn Asp Leu
                 20                  25                  30

Gly Trp Tyr Gln Gln Lys Pro Gly Lys Ala Pro Lys Arg Leu Ile Tyr
            35                  40                  45

Ala Thr Ser Ser Leu Gln Ser Gly Val Pro Ser Arg Phe Ser Gly Ser
 50                  55                  60

Gly Ser Gly Thr Glu Phe Thr Leu Thr Ile Asn Ser Leu Gln Pro Glu
 65                  70                  75                  80

Asp Ser Ala Thr Tyr Tyr Cys Leu Gln His Asn Ser Phe Pro Trp Thr
                 85                  90                  95

Phe Gly Gln Gly Thr Lys Val Glu Ile Lys Arg
            100                 105

<210> SEQ ID NO 30
<211> LENGTH: 112
<212> TYPE: PRT
<213> ORGANISM: Homo sapiens
<220> FEATURE:
<223> OTHER INFORMATION: anti-Rh(D) chain G01

<400> SEQUENCE: 30

Ala Glu Leu Thr Gln Ser Pro Leu Ser Leu Pro Val Thr Pro Gly Glu
  1               5                  10                  15

Pro Ala Ser Ile Ser Cys Arg Ser Ser Gln Ser Leu Leu His Ser Ser
                 20                  25                  30

Gly Phe Asn Phe Leu Asp Trp Tyr Leu Gln Lys Pro Gly Gln Ser Pro
            35                  40                  45

Gln Leu Leu Ile Tyr Met Gly Ser Asn Arg Ala Ser Gly Val Pro Asp
 50                  55                  60

Arg Phe Ser Gly Ser Gly Ser Gly Thr Asp Phe Thr Leu Lys Ile Asn
 65                  70                  75                  80

Arg Val Glu Ala Glu Asp Val Gly Val Tyr Tyr Cys Met Gln Ala Leu
                 85                  90                  95

Gln Phe Pro Leu Thr Phe Gly Gly Gly Thr Lys Val Glu Ile Lys Arg
            100                 105                 110

<210> SEQ ID NO 31
<211> LENGTH: 108
<212> TYPE: PRT
<213> ORGANISM: Homo sapiens
<220> FEATURE:
```

<223> OTHER INFORMATION: anti-Rh(D) chain H01

<400> SEQUENCE: 31

Ala Glu Leu Thr Gln Ser Pro Ser Phe Leu Ser Ala Ser Val Gly Asp
1               5                   10                  15

Arg Val Thr Ile Thr Cys Arg Ala Ser Gln Gly Ile Thr Ser Tyr Leu
            20                  25                  30

Ala Trp Tyr Gln Gln Lys Pro Gly Lys Ala Pro Lys Leu Leu Ile Tyr
        35                  40                  45

Ala Ala Ser Thr Leu Gln Ser Gly Val Pro Ser Arg Phe Ser Gly Ser
    50                  55                  60

Gly Ser Gly Thr Glu Phe Thr Leu Thr Ile Ala Ser Leu Gln Pro Asp
65                  70                  75                  80

Asp Phe Ala Thr Tyr Tyr Cys Gln Gln Leu Asn Asn Tyr Pro Pro Phe
                85                  90                  95

Thr Phe Gly Pro Gly Thr Lys Val Asp Ile Lys Arg
            100                 105

<210> SEQ ID NO 32
<211> LENGTH: 108
<212> TYPE: PRT
<213> ORGANISM: Homo sapiens
<220> FEATURE:
<223> OTHER INFORMATION: anti-Rh(D) chain I01

<400> SEQUENCE: 32

Ala Glu Leu Thr Gln Ser Pro Ser Ser Leu Ser Ala Ser Val Gly Asp
1               5                   10                  15

Arg Val Thr Ile Thr Cys Arg Ala Ser Gln Ser Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro Pro Tyr
                85                  90                  95

Thr Phe Gly Gln Gly Thr Lys Leu Glu Ile Lys Arg
            100                 105

<210> SEQ ID NO 33
<211> LENGTH: 107
<212> TYPE: PRT
<213> ORGANISM: Homo sapiens
<220> FEATURE:
<223> OTHER INFORMATION: anti-Rh(D) chain I02

<400> SEQUENCE: 33

Ala Glu Leu Thr Gln Ser Pro Ser Ser Leu Ser Ala Ser Val Gly Asp
1               5                   10                  15

Arg Val Thr Ile Thr Cys Arg Ala Ser Gln Ser Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu

```
                65                  70                  75                  80
Asp Phe Ala Thr Tyr Tyr Cys Gln Gln Ser Tyr Ser Thr Leu Trp Thr
                        85                  90                  95

Phe Gly Gln Gly Thr Lys Val Glu Ile Lys Arg
                100                 105
```

<210> SEQ ID NO 34
<211> LENGTH: 107
<212> TYPE: PRT
<213> ORGANISM: Homo sapiens
<220> FEATURE:
<223> OTHER INFORMATION: anti-Rh(D) chain I03

<400> SEQUENCE: 34

```
Ala Glu Leu Thr Gln Ser Pro Ser Ser Leu Ser Ala Ser Val Ala Asp
 1               5                  10                  15

Arg Val Thr Ile Thr Cys Arg Ser Arg Asn Ile Asn Arg Tyr Leu
                20                  25                  30

Asn Trp Tyr Gln Gln Lys Pro Gly Lys Ala Pro Lys Leu Leu Ile Tyr
            35                  40                  45

Ala Ala Ser Ser Leu Gln Ser Gly Val Pro Ser Arg Phe Ser Gly Ser
        50                  55                  60

Gly Ser Gly Thr Asp Phe Thr Leu Thr Ile Thr Ser Leu Gln Pro Glu
65                  70                  75                  80

Asp Phe Ala Thr Tyr Tyr Cys Gln Gln Ser Tyr Ser Thr Pro Phe Thr
                    85                  90                  95

Phe Gly Pro Gly Thr Lys Val Asp Leu Lys Arg
                100                 105
```

<210> SEQ ID NO 35
<211> LENGTH: 107
<212> TYPE: PRT
<213> ORGANISM: Homo sapiens
<220> FEATURE:
<223> OTHER INFORMATION: anti-Rh(D) chain I04

<400> SEQUENCE: 35

```
Ala Glu Leu Thr Gln Ser Pro Ser Ser Leu Ser Ala Ser Val Gly Asp
 1               5                  10                  15

Arg Val Thr Ile Thr Cys Arg Ala Ser Gln Asn Ile Arg Arg Ser Leu
                20                  25                  30

Asn Trp Tyr Gln Gln Lys Pro Gly Lys Ala Pro Lys Leu Leu Ile Tyr
            35                  40                  45

Ala Ala Ser Ser Leu Gln Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Ser Asn Thr Pro Trp Thr
                    85                  90                  95

Phe Gly Gln Gly Thr Lys Val Glu Ile Lys Arg
                100                 105
```

<210> SEQ ID NO 36
<211> LENGTH: 107
<212> TYPE: PRT
<213> ORGANISM: Homo sapiens
<220> FEATURE:
<223> OTHER INFORMATION: anti-Rh(D) chain I05

<400> SEQUENCE: 36

Ala Glu Leu Thr Gln Ser Pro Ser Ser Leu Ser Ala Ser Val Gly Asp
1               5                   10                  15

Arg Val Thr Ile Thr Cys Arg Ala Ser Gln Ser Ile Arg Arg Tyr Leu
            20                  25                  30

Asn Trp Tyr Gln His Lys Pro Gly Lys Ala Pro Lys Leu Leu Ile Phe
        35                  40                  45

Ala Ala Ser Ser Leu Gln Ser Gly Val Pro Ser Arg Phe Thr Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro Gln Thr
                85                  90                  95

Phe Gly Gln Gly Thr Lys Val Glu Ile Lys Arg
            100                 105

<210> SEQ ID NO 37
<211> LENGTH: 107
<212> TYPE: PRT
<213> ORGANISM: Homo sapiens
<220> FEATURE:
<223> OTHER INFORMATION: anti-Rh(D) chain I06

<400> SEQUENCE: 37

Ala Glu Leu Thr Gln Ser Pro Ser Ser Leu Ser Ala Ser Val Gly Asp
1               5                   10                  15

Arg Val Thr Ile Thr Cys Arg Ala Ser Gln Ser Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro Ile Thr
                85                  90                  95

Phe Gly Gln Gly Thr Arg Leu Glu Ile Lys Arg
            100                 105

<210> SEQ ID NO 38
<211> LENGTH: 107
<212> TYPE: PRT
<213> ORGANISM: Homo sapiens
<220> FEATURE:
<223> OTHER INFORMATION: anti-Rh(D) chain I07

<400> SEQUENCE: 38

Ala Glu Leu Thr Gln Ser Pro Ser Ser Leu Ser Ala Ser Val Gly Asp
1               5                   10                  15

Arg Val Thr Ile Thr Cys Arg Ala Ser Gln Ser Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro Arg Thr

```
                        85                  90                  95

Phe Gly Gly Gly Thr Lys Val Glu Ile Lys Arg
            100                 105

<210> SEQ ID NO 39
<211> LENGTH: 107
<212> TYPE: PRT
<213> ORGANISM: Homo sapiens
<220> FEATURE:
<223> OTHER INFORMATION: anti-Rh(D) chain I08

<400> SEQUENCE: 39

Ala Glu Leu Thr Gln Ser Pro Ser Ser Leu Ser Ala Ser Val Gly Asp
  1               5                  10                  15

Arg Val Thr Ile Thr Cys Arg Ala Ser Gln Ser Ile Ser Ser Tyr Leu
                 20                  25                  30

Asn Trp Tyr Gln Gln Lys Pro Gly Lys Ala Pro Lys Leu Leu Ile Tyr
             35                  40                  45

Ala Ala Ser Ser Leu Gln Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Arg Thr
                 85                  90                  95

Phe Gly Gly Gly Thr Lys Val Glu Ile Lys Arg
            100                 105

<210> SEQ ID NO 40
<211> LENGTH: 107
<212> TYPE: PRT
<213> ORGANISM: Homo sapiens
<220> FEATURE:
<223> OTHER INFORMATION: anti-Rh(D) chain I09

<400> SEQUENCE: 40

Ala Glu Leu Thr Gln Ser Pro Ser Ser Leu Ser Ala Ser Val Gly Asp
  1               5                  10                  15

Arg Val Thr Ile Thr Cys Arg Ala Ser Gln Ser Ile Ser Ser Tyr Leu
                 20                  25                  30

Asn Trp Tyr Gln Gln Lys Pro Gly Lys Ala Pro Lys Leu Leu Ile Tyr
             35                  40                  45

Ala Ala Ser Ser Leu Gln Ser Gly Val Pro Ser Arg Phe Ser Gly Ser
         50                  55                  60

Gly Ser Gly Thr Asp Ser Thr Leu Thr Ile Ser Ser Leu Gln Pro Glu
 65                  70                  75                  80

Asp Phe Ala Thr Tyr Tyr Cys Gln Gln Leu Asn Ser Tyr Pro Tyr Thr
                 85                  90                  95

Phe Gly Gln Gly Thr Lys Leu Glu Ile Lys Arg
            100                 105

<210> SEQ ID NO 41
<211> LENGTH: 108
<212> TYPE: PRT
<213> ORGANISM: Homo sapiens
<220> FEATURE:
<223> OTHER INFORMATION: anti-Rh(D) chain I10

<400> SEQUENCE: 41

Ala Glu Leu Thr Gln Ser Pro Ser Ser Leu Ser Ala Ser Val Gly Asp
  1               5                  10                  15
```

```
Arg Val Thr Ile Thr Cys Arg Ala Ser Gln Asn Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Leu Ser Arg Phe Ser Gly Ser
    50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Pro Tyr
                85                  90                  95

Ser Phe Gly Gln Gly Thr Lys Leu Glu Ile Lys Arg
            100                 105

<210> SEQ ID NO 42
<211> LENGTH: 103
<212> TYPE: PRT
<213> ORGANISM: Homo sapiens
<220> FEATURE:
<223> OTHER INFORMATION: anti-Rh(D) chain I11

<400> SEQUENCE: 42

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Ser Tyr Leu
            20                  25                  30

Asn Trp Tyr Gln Gln Lys Pro Gly Lys Ala Pro Thr Leu Leu Ile Asn
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
 65                  70                  75                  80

Asp Phe Ala Ile Tyr Tyr Cys Gln Gln Arg Glu Thr Phe Gly Gln Gly
                85                  90                  95

Thr Lys Leu Glu Ile Lys Arg
            100

<210> SEQ ID NO 43
<211> LENGTH: 108
<212> TYPE: PRT
<213> ORGANISM: Homo sapiens
<220> FEATURE:
<223> OTHER INFORMATION: anti-Rh(D) chain I12

<400> SEQUENCE: 43

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Pro Tyr
                85                  90                  95

Thr Phe Gly Gln Gly Thr Lys Leu Glu Ile Lys Arg
```

-continued

```
               100                 105

<210> SEQ ID NO 44
<211> LENGTH: 107
<212> TYPE: PRT
<213> ORGANISM: Homo sapiens
<220> FEATURE:
<223> OTHER INFORMATION: anti-Rh(D) chain I13

<400> SEQUENCE: 44

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Arg Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Gly Thr Pro His Ser
                85                  90                  95

Phe Gly Arg Gly Thr Lys Leu Glu Ile Lys Arg
            100                 105

<210> SEQ ID NO 45
<211> LENGTH: 107
<212> TYPE: PRT
<213> ORGANISM: Homo sapiens
<220> FEATURE:
<223> OTHER INFORMATION: anti-Rh(D) chain I15

<400> SEQUENCE: 45

Ala Glu Leu Thr Gln Ser Pro Ser Ser Leu Ser Ala Ser Val Gly Asp
 1               5                  10                  15

Arg Val Thr Ile Thr Cys Arg Ala Asn Gln Asn Ile Arg Arg Ser Leu
            20                  25                  30

Asn Trp Tyr Gln Gln Lys Pro Gly Lys Ala Pro Asn Leu Leu Ile Tyr
        35                  40                  45

Ala Ala Ser Thr Leu Gln Gly Gly Val Pro Ser Arg Phe Ser Gly Ser
    50                  55                  60

Gly Ser Gly Thr Asp Phe Thr Leu Thr Ile Ser Ser Leu Gln Leu Ala
65                  70                  75                  80

Asp Phe Ala Thr Tyr Tyr Cys Gln Gln Thr Ser Ala Thr Pro Trp Thr
                85                  90                  95

Phe Gly Gln Gly Thr Lys Val Glu Ile Lys Arg
            100                 105

<210> SEQ ID NO 46
<211> LENGTH: 107
<212> TYPE: PRT
<213> ORGANISM: Homo sapiens
<220> FEATURE:
<223> OTHER INFORMATION: anti-Rh(D) chain I16

<400> SEQUENCE: 46

Ala Glu Leu Thr Gln Ser Pro Ser Ser Leu Pro Ala Ser Val Gly Asp
 1               5                  10                  15

Arg Val Thr Ile Thr Cys Arg Ala Ser Gln Thr Ile Gly Phe Asn Leu
            20                  25                  30
```

```
Asn Trp Tyr Gln Gln Thr Ser Gly Lys Pro Lys Leu Leu Ile Tyr
         35                  40                  45

Gly Val Ser Lys Leu Gln Asn Gly Val Pro Ser Arg Phe Ser Gly Ser
 50                  55                  60

Gly Ser Gly Thr Glu Phe Thr Leu Thr Ile Ser Ser Leu Gln Pro Glu
 65                  70                  75                  80

Asp Phe Ala Thr Tyr Tyr Cys Gln Gln Thr Asn Asp Ala Leu Trp Thr
                 85                  90                  95

Phe Gly Gln Gly Thr Lys Val Glu Val Arg Arg
                100                 105
```

<210> SEQ ID NO 47
<211> LENGTH: 106
<212> TYPE: PRT
<213> ORGANISM: Homo sapiens
<220> FEATURE:
<223> OTHER INFORMATION: anti-Rh(D) chain J01

<400> SEQUENCE: 47

```
Ala Glu Leu Gln Asp Pro Val Val Ser Val Ala Leu Gly Gln Thr Val
 1               5                  10                  15

Arg Ile Thr Cys Gln Gly Asp Gly Leu Arg Ser Tyr Tyr Ala Ser Trp
             20                  25                  30

Tyr Gln Gln Lys Pro Gly Gln Ala Pro Lys Leu Val Met Tyr Gly Arg
         35                  40                  45

Asn Asn Arg Pro Ser Gly Ile Pro Gly Arg Phe Ser Gly Ser Ser Ser
 50                  55                  60

Gly Gln Thr Ala Ala Leu Thr Ile Thr Gly Thr Gln Ala Glu Asp Glu
 65                  70                  75                  80

Ala Asp Tyr Tyr Cys Gln Ser Arg Ala Thr Ser Gly Asn Pro Val Val
                 85                  90                  95

Phe Gly Gly Gly Thr Lys Leu Thr Val Leu
                100                 105
```

<210> SEQ ID NO 48
<211> LENGTH: 106
<212> TYPE: PRT
<213> ORGANISM: Homo sapiens
<220> FEATURE:
<223> OTHER INFORMATION: anti-Rh(D) chain J02

<400> SEQUENCE: 48

```
Ala Glu Leu Gln Asp Pro Val Val Ser Val Ala Leu Gly Gln Thr Val
 1               5                  10                  15

Arg Ile Thr Cys Gln Gly Asp Gly Leu Arg Ser Tyr Tyr Ala Ser Trp
             20                  25                  30

Tyr Gln Gln Lys Pro Gly Gln Ala Pro Lys Leu Val Met Tyr Gly Arg
         35                  40                  45

Asn Asn Arg Pro Ser Gly Ile Pro Asp Arg Phe Ser Gly Ser Ser Ser
 50                  55                  60

Gly Gln Thr Ala Ala Leu Thr Ile Thr Gly Thr Gln Ala Glu Asp Glu
 65                  70                  75                  80

Ala Asp Tyr Tyr Cys Gln Ser Arg Ala Thr Ser Gly Asn Pro Val Val
                 85                  90                  95

Phe Gly Gly Gly Thr Lys Leu Thr Val Leu
                100                 105
```

```
<210> SEQ ID NO 49
<211> LENGTH: 104
<212> TYPE: PRT
<213> ORGANISM: Homo sapiens
<220> FEATURE:
<223> OTHER INFORMATION: anti-Rh(D) chain J04

<400> SEQUENCE: 49

Ala Glu Leu Gln Asp Pro Val Val Ser Val Ala Leu Gly Gln Thr Val
 1               5                  10                  15

Arg Ile Thr Cys Gln Gly Asp Ser Leu Arg Ser Tyr Tyr Ala Ser Trp
             20                  25                  30

Tyr Gln Gln Lys Pro Gly Gln Ala Pro Val Leu Val Ile Tyr Gly Lys
         35                  40                  45

Asn Ser Arg Pro Ser Gly Ile Pro Asp Arg Phe Ser Gly Ser Ser Ser
 50                  55                  60

Gly Asn Thr Ala Ser Leu Thr Ile Thr Gly Ala Gln Ala Glu Asp Glu
 65                  70                  75                  80

Ala Asp Tyr Tyr Cys Ser Ser Arg Gly Ser Pro His Val Ala Phe Gly
                 85                  90                  95

Gly Gly Thr Lys Leu Thr Val Leu
            100

<210> SEQ ID NO 50
<211> LENGTH: 106
<212> TYPE: PRT
<213> ORGANISM: Homo sapiens
<220> FEATURE:
<223> OTHER INFORMATION: anti-Rh(D) chain J05

<400> SEQUENCE: 50

Ala Glu Leu Gln Asp Pro Val Val Ser Val Ala Leu Gly Gln Thr Val
 1               5                  10                  15

Lys Ile Thr Cys Gln Gly Asp Ser Leu Arg Lys Tyr Tyr Ala Ser Trp
             20                  25                  30

Tyr Gln Gln Lys Pro Gly Gln Ala Pro Val Leu Val Phe Tyr Ala Arg
         35                  40                  45

Asn Ser Arg Pro Ser Gly Ile Pro Asp Arg Phe Ser Gly Ser Asn Ser
 50                  55                  60

Gly Thr Thr Ala Ser Leu Thr Ile Ala Gly Ala Arg Ala Glu Asp Glu
 65                  70                  75                  80

Ala Asp Tyr Tyr Cys His Ser Asp Ser Asn Gly His His Arg Val
                 85                  90                  95

Phe Gly Gly Gly Thr Lys Leu Thr Val Leu
            100                 105

<210> SEQ ID NO 51
<211> LENGTH: 108
<212> TYPE: PRT
<213> ORGANISM: Homo sapiens
<220> FEATURE:
<223> OTHER INFORMATION: anti-Rh(D) chain K01

<400> SEQUENCE: 51

Ala Glu Leu Thr Gln Glu Pro Ser Leu Thr Val Ser Pro Gly Gly Thr
 1               5                  10                  15

Val Thr Leu Thr Cys Ala Ser Ser Thr Gly Ala Val Thr Ser Arg Tyr
             20                  25                  30

Phe Pro Asn Trp Phe Gln Gln Lys Pro Gly Gln Ala Pro Arg Pro Leu
         35                  40                  45
```

```
Ile Tyr Ser Ala Ser Asn Lys His Ser Trp Thr Pro Ala Arg Phe Ser
        50                  55                  60

Gly Ser Leu Leu Gly Gly Lys Ala Ala Leu Thr Leu Ser Gly Val Gln
 65                  70                  75                  80

Pro Glu Asp Glu Ala Glu Tyr Tyr Cys Leu Leu Tyr Tyr Ser Gly Ala
                85                  90                  95

Trp Val Phe Gly Gly Gly Thr Lys Leu Thr Val Leu
                100                 105
```

<210> SEQ ID NO 52
<211> LENGTH: 108
<212> TYPE: PRT
<213> ORGANISM: Homo sapiens
<220> FEATURE:
<223> OTHER INFORMATION: anti-Rh(D) chain K02

<400> SEQUENCE: 52

```
Ala Glu Leu Thr Gln Glu Pro Ser Leu Thr Val Ser Pro Gly Gly Thr
  1               5                  10                  15

Val Thr Leu Thr Cys Ala Ser Ser Thr Gly Ala Val Thr Ser Arg Tyr
                20                  25                  30

Phe Pro Asn Trp Phe Gln Gln Lys Pro Gly Gln Ala Pro Arg Pro Leu
            35                  40                  45

Ile Tyr Ser Ala Ser Asn Lys His Ser Trp Thr Pro Ala Arg Phe Ser
        50                  55                  60

Gly Ser Leu Leu Gly Gly Lys Ala Ala Leu Thr Leu Ser Gly Val Gln
 65                  70                  75                  80

Pro Glu Asp Glu Ala Glu Tyr Tyr Cys Leu Leu Tyr Tyr Ser Gly Ala
                85                  90                  95

Trp Val Phe Gly Gly Gly Thr Lys Leu Thr Val Leu
                100                 105
```

<210> SEQ ID NO 53
<211> LENGTH: 108
<212> TYPE: PRT
<213> ORGANISM: Homo sapiens
<220> FEATURE:
<223> OTHER INFORMATION: anti-Rh(D) chain K03

<400> SEQUENCE: 53

```
Ala Glu Leu Thr Gln Pro Pro Ser Leu Thr Val Ser Pro Gly Gly Thr
  1               5                  10                  15

Val Thr Leu Thr Cys Ala Ser Ser Thr Gly Ala Val Thr Ser Arg Tyr
                20                  25                  30

Phe Pro Asn Trp Phe Gln Gln Lys Pro Gly Gln Ala Pro Arg Ala Leu
            35                  40                  45

Ile Tyr Gly Ser Asn Asn Lys His Ser Trp Thr Pro Ala Arg Phe Ser
        50                  55                  60

Gly Ser Leu Leu Gly Gly Lys Ala Ala Leu Thr Leu Ser Gly Val Gln
 65                  70                  75                  80

Pro Glu Asp Glu Ala Glu Tyr Tyr Cys Leu Leu Phe Tyr Ala Gly Ala
                85                  90                  95

Trp Ala Phe Gly Gly Trp Thr Lys Leu Thr Val Leu
                100                 105
```

<210> SEQ ID NO 54
<211> LENGTH: 109
<212> TYPE: PRT

<213> ORGANISM: Homo sapiens
<220> FEATURE:
<223> OTHER INFORMATION: anti-Rh(D) chain L01

<400> SEQUENCE: 54

Ala Glu Leu Thr Gln Pro Pro Ser Ala Ser Gly Thr Pro Gly Gln Arg
 1               5                  10                  15

Val Thr Ile Ser Cys Ser Gly Gly Ser Ser Asn Ile Ala Ser Asn Thr
            20                  25                  30

Val Asn Trp Tyr Gln Gln Leu Pro Gly Thr Ala Pro Lys Leu Leu Ile
        35                  40                  45

Tyr Ser Asn Asn Gln Arg Pro Ser Gly Val Pro Asp Arg Phe Ser Gly
    50                  55                  60

Ser Lys Ser Gly Thr Ser Ala Thr Leu Val Ile Thr Gly Leu Gln Thr
65                  70                  75                  80

Gly Asp Glu Ala Asp Tyr Tyr Cys Gly Thr Trp Asp His Ser Arg Ser
                85                  90                  95

Gly Ala Val Phe Gly Gly Gly Thr Lys Leu Thr Val Leu
                100                 105

<210> SEQ ID NO 55
<211> LENGTH: 109
<212> TYPE: PRT
<213> ORGANISM: Homo sapiens
<220> FEATURE:
<223> OTHER INFORMATION: anti-Rh(D) chain L03

<400> SEQUENCE: 55

Ala Glu Leu Thr Gln Pro Pro Ser Ala Ser Gly Thr Pro Gly Gln Arg
 1               5                  10                  15

Val Thr Ile Ser Cys Ser Gly Ser Ser Asn Ile Gly Asn Asn His
            20                  25                  30

Val Ser Trp Tyr Gln Gln Leu Pro Gly Met Ala Pro Lys Leu Leu Ile
        35                  40                  45

Tyr Ser Asn Gly Gln Arg Pro Ser Gly Val Pro Asp Arg Phe Ser Gly
    50                  55                  60

Ser Lys Ser Gly Thr Ser Ala Ser Leu Ala Ile Ser Gly Leu Gln Ser
65                  70                  75                  80

Glu Asp Glu Ala Asp Tyr Tyr Cys Ala Ala Trp His Asp Ser Leu Tyr
                85                  90                  95

Gly Pro Val Phe Gly Gly Gly Thr Lys Leu Thr Val Leu
                100                 105

<210> SEQ ID NO 56
<211> LENGTH: 109
<212> TYPE: PRT
<213> ORGANISM: Homo sapiens
<220> FEATURE:
<223> OTHER INFORMATION: anti-Rh(D) chain L04

<400> SEQUENCE: 56

Ala Glu Leu Thr Gln Pro Pro Ser Ala Ser Gly Thr Pro Gly Gln Arg
 1               5                  10                  15

Val Ser Ile Ser Cys Ser Gly Ser Ser Asn Ile Gly Ser Asn Thr
            20                  25                  30

Val Asn Trp Tyr Gln Gln Leu Pro Gly Thr Ala Pro Lys Leu Leu Ile
        35                  40                  45

Ser Thr Asn Asn Gln Gly Pro Ser Gly Val Pro Asp Arg Phe Ser Gly
    50                  55                  60

```
Ser Lys Ser Gly Thr Ser Ser Leu Ala Ile Ser Gly Leu Arg Ser
 65                  70                  75                  80

Glu Ala Glu Asp Asp Tyr Tyr Cys Ala Ala Trp Asp Thr Leu Asn
                 85                  90                  95

Gly Val Val Phe Gly Gly Gly Thr Lys Leu Thr Val Leu
                100                 105

<210> SEQ ID NO 57
<211> LENGTH: 109
<212> TYPE: PRT
<213> ORGANISM: Homo sapiens
<220> FEATURE:
<223> OTHER INFORMATION: anti-Rh(D) chain L05

<400> SEQUENCE: 57

Ala Glu Leu Thr Gln Pro Pro Ser Ala Ser Gly Thr Pro Gly Leu Arg
 1               5                  10                  15

Val Thr Ile Ser Cys Ser Gly Ser Ser Asn Ile Gly Ser Asn Ile
                 20                  25                  30

Val Asn Trp Tyr Gln Gln Leu Pro Gly Thr Ala Pro Lys Leu Leu Ile
             35                  40                  45

Phe Ser Asn Asn Lys Arg Pro Ser Gly Val Pro Asp Arg Phe Ser Gly
 50                  55                  60

Ser Lys Ser Gly Thr Ser Ala Ser Leu Ala Ile Ser Gly Leu Gln Ser
 65                  70                  75                  80

Glu Asp Glu Ala Asp Tyr Tyr Cys Ala Thr Trp Asp Ser Leu Asn
                 85                  90                  95

Gly Arg Val Phe Gly Gly Gly Thr Lys Leu Thr Val Leu
                100                 105

<210> SEQ ID NO 58
<211> LENGTH: 109
<212> TYPE: PRT
<213> ORGANISM: Homo sapiens
<220> FEATURE:
<223> OTHER INFORMATION: anti-Rh(D) chain M01

<400> SEQUENCE: 58

Ala Glu Leu Thr Gln Pro Pro Ser Ala Ser Gly Thr Pro Gly Gln Arg
 1               5                  10                  15

Val Thr Ile Ser Cys Ser Gly Ser Asn Phe Asn Ile Gly Ser Asn Tyr
                 20                  25                  30

Val Phe Trp Tyr Gln His Val Pro Gly Thr Ala Pro Lys Leu Leu Ile
             35                  40                  45

Tyr Asn Asn Asn Gln Arg Pro Ser Gly Val Pro Asp Arg Leu Ser Gly
 50                  55                  60

Ser Lys Ser Gly Ala Ser Ala Ser Leu Ala Ile Asn Gly Leu Arg Ser
 65                  70                  75                  80

Asp Asp Glu Ala Asp Tyr Tyr Cys Thr Gly Trp Asp Asp Arg Leu Ser
                 85                  90                  95

Gly Leu Ile Phe Gly Gly Gly Pro Lys Val Thr Val Leu
                100                 105

<210> SEQ ID NO 59
<211> LENGTH: 109
<212> TYPE: PRT
<213> ORGANISM: Homo sapiens
<220> FEATURE:
<223> OTHER INFORMATION: anti-Rh(D) chain M02
```

<400> SEQUENCE: 59

```
Ala Glu Leu Thr Gln Pro Pro Ser Ala Ser Gly Thr Pro Gly Gln Arg
 1               5                  10                  15

Val Thr Ile Ser Cys Ser Gly Ser Ser Asn Ile Gly Ser Asn Tyr
            20                  25                  30

Val Tyr Trp Tyr Gln Gln Leu Pro Gly Thr Ala Pro Lys Leu Leu Ile
            35                  40                  45

Tyr Arg Asn Asn Gln Arg Pro Ser Gly Val Pro Asp Arg Phe Ser Gly
 50                  55                  60

Ser Lys Ser Gly Thr Ser Ala Ser Leu Ala Ile Ser Gly Leu Arg Ser
 65                  70                  75                  80

Glu Asp Glu Ala Asp Tyr Tyr Cys Ala Ala Trp Asp Asp Ser Leu Ser
                 85                  90                  95

Gly Trp Val Phe Gly Gly Gly Thr Lys Leu Thr Val Leu
                100                 105
```

<210> SEQ ID NO 60
<211> LENGTH: 110
<212> TYPE: PRT
<213> ORGANISM: Homo sapiens
<220> FEATURE:
<223> OTHER INFORMATION: anti-Rh(D) chain M03

<400> SEQUENCE: 60

```
Ala Glu Leu Thr Gln Pro Pro Ser Ala Ser Gly Thr Pro Gly Gln Arg
 1               5                  10                  15

Val Thr Ile Ser Cys Ser Gly Ser Ser Asn Ile Gly Ser Asn Tyr
            20                  25                  30

Val Tyr Trp Tyr Gln Gln Leu Pro Gly Thr Ala Pro Lys Leu Leu Ile
            35                  40                  45

Tyr Arg Asn Asn Gln Arg Pro Ser Gly Val Pro Asp Arg Phe Ser Gly
 50                  55                  60

Ser Lys Ser Gly Thr Ser Ala Ser Leu Ala Ile Ser Gly Leu Arg Ser
 65                  70                  75                  80

Glu Ala Glu Ala Asp Tyr Tyr Cys Ala Ala Trp Asp Asp Ser Leu Ser
                 85                  90                  95

Ala Val Val Phe Gly Gly Gly Thr Lys Leu Thr Val Leu Leu
                100                 105                 110
```

<210> SEQ ID NO 61
<211> LENGTH: 109
<212> TYPE: PRT
<213> ORGANISM: Homo sapiens
<220> FEATURE:
<223> OTHER INFORMATION: anti-Rh(D) chain N01

<400> SEQUENCE: 61

```
Ala Glu Leu Thr Gln Pro Pro Ser Val Ser Ala Ala Pro Gly Gln Lys
 1               5                  10                  15

Val Thr Ile Ser Cys Ser Gly Ser Ser Asn Ile Asp Ser Asn Tyr
            20                  25                  30

Val Ser Trp Tyr Gln Gln Leu Pro Gly Thr Ala Pro Lys Leu Leu Ile
            35                  40                  45

Phe Asp Asn Tyr Arg Arg Pro Ser Gly Ile Pro Asp Arg Phe Ser Gly
 50                  55                  60

Ser Lys Ser Gly Thr Ser Ala Thr Leu Gly Ile Thr Gly Leu Gln Thr
 65                  70                  75                  80
```

Gly Asp Glu Ala Asp Tyr Tyr Cys Ala Thr Trp Asp Ser Leu Asn
            85                  90                  95

Gly Arg Val Phe Gly Gly Gly Thr Lys Leu Thr Val Leu
            100                 105

<210> SEQ ID NO 62
<211> LENGTH: 114
<212> TYPE: PRT
<213> ORGANISM: Homo sapiens
<220> FEATURE:
<223> OTHER INFORMATION: anti-Rh(D) chain N02

<400> SEQUENCE: 62

Ala Glu Leu Thr Gln Pro Pro Ser Val Ser Ala Ala Pro Gly Gln Lys
 1               5                  10                  15

Val Thr Ile Ser Cys Ser Gly Ser Ser Ser Asn Ile Gly Asn Asn Tyr
                20                  25                  30

Val Ser Trp Tyr Gln Gln Leu Pro Gly Thr Ala Pro Lys Leu Leu Ile
            35                  40                  45

Tyr Asp Asn Asn Lys Arg Pro Ser Gly Ile Pro Asp Arg Phe Ser Gly
        50                  55                  60

Ser Lys Ser Gly Thr Ser Ala Thr Leu Gly Ile Thr Gly Leu Gln Thr
65                  70                  75                  80

Gly Asp Glu Ala Asp Tyr Tyr Cys Gly Thr Trp Asp Ser Ser Leu Ser
                85                  90                  95

Ala Gly Arg Val Arg Arg Met Phe Gly Gly Gly Thr Lys Leu Thr Val
            100                 105                 110

Leu Gly

<210> SEQ ID NO 63
<211> LENGTH: 110
<212> TYPE: PRT
<213> ORGANISM: Homo sapiens
<220> FEATURE:
<223> OTHER INFORMATION: anti-Rh(D) chain O01

<400> SEQUENCE: 63

Ala Glu Leu Thr Gln Pro Pro Ser Val Ser Gly Ala Pro Gly Gln Arg
 1               5                  10                  15

Val Thr Ile Ser Cys Thr Gly Ser Ser Ser Asn Ile Gly Ala Pro Tyr
                20                  25                  30

Gly Val His Trp Tyr Gln Gln Phe Pro Gly Thr Ala Pro Lys Leu Val
            35                  40                  45

Ile Tyr Asn Asp Asn Asn Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Arg Val Phe Gly Gly Gly Thr Lys Leu Thr Val Leu
            100                 105                 110

<210> SEQ ID NO 64
<211> LENGTH: 112
<212> TYPE: PRT
<213> ORGANISM: Homo sapiens
<220> FEATURE:
<223> OTHER INFORMATION: anti-Rh(D) chain O02

```
<400> SEQUENCE: 64

Ala Glu Leu Thr Gln Pro Pro Ser Val Ser Gly Ala Pro Gly Gln Thr
  1               5                  10                  15

Val Thr Ile Ser Cys Thr Gly Ser Ser Ser Ile Gly Ala Arg Tyr
             20                  25                  30

Asp Val His Trp Tyr Gln His Leu Pro Gly Thr Ala Pro Lys Leu Leu
             35                  40                  45

Ile Tyr Gly Asn His Asn Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ala Glu Asp Glu Ala Glu Tyr Tyr Cys Gln Ser Tyr Asp Asn Ser Leu
             85                  90                  95

Ser Gly Ser Ser Val Phe Phe Gly Gly Gly Thr Lys Leu Thr Val Leu
            100                 105                 110

<210> SEQ ID NO 65
<211> LENGTH: 110
<212> TYPE: PRT
<213> ORGANISM: Homo sapiens
<220> FEATURE:
<223> OTHER INFORMATION: anti-Rh(D) chain O03

<400> SEQUENCE: 65

Ala Glu Leu Thr Gln Pro Pro Ser Gly Ala Pro Gly Gln Thr Val Thr
  1               5                  10                  15

Ile Ser Cys Thr Gly Ser Ser Ser Asn Ile Gly Ala Gly Tyr Asp Val
             20                  25                  30

His Trp Tyr Gln Gln Leu Pro Gly Thr Ala Pro Lys Leu Leu Ile Tyr
             35                  40                  45

Gly Asn Ser Asn Arg Pro Ser Gly Val Pro Asp Arg Phe Ser Gly Ser
 50                  55                  60

Lys Ser Gly Thr Ser Ala Ser Leu Ala Ile Thr Gly Leu Gln Ala Glu
 65                  70                  75                  80

Asp Glu Ala Asp Tyr Tyr Cys Gln Ser Tyr Asp Ser Ser Leu Ser Gly
             85                  90                  95

Pro Tyr Val Val Phe Gly Gly Gly Thr Lys Leu Thr Val Leu
            100                 105                 110

<210> SEQ ID NO 66
<211> LENGTH: 108
<212> TYPE: PRT
<213> ORGANISM: Homo sapiens
<220> FEATURE:
<223> OTHER INFORMATION: anti-Rh(D) chain P01

<400> SEQUENCE: 66

Ala Glu Leu Thr Gln Pro Pro Ser Val Ser Val Ala Pro Arg Gln Thr
  1               5                  10                  15

Ala Arg Ile Thr Cys Gly Gly Asp Lys Ile Gly Ser Asn Thr Val His
             20                  25                  30

Trp Tyr Arg Gln Met Ser Gly Gln Ala Pro Val Leu Val Ile Tyr Glu
             35                  40                  45

Asp Lys Lys Arg Pro Pro Gly Ile Pro Glu Arg Phe Ser Gly Ser Thr
 50                  55                  60

Ser Gly Thr Thr Ala Thr Leu Ser Ile Ser Gly Ala Gln Val Glu Asp
 65                  70                  75                  80
```

Glu Ala Asp Tyr Tyr Cys Tyr Ser Arg Asp Asn Ser Gly Asp Gln Arg
                85                  90                  95

Arg Val Phe Gly Ala Gly Thr Lys Leu Thr Val Leu
            100                 105

<210> SEQ ID NO 67
<211> LENGTH: 110
<212> TYPE: PRT
<213> ORGANISM: Homo sapiens
<220> FEATURE:
<223> OTHER INFORMATION: anti-Rh(D) chain Q01

<400> SEQUENCE: 67

Ala Glu Leu Thr Gln Pro Pro Ser Ala Thr Ala Ser Leu Gly Gly Ser
1               5                   10                  15

Val Lys Leu Thr Cys Ile Leu Gln Ser Gly His Arg Asn Tyr Ala Val
            20                  25                  30

Ala Trp His His Gln Glu Ala Gly Lys Gly Pro Arg Phe Leu Met Thr
        35                  40                  45

Val Thr Asn Asp Gly Arg His Ile Lys Gly Asp Gly Ile Pro Asp Arg
    50                  55                  60

Phe Ser Gly Ser Ala Ser Gly Ala Glu Arg Tyr Leu Ser Ile Ser Gly
65                  70                  75                  80

Leu Gln Ser Glu Asp Glu Gly Asp Tyr Tyr Cys Gln Thr Trp Gly Thr
                85                  90                  95

Gly Met His Val Phe Gly Gly Gly Thr Lys Leu Thr Val Leu
            100                 105                 110

<210> SEQ ID NO 68
<211> LENGTH: 108
<212> TYPE: PRT
<213> ORGANISM: Homo sapiens
<220> FEATURE:
<223> OTHER INFORMATION: anti-Rh(D) chain R01

<400> SEQUENCE: 68

Ala Glu Leu Thr Gln Pro Pro Ser Ala Ser Gly Ser Pro Gly Gln Ser
1               5                   10                  15

Val Thr Ile Ser Cys Thr Gly Ala Ser Ser Asp Val Gly Ala Tyr Lys
            20                  25                  30

His Val Ser Trp Tyr Gln Gln His Pro Gly Lys Ala Pro Lys Leu Leu
        35                  40                  45

Thr His Glu Gly Thr Lys Arg Pro Ser Gly Val Pro Asp Arg Phe Ser
    50                  55                  60

Gly Ser Lys Ser Gly Asn Thr Ala Ser Leu Thr Val Ser Gly Leu Gln
65                  70                  75                  80

Ala Glu Asp Glu Ala Asp Tyr Tyr Cys Ser Ser Phe Ala Gly Asn Ser
                85                  90                  95

Val Ile Phe Gly Gly Gly Thr Lys Leu Thr Val Leu
            100                 105

<210> SEQ ID NO 69
<211> LENGTH: 104
<212> TYPE: PRT
<213> ORGANISM: Homo sapiens
<220> FEATURE:
<223> OTHER INFORMATION: anti-Rh(D) chain S01

<400> SEQUENCE: 69

Ala Glu Leu Thr Gln Pro Pro Ser Val Ser Gly Ser Pro Gly Gln Ser

```
                1               5                   10                  15
            Ile Thr Ile Ser Cys Ser Asp Val Gly Asn Tyr Asn Leu Val Ser Trp
                            20                  25                  30

Tyr Gln Gln Tyr Pro Gly Lys Ala Pro Lys Leu Ile Ile Tyr Glu Gly
                        35                  40                  45

Ser Lys Arg Pro Ser Gly Val Ser Ser Arg Phe Ser Gly Ser Arg Ser
                    50                  55                  60

Gly Asn Thr Ala Ser Leu Thr Ile Ser Gly Leu Gln Ala Glu Asp Glu
                65                  70                  75                  80

Ala Asp Tyr His Cys Cys Ser Tyr Ala Ile Ser Ser Arg Ile Phe Gly
                            85                  90                  95

Gly Gly Thr Lys Leu Thr Val Leu
                        100
```

<210> SEQ ID NO 70
<211> LENGTH: 384
<212> TYPE: DNA
<213> ORGANISM: Homo sapiens
<220> FEATURE:
<223> OTHER INFORMATION: anti-Rh(D) chain B01

<400> SEQUENCE: 70

```
gaggtgcagc tgctcgagtc tggggggaggc gtggtccagc ctgggaggtc cctgagactc      60
tcctgtgcag cctctggatt caccttcagg agctatgcta tgcactgggt ccgccaggct     120
ccaggcaagg ggctggagtg ggtggcagct acagcatatg atggaaaaaa taaatactac     180
gcagactccg tgaagggccg attcaccatc tccagagaca attccaagaa cacgctgttt     240
ctgcaaatga acagcctgag agctgaggac acggctgtgt tttactgtgc gagaggcgga     300
ttttactatg atagtagtgg ttattacggc ttgaggcact actttgactc ctggggccag     360
ggaaccctgg tcaccgtctc ctca                                            384
```

<210> SEQ ID NO 71
<211> LENGTH: 372
<212> TYPE: DNA
<213> ORGANISM: Homo sapiens
<220> FEATURE:
<223> OTHER INFORMATION: anti-Rh(D) chain C03

<400> SEQUENCE: 71

```
gaggtgcagc tgctcgagtc tggggggaggc gtggtccagc ctgggaggtc cctgagactc      60
tcctgtgcag cctctggatt ctccttcagt agctatggca tgcactgggt ccgccaggct     120
ccaggcaagg ggctggagtg ggtgtcagtt atatcatatg atggacatca taaaaactat     180
gcagactccg tgaagggccg attcaccatc tccagagaca attccaagaa aacgctgtac     240
ctgcaaatga acagcctgag acctgaggac acggctgtat attactgtgc gaacctaagg     300
ggggaagtaa ctcgtcgtgc gtctgttccc tttgatatct ggggcccagg gacaatggtc     360
accgtctctt ca                                                         372
```

<210> SEQ ID NO 72
<211> LENGTH: 372
<212> TYPE: DNA
<213> ORGANISM: Homo sapiens
<220> FEATURE:
<223> OTHER INFORMATION: anti-Rh(D) chain C01

<400> SEQUENCE: 72

```
gaggtgcagc tgctcgagtc gggggggaggt gtggtccagc atgggaggtc cctgagactg      60
```

```
tcctgtgcag cctctggatt ctccttcagt agctatggca tgcactgggt ccgccaggct    120
ccaggcaagg gctggagtg gtgtcagtt atatcatatg atggacatca taaaaactat     180
gcagactccg tgaagggccg attcaccatc tccagagaca attccaagaa aacgctgtac    240
ctgcaaatga acagcctgag acctgaggac acggctgtat attactgtgc gaacctaagg    300
ggggaagtaa ctcgtcgtgc gtctgttccc tttgatatat ggggccagg gacaatggtc    360 accgtgtctt ca                                                        372

<210> SEQ ID NO 73
<211> LENGTH: 372
<212> TYPE: DNA
<213> ORGANISM: Homo sapiens
<220> FEATURE:
<223> OTHER INFORMATION: anti-Rh(D) chain C04

<400> SEQUENCE: 73
gaggtgcagc tgctcgagtc tgggggaggc gtggtccagc ctgggaggtc cctgagactc     60
tcctgtgcag cctctggatt ctccttcagt acctatggca tgcactgggt ccgccaggct    120
ccaggcaagg gctggagtg gtgtcagtt atatcatatg atggacataa taaaaactat     180
gcagactccg tgaagggccg attcaccatc tccagagaca attccaagaa aacgctgtac    240
ctgcaaatga acagcctgag acctgaggac acggctgtgt attactgtgc gaacctaagg    300
ggggaagtaa ctcgtcgtgc gtctattcct tttgatatct ggggccaagg gacaatggtc    360
accgtctctt ca                                                        372

<210> SEQ ID NO 74
<211> LENGTH: 372
<212> TYPE: DNA
<213> ORGANISM: Homo sapiens
<220> FEATURE:
<223> OTHER INFORMATION: anti-Rh(D) chain C05

<400> SEQUENCE: 74
gaggtgcagc tgctcgagtc gggggaggc gtggtccagc ctgggaggtc cctgagactc     60
tcctgtgcag cctctggatt cagcttcagt agttatggca tgcactgggt ccgccaggct    120
ccaggcaagg gctggagtg ggtggcagtt atatcgtatg atggaactaa taaatacttt    180
gcagactccg tgaagggccg attcaccatc tccagagaca attccaagaa aacgctgtat    240
ctgcaaatga ccagcctgag acctgaggac acggctgtgt atttctgtgc gaacctaagg    300
ggggaagtaa ctcgtcgtgc gtccgtacct cttgatatct ggggccaagg gacaatggtc    360
accgtctctt ca                                                        372

<210> SEQ ID NO 75
<211> LENGTH: 372
<212> TYPE: DNA
<213> ORGANISM: Homo sapiens
<220> FEATURE:
<223> OTHER INFORMATION: anti-Rh(D) chain C08

<400> SEQUENCE: 75
gaggtgcagc tgctcgagtc gggggaggc gtggtccagc ctgggaggtc cctgagactc     60
tcctgtgcag cctctggatt cagcttcagt agttatggca tgcactgggt ccgccaggct    120
ccaggcaagg gctggagtg ggtggcagtt atatcgtatg atggaactaa taaatacttt    180
gcagactccg tgaagggccg attcaccatc tccagagaca attccaagaa aacgctgtat    240
```

```
ctgcaaatga ccagcctgag acctgaggac acggctgtgt atttctgtgc gaacctaagg      300
ggggaagtaa ctcgtcgtgc gtctgtacct cttgatatct ggggccaagg gacaatggtc      360
accgtctctt ca                                                           372
```

<210> SEQ ID NO 76
<211> LENGTH: 372
<212> TYPE: DNA
<213> ORGANISM: Homo sapiens
<220> FEATURE:
<223> OTHER INFORMATION: anti-Rh(D) chain C10

<400> SEQUENCE: 76

```
gaggtgcagc tgctcgagtc tgggggaggc gtggtccagc ctgggaggtc cctgagactc      60
tcctgtgcag cctctggatt ctccttcagt agctatggca tgcactgggt ccgccaggct     120
ccaggcaagg ggctggagtg ggtgtcagtt atatcatatg atggacatca taaaaactat     180
gcagactccg tgaagggccg attcaccatc tccagagaca attccaagaa aacgctgtac     240
ctgcaaatga acagcctgag acctgaggac acggctgtat attactgtgc gaacctaagg     300
ggggaagtaa ctcgtcgtgc gtctgttccc tttgatatct ggggcccagg gacattggtc     360
accgtctctt ca                                                           372
```

<210> SEQ ID NO 77
<211> LENGTH: 375
<212> TYPE: DNA
<213> ORGANISM: Homo sapiens
<220> FEATURE:
<223> OTHER INFORMATION: anti-Rh(D) chain D01

<400> SEQUENCE: 77

```
gaggtgcagc tgctcgagtc tgggggaggc gtggtccagc ctgggaggtc cctgagactc      60
tcctgtgtag tgtctggttt caccttcaat aactatggca tgcactgggt ccgccaggct     120
ccaggcaagg ggctggagtg ggtggcagtt atttggtttg atggaagtaa taaatactat     180
gcagactccg tgaagggccg attcaccatc tccagagaca attccaagaa cacactgtac     240
ctgcaaatga acagcctgag agccgaggac acggctgtat attactgtgc gagagagaac     300
cagataaagc tatggtcccg ataccttttac tactttgatt actggggcca gggaaccctg     360
gtcaccgtct cctca                                                        375
```

<210> SEQ ID NO 78
<211> LENGTH: 375
<212> TYPE: DNA
<213> ORGANISM: Homo sapiens
<220> FEATURE:
<223> OTHER INFORMATION: anti-Rh(D) chain D03

<400> SEQUENCE: 78

```
gaggtgcagc tgctcgagtc tgggggaggc gtggtccagc ctgggaggtc cctgagactc      60
tcctgtgcag cgtctggatt caccttcagt acctatggca tgcactgggt ccgccaggct     120
ccaggcaagg gactggagtg ggtggcagtt atatggtttg atggaagtaa taaggaatat     180
gcagactccg tgaagggccg attcaccgtc tccagagaca attccaagaa cacgctgtat     240
ctacaaatga acagcctgag agccgaggac acggctgtgt attactgtgc gagagaagaa     300
gtggttcggg gagttatctt atggtctcgg aagtttgact actggggcca gggaaccctg     360
gtcaccgtct cctca                                                        375
```

```
<210> SEQ ID NO 79
<211> LENGTH: 378
<212> TYPE: DNA
<213> ORGANISM: Homo sapiens
<220> FEATURE:
<223> OTHER INFORMATION: anti-Rh(D) chain D04

<400> SEQUENCE: 79
gaggtgcagc tgctcgagtc ggggggaggc gtggcccagc ctggggaggtc cctgagactc      60 tcctgtgtag cgtctggatt cagcctcagg agctatggca tgcactgggt ccgccaggct     120
cctggcaagg ggctggagtg ggtggcagat atatggtttg atggaagtaa taaagattat     180
gcagactccg tgaagggccg attcaccatc tccagagaca attccaagaa cacgttgtat     240
cttcaaatga acagcctgag agccgaggat acggctgtgt attattgtgc gagagattgg     300
agggtgcggg cctttagtag tggctggtta agtgcttttg atatctgggg ccaagggaca     360
atggtcaccg tctcctca                                                   378

<210> SEQ ID NO 80
<211> LENGTH: 381
<212> TYPE: DNA
<213> ORGANISM: Homo sapiens
<220> FEATURE:
<223> OTHER INFORMATION: anti-Rh(D) chain D05

<400> SEQUENCE: 80
gaggtgcagc tgctcgagga gtctggggga ggcgtggccc agcctgggag gtccctgaga      60
ctctcctgtg tagcgtctgg attcagcctc aggagctatg catgcactg ggtccgccag      120 gctcctggca aggggctgga gtgggtggca gatatatggt ttgatggaag taataaagat     180
tatgcagact ccgtgaaggg ccgattcacc atctccagag acaattccaa gaacacgttg     240
tatcttcaaa tgaacagcct gagagccgag gacacggctg tgtattattg tgcgagagat     300
tggagggtgc gggcctttag tagtggctgg ttaagtgctt ttgatatctg gggccaaggg     360
accacggtca gcgtctcctc a                                               381

<210> SEQ ID NO 81
<211> LENGTH: 375
<212> TYPE: DNA
<213> ORGANISM: Homo sapiens
<220> FEATURE:
<223> OTHER INFORMATION: anti-Rh(D) chain D07

<400> SEQUENCE: 81
gaggtgcagc tgctcgagtc tgggggaggc gtggtccagc ctggggaggtc cctgagactc      60 tcctgtgcag tgtctggatt caccctaact aattatggca tgcactgggt ccgccaggct     120
ccaggcaagg ggctggagtg ggtggcacat gtctggtatg atggaagtaa aacagaatat     180
gcagactccg tcaagggccg attcgccgtc tccagagaca atccaagaa cacactgttt      240 ctgcaaatga acagcctgac agccgaggac acggctattt attactgtgc gagagagagg     300
agagagaaag tctatatatt gttctactcg tggctcgacc gctggggcca gggaaccctg     360
gtcaccgtct cctca                                                      375

<210> SEQ ID NO 82
<211> LENGTH: 378
<212> TYPE: DNA
<213> ORGANISM: Homo sapiens
<220> FEATURE:
<223> OTHER INFORMATION: anti-Rh(D) chain D08
```

<400> SEQUENCE: 82

```
gaggtgcagc tgctcgagga gtctggggga ggcgtggtcc agcctgggag gtccctgaga      60
ctctcctgtg cagcgtctgg gttcaccttc agtagctatg catgcactg ggtccgccag      120
gctccaggca gggggctgga gtgggtggct cttatatggt acgatggagg taacaaagag    180
tatgcagact ccgtgaaggg ccgcttcagc atctccagag acaattccaa gaacactctg    240
tatctgcaag tgaacagcct gagagccgac gacacggctg tctattactg tgcgagagac    300
cagagagcag cagcgggtat cttttattat tcccgtatgg acgtctgggg ccaagggacc    360
acggtcaccg tctcctca                                                   378
```

<210> SEQ ID NO 83
<211> LENGTH: 378
<212> TYPE: DNA
<213> ORGANISM: Homo sapiens
<220> FEATURE:
<223> OTHER INFORMATION: anti-Rh(D) chain D09

<400> SEQUENCE: 83

```
gaggtgcagc tgctcgagtc tgggggaggc gtggtccagc ctgggaggtc cctgagactc      60
tcctgtgaag cgtctaaatt caccctctac aattatggca tgcactgggt ccgccaggct    120
ccaggcaagg ggctggagtg gtggcattt atatggtttg atggaagtaa taaatactat      180
gaagactccg tgaagggccg attcaccgtc tccagagaca attccaagaa cacgctgtat    240
ctgcaaatga acagcctgag agccgaggac acggctgtgt attactgtgc gagagaagga    300
tctaagaagg tggcactttc taggtattac tattatatgg acgtctgggg ccaggggacc    360
acggtcactg tctcgtca                                                   378
```

<210> SEQ ID NO 84
<211> LENGTH: 378
<212> TYPE: DNA
<213> ORGANISM: Homo sapiens
<220> FEATURE:
<223> OTHER INFORMATION: anti-Rh(D) chain D10

<400> SEQUENCE: 84

```
gaggtgcagc tgctcgagtc tgggggaggc gtggtccagc ctgggaggtc cctgagactc      60
tcctgtgaag cgtctaaatt caccctctac aattatggca tgcactgggt ccgccaggct    120
ccaggcaagg ggctggagtg gtggcattt atatggtttg atggaagtaa taaatactat      180
gaagactccg tgaagggccg attcaccgtc tccagagaca attccaagaa cacgctgtat    240
ctgcaaatga acagcctgag agccgaggac acggctgtgt attactgtgc gagagaagta    300
tctaagaagg tggcactttc taggtattac tactatatgg acgtctgggg ccaggggacc    360
acggtcactg tctcctca                                                   378
```

<210> SEQ ID NO 85
<211> LENGTH: 378
<212> TYPE: DNA
<213> ORGANISM: Homo sapiens
<220> FEATURE:
<223> OTHER INFORMATION: anti-Rh(D) chain D11

<400> SEQUENCE: 85

```
gaggtgcagc tgctcgagtc tgggggaggc gtggtccagc ctgggaggtc cctgagactc      60
tcctgtgaag cgtctaaatt caccctctac aattatggca tgcactgggt ccgccaggct    120
ccaggcgaag ggctggagtg gtggcattt atatggtttg atggaagtaa taaatactat      180
```

```
gcagactccg tgaagggccg attcaccgtc tccagagaca attccaagaa cacgctgtat      240
ctgcaaatga acagcctgag agccgaggac acggctgtgt attactgtgc gagagaagta      300
tctaagaagc tggcactttc taggtactac tactatatgg acgtctgggg ccaggggacc      360
acggtcactg tctcctca                                                    378

<210> SEQ ID NO 86
<211> LENGTH: 378
<212> TYPE: DNA
<213> ORGANISM: Homo sapiens
<220> FEATURE:
<223> OTHER INFORMATION: anti-Rh(D) chain D12

<400> SEQUENCE: 86
gaggtgcagc tgctcgagtc ggggggaggc gtggtccagc ctggagggtc cctgagactc      60
gcctgtgcag cgtctggatt cagcttcagg agctatggca tgcactgggt ccgccaggct      120
ccaggcaggg ggctggagtg ggtggcattt acatggtttg atggaagcaa taaatattat      180
gtagactccg tgaagggccg attcaccatc tccagagaca attccaagaa cacgctgtat      240
ctggaaatga acagcctgag agtcgatgac acggctgtat attactgtgc gagagaggcg      300
tctatgcttc gcggaattag cagatactac tacgcgatgg acgtctgggg cccagggacc      360
acggtcaccg tctcctca                                                    378

<210> SEQ ID NO 87
<211> LENGTH: 381
<212> TYPE: DNA
<213> ORGANISM: Homo sapiens
<220> FEATURE:
<223> OTHER INFORMATION: anti-Rh(D) chain D13

<400> SEQUENCE: 87
gaggtgcagc tgctcgagtc tggggggagc gtggtccagc ctggagggtc cctgagactc      60
tcctgtgcag cgtctggatt caccttcagt acttatggca tgcactgggt ccgccaggct      120
ccaggcaagg ggctggagtg ggtggcagtt atatggtttg atggaagtaa cagagactat      180
gcagagtccg tgaagggccg attcaccatc tccagagaca gtccaagaa cacactgtat       240 ctgcaaatga acagcctgag agccgaggac tcggctgtgt attattgtgc gagagaaaat      300
gtggctcgtg ggggggggg cgttcgatac aagtactact ttgactactg gggccaggga      360
accctggtca ccgtctcctc a                                                381

<210> SEQ ID NO 88
<211> LENGTH: 381
<212> TYPE: DNA
<213> ORGANISM: Homo sapiens
<220> FEATURE:
<223> OTHER INFORMATION: anti-Rh(D) chain D14

<400> SEQUENCE: 88
gaggtgcagc tgctcgagtc gggggagc ttggtacagc ctgggggtc cctgagactc         60 tcctgtgcag cgtctggatt caccttcagt acttatggca tgcactgggt ccgccaggct      120
ccaggcaagg ggctggagtg ggtggcagtt atatggtttg atggaagtaa gagagactat      180
gcagagtccg tgaagggccg attcaccatc tccagagaca actccaagaa cacactgtat      240
ctgcaaatga acagcctgag agccgaggac tcggctgtgt attactgtgc gagagaaaat      300
gtggctcgtg ggggggggg cattcgatac aagtactact ttgactactg gggccaggga      360
```

```
accctggtca ccgtctcctc a                                              381

<210> SEQ ID NO 89
<211> LENGTH: 375
<212> TYPE: DNA
<213> ORGANISM: Homo sapiens
<220> FEATURE:
<223> OTHER INFORMATION: anti-Rh(D) chain D15

<400> SEQUENCE: 89
gaggtgcagc tgctcgagtc tgggggaggc gtggtccagc ctggggaggtc cctgagactc    60 tcctgtgtag tgtctggatt caccttcaat aactatggca tgcactgggt ccgccaggct   120
ccaggcaagg ggctggagtg ggtggcagtt atttggtttg atggaagtaa taaatactat   180
gcagactccg tgaagggccg attcaccatc tccagagaca attccaagaa cacactgtac   240
ctgcaaatga acagcctgag agccgaggac acggctgtat attactgtgc gagagagaac   300
cagataaagc tatggtcccg atacctttac tactttgact actggggcca gggaaccctg   360
gtcaccgtct cctca                                                     375

<210> SEQ ID NO 90
<211> LENGTH: 375
<212> TYPE: DNA
<213> ORGANISM: Homo sapiens
<220> FEATURE:
<223> OTHER INFORMATION: anti-Rh(D) chain D16

<400> SEQUENCE: 90
gaggtgcagc tgctcgagtc tgggggaggc gtggtccagc ctggggaggtc cctgagactc    60 tcctgtgtag tgtctggttt caccttcaat aactatggca tgcactgggt ccgccaggct   120
ccaggcaagg ggctggagtg ggtggcagtt atttggtttg atggaagtaa taaatactat   180
gcagactccg tgaagggccg attcaccatc tccagagaca attccaagaa cacactgtac   240
ctgcaaatga acagcctgag agccgaggac acggctgtat attactgtgc gagagagaac   300
cagataaagc tatggtcccg atacctttac tactttgact actggggcca gggaaccctg   360
gtcaccgtct cctca                                                     375

<210> SEQ ID NO 91
<211> LENGTH: 375
<212> TYPE: DNA
<213> ORGANISM: Homo sapiens
<220> FEATURE:
<223> OTHER INFORMATION: anti-Rh(D) chain D17

<400> SEQUENCE: 91
gaggtgcagc tgctcgagtc tgggggaggc gtggtccagc ctggggaggtc cctgagactc    60 tcctgtgtag tgtctggttt caccttcaat aactatggca tgcactgggt ccgccaggct   120
ccaggcaagg ggctggagtg ggtggcagtt atttggtttg atggaagtaa taaatactat   180
gcagactccg tgaagggccg attcaccatc tccagagaca attccaagaa cacactgtac   240
ctgcaaatga acagcctgag agccgaggac acggctgtat attactgtgc gagagagaac   300
cagataaagc tatggtcccg atacctttac tactttgact actggggcca gggaaccctg   360
gtcaccgtct cctcc                                                     375

<210> SEQ ID NO 92
<211> LENGTH: 375
<212> TYPE: DNA
<213> ORGANISM: Homo sapiens
```

```
<220> FEATURE:
<223> OTHER INFORMATION: anti-Rh(D) chain D18

<400> SEQUENCE: 92
gaggtgcagc tgctcgagtc tgggggaggc gtggtccagc ctgggaggtc cctgagactc      60
tcctgtgtag tgtctggttt caccttcaat aactatggca tgcactgggt ccgccaggct     120
tcaggcaagg ggttggagtg ggtggcagtt atttggtttg atggaagtaa taaatactat     180
gcagactccg tgaagggccg attcaccatc tccagagaca attccaagaa cacactgtac     240
ctgcaaatga acagcctgag agccgaggac acggctgtat attactgtgc gagagagaac     300
cagataaagc tatggtcccg atacctttac tactttgact actggggcca gggaaccctg     360
gtcaccgtgt cctca                                                      375

<210> SEQ ID NO 93
<211> LENGTH: 375
<212> TYPE: DNA
<213> ORGANISM: Homo sapiens
<220> FEATURE:
<223> OTHER INFORMATION: anti-Rh(D) chain D20

<400> SEQUENCE: 93
gaggtgcagc tgctcgagtc gggggggaggc gtggtccagc ctggaggtc cctgagactc      60 tcctgtgcag cgtctggatt caccttcagt acctatggca tgcactgggt ccgccaggct     120
ccaggcaagg gactggagtg ggtggcagtt atatggtttg atggaagtaa taaggaatat     180
gcagactccg tgaagggccg attcaccatc tccagagaca attccaagaa cacgctgtat     240
ctacaaatga acagcctgag agccgaggac acggctgtgt attactgtgc gagagaagaa     300
gtggttcggg gagttatctt atggtctcgg aagtttgact actggggcca gggaaccctg     360
gtcaccgtct cctca                                                      375

<210> SEQ ID NO 94
<211> LENGTH: 378
<212> TYPE: DNA
<213> ORGANISM: Homo sapiens
<220> FEATURE:
<223> OTHER INFORMATION: anti-Rh(D) chain D30

<400> SEQUENCE: 94
gaggtgcagc tgctcgagtc gggggggaggc gtggtccagc ctggaggtc cctgagactc      60 tcctgtgcag cgtctggatt caccttcagt agctatggca tgcgctgggt ccggcaggct     120
ccaggcaagg ggctggagtg ggtggcagtt gtctactatg atggaagtaa caaacactat     180
tcagactccg tgaagggccg attcaccatc tccagagaca actccaagaa cacgctgtat     240
ctacaaatgg acagcctgag agccgaggac acggctgtgt attactgtgc gagagaaaga     300
aattttcgga gtggttattc ccgctactac tacggtatgg acgtctgggg cccagggacc     360
acggtcaccg tctcctca                                                   378

<210> SEQ ID NO 95
<211> LENGTH: 378
<212> TYPE: DNA
<213> ORGANISM: Homo sapiens
<220> FEATURE:
<223> OTHER INFORMATION: anti-Rh(D) chain D31

<400> SEQUENCE: 95
gaggtgcagc tgctcgagtc tgggggaggc gtggtccagc ctggaggtc cctgagactc       60
```

```
tcctgtgcag cgtctggatt caccttcagt agctatggca tgcactgggt ccggcaggct      120
ccaggcaagg gctggagtg gtggcagtt gtctactatg atggaagtaa caaacactat       180
tcagactccg tgaagggccg attcaccatc tccagagaca actccaagaa cacgctgtat     240
ctacaaatgg acagcctgag agccgaggac acggctgtgt attactgtgc gagagaaaga    300
aattttcgga gtggttattc ccgctactac tacggtatgg acgtctgggg cccagggacc    360
acggtcaccg tctcctca                                                   378
```

<210> SEQ ID NO 96
<211> LENGTH: 381
<212> TYPE: DNA
<213> ORGANISM: Homo sapiens
<220> FEATURE:
<223> OTHER INFORMATION: anti-Rh(D) chain E01

<400> SEQUENCE: 96

```
gaggtgcagc tgctcgagtc tgggggaggc ctggtcaagc ctgggggggtc cctgagactc    60 tcctgtgcag cctctggatt caccttcagt agctatagca tgcactgggt ccgccaggct    120
ccagggaagg gctggagtg gtctcatcc attagtaata gtaatactta catatactac      180
gcagacgcga tgaagggccg attcaccatc tccagagaca acgccaagaa ctcactgtat    240
ctgcaaatga acagcctgag agccgaggac acggctgtgt actactgtgc gagagattct    300
agatacagta atttcctccg ttgggttcgg agcgacggta tggacgtctg gggccaaggg    360
accacggtca tcgtctcctc a                                               381
```

<210> SEQ ID NO 97
<211> LENGTH: 393
<212> TYPE: DNA
<213> ORGANISM: Homo sapiens
<220> FEATURE:
<223> OTHER INFORMATION: anti-Rh(D) chain E03

<400> SEQUENCE: 97

```
gaggtgcagc tgctcgagtc tgggtggag tctgggggag gcctggtcaa gcctgggggg     60
tccctgagac tctcctgtgc agcctctgga ttcaccttca gtagctatag catgcactgg    120
gtccgccagg tccagggaa ggggctggag tgggtctcat ccattagtaa tagtaatact     180
tacatatact acgcagacgc agtgaagggc cgattcacca tctccagaga caacgccaag    240
aactcactgt atctgcaaat gaacagcctg agagccgagc acacggctgt gtactactgt    300
gcgagagatt ctagatacag taatttcctc cgttgggttc ggagcgacgg tatggacgtc    360
tggggccaag ggaccacggt catcgtctcc tca                                  393
```

<210> SEQ ID NO 98
<211> LENGTH: 321
<212> TYPE: DNA
<213> ORGANISM: Homo sapiens
<220> FEATURE:
<223> OTHER INFORMATION: anti-Rh(D) chain F01

<400> SEQUENCE: 98

```
gccgagctca cccagtctcc atcctccctg tctgcatctg taggagacag agtcaccatc    60
acttgccggg caagtcaggg ctttagaaat gatttaggct ggtatcagca gaaaccaggg    120
aaagccccta gcgcctgat ctatgctaca tccagtttgc aaagtggggt cccatcaagg    180
ttcagcggca gtggatctgg gacagaattc actctcacaa tcaacagcct gcagcctgaa    240
gattctgcaa cttattactg tctacagcat aatagttttcc cgtggacgtt cggccaaggg    300
```

```
accaaggtgg aaatcaaacg a                                              321
```

<210> SEQ ID NO 99
<211> LENGTH: 336
<212> TYPE: DNA
<213> ORGANISM: Homo sapiens
<220> FEATURE:
<223> OTHER INFORMATION: anti-Rh(D) chain G01

<400> SEQUENCE: 99

```
gccgagctca ctcagtctcc actctccctg cccgtcaccc tggagagcc ggcctccatc      60
tcctgcaggt ctagtcagag cctcctgcat agtagtggat tcaacttttt ggattggtac    120
ctgcagaagc cagggcagtc tccacagctc ctgatctata tgggttctaa tcgggcctcc   180
ggggtccctg acaggttcag tggcagtgga tcaggcacag attttacact gaaaatcaac   240
agagtggagg ctgaggatgt tggggtttat tactgcatgc aagctctaca atttcctctc   300
actttcggcg gagggaccaa ggtggagatc aaacga                             336
```

<210> SEQ ID NO 100
<211> LENGTH: 324
<212> TYPE: DNA
<213> ORGANISM: Homo sapiens
<220> FEATURE:
<223> OTHER INFORMATION: anti-Rh(D) chain H01

<400> SEQUENCE: 100

```
gccgagctca cccagtctcc atccttcctg tctgcatctg taggagacag agtcaccatc     60
acttgccggg ccagtcaggg cattacgagt tatttagcct ggtatcagca aaaaccaggg    120
aaagccccta agctcctaat ctatgctgca tccactttgc aaagtggggt cccatcaagg   180
ttcagcggca gtggatctgg gacagaattc actctcacaa cgccagcct gcagcctgat    240
gattttgcaa cttattactg tcaacagctt ataattacc ccctttcac tttcggccct     300
gggaccaaag tggatatcaa acga                                           324
```

<210> SEQ ID NO 101
<211> LENGTH: 324
<212> TYPE: DNA
<213> ORGANISM: Homo sapiens
<220> FEATURE:
<223> OTHER INFORMATION: anti-Rh(D) chain I01

<400> SEQUENCE: 101

```
gccgagctca cccagtctcc atcctcccta tctgcatctg taggagacag agtcaccatc     60
acttgccggg caagtcagag cattagcagc tatttaaatt ggtatcagca gaaaccaggg    120
aaagcccta agctcctgat ctatgctgca tccagtttgc aaagtgggt cccatcaagg     180
ttcagtggca gtggatctgg gacagatttc actctcacca tcagcagtct gcaacctgaa   240
gattttgcaa cttactactg tcaacagagt tacagtaccc ctccgtacac ttttggccag   300
gggaccaagc tggagatcaa acga                                           324
```

<210> SEQ ID NO 102
<211> LENGTH: 321
<212> TYPE: DNA
<213> ORGANISM: Homo sapiens
<220> FEATURE:
<223> OTHER INFORMATION: anti-Rh(D) chain I02

<400> SEQUENCE: 102

```
gccgagctca cccagtctcc atcctccctg tctgcatctg taggagacag agtcaccatc    60
acttgccggg caagtcagag cattagcagc tatttaaatt ggtatcagca gaaaccaggg   120
aaagccccta agctcctgat ctatgctgca tccagtttgc aaagtggggt cccatcaagg   180
ttcagtggca gtggatctgg gacagatttc actctcacca tcagcagtct gcaacctgaa   240
gattttgcaa cttactactg tcaacagagt tacagtaccc tgtggacgtt cggccaaggg   300
accaaggtgg aaatcaaacg a                                             321

<210> SEQ ID NO 103
<211> LENGTH: 321
<212> TYPE: DNA
<213> ORGANISM: Homo sapiens
<220> FEATURE:
<223> OTHER INFORMATION: anti-Rh(D) chain I03

<400> SEQUENCE: 103
gccgagctca cccagtctcc atcctccctg tctgcatctg tagcggacag agtcaccatc    60
acttgccgga caagtcggaa cattaacaga tacttaaatt ggtatcagca gaaaccaggg   120
aaagccccta agctcctgat ttatgctgca tccagtttgc aaagtggggt cccatcaagg   180
ttcagtggca gtggatctgg gacagatttc actctcacca tcaccagtct gcaacctgaa   240
gattttgcca cttactactg tcaacagagt tacagtaccc ctttcacttt cggccctggg   300
accaaagtgg atctcaaacg a                                             321

<210> SEQ ID NO 104
<211> LENGTH: 321
<212> TYPE: DNA
<213> ORGANISM: Homo sapiens
<220> FEATURE:
<223> OTHER INFORMATION: anti-Rh(D) chain I04

<400> SEQUENCE: 104
gccgagctca ctcagtctcc atcctccctg tctgcatctg taggagacag agtcaccatc    60
acttgccggg caagtcagaa cattaggagg tcttttaaatt ggtatcaaca gaaaccaggg   120
aaagccccta agctcctgat ctatgctgca tccagtttgc aaagtggggt cccatcaagg   180
ttcagtggca gtggatctgg gacagatttc actctcacca tcagcagtct gcaacctgaa   240
gattttgcaa cttactactg tcagcagagt tccaataccc cgtggacgtt cggccaaggg   300
accaaggtgg aaatcaaacg a                                             321

<210> SEQ ID NO 105
<211> LENGTH: 321
<212> TYPE: DNA
<213> ORGANISM: Homo sapiens
<220> FEATURE:
<223> OTHER INFORMATION: anti-Rh(D) chain I05

<400> SEQUENCE: 105
gccgagctca cccagtctcc atcctccctg tctgcatctg taggagacag agtcaccatc    60
acttgccggg caagtcagag cattaggagg tatttaaatt ggtatcagca caaaccaggg   120
aaagccccta agctcctgat ctttgctgca tccagtttgc aaagtggggt cccatcaagg   180
ttcactggca gtggatctgg gacagatttc actctcacca tcagcagtct gcaacctgaa   240
gattttgcaa cttactactg tcaacagagt tacagtaccc ctcaaacgtt cggccaaggg   300
accaaggtgg aaatcaaacg a                                             321
```

<210> SEQ ID NO 106
<211> LENGTH: 321
<212> TYPE: DNA
<213> ORGANISM: Homo sapiens
<220> FEATURE:
<223> OTHER INFORMATION: anti-Rh(D) chain I06

<400> SEQUENCE: 106

```
gccgagctca cccagtctcc atcctccctg tctgcatctg taggagacag agtcaccatc      60
acttgccggg caagtcagag cattagcagc tatttaaatt ggtatcagca gaaaccaggg     120
aaagccccta agctcctgat ctatgccgca tccagtttgc aaagtggggt cccatcaagg     180
ttcagtggca gtggatctgg gacagatttc actctcacca tcagcagtct gcaacctgaa     240
gattttgcaa cttactactg tcaacagagt tacagtaccc cgatcacctt cggccaaggg     300
acacgactgg agattaaacg a                                               321
```

<210> SEQ ID NO 107
<211> LENGTH: 321
<212> TYPE: DNA
<213> ORGANISM: Homo sapiens
<220> FEATURE:
<223> OTHER INFORMATION: anti-Rh(D) chain I07

<400> SEQUENCE: 107

```
gccgagctca cccagtctcc atcctccctg tctgcatctg taggagacag agtcaccatc      60
acttgccggg caagtcagag cattagcagc tatttaaatt ggtatcagca gaaaccaggg     120
aaagccccta agctcctgat ctatgctgca tccagtttgc aaagtggggt cccatcaagg     180
ttcagtggca gtggatctgg gacagatttc actctcacca tcagcagtct gcaacctgaa     240
gattttgcaa cttactactg tcaacagagt tacagtaccc ctcgaacttt cggcggaggg     300
accaaggtgg agatcaaacg a                                               321
```

<210> SEQ ID NO 108
<211> LENGTH: 321
<212> TYPE: DNA
<213> ORGANISM: Homo sapiens
<220> FEATURE:
<223> OTHER INFORMATION: anti-Rh(D) chain I08

<400> SEQUENCE: 108

```
gccgagctca cccagtctcc attctccctg tctgcatctg tcggagacag agtcaccata      60
acttgccggg caagtcagac cattagcagg tctttaaatt ggtatcagca taaaccaggg     120
gaagccccta agctcctgat ctatgctgca tccagtctgc agcgtggggt cccacccagg     180
ttcagtggca gtggatctgg gacagatttc actctcacca tcagcagtct gcaacctgaa     240
gactttgcga cttacttctg tcaacagagt gtcagaatcc cgtacagttt tggccagggg     300
accaagctgg agatcaaacg a                                               321
```

<210> SEQ ID NO 109
<211> LENGTH: 321
<212> TYPE: DNA
<213> ORGANISM: Homo sapiens
<220> FEATURE:
<223> OTHER INFORMATION: anti-Rh(D) chain I09

<400> SEQUENCE: 109

```
gccgagctca cccagtctcc atcctccctg tctgcatctg taggagacag agtcaccatc      60
acttgccggg caagtcagag cattagcagc tatttaaatt ggtatcagca gaaaccaggg     120
```

```
aaagccccta agctcctgat ctatgctgca tccagtttgc aaagtggggt cccatcaagg      180
ttcagtggca gtggatctgg gacagattcc actctcacca tcagcagtct gcaacctgaa      240
gattttgcaa cttattactg tcaacagctt aatagttacc cgtacacttt tggccagggg      300
accaagctgg agatcaaacg a                                                321
```

```
<210> SEQ ID NO 110
<211> LENGTH: 324
<212> TYPE: DNA
<213> ORGANISM: Homo sapiens
<220> FEATURE:
<223> OTHER INFORMATION: anti-Rh(D) chain I10

<400> SEQUENCE: 110
gccgagctca cccagtctcc atcctccctg tctgcatctg taggagacag agtcaccatc      60
acttgccggg caagtcagaa cattagcagc tatttaaatt ggtatcagca gaaaccaggg     120
aaagccccta agctcctgat ctatgctgca tccagtttgc aaagtggggt cctatcaagg     180
ttcagtggca gtggatctgg gacagattcc actctcacca tcagcagtct gcaacctgaa     240
gattttgcaa cttactactg tcaacagagt tacagtaccc ctccgtatag ttttggccag     300
gggaccaagc tggagatcaa acga                                            324
```

```
<210> SEQ ID NO 111
<211> LENGTH: 309
<212> TYPE: DNA
<213> ORGANISM: Homo sapiens
<220> FEATURE:
<223> OTHER INFORMATION: anti-Rh(D) chain I11

<400> SEQUENCE: 111
gccgagctca cccagtctcc atcctccctg tctgcatctg taggagacag agtcaccatc      60
acttgccggg caagtcagag cattagcagc tatttaaatt ggtatcagca gaaaccaggg     120
aaagccccta cgctcctgat caatgctgca tccagtttgc aaagtggggt cccatcaagg     180
ttcagtggca gtggatctgg gacagatttc actctcacca ttagcagtct gcaacctgaa     240
gatttcgcaa tttactactg tcaacagaga gaaacttttg gccaggggac caagctggag     300
atcaaacga                                                             309
```

```
<210> SEQ ID NO 112
<211> LENGTH: 324
<212> TYPE: DNA
<213> ORGANISM: Homo sapiens
<220> FEATURE:
<223> OTHER INFORMATION: anti-Rh(D) chain I12

<400> SEQUENCE: 112
gccgagctca cccagtctcc atcctcccta tctgcatctg taggagacag agtcaccatc      60
acttgccggg caagtcagag cattagcagc tatttaaatt ggtatcagca gaaaccaggg     120
aaagccccta agctcctgat ctatgctgca tccagtttgc aaagtggggt cccatcaagg     180
ttcagtggca gtggatctgg gacagatttc actctcacca tcagcagtct gcaacctgaa     240
gattttgcaa cttactactg tcaacagagt tacagtaccc ctccgtacac ttttggccag     300
gggaccaagc tggagatcaa acga                                            324
```

```
<210> SEQ ID NO 113
<211> LENGTH: 321
<212> TYPE: DNA
<213> ORGANISM: Homo sapiens
```

```
<220> FEATURE:
<223> OTHER INFORMATION: anti-Rh(D) chain I13

<400> SEQUENCE: 113
gccgagctca cccagtctcc atcctccctg tctgcctctg taggagacag agtcaccatc      60
acttgccggg caagtcagag cattagcagg tatttaaatt ggtatcagca gaaaccaggg     120
aaagccccta agctcctgat ctatgctgca tccagtttgc aaagtggggt cccatcaagg     180
ttcagtggca gtggatctgg gacagatttc actctcacca tcagcagtct gcaacctgaa     240
gattttgcaa cttactactg tcaacagagt acggtaccc  ctcacagttt tggccggggg    300
accaagctgg agatcaaacg a                                              321

<210> SEQ ID NO 114
<211> LENGTH: 321
<212> TYPE: DNA
<213> ORGANISM: Homo sapiens
<220> FEATURE:
<223> OTHER INFORMATION: anti-Rh(D) chain I15

<400> SEQUENCE: 114
gccgagctca cccagtctcc ttcctccctg tctgcatctg taggagacag agtcaccatc      60
acttgccggg caaatcagaa cattcgtaga tctttaaatt ggtatcagca gaaaccaggg     120
aaagccccta acctcctgat ctatgctgca tccacattgc aaggtggggt cccatcaagg     180
ttcagtggca gtggatctgg gacagatttc actctcacca tcagcagtct gcaacttgcg     240
gattttgcaa cttactactg tcaacagact ccgctaccc  cgtggacgtt cggccaaggg    300
accaaggtgg aaatcaaacg a                                              321

<210> SEQ ID NO 115
<211> LENGTH: 321
<212> TYPE: DNA
<213> ORGANISM: Homo sapiens
<220> FEATURE:
<223> OTHER INFORMATION: anti-Rh(D) chain I16

<400> SEQUENCE: 115
gccgagctca cccagtctcc atcgtccctg cctgcatctg tgggagacag agtcaccatc      60
acttgccggg caagtcagac tattggtttt aatttaaatt ggtatcagca aacatctggg     120 aagccccta aactcctaat ctatggtgtt tccaagttgc aaaatgggt  cccttcacgg    180 ttcagtggca gtgggtccgg gacggaattc accctcacaa tcagcagtct gcagcctgag     240
gattttgcga cttattattg tcaacagact aacgatgcgt tgtggacgtt cggccaaggg     300
accaaagtgg aagtcagacg a                                              321

<210> SEQ ID NO 116
<211> LENGTH: 318
<212> TYPE: DNA
<213> ORGANISM: Homo sapiens
<220> FEATURE:
<223> OTHER INFORMATION: anti-Rh(D) chain J01

<400> SEQUENCE: 116
gccgagctcc aggaccctgt tgtgtctgtg gccttgggac agacagtcag gatcacttgc      60
caaggagacg gcctcagaag ttattatgca agctggtacc agcagaagcc gggacaggcc     120
ccgaaacttg tcatgtacgg tagaaacaac cggccctcag ggatcccagg ccgattctct     180
ggctccagct caggggcagac agctgccttg accatcacgg ggactcaggc ggaggatgag     240
```

```
gctgactatt actgtcagtc ccgtgccacc agcggtaacc ctgtggtgtt cggcggaggg    300
actaagctga ccgtcctg                                                  318

<210> SEQ ID NO 117
<211> LENGTH: 318
<212> TYPE: DNA
<213> ORGANISM: Homo sapiens
<220> FEATURE:
<223> OTHER INFORMATION: anti-Rh(D) chain J02

<400> SEQUENCE: 117
gccgagctcc aggaccctgt tgtgtctgtg gccttgggac agacagtcag gatcacttgc     60
caaggagacg gcctcagaag ttattatgca agctggtacc agcagaagcc gggacaggcc    120
ccgaaacttg tcatgtacgg tagaaacaac cggccctcag ggatcccaga ccgattctct    180
ggctccagct cagggcagac agctgccttg accatcacgg ggactcaggc ggaggatgag    240
gctgactatt actgtcagtc ccgtgccacc agcggtaacc ctgtggtgtt cggcggaggg    300
actaagctga ccgtcctg                                                  318

<210> SEQ ID NO 118
<211> LENGTH: 312
<212> TYPE: DNA
<213> ORGANISM: Homo sapiens
<220> FEATURE:
<223> OTHER INFORMATION: anti-Rh(D) chain J04

<400> SEQUENCE: 118
gccgagctcc aggaccctgt tgtgtctgtg gccttgggac agacagtcag gatcacatgc     60
caaggagaca gcctcagaag ctattatgca agctggtacc agcagaagcc aggacaggcc    120
cctgtacttg tcatctatgg taaaaacagc cggccctcag ggatcccaga ccgattctct    180
ggctccagct caggaaacac agcttcgttg accatcactg ggctcaggc ggaagatgag     240 gcggactatt attgtagttc gcgggcagc ccccacgtgg cattcggcgg agggaccaaa    300
ctgaccgtcc tg                                                        312

<210> SEQ ID NO 119
<211> LENGTH: 318
<212> TYPE: DNA
<213> ORGANISM: Homo sapiens
<220> FEATURE:
<223> OTHER INFORMATION: anti-Rh(D) chain J05

<400> SEQUENCE: 119
gccgagctcc aggaccctgt tgtgtctgtg gccttgggac agacagtcaa gatcacatgc     60
cagggagaca gcctcagaaa gtattatgca agctggtacc agcagaagcc aggacaggcc    120
cctgtgcttg tcttctatgc tagaaatagc cggccctcag ggatcccaga ccgattctct    180
ggctccaact caggaaccac agcttccttg accatcgctg gggctcgggc ggaagatgag    240
gctgactatt actgtcactc ccgggacagc aatggtcacc atcgggtgtt cggcggaggg    300
accaagctga ccgtccta                                                  318

<210> SEQ ID NO 120
<211> LENGTH: 324
<212> TYPE: DNA
<213> ORGANISM: Homo sapiens
<220> FEATURE:
<223> OTHER INFORMATION: anti-Rh(D) chain K01

<400> SEQUENCE: 120
```

```
gccgagctca ctcaggagcc ctcactgact gtgtccccag gagggacagt cactctcacc      60
tgtgcttcca gcactggagc agtcaccagt cgttactttc caaactggtt ccagcagaaa     120
cctggacaag cacccaggcc actgatttat agtgcaagca acaaacactc ctggacccct     180
gcccggttct caggctccct ccttgggggc aaagctgccc tgacactgtc aggtgtgcag     240
cctgaggacg aggctgagta ttactgcctg ctctactata gtggtgcttg ggtgttcggc     300
ggagggacca agttgaccgt cctt                                            324
```

```
<210> SEQ ID NO 121
<211> LENGTH: 324
<212> TYPE: DNA
<213> ORGANISM: Homo sapiens
<220> FEATURE:
<223> OTHER INFORMATION: anti-Rh(D) chain K02

<400> SEQUENCE: 121
```

```
gccgagctca ctcaggagcc ctcactgact gtgtccccag gagggacagt cactctcacc      60
tgtgcttcca gcactggagc agtcaccagt cgttactttc caaactggtt ccagcagaaa     120
cctggacaag cacccaggcc actgatttat agtgcaagca acaaacactc ctggacccct     180
gcccggttct caggctccct ccttgggggc aaagctgccc tgacactgtc aggtgtgcag     240
cctgaggacg aggctgagta ttactgcctg ctctactata gtggtgcttg ggtgttcggc     300
ggagggacca agctgaccgt ccta                                            324
```

```
<210> SEQ ID NO 122
<211> LENGTH: 324
<212> TYPE: DNA
<213> ORGANISM: Homo sapiens
<220> FEATURE:
<223> OTHER INFORMATION: anti-Rh(D) chain K03

<400> SEQUENCE: 122
```

```
gccgagctca ctcagccacc ctcactgact gtgtccccag gagggacagt cactctcacc      60
tgtgcttcca gcactggagc agtcaccagt cgttactttc caaactggtt ccagcagaaa     120
cctggccagg cacccaggc actgatttat ggttcaaaca acaaacactc ctggacccct      180
gcccggttct caggctccct ccttgggggc aaagctgccc tgacactgtc aggtgtgcag     240
cctgaggacg aggcggagta ttactgcctg ctcttctatg ctggtgcttg ggcgttcggc     300
ggatggacca agctgaccgt ccta                                            324
```

```
<210> SEQ ID NO 123
<211> LENGTH: 327
<212> TYPE: DNA
<213> ORGANISM: Homo sapiens
<220> FEATURE:
<223> OTHER INFORMATION: anti-Rh(D) chain L01

<400> SEQUENCE: 123
```

```
gccgagctca cgcagccgcc ctcagcgtct gggaccccg gcagagggt caccatctct        60 tgttctggag gcagctccaa catcgcaagt aatactgtaa actggtacca gcaactccca     120
ggaacggccc ccaaactcct catctatagt aataatcagc ggccctcagg ggtccctgac     180
cgattctctg gctccaagtc tggcacctca gccaccctgg tcatcaccgg ctccagact     240 ggggacgagg ccgattatta ctgcggaaca tgggatcaca gccggagtgg tgcggtgttc     300
ggcggaggga ccaaactgac cgtctta                                         327
```

<210> SEQ ID NO 124
<211> LENGTH: 327
<212> TYPE: DNA
<213> ORGANISM: Homo sapiens
<220> FEATURE:
<223> OTHER INFORMATION: anti-Rh(D) chain L03

<400> SEQUENCE: 124

| | | | | | |
|---|---|---|---|---|---|
| gccgagctca | ctcagccacc | ctcagcgtct | gggacccccg | ggcagagggt | caccatctct | 60 |
| tgttctggca | gtagctccaa | catcggaaat | aatcatgtaa | gctggtacca | gcaactccca | 120 |
| ggaatggccc | ccaaactcct | catctattct | aatggtcagc | ggccctcagg | ggtccctgac | 180 |
| cgattctctg | gctccaagtc | tggcacctca | gcctccctgg | ccatcagcgg | cctccagtct | 240 |
| gaggatgagg | ctgattatta | ttgtgcagca | tggcatgaca | gcctctatgg | tccggtgttc | 300 |
| ggcggaggga | ccaagctgac | cgtcctc | | | | 327 |

<210> SEQ ID NO 125
<211> LENGTH: 327
<212> TYPE: DNA
<213> ORGANISM: Homo sapiens
<220> FEATURE:
<223> OTHER INFORMATION: anti-Rh(D) chain L04

<400> SEQUENCE: 125

| | | | | | |
|---|---|---|---|---|---|
| gccgagctca | ctcagccacc | ctcagcgtct | gggacccccg | ggcagagggt | cagcatctct | 60 |
| tgttctggaa | gcagctccaa | catcggaagt | aatactgtaa | actggtacca | gcagctccca | 120 |
| ggaacagccc | ccaaactcct | catctctact | aataatcagg | ggccctcagg | agtccctgac | 180 |
| cgattctctg | gctccaagtc | tggcacctca | tcctccctgg | ccatcagtgg | gctccggtca | 240 |
| gaggctgagg | atgattatta | ctgtgcagca | tgggatgaca | ccctgaatgg | tgtggtattc | 300 |
| ggcggaggga | ccaaactgac | cgtccta | | | | 327 |

<210> SEQ ID NO 126
<211> LENGTH: 327
<212> TYPE: DNA
<213> ORGANISM: Homo sapiens
<220> FEATURE:
<223> OTHER INFORMATION: anti-Rh(D) chain L05

<400> SEQUENCE: 126

| | | | | | |
|---|---|---|---|---|---|
| gccgagctca | ctcagccacc | ctcagcgtct | gggactcccg | ggctgagggt | caccatctct | 60 |
| tgttctggaa | gcagctccaa | catcggaagt | aatattgtaa | actggtacca | gcagctccca | 120 |
| ggaacggccc | ccaaactcct | catctttagt | aataataagc | ggccctcagg | ggtccctgac | 180 |
| cgattctctg | gctccaagtc | tggcacctca | gcctccctgg | ccatcagtgg | gctccagtct | 240 |
| gaggatgagg | ctgattatta | ctgtgctaca | tgggatgaca | gcctgaatgg | tcgggtgttc | 300 |
| ggcggaggga | ccaagctgac | cgtccta | | | | 327 |

<210> SEQ ID NO 127
<211> LENGTH: 327
<212> TYPE: DNA
<213> ORGANISM: Homo sapiens
<220> FEATURE:
<223> OTHER INFORMATION: anti-Rh(D) chain M01

<400> SEQUENCE: 127

| | | | | | |
|---|---|---|---|---|---|
| gccgagctca | ctcagccacc | ctcagcgtct | gggacccccg | ggcagcgggt | caccatctct | 60 |
| tgttctggga | gcaacttcaa | catcggaagt | aattatgtat | cctggtacca | gcatgttcca | 120 |

```
ggaacggccc caaaactcct catctataat aataatcaac gccctctgg ggtccctgac        180 cgactctctg gctccaagtc tggcgcctca gcctccctgg ccatcaatgg gctccggtcc        240
gatgatgagg ctgattatta ctgtacagga tgggatgacc gcctgagtgg cctgattttc        300
ggcggagggc caaaagtgac cgtccta                                             327
```

<210> SEQ ID NO 128
<211> LENGTH: 327
<212> TYPE: DNA
<213> ORGANISM: Homo sapiens
<220> FEATURE:
<223> OTHER INFORMATION: anti-Rh(D) chain M02

<400> SEQUENCE: 128

```
gccgagctca cgcagccgcc ctcagcgtct gggaccccg ggcagagggt caccatctct         60
tgttctggaa gcagctccaa catcggaagt aattatgtat attggtacca gcagctccca       120
ggaacggccc ccaaactcct catctatagg aataatcagc ggccctcagg gtccctgac        180 cgattctctg gctccaagtc tggcacctca gcctccctgg ccatcagtgg gctccggtcc        240
gaggatgagg ctgattatta ctgtgcagca tgggatgaca gcctgagtgg ttgggtgttc       300
ggcggaggga ccaagctgac cgtccta                                             327
```

<210> SEQ ID NO 129
<211> LENGTH: 327
<212> TYPE: DNA
<213> ORGANISM: Homo sapiens
<220> FEATURE:
<223> OTHER INFORMATION: anti-Rh(D) chain M03

<400> SEQUENCE: 129

```
gccgagctca ctcagccacc ctcagcgtct gggaccccg ggcagagggt caccatctct         60
tgttctggaa gcagctccaa catcggaagt aattatgtat actggtacca gcagctccca       120
ggaacggccc ccaaactcct catctatagg aataatcagc ggccctcagg ggtccctgac       180
cgattctctg gctccaagtc tggcacctca gcctccctgg ccatcagtgg gctccggtcc        240
gaggctgagg ctgattatta ctgtgcggca tgggatgaca gcctgagtgc cgtggtattc       300
ggcggaggga ccaaactgac cgtccta                                             327
```

<210> SEQ ID NO 130
<211> LENGTH: 327
<212> TYPE: DNA
<213> ORGANISM: Homo sapiens
<220> FEATURE:
<223> OTHER INFORMATION: anti-Rh(D) chain N01

<400> SEQUENCE: 130

```
gccgagctca cgcagccgcc ctcagtgtct gcggccccag gacagaaggt caccatctcc         60
tgctctggaa gcagctccaa cattgacagt aactatgtat cctggtacca gcagctccca       120
ggaacagccc ccaaactcct cattttgac aattataggc gacctcagg gattcctgac         180 cgattctcag gctccaagtc tggcacgtca gccaccctgg gcatcaccgg actccagact        240
ggggacgagg ccgattatta ctgtgcaaca tgggatgaca gcctgaatgg tcgggtgttc       300
ggcggaggga ccaagctgac cgtccta                                             327
```

<210> SEQ ID NO 131
<211> LENGTH: 342
<212> TYPE: DNA

<210> SEQ ID NO 131
<211> LENGTH: 342
<212> TYPE: DNA
<213> ORGANISM: Homo sapiens
<220> FEATURE:
<223> OTHER INFORMATION: anti-Rh(D) chain N02

<400> SEQUENCE: 131

| | | | | | |
|---|---|---|---|---|---|
| gccgagctca | cgcagccgcc | ctcagtgtct | gcggcccag | acagaaggt | caccatctcc | 60 |
| tgctctggaa | gcagctccaa | cattgggaat | aattatgtgt | cctggtacca | gcaactccca | 120 |
| ggaacagccc | ccaaactcct | catttatgac | aataataagc | gaccctcagg | gattcctgac | 180 |
| cgattctctg | gctccaagtc | tggcacgtca | gccaccctgg | gcatcaccgg | actccagact | 240 |
| ggggacgagg | ccgattatta | ctgcggaaca | tgggatagca | gcctgagtgc | tggccgcgtt | 300 |
| cggcggatgt | tcggcggagg | gaccaagttg | accgtcctgg | gt | | 342 |

<210> SEQ ID NO 132
<211> LENGTH: 330
<212> TYPE: DNA
<213> ORGANISM: Homo sapiens
<220> FEATURE:
<223> OTHER INFORMATION: anti-Rh(D) chain O01

<400> SEQUENCE: 132

| | | | | | |
|---|---|---|---|---|---|
| gccgagctca | cgcagccgcc | ctcagtgtct | ggggcccag | ggcagagggt | caccatctcc | 60 |
| tgcactggga | gcagctccaa | catcggggca | ccttatggtg | tacactggta | ccagcagttt | 120 |
| ccaggaacag | cccccaaact | cgtcatctac | aatgacaaca | atcggccctc | agggtccct | 180 |
| gaccgattct | ctggctccaa | gtctggcacc | tcagcctccc | tggccatcac | tgggctccag | 240 |
| gctgaggatg | aggctgatta | ttactgccag | tcctatgaca | gcagcctgag | tggaagggtg | 300 |
| ttcggcggag | ggaccaagct | gaccgtccta | | | | 330 |

<210> SEQ ID NO 133
<211> LENGTH: 336
<212> TYPE: DNA
<213> ORGANISM: Homo sapiens
<220> FEATURE:
<223> OTHER INFORMATION: anti-Rh(D) chain O02

<400> SEQUENCE: 133

| | | | | | |
|---|---|---|---|---|---|
| gccgagctca | cgcagccgcc | ctcagtgtct | ggggcccag | ggcagacggt | caccatctcc | 60 |
| tgcactggga | gcagctccag | catcggggca | cgttatgatg | tacactggta | ccaacacctt | 120 |
| ccaggaacag | cccccaaact | cctcatctat | ggtaaccaca | atcggccctc | agggtccct | 180 |
| gaccgattct | ctggctccaa | gtctggcacc | tcagcctccc | tggccatcac | tgggctccag | 240 |
| gctgaggatg | aggctgaata | ttattgccag | tcctatgaca | acagcctgag | tggttcgtct | 300 |
| gtcttttcg | gcggagggac | caagctgacc | gtccta | | | 336 |

<210> SEQ ID NO 134
<211> LENGTH: 330
<212> TYPE: DNA
<213> ORGANISM: Homo sapiens
<220> FEATURE:
<223> OTHER INFORMATION: anti-Rh(D) chain O03

<400> SEQUENCE: 134

| | | | | | |
|---|---|---|---|---|---|
| gccgagctca | cgcagccgcc | ctctggggcc | ccaggccaga | cggtcaccat | ctcctgcact | 60 |
| gggagcagct | ccaacatcgg | ggcaggttat | gatgtacact | ggtaccagca | gcttccagga | 120 |
| acagcccca | aactcctcat | ctatggtaac | agcaatcggc | cctcagggt | ccctgaccga | 180 |
| ttctctggct | ccaagtctgg | cacctcagcc | tccctggcca | tcactgggct | ccaggctgag | 240 |

```
gatgaggctg attattactg ccagtcctat gacagcagcc tgagtggtcc ctatgtggta      300
ttcggcggag ggaccaagct gaccgtccta                                      330
```

<210> SEQ ID NO 135
<211> LENGTH: 324
<212> TYPE: DNA
<213> ORGANISM: Homo sapiens
<220> FEATURE:
<223> OTHER INFORMATION: anti-Rh(D) chain P01

<400> SEQUENCE: 135

```
gccgagctca ctcagccacc ctcggtgtca gtggccccaa gacagacggc caggattacc      60 tgtgggggg acaaaatcgg aagtaacact gtgcattggt accggcagat gtcaggccag      120
gcccctgttc tggtcatcta tgaagacaaa aaacgacccc ccgggatccc tgagagattc     180
tctggttcca cctcagggac aacggccacc ttgagtatca gtggggccca ggttgaggat     240
gaagctgact actactgtta ttcaagagac aacagtggtg atcagagaag ggtgttcggc     300
gcagggacca agctgaccgt ccta                                            324
```

<210> SEQ ID NO 136
<211> LENGTH: 330
<212> TYPE: DNA
<213> ORGANISM: Homo sapiens
<220> FEATURE:
<223> OTHER INFORMATION: anti-Rh(D) chain Q01

<400> SEQUENCE: 136

```
gccgagctca ctcagccacc ctccgccact gcctccctgg gaggctcggt caaactcacc     60
tgcattctgc agagtggcca cagaaattac gccgtcgctt ggcatcacca agaagcaggg     120
aagggcccgc gattttgat gacggttacc aatgatggca gcacatcaa ggggacggg       180 atccctgatc gcttctcagg ctccgcctct ggggctgaac gctacctctc catctccggc     240
ctccagtctg aggatgaggg tgactactac tgtcagacct ggggcactgg catgcatgtg    300
ttcggcggag ggaccaaact gaccgtccta                                      330
```

<210> SEQ ID NO 137
<211> LENGTH: 324
<212> TYPE: DNA
<213> ORGANISM: Homo sapiens
<220> FEATURE:
<223> OTHER INFORMATION: anti-Rh(D) chain R01

<400> SEQUENCE: 137

```
gccgagctca ctcagcctcc ctccgcgtcc gggtctcctg gacagtcagt caccatctcc     60
tgcactggag ccagcagtga cgttggtgct tataagcacg tctcctggta ccaacaacac    120
ccaggcaaag cccccaaact cctgactcat gagggcacta gcggccctc aggggtccct     180 gatcgcttct ctggctccaa gtctggcaac acggcctccc tgaccgtctc tgggctccag    240
gctgaggatg aggctgatta ttactgcagc tcatttgcag gtaattccgt gatattcggc    300
ggagggacca agctgaccgt ccta                                            324
```

<210> SEQ ID NO 138
<211> LENGTH: 312
<212> TYPE: DNA
<213> ORGANISM: Homo sapiens
<220> FEATURE:
<223> OTHER INFORMATION: anti-Rh(D) chain S01

-continued

```
<400> SEQUENCE: 138
gccgagctca ctcagcctcc ctccgtgtct gggtctcctg gacagtcgat caccatctcc      60
tgcagtgatg ttgggaatta taaccttgtc tcctggtacc aacagtaccc aggcaaggcc     120
cccaaactca taatttatga gggcagtaag cggccctcag gggtttctag tcgcttctct     180
ggctccaggt ctggcaacac ggcctccctg acaatctctg gctccaggc tgaggacgag      240 gctgattatc actgctgctc atatgcaatt agtagcagga ttttcggcgg agggaccaag     300
ctgaccgtcc ta                                                         312

<210> SEQ ID NO 139
<211> LENGTH: 127
<212> TYPE: PRT
<213> ORGANISM: Homo sapiens
<220> FEATURE:
<223> OTHER INFORMATION: anti-Rh(D) antibody clone SH10

<400> SEQUENCE: 139

Glu Val Gln Leu Leu Glu Glu Ser Gly Gly Val Val Gln Pro Gly
 1               5                  10                  15

Arg Ser Leu Arg Leu Ser Cys Ala Ala Ser Gly Phe Thr Phe Ser Arg
            20                  25                  30

Asn Gly Met His Trp Val Arg Gln Ala Pro Gly Lys Gly Leu Glu Trp
        35                  40                  45

Val Ala Phe Ile Trp Phe Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Asp Asp Thr Ala Val Tyr Tyr
                85                  90                  95

Cys Ala Arg Glu Glu Ala Leu Phe Arg Gly Leu Thr Arg Trp Ser Tyr
            100                 105                 110

Gly Met Asp Val Trp Gly Gln Gly Thr Thr Val Ser Val Ser Ser
        115                 120                 125

<210> SEQ ID NO 140
<211> LENGTH: 125
<212> TYPE: PRT
<213> ORGANISM: Homo sapiens
<220> FEATURE:
<223> OTHER INFORMATION: anti-Rh(D) antibody clone SH16

<400> SEQUENCE: 140

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Arg Gly Leu Glu Trp Val
        35                  40                  45

Ala Leu Ile Trp Tyr Asp Gly Ser Asn Lys Glu Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Val Asn Ser Leu Arg Ala Asp Asp Thr Ala Val Tyr Tyr Cys
                85                  90                  95

Ala Arg Asp Gln Arg Ala Ala Ala Gly Ile Phe Tyr Tyr Ser Arg Met
            100                 105                 110
```

```
Asp Val Trp Gly Gln Gly Thr Thr Val Thr Val Ser Ser
        115                 120                 125

<210> SEQ ID NO 141
<211> LENGTH: 117
<212> TYPE: PRT
<213> ORGANISM: Homo sapiens
<220> FEATURE:
<223> OTHER INFORMATION: anti-Rh(D) antibody clone SH17

<400> SEQUENCE: 141

Glu Val Gln Leu Leu Glu Ser Gly Gly Gly Leu Val Gln Pro Gly Gly
 1               5                  10                  15

Ser Leu Arg Leu Ser Cys Gly Ala Ser Gly Ile Pro Phe Val Ser Ser
            20                  25                  30

Trp Met Ala Trp Val Arg Gln Ala Pro Gly Lys Gly Leu Glu Trp Val
        35                  40                  45

Ala Asn Ile Lys Gln Asp Gly Ser Lys Lys Asn Tyr Val Asp Ser Val
    50                  55                  60

Glu Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Arg Ile Tyr Tyr Cys
                85                  90                  95

Ala Arg Asp Ser Leu Thr Cys Phe Asp Tyr Trp Gly Gln Gly Ala Leu
            100                 105                 110

Val Thr Val Ser Ser
        115

<210> SEQ ID NO 142
<211> LENGTH: 128
<212> TYPE: PRT
<213> ORGANISM: Homo sapiens
<220> FEATURE:
<223> OTHER INFORMATION: anti-Rh(D) antibody clone SH18

<400> SEQUENCE: 142

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
            20                  25                  30

Ala Met His Trp Val Arg Gln Ala Pro Gly Lys Gly Leu Glu Trp Val
        35                  40                  45

Ala Ala Thr Ala Tyr Asp Gly Lys Asn Lys Tyr Tyr Ala Asp Ser Val
    50                  55                  60

Lys Gly Arg Phe Thr Ile Ser Arg Asp Asn Ser Met Asn Thr Leu Phe
65                  70                  75                  80

Leu Gln Met Asn Ser Leu Arg Ala Glu Asp Thr Ala Val Phe Tyr Cys
                85                  90                  95

Ala Arg Gly Gly Phe Tyr Tyr Asp Ser Ser Gly Tyr Tyr Gly Leu Arg
            100                 105                 110

His Tyr Phe Asp Ser Trp Gly Gln Gly Thr Leu Val Thr Val Ser Ser
        115                 120                 125

<210> SEQ ID NO 143
<211> LENGTH: 129
<212> TYPE: PRT
<213> ORGANISM: Homo sapiens
<220> FEATURE:
<223> OTHER INFORMATION: anti-Rh(D) antibody clone SH20
```

```
<400> SEQUENCE: 143

Glu Val Gln Leu Leu Glu Ser Gly Gly Gly Val Val Gln Pro Gly
 1               5                  10                  15

Arg Ser Leu Arg Leu Ser Cys Ala Ala Ser Gly Phe Thr Phe Arg Ser
                20                  25                  30

Tyr Ala Met His Trp Val Arg Gln Ala Pro Gly Lys Gly Leu Glu Trp
            35                  40                  45

Val Ala Val Ile Ser Tyr Asp Gly Ser Thr Ile Tyr Tyr Ala Asp Ser
 50                  55                  60

Val Lys Gly Arg Phe Thr Ile Ser Arg Ala Asn Ser Lys Asn Thr Leu
 65                  70                  75                  80

Phe Leu Gln Met Asn Ser Leu Arg Thr Glu Asp Thr Ala Val Tyr Tyr
                85                  90                  95

Cys Thr Arg Gly Gly Phe Tyr Tyr Asp Ser Ser Gly Tyr Tyr Gly Leu
                100                 105                 110

Arg His Tyr Phe Asp Tyr Trp Gly Gln Gly Thr Leu Val Thr Val Ser
            115                 120                 125

Ser

<210> SEQ ID NO 144
<211> LENGTH: 126
<212> TYPE: PRT
<213> ORGANISM: Homo sapiens
<220> FEATURE:
<223> OTHER INFORMATION: anti-Rh(D) antibody clone SH24

<400> SEQUENCE: 144

Glu Val Gln Leu Leu Glu Ser Gly Gly Gly Val Ala Gln Pro Gly Arg
 1               5                  10                  15

Ser Leu Arg Leu Ser Cys Val Ala Ser Gly Phe Ser Leu Arg Ser Tyr
                20                  25                  30

Gly Met His Trp Val Arg Gln Ala Pro Gly Lys Gly Leu Glu Trp Val
            35                  40                  45

Ala Asp Ile Trp Phe Asp Gly Ser Asn Lys Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Trp Arg Val Arg Ala Phe Ser Ser Gly Trp Leu Ser Ala
                100                 105                 110

Phe Asp Ile Trp Gly Gln Gly Thr Met Val Thr Val Ser Ser
            115                 120                 125

<210> SEQ ID NO 145
<211> LENGTH: 127
<212> TYPE: PRT
<213> ORGANISM: Homo sapiens
<220> FEATURE:
<223> OTHER INFORMATION: anti-Rh(D) antibody clone SH25

<400> SEQUENCE: 145

Glu Val Gln Leu Leu Glu Ser Gly Gly Gly Val Val Gln Pro Gly
 1               5                  10                  15

Arg Ser Leu Arg Leu Ala Cys Ala Ala Ser Gly Phe Ser Phe Arg Ser
                20                  25                  30

Tyr Gly Met His Trp Val Arg Gln Ala Pro Gly Arg Gly Leu Glu Trp
```

```
                   35                  40                  45

Val Ala Phe Thr Trp Phe Asp Gly Ser Asn Lys Tyr Tyr Val Asp Ser
        50                  55                  60

Val Lys Gly Arg Phe Thr Ile Ser Arg Asp Asn Ser Lys Asn Thr Leu
 65                  70                  75                  80

Tyr Leu Glu Met Asn Ser Leu Arg Val Asp Asp Thr Ala Val Tyr Tyr
                85                  90                  95

Cys Ala Arg Glu Ala Pro Met Leu Arg Gly Ile Ser Arg Tyr Tyr Tyr
                100                 105                 110

Ala Met Asp Val Trp Gly Pro Gly Thr Thr Val Thr Val Ser Ser
                115                 120                 125

<210> SEQ ID NO 146
<211> LENGTH: 126
<212> TYPE: PRT
<213> ORGANISM: Homo sapiens
<220> FEATURE:
<223> OTHER INFORMATION: anti-Rh(D) antibody clone SH28, SH50, and SH53

<400> SEQUENCE: 146

Glu Val Gln Leu Leu Glu Ser Gly Gly Gly Val Gln Pro Gly Arg
  1               5                  10                  15

Ser Leu Arg Leu Ser Cys Ala Ala Ser Gly Phe Thr Phe Asn Ser Tyr
                 20                  25                  30

Ala Met Tyr Trp Val Arg Gln Pro Pro Gly Lys Gly Leu Glu Trp Val
                35                  40                  45

Ala Ala Ile Trp Tyr Asp Gly Ser Asn Lys Glu Tyr Ala Asp Phe Val
        50                  55                  60

Lys Gly Arg Phe Thr Ile Ser Arg Asp Asn Ser Lys Asn Thr Leu Ser
 65                  70                  75                  80

Leu Gln Met Asn Ser Leu Arg Asp Glu Asp Thr Ala Val Tyr Tyr Cys
                85                  90                  95

Ala Arg Glu Ala Asn Leu Leu Arg Gly Trp Ser Arg Tyr Tyr Tyr Gly
                100                 105                 110

Met Asp Val Trp Gly Gln Gly Thr Thr Val Thr Val Ser Ser
                115                 120                 125

<210> SEQ ID NO 147
<211> LENGTH: 126
<212> TYPE: PRT
<213> ORGANISM: Homo sapiens
<220> FEATURE:
<223> OTHER INFORMATION: anti-Rh(D) antibody clone SH32

<400> SEQUENCE: 147

Glu Val Gln Leu Leu Glu Ser Gly Gly Gly Val Val Gln Pro Gly Arg
  1               5                  10                  15

Ser Leu Arg Leu Ser Cys Glu Ala Ser Lys Phe Thr Leu Tyr Asn Tyr
                 20                  25                  30

Gly Met His Trp Val Arg Gln Ala Pro Gly Lys Gly Leu Glu Trp Val
                35                  40                  45

Ala Phe Ile Trp Phe Asp Gly Ser Asn Lys Tyr Tyr Glu Asp Ser Val
        50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

```
Ala Arg Glu Leu Ser Lys Lys Val Ala Leu Ser Arg Tyr Tyr Tyr Tyr
            100                 105                 110

Met Asp Val Trp Gly Gln Gly Thr Thr Val Thr Val Ser Ser
            115                 120                 125

<210> SEQ ID NO 148
<211> LENGTH: 126
<212> TYPE: PRT
<213> ORGANISM: Homo sapiens
<220> FEATURE:
<223> OTHER INFORMATION: anti-Rh(D) antibody clone SH37

<400> SEQUENCE: 148

Glu Val Gln Leu Leu Glu Ser Gly Gly Val Val Gln Pro Gly Arg
  1               5                  10                  15

Ser Leu Arg Leu Ser Cys Glu Ala Ser Lys Phe Thr Leu Tyr Asn Tyr
            20                  25                  30

Gly Met His Trp Val Arg Gln Ala Pro Gly Lys Gly Leu Glu Trp Val
            35                  40                  45

Ala Phe Ile Trp Phe Asp Gly Ser Asn Lys Tyr Tyr Glu Asp Ser Val
        50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Glu Leu Ser Lys Lys Val Ala Leu Ser Arg Tyr Tyr Tyr Tyr
            100                 105                 110

Met Asp Val Trp Gly Gln Gly Thr Thr Val Thr Val Ser Ser
            115                 120                 125

<210> SEQ ID NO 149
<211> LENGTH: 126
<212> TYPE: PRT
<213> ORGANISM: Homo sapiens
<220> FEATURE:
<223> OTHER INFORMATION: anti-Rh(D) antibody clone SH39

<400> SEQUENCE: 149

Glu Val Gln Leu Leu Glu Gln Ser Gly Gly Val Val Gln Pro Gly
  1               5                  10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Gly Lys Gly Leu Glu Trp
            35                  40                  45

Val Ala Val Ile Trp Phe Asp Gly Ser Asn Lys Glu Tyr Ala Asp Ser
        50                  55                  60

Val Lys Gly Arg Phe Thr Ile Ser Arg Asp Asn Ser Lys Asn Thr Leu
 65                  70                  75                  80

Tyr Leu Gln Met Asn Ser Leu Arg Ala Glu Asp Thr Ala Val Tyr Tyr
                85                  90                  95

Cys Ala Arg Glu Glu Val Val Arg Gly Val Ile Leu Trp Ser Arg Lys
            100                 105                 110

Phe Asp Tyr Trp Gly Gln Gly Thr Leu Val Thr Val Ser Ser
            115                 120                 125

<210> SEQ ID NO 150
<211> LENGTH: 126
<212> TYPE: PRT
<213> ORGANISM: Homo sapiens
```

```
<220> FEATURE:
<223> OTHER INFORMATION: anti-Rh(D) antibody clone SH44

<400> SEQUENCE: 150

Glu Val Gln Leu Leu Glu Ser Gly Gly Gly Val Ala Gln Pro Gly Arg
 1               5                  10                  15

Ser Leu Arg Leu Ser Cys Val Ala Ser Gly Phe Ser Leu Arg Ser Tyr
            20                  25                  30

Gly Met His Trp Val Arg Gln Ala Pro Gly Lys Gly Leu Glu Trp Val
        35                  40                  45

Ala Asp Ile Trp Phe Asp Gly Ser Asn Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Arg Val Arg Ala Phe Ser Ser Gly Trp Leu Ser Ala
            100                 105                 110

Phe Asp Ile Trp Gly Gln Gly Thr Met Val Thr Val Ser Ser
        115                 120                 125

<210> SEQ ID NO 151
<211> LENGTH: 125
<212> TYPE: PRT
<213> ORGANISM: Homo sapiens
<220> FEATURE:
<223> OTHER INFORMATION: anti-Rh(D) antibody clone SH47

<400> SEQUENCE: 151

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Ser Phe Ser Asn Tyr
            20                  25                  30

Ala Met His Trp Val Arg Gln Ala Pro Gly Lys Gly Leu Glu Trp Val
        35                  40                  45

Ala Val Thr Ser Phe Asp Gly Ser Ile Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Glu Arg Gly Met Ile Val Val Arg Arg Arg Asn Ala Phe
            100                 105                 110

Asp Ile Trp Gly Gln Gly Thr Met Val Thr Val Ser Ser
        115                 120                 125

<210> SEQ ID NO 152
<211> LENGTH: 126
<212> TYPE: PRT
<213> ORGANISM: Homo sapiens
<220> FEATURE:
<223> OTHER INFORMATION: anti-Rh(D) antibody clone SH54

<400> SEQUENCE: 152

Glu Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Arg Asn
            20                  25                  30
```

```
Gly Met His Trp Val Arg Gln Ala Pro Gly Lys Gly Leu Glu Trp Val
            35                  40                  45

Ala Phe Ile Trp Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Asp Asp Thr Ala Val Tyr Tyr Cys
                85                  90                  95

Ala Arg Glu Glu Ala Leu Phe Arg Gly Leu Thr Arg Trp Ser Tyr Gly
            100                 105                 110

Met Asp Val Trp Gly Gln Gly Thr Thr Val Ser Val Ser Ser
            115                 120                 125

<210> SEQ ID NO 153
<211> LENGTH: 126
<212> TYPE: PRT
<213> ORGANISM: Homo sapiens
<220> FEATURE:
<223> OTHER INFORMATION: anti-Rh(D) antibody clone SH56

<400> SEQUENCE: 153

Glu Val Gln Leu Leu Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Val Tyr Tyr Asp Gly Ser Asn Lys His Tyr Ser Asp Ser Val
        50                  55                  60

Lys Gly Arg Phe Thr Ile Phe Arg Asp Asn Ser Lys Asn Thr Leu Tyr
 65                 70                  75                  80

Leu Gln Met Asp Ser Leu Arg Ala Glu Asp Thr Ala Val Tyr Tyr Cys
                85                  90                  95

Ala Arg Glu Arg Asn Phe Arg Ser Gly Tyr Ser Arg Tyr Tyr Tyr Gly
            100                 105                 110

Met Asp Val Trp Gly Pro Gly Thr Thr Val Thr Val Ser Ser
            115                 120                 125

<210> SEQ ID NO 154
<211> LENGTH: 107
<212> TYPE: PRT
<213> ORGANISM: Homo sapiens
<220> FEATURE:
<223> OTHER INFORMATION: anti-Rh(D) antibody clone SH8

<400> SEQUENCE: 154

Ala Glu Leu Thr Gln Ser Pro Ser Ser Leu Ala Ala Ser Val Gly Asp
 1               5                  10                  15

Arg Val Thr Ile Thr Cys Arg Ala Asn Gln Thr Ile Arg Thr Ser Leu
            20                  25                  30

Asn Trp Tyr Gln Gln Arg Pro Gly Lys Ala Pro Asn Leu Leu Ile Tyr
            35                  40                  45

Gly Ala Ser Arg Leu His Ser Gly Val Pro Ser Arg Phe Ser Gly Gly
        50                  55                  60

Ile Ser Gly Ala Asp Phe Thr Leu Thr Ile Ser Ser Leu Gln Pro Glu
 65                 70                  75                  80

Asp Phe Ala Thr Tyr Tyr Cys Gln Gln Thr Tyr Gly Tyr Ser Arg Thr
                85                  90                  95
```

```
Phe Gly Gln Gly Thr Lys Val Asp Ile Lys Arg
            100                 105
```

<210> SEQ ID NO 155
<211> LENGTH: 107
<212> TYPE: PRT
<213> ORGANISM: Homo sapiens
<220> FEATURE:
<223> OTHER INFORMATION: anti-Rh(D) antibody clone SH12

<400> SEQUENCE: 155

```
Ala Glu Leu Thr Gln Ser Pro Phe Ser Leu Ser Ala Ser Val Gly Asp
  1               5                  10                  15

Arg Val Thr Ile Thr Cys Arg Ala Ser His Asn Ile Tyr Arg Ser Leu
             20                  25                  30

Asn Trp Phe Gln His Lys Pro Gly Glu Ala Pro Lys Leu Leu Val Tyr
         35                  40                  45

Ala Ala Ser Ser Leu Gln Arg Gly Val Pro Thr Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Ser Ala Thr Tyr Phe Cys Gln Gln Ser Val Thr Phe Pro Tyr Thr
                 85                  90                  95

Phe Gly Gln Gly Thr Lys Leu Glu Ile Arg Arg
            100                 105
```

<210> SEQ ID NO 156
<211> LENGTH: 107
<212> TYPE: PRT
<213> ORGANISM: Homo sapiens
<220> FEATURE:
<223> OTHER INFORMATION: anti-Rh(D) antibody clone SH13

<400> SEQUENCE: 156

```
Ala Glu Leu Thr Gln Ser Pro Ser Ser Leu Ser Ala Ser Val Gly Asp
  1               5                  10                  15

Arg Val Thr Ile Thr Cys Arg Ala Ser Gln Ser Ile Ser Ser Tyr Leu
             20                  25                  30

Asn Trp Tyr Gln Gln Lys Pro Gly Lys Ala Pro Lys Leu Leu Ile Tyr
         35                  40                  45

Ala Ala Ser Ser Leu Arg Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Tyr Thr
                 85                  90                  95

Phe Gly Gln Gly Thr Lys Leu Glu Ile Lys Arg
            100                 105
```

<210> SEQ ID NO 157
<211> LENGTH: 107
<212> TYPE: PRT
<213> ORGANISM: Homo sapiens
<220> FEATURE:
<223> OTHER INFORMATION: anti-Rh(D) antibody clone SH14

<400> SEQUENCE: 157

```
Ala Glu Leu Thr Gln Ser Pro Ser Ser Leu Ser Ala Ser Val Gly Asp
  1               5                  10                  15
```

-continued

```
Arg Val Thr Ile Thr Cys Arg Ala Ser Gln Asn Ile Arg Arg Ser Leu
             20                  25                  30

Asn Trp Tyr Gln His Lys Pro Gly Arg Ala Pro Arg Leu Leu Ile Tyr
         35                  40                  45

Ala Ala Ser Thr Leu Gln Ser Gly Val Pro Ser Arg Phe Arg Gly Ser
     50                  55                  60

Gly Ser Gly Thr Asp Phe Thr Leu Thr Ile Asn Ser Leu Gln Pro Ala
 65                  70                  75                  80

Asp Phe Ala Thr Tyr Tyr Cys Gln Gln Ser Ser Asn Thr Pro Trp Thr
                 85                  90                  95

Phe Gly His Gly Thr Lys Val Glu Ile Lys Arg
            100                 105
```

<210> SEQ ID NO 158
<211> LENGTH: 107
<212> TYPE: PRT
<213> ORGANISM: Homo sapiens
<220> FEATURE:
<223> OTHER INFORMATION: anti-Rh(D) antibody clone SH16

<400> SEQUENCE: 158

```
Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Ser Tyr Leu
             20                  25                  30

Asn Trp Tyr Gln Gln Lys Pro Gly Lys Ala Pro Lys Leu Leu Ile Tyr
         35                  40                  45

Ala Ala Ser Ser Leu Gln Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Pro Thr
                 85                  90                  95

Phe Gly Gly Gly Thr Lys Val Glu Ile Lys Arg
            100                 105
```

<210> SEQ ID NO 159
<211> LENGTH: 106
<212> TYPE: PRT
<213> ORGANISM: Homo sapiens
<220> FEATURE:
<223> OTHER INFORMATION: anti-Rh(D) antibody clone SH18

<400> SEQUENCE: 159

```
Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Ile Ala Leu
             20                  25                  30

Asn Trp Tyr Gln Gln Arg Pro Gly Lys Ala Pro Lys Leu Leu Met Tyr
         35                  40                  45

Ala Thr Ser Thr Leu Gln Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Tyr Tyr Asn Lys Pro Thr Phe
                 85                  90                  95

Gly Pro Gly Thr Lys Val Asp Ile Lys Arg
            100                 105
```

```
<210> SEQ ID NO 160
<211> LENGTH: 107
<212> TYPE: PRT
<213> ORGANISM: Homo sapiens
<220> FEATURE:
<223> OTHER INFORMATION: anti-Rh(D) antibody clone SH20

<400> SEQUENCE: 160

Ala Glu Leu Thr Gln Ser Pro Phe Ser Leu Ser Ala Ser Val Gly Asp
 1               5                  10                  15

Arg Val Thr Ile Thr Cys Arg Ala Ser Gln Ser Ile Ser Arg Ser Leu
             20                  25                  30

Asn Trp Tyr Gln His Lys Pro Gly Glu Ala Pro Lys Leu Leu Ile Tyr
         35                  40                  45

Ala Ala Ser Ser Leu Gln Arg Gly Val Pro Pro Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Phe Cys Gln Gln Ser Val Arg Ile Pro Tyr Ser
                 85                  90                  95

Phe Gly Gln Gly Thr Lys Leu Glu Ile Lys Arg
            100                 105

<210> SEQ ID NO 161
<211> LENGTH: 108
<212> TYPE: PRT
<213> ORGANISM: Homo sapiens
<220> FEATURE:
<223> OTHER INFORMATION: anti-Rh(D) antibody clone SH21

<400> SEQUENCE: 161

Ala Glu Leu Thr Gln Ser Pro Ser Phe Leu Ser Ala Ser Val Gly Asp
 1               5                  10                  15

Arg Val Thr Ile Thr Cys Arg Ala Ser Gln Gly Ile Arg Ser Tyr Leu
             20                  25                  30

Ala Trp Tyr Gln Gln Lys Pro Gly Lys Ala Pro Lys Leu Leu Ile Tyr
         35                  40                  45

Ala Ala Ser Thr Leu Gln Ser Gly Val Pro Ser Arg Phe Ser Gly Ser
     50                  55                  60

Gly Ser Gly Thr Glu Phe Thr Leu Thr Ile Ala Ser Leu Gln Pro Asp
 65                  70                  75                  80

Asp Phe Ala Thr Tyr Tyr Cys Gln Gln Leu Asn Asn Tyr Pro Pro Phe
                 85                  90                  95

Thr Phe Gly Pro Gly Thr Lys Val Asp Ile Lys Arg
            100                 105

<210> SEQ ID NO 162
<211> LENGTH: 107
<212> TYPE: PRT
<213> ORGANISM: Homo sapiens
<220> FEATURE:
<223> OTHER INFORMATION: anti-Rh(D) antibody clone SH24

<400> SEQUENCE: 162

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Thr Tyr Leu
             20                  25                  30
```

```
Asn Trp Tyr Gln Gln Arg Pro Gly Lys Ala Pro Asn Leu Leu Ile Tyr
            35                  40                  45

Ala Ala Ser Thr Leu Gln Arg Gly Val Pro Ser Arg Phe Thr Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Thr Thr Leu Trp Thr
                 85                  90                  95

Phe Gly Gln Gly Thr Lys Met Glu Ile Arg Arg
            100                 105

<210> SEQ ID NO 163
<211> LENGTH: 108
<212> TYPE: PRT
<213> ORGANISM: Homo sapiens
<220> FEATURE:
<223> OTHER INFORMATION: anti-Rh(D) antibody clone SH26

<400> SEQUENCE: 163

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Ser Tyr Leu
                 20                  25                  30

Asn Trp Tyr Gln Gln Lys Pro Gly Lys Ala Pro Lys Leu Leu Ile Tyr
            35                  40                  45

Ala Ala Ser Ser Leu Gln Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Phe Arg Arg Tyr
                 85                  90                  95

Ser Phe Gly Gln Gly Thr Lys Leu Glu Ile Lys Arg
            100                 105

<210> SEQ ID NO 164
<211> LENGTH: 107
<212> TYPE: PRT
<213> ORGANISM: Homo sapiens
<220> FEATURE:
<223> OTHER INFORMATION: anti-Rh(D) antibody clone SH28

<400> SEQUENCE: 164

Ala Glu Leu Thr Gln Ser Pro Ser Ser Leu Ser Ala Ser Val Gly Asp
 1               5                  10                  15

Arg Val Thr Ile Thr Cys Arg Ala Asp Gln Asn Ile Arg Arg Ser Leu
                 20                  25                  30

Asn Trp Phe Gln Gln Lys Pro Gly Lys Ala Pro Lys Leu Leu Ile Tyr
            35                  40                  45

Ala Ala Ser Ser Leu Gln Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Ser Thr Pro Trp Thr
                 85                  90                  95

Phe Gly Arg Gly Thr Lys Val Glu Ile Lys Arg
            100                 105

<210> SEQ ID NO 165
```

```
<211> LENGTH: 106
<212> TYPE: PRT
<213> ORGANISM: Homo sapiens
<220> FEATURE:
<223> OTHER INFORMATION: anti-Rh(D) antibody clone SH30

<400> SEQUENCE: 165

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Arg Arg Ser Leu
             20                  25                  30

Asn Trp Tyr Gln Gln Ser Pro Gly Lys Thr Pro Lys Leu Leu Ile Tyr
         35                  40                  45

Ala Ala Ser Ser Leu Gln Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Leu Thr Phe
                 85                  90                  95

Gly Gly Gly Thr Lys Val Glu Ile Lys Arg
            100                 105

<210> SEQ ID NO 166
<211> LENGTH: 108
<212> TYPE: PRT
<213> ORGANISM: Homo sapiens
<220> FEATURE:
<223> OTHER INFORMATION: anti-Rh(D) antibody clone SH32

<400> SEQUENCE: 166

Ala Glu Leu Thr Gln Glu Pro Ser Leu Thr Val Ser Pro Gly Gly Thr
 1               5                  10                  15

Val Thr Leu Thr Cys Ala Ser Ser Thr Gly Ala Val Thr Ser Arg Tyr
             20                  25                  30

Phe Pro Asn Trp Phe Gln Gln Lys Pro Gly Gln Ala Pro Arg Ala Leu
         35                  40                  45

Ile Tyr Gly Ser Asn Asn Lys His Ser Trp Thr Pro Ala Arg Phe Ser
     50                  55                  60

Gly Ser Leu Leu Gly Gly Lys Ala Ala Leu Thr Leu Ser Gly Val Gln
 65                  70                  75                  80

Pro Glu Asp Glu Ala Glu Tyr Tyr Cys Leu Leu Phe Tyr Ala Gly Ala
                 85                  90                  95

Trp Ala Phe Gly Gly Gly Thr Lys Leu Thr Val Leu
            100                 105

<210> SEQ ID NO 167
<211> LENGTH: 108
<212> TYPE: PRT
<213> ORGANISM: Homo sapiens
<220> FEATURE:
<223> OTHER INFORMATION: anti-Rh(D) antibody clone SH34

<400> SEQUENCE: 167

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Ser Tyr Leu
             20                  25                  30

Asn Trp Tyr Gln Gln Lys Pro Gly Lys Ala Pro Lys Leu Leu Ile Tyr
         35                  40                  45
```

```
Ala Ala Ser Gly Leu Gln Ser Gly Val Pro Ser Arg Phe Ser Gly Ser
        50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Pro Tyr
                 85                  90                  95

Thr Phe Gly Gln Gly Thr Lys Leu Glu Ile Lys Arg
            100                 105
```

<210> SEQ ID NO 168
<211> LENGTH: 107
<212> TYPE: PRT
<213> ORGANISM: Homo sapiens
<220> FEATURE:
<223> OTHER INFORMATION: anti-Rh(D) antibody clone SH36

<400> SEQUENCE: 168

```
Ala Glu Leu Thr Gln Ser Pro Ser Ser Leu Ser Ala Ser Val Gly Asp
 1               5                  10                  15

Arg Val Thr Ile Thr Cys Arg Ala Ser Gln Ser Ile Ser Ser Tyr Leu
                 20                  25                  30

Asn Trp Tyr Gln Gln Lys Pro Gly Lys Ser Pro Lys Leu Leu Ile Tyr
             35                  40                  45

Ala Ala Ser Ser Leu Gln Ser Gly Val Pro Ser Arg Phe Ser Gly Ser
        50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Pro Ala
                 85                  90                  95

Phe Gly Pro Gly Thr Lys Val Asp Ile Lys Arg
            100                 105
```

<210> SEQ ID NO 169
<211> LENGTH: 107
<212> TYPE: PRT
<213> ORGANISM: Homo sapiens
<220> FEATURE:
<223> OTHER INFORMATION: anti-Rh(D) antibody clone SH39

<400> SEQUENCE: 169

```
Ala Glu Leu Thr Gln Ser Pro Ser Ser Leu Ser Ala Ser Val Gly Asp
 1               5                  10                  15

Arg Val Thr Ile Thr Cys Arg Ala Ser Gln Thr Ile Gly Arg Tyr Leu
                 20                  25                  30

Asn Trp Tyr Gln Gln Arg Pro Gly Lys Ala Pro Lys Leu Leu Val Tyr
             35                  40                  45

Ala Val Ser Ser Leu Gln Ser Gly Ala Pro Ser Arg Phe Ser Gly Ser
        50                  55                  60

Gly Ser Gly Thr His Phe Thr Leu Thr Ile Thr Ser Leu Gln Pro Glu
 65                  70                  75                  80

Asp Phe Ala Thr Tyr Phe Cys Gln Gln Ser Tyr Ser Ser Pro Phe Thr
                 85                  90                  95

Phe Gly Gln Gly Thr Lys Val Glu Ile Lys Arg
            100                 105
```

<210> SEQ ID NO 170
<211> LENGTH: 107
<212> TYPE: PRT
<213> ORGANISM: Homo sapiens

```
<220> FEATURE:
<223> OTHER INFORMATION: anti-Rh(D) antibody clone SH41

<400> SEQUENCE: 170

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Asn Ile Arg Arg Ser Leu
             20                  25                  30

Asn Trp Tyr Gln His Lys Pro Gly Arg Ala Pro Arg Leu Leu Ile Tyr
         35                  40                  45

Ala Ala Ser Thr Leu Gln Ser Gly Val Pro Ser Arg Phe Arg Gly Ser
     50                  55                  60

Gly Ser Gly Thr Asp Phe Thr Leu Thr Ile Asn Ser Leu Gln Pro Ala
 65                  70                  75                  80

Asp Phe Ala Thr Tyr Tyr Cys Gln Gln Ser Ser Asn Thr Pro Trp Thr
                 85                  90                  95

Phe Gly His Gly Thr Lys Val Glu Ile Lys Arg
            100                 105

<210> SEQ ID NO 171
<211> LENGTH: 106
<212> TYPE: PRT
<213> ORGANISM: Homo sapiens
<220> FEATURE:
<223> OTHER INFORMATION: anti-Rh(D) antibody clone SH44

<400> SEQUENCE: 171

Ala Glu Leu Thr Gln Ser Pro Ser Ser Leu Ser Ala Ser Val Gly Asp
 1               5                  10                  15

Arg Val Ile Ile Thr Cys Arg Ala Ser Gln Thr Ile Pro Arg Phe Leu
             20                  25                  30

Asn Trp Tyr Gln Gln Lys Pro Gly Lys Ala Pro Val Leu Leu Ile His
         35                  40                  45

Ser Ile Ser Ser Leu Gln Ser Gly Val Pro Ser Arg Phe Ser Ala Ser
     50                  55                  60

Gly Ser Gly Thr Glu Phe Thr Leu Thr Ile Ser Ser Leu Gln Pro Glu
 65                  70                  75                  80

Asp Phe Ala Thr Tyr Tyr Cys Gln Gln Ser Tyr Ser Asn Leu Ser Phe
                 85                  90                  95

Gly Pro Gly Thr Thr Val Asp Ile Arg Arg
            100                 105

<210> SEQ ID NO 172
<211> LENGTH: 107
<212> TYPE: PRT
<213> ORGANISM: Homo sapiens
<220> FEATURE:
<223> OTHER INFORMATION: anti-Rh(D) antibody clone SH46

<400> SEQUENCE: 172

Ala Glu Leu Thr Gln Ser Pro Ser Ser Leu Ser Ala Ser Val Gly Asp
 1               5                  10                  15

Arg Val Thr Ile Thr Cys Arg Ala Ser Gln Tyr Ile Ser Ser Tyr Leu
             20                  25                  30

Asn Trp Tyr Gln Gln Lys Pro Gly Lys Ala Pro Asn Leu Leu Ile Tyr
         35                  40                  45

Ala Ala Ser Ser Leu Gln Ser Gly Val Pro Ser Arg Phe Ser Gly Ser
     50                  55                  60
```

```
Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Thr Tyr Ser Ser Pro Ser Thr
                 85                  90                  95

Phe Gly Pro Gly Thr Lys Val Asp Ile Lys Arg
            100                 105
```

<210> SEQ ID NO 173
<211> LENGTH: 107
<212> TYPE: PRT
<213> ORGANISM: Homo sapiens
<220> FEATURE:
<223> OTHER INFORMATION: anti-Rh(D) antibody clone SH47

<400> SEQUENCE: 173

```
Ala Glu Leu Thr Gln Ser Pro Ser Ser Leu Ser Ala Ser Val Gly Asp
  1               5                  10                  15

Arg Val Thr Ile Thr Cys Arg Ala Ser Gln Ser Ile Ser Asn Tyr Leu
                 20                  25                  30

Asn Trp Tyr Gln Gln Lys Pro Gly Lys Ala Pro Asn Leu Leu Ile Tyr
             35                  40                  45

Ala Ala Ser Ser Leu Gln Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Tyr Pro Arg Thr
                 85                  90                  95

Phe Gly Gln Gly Thr Lys Val Glu Ile Arg Arg
            100                 105
```

<210> SEQ ID NO 174
<211> LENGTH: 107
<212> TYPE: PRT
<213> ORGANISM: Homo sapiens
<220> FEATURE:
<223> OTHER INFORMATION: anti-Rh(D) antibody clone SH48

<400> SEQUENCE: 174

```
Ala Glu Leu Thr Gln Ser Pro Ser Ser Leu Ser Ala Ser Val Gly Asp
  1               5                  10                  15

Arg Val Thr Ile Thr Cys Arg Ala Ser Gln Tyr Ile Ser Ser Tyr Leu
                 20                  25                  30

Asn Trp Tyr Gln Gln Lys Pro Gly Lys Ala Pro Asn Leu Leu Ile Tyr
             35                  40                  45

Ala Ala Ser Ser Leu Gln Ser Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Thr Tyr Ser Ser Pro Ser Thr
                 85                  90                  95

Phe Gly Pro Gly Thr Lys Val Asp Ile Lys Arg
            100                 105
```

<210> SEQ ID NO 175
<211> LENGTH: 107
<212> TYPE: PRT
<213> ORGANISM: Homo sapiens
<220> FEATURE:
<223> OTHER INFORMATION: anti-Rh(D) antibody clone SH49

-continued

```
<400> SEQUENCE: 175

Ala Glu Leu Thr Gln Ser Pro Ser Leu Ser Ala Ser Val Gly Asp
 1               5                  10                  15

Arg Val Thr Val Thr Cys Arg Ala Ser Gln Ser Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro Trp Thr
                85                  90                  95

Phe Gly Gln Gly Thr Lys Val Glu Ile Lys Arg
            100                 105

<210> SEQ ID NO 176
<211> LENGTH: 107
<212> TYPE: PRT
<213> ORGANISM: Homo sapiens
<220> FEATURE:
<223> OTHER INFORMATION: anti-Rh(D) antibody clone SH50

<400> SEQUENCE: 176

Ala Glu Leu Thr Gln Ser Pro Ser Leu Ser Ala Ser Val Gly Asp
 1               5                  10                  15

Arg Val Thr Val Thr Cys Arg Ala Ser Gln Ser Ile Ser Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro Trp Thr
                85                  90                  95

Phe Gly Gln Gly Thr Lys Val Glu Ile Lys Arg
            100                 105

<210> SEQ ID NO 177
<211> LENGTH: 108
<212> TYPE: PRT
<213> ORGANISM: Homo sapiens
<220> FEATURE:
<223> OTHER INFORMATION: anti-Rh(D) antibody clone SH51

<400> SEQUENCE: 177

Ala Glu Leu Thr Gln Ser Pro Ser Phe Leu Ser Ala Ser Val Gly Asp
 1               5                  10                  15

Arg Val Thr Ile Thr Cys Arg Ala Ser Gln Gly Ile Arg Ser Tyr Leu
            20                  25                  30

Ala Trp Tyr Gln Gln Lys Pro Gly Lys Ala Pro Lys Leu Leu Ile Tyr
        35                  40                  45

Ala Ala Ser Thr Leu Gln Ser Gly Val Pro Ser Arg Phe Ser Gly Ser
    50                  55                  60

Gly Ser Gly Thr Glu Phe Thr Leu Thr Ile Ser Ser Leu Gln Pro Glu
65                  70                  75                  80
```

```
Asp Phe Ala Thr Tyr Tyr Cys Gln Gln Leu Asn Asn Tyr Pro Pro Phe
                85                  90                  95

Thr Phe Gly Pro Gly Thr Lys Val Asp Ile Lys Arg
            100                 105

<210> SEQ ID NO 178
<211> LENGTH: 108
<212> TYPE: PRT
<213> ORGANISM: Homo sapiens
<220> FEATURE:
<223> OTHER INFORMATION: anti-Rh(D) antibody clone SH52

<400> SEQUENCE: 178

Ala Glu Leu Thr Gln Ser Pro Gly Thr Leu Ser Leu Ser Pro Gly Glu
  1               5                  10                  15

Arg Ala Thr Leu Ser Cys Arg Ala Ser Gln Ser Ile Ser Ser Ser Tyr
                 20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Pro Trp
                 85                  90                  95

Thr Phe Gly Gln Gly Thr Lys Val Glu Ile Lys Arg
            100                 105

<210> SEQ ID NO 179
<211> LENGTH: 107
<212> TYPE: PRT
<213> ORGANISM: Homo sapiens
<220> FEATURE:
<223> OTHER INFORMATION: anti-Rh(D) antibody clone SH54

<400> SEQUENCE: 179

Ala Glu Leu Thr Gln Ser Pro Ser Ser Met Ser Ala Ser Val Gly Asp
  1               5                  10                  15

Arg Val Thr Ile Thr Cys Arg Ala Ser Gln Ser Ile Gly Thr Tyr Leu
                 20                  25                  30

Asn Trp Tyr Gln Gln Lys Pro Gly Lys Ala Pro Lys Leu Leu Ile Tyr
             35                  40                  45

Ala Ala Ser Ser Leu Gln Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ser Tyr Ser Thr Pro Trp Thr
                 85                  90                  95

Phe Gly Gln Gly Thr Lys Val Glu Ile Lys Arg
            100                 105

<210> SEQ ID NO 180
<211> LENGTH: 109
<212> TYPE: PRT
<213> ORGANISM: Homo sapiens
<220> FEATURE:
<223> OTHER INFORMATION: anti-Rh(D) antibody clone SH55

<400> SEQUENCE: 180

Ala Glu Leu Thr Gln Pro Pro Ser Ala Ser Gly Thr Pro Gly Gln Arg
```

```
                1               5                   10                  15
            Val Thr Ile Ser Cys Ser Gly Ser Ser Ser Asn Ile Gly Ser Lys Tyr
                            20                  25                  30

Val Tyr Trp Tyr Gln Gln Leu Pro Gly Thr Ala Pro Lys Leu Leu Ile
                        35                  40                  45

Tyr Ser Asn Asn Gln Arg Pro Ser Gly Val Pro Asp Arg Phe Ser Ala
                    50                  55                  60

Phe Lys Ser Gly Thr Ser Ala Ser Leu Ala Ile Thr Gly Leu Gln Ala
                65                  70                  75                  80

Glu Asp Glu Ala Asn Tyr Tyr Cys Gln Ser Tyr Asp Ser Gly Leu Ser
                            85                  90                  95

Gly Trp Val Phe Gly Gly Gly Thr Lys Leu Thr Val Leu
                        100                 105

<210> SEQ ID NO 181
<211> LENGTH: 108
<212> TYPE: PRT
<213> ORGANISM: Homo sapiens
<220> FEATURE:
<223> OTHER INFORMATION: anti-Rh(D) antibody clone SH56

<400> SEQUENCE: 181

Ala Glu Leu Thr Gln Ser Pro Ser Ser Leu Ser Ala Ser Val Gly Asp
            1               5                   10                  15

Arg Val Thr Ile Thr Cys Arg Ala Ser Gln Ser Ile Ser Arg Tyr Leu
                            20                  25                  30

Asn Trp Tyr Gln Gln Lys Pro Gly Lys Ala Pro Lys Leu Leu Ile Tyr
                        35                  40                  45

Ala Ala Ser Ser Leu Gln Ser Gly Val Pro Ser Arg Phe Ser Gly Ser
                    50                  55                  60

Gly Ser Gly Thr Asp Phe Ala Leu Thr Ile Ser Ser Leu Leu Pro Glu
                65                  70                  75                  80

Asp Phe Ala Thr Tyr Tyr Cys Gln Gln Gly Tyr Ser Thr Pro Pro Tyr
                            85                  90                  95

Ser Phe Gly Gln Gly Thr Lys Leu Glu Ile Lys Arg
                        100                 105

<210> SEQ ID NO 182
<211> LENGTH: 381
<212> TYPE: DNA
<213> ORGANISM: Homo sapiens
<220> FEATURE:
<223> OTHER INFORMATION: anti-Rh(D) antibody clone SH10

<400> SEQUENCE: 182
gaggtgcagc tgctcgagga gtctggggga ggcgtggtcc agcctgggag gtccctgaga      60
ctctcctgtg cagcgtctgg gttcaccttc agtaggaatg gcatgcactg ggtccgccag     120
gctcctggca aggggctgga gtgggtggca tttatatggt ttgatggaag taataaatac     180
tatgcagact ccgtgaaggg ccgattcacc atctccagac acaattccaa gaacacgctg     240
tatctgcaaa tgaacagcct gagagccgac gacacggctg tgtattactg cgagagag      300 gaggctctgt ttcggggact tactcggtgg tcctacggca tggacgtctg gggccaaggg     360
accacggtca gcgtctcctc a                                               381

<210> SEQ ID NO 183
<211> LENGTH: 375
<212> TYPE: DNA
```

<213> ORGANISM: Homo sapiens
<220> FEATURE:
<223> OTHER INFORMATION: anti-Rh(D) antibody clone SH16

<400> SEQUENCE: 183

```
gaggtgcagc tgctcgagtc tgggggaggc gtggtccagc ctggaggtc cctgagactc      60
tcctgtgcag cgtctggqtt caccttcagt agctatggca tgcactgggt ccgccaggct    120
ccaggcaggg ggctggagtg ggtggctctt atatggtacg atggaggtaa caaagagtat    180
gcagactccg tgaagggccg cttcagcatc tccagagaca actccaagaa cactctgtat    240
ctgcaagtga acagcctgag agccgacgac acggctgtct attactgtgc gagagaccag    300
agagcagcag cgggtatctt ttattattcc cgtatggacg tctggggcca agggaccacg    360
gtcaccgtct cctca                                                     375
```

<210> SEQ ID NO 184
<211> LENGTH: 351
<212> TYPE: DNA
<213> ORGANISM: Homo sapiens
<220> FEATURE:
<223> OTHER INFORMATION: anti-Rh(D) antibody clone SH17
<220> FEATURE:
<223> OTHER INFORMATION: anti-Rh(D) antibody clone SH17

<400> SEQUENCE: 184

```
gaggtgcagc tgctcgagtc tgggggaggc ttggtccagc cggggggqtc cctgagactc      60
tcctgtggtg cctctggaat ccccttigtt tcctcttgga tggcctgggt ccgccaggcc    120
ccagggaagg ggctggagtg ggtggccaac ataaaacaag atggaagtaa gaaaaactat    180
gtggactctg tggagggccg attcaccatc tccagagaca acgcgaagaa ctcactttat    240
ctgcaaatgg acagcctgag agccgaggac acgcggatat attactgtgc gcgagattca    300
cttacttgtt ttgactactg gggccaggga gccctggtca ccgtctcctc a             351
```

<210> SEQ ID NO 185
<211> LENGTH: 384
<212> TYPE: DNA
<213> ORGANISM: Homo sapiens
<220> FEATURE:
<223> OTHER INFORMATION: anti-Rh(D) antibody clone SH18

<400> SEQUENCE: 185

```
gaggtgcagc tgctcgagtc tgggggaggc gtggtccagc ctggaggtc cctgagactc      60
tcctgtgcag cctctggatt caccttcagg agctatgcta tgcactgggt ccgccaggct    120
ccaggcaagg ggctggagtg ggtggcagct acagcatatg atggaaaaaa taaatactac    180
gcagactccg tgaagggccg attcaccatc tccagagaca attccatgaa cacgctgttt    240
ctgcaaatga acagcctgag agctgaggac acggctgtgt tttactgtgc gagaggcgga    300
ttttactatg atagtagtgg ttattacggc ttgaggcact actttgactc tgggggccag    360
ggaaccctgg tcaccgtctc ctca                                           384
```

<210> SEQ ID NO 186
<211> LENGTH: 387
<212> TYPE: DNA
<213> ORGANISM: Homo sapiens
<220> FEATURE:
<223> OTHER INFORMATION: anti-Rh(D) antibody clone SH20

<400> SEQUENCE: 186

```
gaggtgcagc tgctcgagga gtctgqggga ggcgtggtcc agcctgggag gtccctgaga      60
```

```
ctctcctgtg cagcctctgg attcaccttc agaagttatg ctatgcactg ggtccgccag    120
gctccaggca aggggctgga gtgggtggcg gttatatcat atgatggaag tactatatac    180
tacgcagact ccgtgaaggg ccgattcacc atctccagag ccaattccaa gaacacgctg    240
tttctgcaaa tgaacagcct cagaactgag gacacggctg tatattactg tacgagaggg    300
gggtttract atgacagtag tggttattac gggttgaggc actactttga ctactgggc    360 cagggaaccc tggtcaccgt ctcttca                                        387

<210> SEQ ID NO 187
<211> LENGTH: 378
<212> TYPE: DNA
<213> ORGANISM: Homo sapiens
<220> FEATURE:
<223> OTHER INFORMATION: anti-Rh(D) antibody clone SH24

<400> SEQUENCE: 187
gaggtgcagc tgctcgagtc ggggggaggc gtggcccagc ctggaggtc cctgagactc      60 tcctgtgtag cgtctggatt cagcctcagg agctatggca tgcactgggt ccgccaggct    120
cctggcaagg ggctggagtg gtggcagat atatggtttg atggaagtaa taagattat    180 gcagactccg tgaagggccg attcaccatc tccagagaca attccaagaa cacgttgtat    240
cttcaaatga acagcctgag agccgaggac acggctgtgt attattgtgc gagagattgg    300
agggtgcggg cctttagtag tggctggtta agtgcttttg atatctgggg ccaagggaca    360
atggtcaccg tctcttca                                                  378

<210> SEQ ID NO 188
<211> LENGTH: 381
<212> TYPE: DNA
<213> ORGANISM: Homo sapiens
<220> FEATURE:
<223> OTHER INFORMATION: anti-Rh(D) antibody clone SH25

<400> SEQUENCE: 188
gaggtgcagc tgctcgagga gtctggggga ggcgtggtcc agcctgggag gtccctgaga     60
ctcgcctgtg cagcgtctgg attcagcttc aggagctatg catgcactgg ggtccgccag   120
gctccaggca gggggctgga gtgggtggca tttacatggt ttgatggaag caataaatat    180
tatgtagact ccgtgaaggg ccgattcacc atctccagag acaattccaa gaacacgctg    240
tatctggaaa tgaacagcct gagagtcgat gacacggctg tatattactg tgcgagagag    300
gcgcctatgc ttcgcggaat tagcagatac tactacgcga tggacgtctg ggggcccaggg   360 accacggtca ccgtctcctc a                                              381

<210> SEQ ID NO 189
<211> LENGTH: 378
<212> TYPE: DNA
<213> ORGANISM: Homo sapiens
<220> FEATURE:
<223> OTHER INFORMATION: anti-Rh(D) antibody clone SH28, SH50, and SH53

<400> SEQUENCE: 189
gaggtgcagc tgctcgagtc tgggggaggc gggtccagc ctggaggtc cctgcgactc       60 tcctgtgcgg cgtctggatt caccttcaat agttatgcca tgtactgggt ccgccagcct    120
ccaggcaagg ggctggagtg gtggcagct atatggtatg atggaagtaa taagaatat    180 gcagattttg tgaagggccg cttcaccatc tccagagaca attccaagaa cacgctgtct    240
```

```
ctgcaaatga acagcctgag agacgaggac acggctgtgt attactgtgc gagagaggcg    300
aatctcctcc gtggctggtc tcgatactac tacggtatgg acgtctgggg ccaagggacc    360
acggtcaccg tctcctca                                                   378
```

<210> SEQ ID NO 190
<211> LENGTH: 378
<212> TYPE: DNA
<213> ORGANISM: Homo sapiens
<220> FEATURE:
<223> OTHER INFORMATION: anti-Rh(D) antibody clone SH32

<400> SEQUENCE: 190

```
gaggtgcagc tgctcgagtc ggggggaggc gtggtccagc ctgggaggtc cctgagactc    60
tcctgtgaag cgtctaaatt caccctctac aattatggca tgcactgggt ccgccaggct    120
ccaggcaagg ggctggagtg ggtggcattt atatggtttg atggaagtaa taatactat    180 gaagactccg tgaagggccg attcaccgtc tccagagaca attccaagaa cacgctgtat    240
ctgcaaatga acagcctgag agccgaggac acggctgtgt attactgtgc gagagaacta    300
tctaagaagg tggcactttc taggtattac tactatatgg acgtctgggg caggggacc    360 acggtcactg tctcgtca                                                   378
```

<210> SEQ ID NO 191
<211> LENGTH: 378
<212> TYPE: DNA
<213> ORGANISM: Homo sapiens
<220> FEATURE:
<223> OTHER INFORMATION: anti-Rh(D) antibody clone SH37

<400> SEQUENCE: 191

```
gaggtgcagc tgctcgagga gtctggggga ggcgtggtcc agcctgggag gtccctgaga    60
ctctcctgtg cagtgtctgg attcacccta actaattatg catgcactg ggtccgccag    120 gctccaggca aggggctgga gtgggtggca catgtctggt atgatggaag taaaacagaa    180
tacgcagact ccgtcaaggg ccgattcgcc gtctccagag acaaatccaa gaacacactg    240
tttctgcaaa tgaacagcct gacagccgag gacacggcta tttattactg tgcgagagag    300
aggagagaga aagtctatat attgttctac tcgtggctcg accgctgggg ccagggaaacc    360 ctggtcaccg tctcctca                                                   378
```

<210> SEQ ID NO 192
<211> LENGTH: 378
<212> TYPE: DNA
<213> ORGANISM: Homo sapiens
<220> FEATURE:
<223> OTHER INFORMATION: anti-Rh(D) antibody clone SH39

<400> SEQUENCE: 192

```
gaggtgcagc tgctcgagca gtctggggga ggcgtggtcc agcctgggag gtccctgaga    60
ctctcctgtg cagcgtctgg attcaccttc agtagctatg catgcactg ggtccgccag    120 gctccaggca agggactgga gtgggtggca gttatatggt ttgatggaag taataaggaa    180
tatgcagact ccgtgaaggg ccgattcacc atctccagag acaattccaa gaacacgctg    240
tatctacaaa tgaacagcct gagagccgag gacacggctg tgtattactg tgcgagagaa    300
gaagtggttc ggggagttat cttatggtct cggaagtttg actactgggg ccagggaaacc    360 ctggtcaccg tctcctca                                                   378
```

<210> SEQ ID NO 193
<211> LENGTH: 378
<212> TYPE: DNA
<213> ORGANISM: Homo sapiens
<220> FEATURE:
<223> OTHER INFORMATION: anti-Rh(D) antibody clone SH44

<400> SEQUENCE: 193

| | | |
|---|---|---|
| gaggtgcagc tgctcgagtc ggggggaggc gtggcccagc ctgggaggtc cctgagactc | 60 |
| tcctgtgtag cgtctggatt cagcctcagg agctatggca tgcactgggt ccgccaggct | 120 |
| cctggcaagg ggctggagtg gtggcagat atatggtttg atggaagtaa taagattat | 180 |
| gcagactccg tgaagggccg attcaccatc tccagagaca attccaagaa cacgttgtat | 240 |
| cttcaaatga acagcctgag agccgaggat acggctgtgt attattgtgc gagagattgg | 300 |
| agggtgcggg cctttagtag tggctggtta agtgcttttg atatctgggg ccaagggaca | 360 |
| atggtcaccg tctcttca | 378 |

<210> SEQ ID NO 194
<211> LENGTH: 375
<212> TYPE: DNA
<213> ORGANISM: Homo sapiens
<220> FEATURE:
<223> OTHER INFORMATION: anti-Rh(D) antibody clone SH47

<400> SEQUENCE: 194

| | | |
|---|---|---|
| gaggtgcagc tgctcgagtc tgggggaggc gtggtccagc ctgggaggtc cctgcgactc | 60 |
| tcttgtgcag cctctggatt cagcttcagt aactatgcta tgcactgggt ccgccaggct | 120 |
| ccaggcaagg ggctggagtg gtggcagtt acatcatttg atggaagcat taaagactac | 180 |
| gcagactccg tgaagggccg attcaccatc tccagagaca attccaagaa cacactatat | 240 |
| ctgcaaatga acagcctgag agatgaggac acggctgtat attactgtgc gagagagcgg | 300 |
| gggatgatag tcgtggtccg tcgcagaaat gcttttgata tttggggcca agggacaatg | 360 |
| gtcaccgtct cttca | 375 |

<210> SEQ ID NO 195
<211> LENGTH: 378
<212> TYPE: DNA
<213> ORGANISM: Homo sapiens
<220> FEATURE:
<223> OTHER INFORMATION: anti-Rh(D) antibody clone SH54

<400> SEQUENCE: 195

| | | |
|---|---|---|
| gaggtgcagc tgctcgagtc ggggggaggc gtggtccagc ctgggaggtc cctgagactc | 60 |
| tcctgtgcag cgtctgggtt caccttcagt aggaatggca tgcactgggt ccgccaggct | 120 |
| cctggcaagg ggctggagtg gtggcatt atatggtttg atggaagtaa taatactat | 180 |
| gcagactccg tgaagggccg attcaccatc tccagagaca attccaagaa cacgctgtat | 240 |
| ctgcaaatga acagcctgag agccgacgac acggctgtgt attactgtgc gagagaggag | 300 |
| gctctgtttc gggacttac tcggtggtcc tacggtatgg acgtctgggg ccaagggacc | 360 |
| acggtcagcg tctcctca | 378 |

<210> SEQ ID NO 196
<211> LENGTH: 378
<212> TYPE: DNA
<213> ORGANISM: Homo sapiens
<220> FEATURE:
<223> OTHER INFORMATION: anti-Rh(D) antibody clone SH56

<400> SEQUENCE: 196

```
gaggtgcagc tgctcgagtc ggggggaggc gtggtccagc ctgggaggtc cctgagactc      60
tcctgtgcag cgtctggatt caccttcagt agctatggca tgcactgggt ccggcaggct     120
ccaggcaagg ggctggagtg ggtggcagtt gtctactatg atggaagtaa caaacactat     180
tcagactccg tgaagggccg attcaccatc ttcagagaca actccaagaa cacgctgtat     240
ctacaaatgg acagcctgag agccgaggac acggctgtgt attactgtgc gagagaaaga     300
aattttcgga gtggttattc ccgctactac tacggtatgg acgtctgggg cccagggacc     360
acggtcaccg tctcctca                                                   378
```

<210> SEQ ID NO 197
<211> LENGTH: 321
<212> TYPE: DNA
<213> ORGANISM: Homo sapiens
<220> FEATURE:
<223> OTHER INFORMATION: anti-Rh(D) antibody clone SH8

<400> SEQUENCE: 197

```
gccgagctca cccagtctcc atcctccctg ctgcgtctg tcggagacag agtcaccatc       60
acttgccggg caaatcagac catcagaacc tctttaaatt ggtatcaaca aagacctggg     120
aaagcccta acctcctgat ctatggtgca tccaggttgc atagtgggt cccatcaagg      180
tttagtggcg gtatttctgg ggcagacttc actctcacca tcagcagtct gcaacctgaa     240
gattttgcaa cttactactg tcagcagact acggttatt ctcgaacgtt cggccaaggg      300
accaaggtgg atatcaaacg a                                               321
```

<210> SEQ ID NO 198
<211> LENGTH: 321
<212> TYPE: DNA
<213> ORGANISM: Homo sapiens
<220> FEATURE:
<223> OTHER INFORMATION: anti-Rh(D) antibody clone SH12

<400> SEQUENCE: 198

```
gccgagctca cccagtctcc attctccctg tctgcatctg taggagacag agtcaccata      60
acttgccggg caagtcacaa catttacagg tctttaaatt ggtttcagca taaaccaggg     120
gaagccccta agctcctggt ctatgctgca tccagtctgc agcgtggggt cccaaccagg     180
ttcagtggca gtggatctgg gacagatttc actctcacca tcagcagtct caacctgaa      240
gactctgcga cttacttctg tcaacagagt gtcacattcc cctacacttt tggccagggg    300
accaagctgg agatcagacg a                                               321
```

<210> SEQ ID NO 199
<211> LENGTH: 321
<212> TYPE: DNA
<213> ORGANISM: Homo sapiens
<220> FEATURE:
<223> OTHER INFORMATION: anti-Rh(D) antibody clone SH13

<400> SEQUENCE: 199

```
gccgagctca cccagtctcc atcctccctg tctgcatctg taggagacag agtcaccatc      60
acttgccggg caagtcagag cattagcagc tatttaaatt ggtatcagca gaaaccaggg     120
aaagcccta agctcctgat ctatgctgca tccagtttgc gaagtgggt cccatcaagg      180
ttcagtggca gtggatctgg gacagatttc actctcacca tcagcagtct gcaacctgaa     240
gattttgcaa cttactactg tcaacagagt tacagtaccc cctacacttt tggccagggg    300
```

```
accaagctgg agatcaaacg a                                              321

<210> SEQ ID NO 200
<211> LENGTH: 321
<212> TYPE: DNA
<213> ORGANISM: Homo sapiens
<220> FEATURE:
<223> OTHER INFORMATION: anti-Rh(D) antibody clone SH14

<400> SEQUENCE: 200
gccgagctca cccagtctcc atcctccctg tctgcatctg taggagacag agtcaccatc     60
acttgccggg caagtcagaa cattaggagg tctttaaatt ggtatcaaca caaaccaggg    120 agagcccta gactcctgat ctatgctgca tccactttgc aaagtggggt cccatcaagg     180
ttcaggggca gtggatctgg gacagatttc actctcacca tcaacagtct gcaacctgca    240
gattttgcaa cttactactg tcagcagagt tccaataccc cgtggacgtt cggccatggg    300
accaaggtgg aaatcaaacg a                                              321

<210> SEQ ID NO 201
<211> LENGTH: 321
<212> TYPE: DNA
<213> ORGANISM: Homo sapiens
<220> FEATURE:
<223> OTHER INFORMATION: anti-Rh(D) antibody clone SH16

<400> SEQUENCE: 201
gccgagctca cccagtctcc atcctccctg tctgcctctg taggagacag agtcaccatc     60
acttgccggg caagtcagag cattagcagc tatttaaatt ggtatcaaca gaaaccaggg    120 aaagcccta agctcctgat ctatgctgca tccagtttgc aaagtggggt cccatcaagg     180
ttcagtggca gtggatctgg gacagatttc actctcacca tcagcagtct gcaacctgaa    240
gattttgcaa cttactactg tcaacagagt tacagtaccc ctccaacttt cggcggaggg    300
accaaggtgg agatcaaacg a                                              321

<210> SEQ ID NO 202
<211> LENGTH: 318
<212> TYPE: DNA
<213> ORGANISM: Homo sapiens
<220> FEATURE:
<223> OTHER INFORMATION: anti-Rh(D) antibody clone SH18

<400> SEQUENCE: 202
gccgagctca cccagtctcc atcctccctc tctgcatctg taggagacag agtcaccatc     60
acttgccggg caagtcagag tattagcatc gctttaaatt ggtatcagca gagaccaggg    120 aaagcccta agctcctgat gtatgctaca tccactttgc aaagtggggt cccatcaagg     180
ttcagtggca gtggatctgg gacagatttc actctcacca tcagcagtct gcaacctgaa    240
gattttgcaa cttactactg tcaacaatat acaataaac ctactttcgg ccctgggacc     300
aaggtggata tcaaacga                                                  318

<210> SEQ ID NO 203
<211> LENGTH: 321
<212> TYPE: DNA
<213> ORGANISM: Homo sapiens
<220> FEATURE:
<223> OTHER INFORMATION: anti-Rh(D) antibody clone SH20

<400> SEQUENCE: 203
```

```
gccgagctca cccagtctcc attctccctg tctgcatctg tcggagacag agtcaccata      60
acttgccggg caagtcagag cattagcagg tctttaaatt ggtatcaaca taaaccaggg     120
gaagccccta agctcctgat ctatgctgca tccagtctgc agcgtggggt cccacccagg     180
ttcagtggca gtggatctgg gacagatttc actctcacca tcagcagtct gcaacctgaa     240
gactttgcga cttacttctg tcaacagagt gtcagaatcc cgtacagttt tggccagggg     300
accaagctgg agatcaaacg a                                               321
```

<210> SEQ ID NO 204
<211> LENGTH: 324
<212> TYPE: DNA
<213> ORGANISM: Homo sapiens
<220> FEATURE:
<223> OTHER INFORMATION: anti-Rh(D) antibody clone SH21

<400> SEQUENCE: 204

```
gccgagctca cccagtctcc atccttcctg tctgcatctg taggagacag agtcaccatc      60
acttgccggg ccagtcaggg cattaggagt tatttagcct ggtatcagca aaaaccaggg     120
aaagccccta agctcctaat ctatgctgca tccactttgc aaagtggggt cccatcaagg     180
ttcagcggca gtggatctgg gacagaattc actctcacaa tcgccagcct gcagcctgat     240
gattttgcaa cttattactg tcaacagctt aataattacc ccccttttcac tttcggccct     300 gggaccaaag tggatatcaa acga                                            324
```

<210> SEQ ID NO 205
<211> LENGTH: 321
<212> TYPE: DNA
<213> ORGANISM: Homo sapiens
<220> FEATURE:
<223> OTHER INFORMATION: anti-Rh(D) antibody clone SH24

<400> SEQUENCE: 205

```
gccgagctca cccagtctcc atcctccctg tctgcatctg taggagacag agtcaccatc      60
acttgccggg caagtcagag cattagcacc tatttaaatt ggtatcagca gagaccaggg     120
aaagccccta acctcctgat ctatgctgca tccactttgc aaaggggggt cccatcaagg     180
ttcactggca gtggatctgg gacagatttc actctcacca tcagcagtct gcaacctgaa     240
gattttgcaa cttactactg tcaacagagt tacactaccc tgtggacgtt cggccaaggg     300
accaagatgg aaatcagacg a                                               321
```

<210> SEQ ID NO 206
<211> LENGTH: 324
<212> TYPE: DNA
<213> ORGANISM: Homo sapiens
<220> FEATURE:
<223> OTHER INFORMATION: anti-Rh(D) antibody clone SH26

<400> SEQUENCE: 206

```
gccgagctca cccagtctcc atcctccctg tctgcatctg taggagacag agtcaccatc      60
acttgccggg caagtcagag cattagcagc tatttaaatt ggtatcagca gaaaccaggg     120
aaagccccta agctcctgat ctatgctgca tccagtttgc aaagtggggt cccatcaagg     180
ttcagtggca gtggatctgg gacagatttc actctcacca tcagcagtct gcaacctgaa     240
gattttgcaa cttactactg tcaacagagt tacagtttcc gaaggtacag ttttggccag     300
gggaccaagc tggagatcaa acga                                            324
```

```
<210> SEQ ID NO 207
<211> LENGTH: 321
<212> TYPE: DNA
<213> ORGANISM: Homo sapiens
<220> FEATURE:
<223> OTHER INFORMATION: anti-Rh(D) antibody clone SH28

<400> SEQUENCE: 207
gccgagctca cccagtctcc atcctccctg tctgcatctg taggagacag agtcaccatc     60
acttgccggg cagatcagaa cattaggagg tctttaaatt ggtttcagca gaaaccaggg    120
aaagccccta agctcctgat ctatgctgca tccagtttgc aaagtggggt cccatcaagg    180
ttcagtggca gtggatctgg gacagatttc actctcacca tcagcagtct gcaacctgaa    240
gattttgcaa cttactactg tcaacagagt tccagtaccc cgtggacgtt cggccgaggg    300
accaaggtgg aaatcaaacg a                                              321

<210> SEQ ID NO 208
<211> LENGTH: 318
<212> TYPE: DNA
<213> ORGANISM: Homo sapiens
<220> FEATURE:
<223> OTHER INFORMATION: anti-Rh(D) antibody clone SH30

<400> SEQUENCE: 208
gccgagctca cccagtctcc atcctccctg tctgcatctg ttggagacag agtcaccatc     60
acttgccggg caagtcagag cattcggagg tctttaaatt ggtatcagca gagtccaggg    120
aaaaccccta agctcctgat ctatgctgca tccagtttgc aaagtggggt cccatcaagg    180
ttcagtggca gtggatctgg gacagatttc actctcacca tcagcagtct gcaacctgaa    240
gattttgcaa cttactactg tcaacagagt tacagtaccc tcactttcgg cggagggacc    300
aaggtggaga tcaaacga                                                  318

<210> SEQ ID NO 209
<211> LENGTH: 324
<212> TYPE: DNA
<213> ORGANISM: Homo sapiens
<220> FEATURE:
<223> OTHER INFORMATION: anti-Rh(D) antibody clone SH32

<400> SEQUENCE: 209
gccgagctca ctcaggagcc ctcactgact gtgtccccag gagggacagt cactctcacc     60
tgtgcttcca gcactggagc agtcaccagt cgttactttc caaactggtt ccagcagaaa    120
cctggccagg cacccagggc actgatttat ggttcaaaca acaaacactc ctggacccct    180
gcccggttct caggctcccc ccttgggggc aaagctgccc tgacactgtc aggtgtgcag    240
cctgaggacg aggcggagta ttactgcctg ctcttctatg ctggtgcttg ggcgttcggc    300
ggagggacca agctgaccgt ccta                                           324

<210> SEQ ID NO 210
<211> LENGTH: 324
<212> TYPE: DNA
<213> ORGANISM: Homo sapiens
<220> FEATURE:
<223> OTHER INFORMATION: anti-Rh(D) antibody clone SH34

<400> SEQUENCE: 210
gccgagctca cccagtctcc atcctccctg tctgcatctg taggagacag agtcaccatc     60
acttgccggg caagtcagag cattagcagc tatttaaatt ggtatcagca gaaaccaggg    120
```

-continued

| | |
|---|---|
| aaagccccta agctcctgat ctatgctgca tccggtttgc aaagtggggt cccatcaagg | 180 |
| ttcagtggca gtggatctgg gacagatttc actctcacca tcagcagtct gcaacctgaa | 240 |
| gattttgcaa cttactactg tcaacagagt tacagtaccc ccccgtacac ttttggccag | 300 |
| gggaccaagc tggagatcaa acga | 324 |

<210> SEQ ID NO 211
<211> LENGTH: 321
<212> TYPE: DNA
<213> ORGANISM: Homo sapiens
<220> FEATURE:
<223> OTHER INFORMATION: anti-Rh(D) antibody clone SH36

<400> SEQUENCE: 211

| | |
|---|---|
| gccgagctca ctcagtctcc atcctccctg tctgcatctg taggagacag agtcaccatc | 60 |
| acttgccggg caagtcagag cattagcagc tatttaaatt ggtatcagca gaaaccaggg | 120 |
| aaatccccta agctcctgat ctatgctgca tccagtttgc aaagtggggt cccatcaagg | 180 |
| ttcagtggca gtggatctgg gacagatttc actctcacca tcagcagtct gcaacctgaa | 240 |
| gattttgcaa cttactactg tcaacagagt tacagtaccc ctccggcttt cggccctggg | 300 |
| accaaagtgg atatcaaacg a | 321 |

<210> SEQ ID NO 212
<211> LENGTH: 321
<212> TYPE: DNA
<213> ORGANISM: Homo sapiens
<220> FEATURE:
<223> OTHER INFORMATION: anti-Rh(D) antibody clone SH39

<400> SEQUENCE: 212

| | |
|---|---|
| gccgagctca cccagtctcc atcctccctg tctgcatctg tgggagacag agtcaccatc | 60 |
| acttgccggg caagtcagac cattgggagg tatttaaatt ggtatcagca gaggccaggg | 120 |
| aaagccccca aactcctggt atatgctgtg tccagtttgc aaagtggggc cccatcaagg | 180 |
| ttcagtggca gtggctctgg gacacatttc actctcacca tcaccagtct gcaacctgaa | 240 |
| gattttgcaa cttacttctg ccaacagagt tacagttctc ctttcacttt tggccagggg | 300 |
| accaaggttg agatcaaacg a | 321 |

<210> SEQ ID NO 213
<211> LENGTH: 321
<212> TYPE: DNA
<213> ORGANISM: Homo sapiens
<220> FEATURE:
<223> OTHER INFORMATION: anti-Rh(D) antibody clone SH41

<400> SEQUENCE: 213

| | |
|---|---|
| gccgagctca cccagtctcc atcctccctg tctgcatctg taggagacag agtcaccatc | 60 |
| acttgccggg caagtcagaa cattaggagg tctttaaatt ggtatcaaca caaaccaggg | 120 |
| agagccccta gactcctgat ctatgctgca tccactttgc aaagtggggt cccatcaagg | 180 |
| ttcaggggca gtggatctgg gacagatttc actctcacca tcaacagtct gcaacctgca | 240 |
| gattttgcaa cttactactg tcagcagagt tccaataccc cgtggacgtt cggccatggg | 300 |
| accaaggtgg aaatcaaacg a | 321 |

<210> SEQ ID NO 214
<211> LENGTH: 318
<212> TYPE: DNA
<213> ORGANISM: Homo sapiens

```
<220> FEATURE:
<223> OTHER INFORMATION: anti-Rh(D) antibody clone SH44

<400> SEQUENCE: 214
gccgagctca cccagtctcc atcgtccctg tctgcatctg taggagacag agtcatcatc    60
acttgccggg caagtcagac cattcccagg ttcttgaatt ggtatcaaca gaagcctgga   120
aaagcccctg ttctcctgat tcatagtata tccagtttac aaagtggggt cccatcaagg   180
ttcagtgcca gtggatctgg gacagagttc actctcacca tcagcagtct gcaacctgaa   240
gatttcgcaa cttactactg ccaacagagt tacagtaatc tctctttcgg ccctgggacc   300
acagtggata ttagacga                                                 318

<210> SEQ ID NO 215
<211> LENGTH: 321
<212> TYPE: DNA
<213> ORGANISM: Homo sapiens
<220> FEATURE:
<223> OTHER INFORMATION: anti-Rh(D) antibody clone SH46

<400> SEQUENCE: 215
gccgagctca cccagtctcc atcctccctg tctgcatctg taggagacag agtcaccatc    60
acttgccggg caagtcagta cattagcagc tatttaaatt ggtatcagca gaaaccaggg   120
aaagccccta atctcctgat ctatgctgca tccagtttgc aaagtggggt cccatcaagg   180
ttcagtggca gtggatctgg gacagatttc actctcacca tcagcagtct gcaacctgaa   240
gattttgcaa cttactactg tcaacagact tacagttccc ctagcacttt cggccctggg   300
accaaagtgg atatcaaacg a                                             321

<210> SEQ ID NO 216
<211> LENGTH: 321
<212> TYPE: DNA
<213> ORGANISM: Homo sapiens
<220> FEATURE:
<223> OTHER INFORMATION: anti-Rh(D) antibody clone SH47

<400> SEQUENCE: 216
gccgagctca cccagtctcc atcctccctg tctgcatctg taggagacag agtcaccatc    60
acttgccggg caagtcagag cattagcaac tatttaaatt ggtatcagca gaaaccagga   120
aaagccccta acctcctgat ctatgctgca tccagtttgc aaagtggggt cccatcaagg   180
ttcagtggca gtggatctgg gacagatttc actctcacca tcagcagtct gcaacctgaa   240
gattttgcaa cttactactg tcaacagagt tacagttatc ctcgcacgtt cggccaaggg   300
accaaggtgg agatcagacg a                                             321

<210> SEQ ID NO 217
<211> LENGTH: 321
<212> TYPE: DNA
<213> ORGANISM: Homo sapiens
<220> FEATURE:
<223> OTHER INFORMATION: anti-Rh(D) antibody clone SH48

<400> SEQUENCE: 217
gccgagctca cccagtctcc atcctccctg tctgcatctg taggagacag agtcaccatc    60
acttgccggg caagtcagta cattagcagc tatttaaatt ggtatcagca gaaaccaggg   120
aaagccccta atctcctgat ctatgctgca tccagtttgc aaagtggggt cccatcaagg   180
ttcagtggca gtggatctgg gacagatttc actctcacca tcagcagtct gcaacctgaa   240
```

```
gattttgcaa cttactactg tcaacagact tacagttccc ctagcacttt cggccctggg    300
accaaagtgg atatcaaacg a                                              321
```

<210> SEQ ID NO 218
<211> LENGTH: 321
<212> TYPE: DNA
<213> ORGANISM: Homo sapiens
<220> FEATURE:
<223> OTHER INFORMATION: anti-Rh(D) antibody clone SH49

<400> SEQUENCE: 218

```
gccgagctca cccagtctcc atcctccctg tctgcatctg taggagacag agtcaccgtc    60
acttgccggg caagtcagag cattagcagc tatttaaatt ggtatcagca gaaaccaggg   120
aaagccccta agctcctgat ctatgctgca tccagtttgc aaagtggggt cccatcaagg   180
ttcagtggca gtggatctgg gacagatttc actctcacca tcagcagtct gcaacctgaa   240
gattttgcaa cttactactg tcaacagagt tacagtaccc cgtggacgtt cggccaaggg   300
accaaggtgg aaatcaaacg a                                              321
```

<210> SEQ ID NO 219
<211> LENGTH: 324
<212> TYPE: DNA
<213> ORGANISM: Homo sapiens
<220> FEATURE:
<223> OTHER INFORMATION: anti-Rh(D) antibody clone SH50

<400> SEQUENCE: 219

```
gccgagctca cccagtctcc atcgtccctg tctgcatctg taggagacag agtcaccatc    60
acttgccgga caagtcagag cattggcacc tatttaaatt ggtatcaaca aaaaccaggg   120
aaagccccta aactcctgat ctatgctgca tccaatgtgc aaagtggggt cccatcaagg   180
ttcagtggcg gtggatctgg gacaggtttc tctctcatca tcagcagtct gcaacctgaa   240
gatttagcaa tttactactg ccaacagagc tacagtgtcc ctccgtacag ctttggcccg   300
gggaccaagc tggagatcaa acga                                           324
```

<210> SEQ ID NO 220
<211> LENGTH: 324
<212> TYPE: DNA
<213> ORGANISM: Homo sapiens
<220> FEATURE:
<223> OTHER INFORMATION: anti-Rh(D) antibody clone SH51

<400> SEQUENCE: 220

```
gccgagctca cacagtctcc atccttcctg tctgcatctg taggagacag agtcaccatc    60
acttgccggg ccagtcaggg cataaggagt tatttagcct ggtatcagca aaaaccaggg   120
aaagccccta agctcctaat ctatgctgca tccactttgc aaagtggggt cccatcaagg   180
ttcagcggca gtggatctgg gacagaattc actctcacaa tcagcagcct gcagcctgaa   240
gattttgcaa cttattactg tcaacagctt aataattacc ccccttttcac tttcggccct   300 gggaccaaag tggatatcaa acga                                           324
```

<210> SEQ ID NO 221
<211> LENGTH: 321
<212> TYPE: DNA
<213> ORGANISM: Homo sapiens
<220> FEATURE:
<223> OTHER INFORMATION: anti-Rh(D) antibody clone SH52

<400> SEQUENCE: 221

```
gccgagctca cccagtctcc atcctccatg tctgcatctg taggagacag agtcaccatc      60
acttgccggg caagtcagag cattggcact tatttaaatt ggtatcagca gaaaccaggg     120 aaagcccta agctcctgat ctatgctgca tccagtttgc aaagtggggt cccatcaagg     180
ttcagtggca gtggatctgg gacagatttc actctcacca tcagcagtct gcaacctgaa     240
gattttgcaa cttactactg tcaacagagt tacagtaccc cgtggacgtt cggccaaggg     300
accaaggtgg aaatcaaacg a                                               321
```

<210> SEQ ID NO 222
<211> LENGTH: 321
<212> TYPE: DNA
<213> ORGANISM: Homo sapiens
<220> FEATURE:
<223> OTHER INFORMATION: anti-Rh(D) antibody clone SH54

<400> SEQUENCE: 222

```
gccgagctca cccagtctcc atcctccatg tctgcatctg taggagacag agtcaccatc      60
acttgccggg caagtcagag cattggcact tatttaaatt ggtatcagca gaaaccaggg     120 aaagcccta agctcctgat ctatgctgca tccagtttgc aaagtggggt cccatcaagg     180
ttcagtggca gtggatctgg gacagatttc actctcacca tcagcagtct gcaacctgaa     240
gattttgcaa cttactactg tcaacagagt tacagtaccc cgtggacgtt cggccaaggg     300
accaaggtgg aaatcaaacg a                                               321
```

<210> SEQ ID NO 223
<211> LENGTH: 327
<212> TYPE: DNA
<213> ORGANISM: Homo sapiens
<220> FEATURE:
<223> OTHER INFORMATION: anti-Rh(D) antibody clone SH55

<400> SEQUENCE: 223

```
gccgagctca cgcagccgcc ctcagcgtct gggaccccg ggcagagggt caccatctct      60
tgttctggaa gcagctccaa catcggaagt aaatatgtat actggtacca gcaactccca     120
ggaacggccc ccaaactcct catttatagt aataatcagc ggccctcagg ggtccctgac     180
cgattctctg ccttcaagtc tggcacctca gcctccctgg ccatcactgg gctccaggct     240
gaggatgagg ctaattatta ctgccagtcc tatgacagcg gcctgagtgg ctgggtgttc     300
ggcggcggga ccaagctgac cgtccta                                         327
```

<210> SEQ ID NO 224
<211> LENGTH: 324
<212> TYPE: DNA
<213> ORGANISM: Homo sapiens
<220> FEATURE:
<223> OTHER INFORMATION: anti-Rh(D) antibody clone SH56

<400> SEQUENCE: 224

```
gccgagctca cccagtctcc atcctccctg tctgcatctg taggagacag agtcaccatc      60
acttgccggg caagtcagag cattagcagg tatttaaatt ggtatcagca gaaaccaggg     120
aaagccccca agctcctgat ctatgctgca tccagtttgc aaagtggggt cccatcaagg     180
ttcagtggca gtggatctgg gacagatttc gctctcacca tcagcagtct gctacctgaa     240
gattttgcaa cttactactg tcaacagggt tacagtaccc ctccgtacag ttttggccag     300
gggaccaagc tggagatcaa acga                                            324
```

RH(D)-BINDING PROTEINS AND MAGNETICALLY ACTIVATED CELL SORTING METHOD FOR PRODUCTION THEREOF

CROSS REFERENCE TO RELATED APPLICATION

This application is entitled to priority pursuant to 35 U.S.C. §119(e) to U.S. provisional patent application No. 60/081,380, which was filed on Apr. 10, 1998, and is a continuation-in-part of U.S. application Ser. No. 08/884, 045, filed Jun. 27, 1997, which (now U.S. Pat. No. 5,876, 925) application is entitled to priority under 35 U.S.C. §119(e) to U.S. Provisional Application No. 60/028,550, filed on Oct. 11,1996.

GOVERNMENT SUPPORT

This invention was supported in part by a grant from the U.S. Government (NIH Grant No. P50-HL54516) and the U.S. Government may therefore have certain rights in the invention.

FIELD OF THE INVENTION

The field of the invention is generation of binding proteins.

BACKGROUND OF THE INVENTION

The ability to produce monoclonal antibodies has revolutionized diagnostic and therapeutic medicine. Monoclonal antibodies are typically produced by immortalization of antibody-producing mouse lymphocytes thus ensuring an endless supply of cells which produce mouse antibodies. However, for many human applications, it is desirable to produce human antibodies. For example, it is preferable that antibodies which are administered to humans for either diagnostic or therapeutic purposes are human antibodies since administration of human antibodies to a human circumvents potential immune reactions to the administered antibody, which reactions may negate the purpose for which the antibody was administered.

In addition, there exists certain situations where, for diagnostic purposes, it is essential that human antibodies be used because other animals are unable to make antibodies against the antigen to be detected in the diagnostic method. For example, in order to determine the Rh phenotype of human red blood cells (RBCs), human sera that contains anti-Rh antibody must be used since other animals cannot make an antibody capable of detecting the human Rh antigen.

The production of human antibodies in vitro by immortalizing human B lymphocytes using Epstein Barr virus (EBV)-mediated transformation or cell fusion has been fraught with technical difficulties due to the relatively low efficiency of both EBV-induced transformation and cell fusion when compared with the murine system. To overcome these problems, processes have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin (Ig) genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab Ig. Thus, in contrast to conventional monoclonal antibody synthesis, this procedure immortalizes DNA encoding human Ig rather than cells which express human Ig.

There are several difficulties associated with the generation of antibodies using bacteriophage. For example, many proteins cannot be purified in a non-denatured state, in that purification procedures necessarily involve solubilization of protein which may render some proteins permanently denatured with concomitant destruction of antigenic sites present thereon. Such proteins thus cannot be bound to a solid phase and therefore cannot be used to pan for phage bearing antibodies which bind to them. An example of such a protein is the human Rh antigen.

To solve the problem, a method was developed wherein intact RBCs were used as the panning antigen (Siegel et al., 1994, Blood 83:2334–2344). However, it was discovered that since phage are inherently "sticky" and RBCs express a multitude of antigens on the cell surface, a sufficient amount of phage which do not express the appropriate antibody on the surface also adhere to the RBCs, thus rendering the method impractical for isolation of phage which express antibody of desired specificity.

De Kruif et al. (1995, Proc. Natl. Acad. Sci. USA 92:3938–3942) disclose a method of isolating phage encoding antibodies, wherein antibody-expressing phage are incubated with a mixture of antigen-expressing cells and cells which do not express antigen. The antibody-expressing phage bind to the antigen-expressing cells. Following binding with phage, a fluorescently labeled antibody is added specifically to the antigen-expressing cells, which cells are removed from the mixture having antibody-expressing phage bound thereto. The isolation of fluorescently labeled cells is accomplished using the technique of fluorescently-activated cell sorting (FACS), an expensive and time-consuming procedure.

There remains a need for a method of isolating recombinant proteins, preferably antibodies, which is rapid and economical, and which will provide a vast array of protein-binding proteins useful for diagnostic and therapeutic applications in humans.

SUMMARY OF THE INVENTION

The invention relates to an isolated protein having an amino acid sequence comprising a sequence selected from the group consisting of SEQ ID NOs: 1–69 and 139–181. In one embodiment, the isolated protein is an antigen-binding protein. In one aspect, the antigen is human Rh(D) protein. In another embodiment, the binding protein has an amino acid sequence selected from the group consisting of SEQ ID NOs: 1–69 and 139–181. In one aspect, the binding protein is an antibody. In another aspect, the said antibody comprises a heavy chain having an amino acid sequence selected from the group consisting of SEQ ID NOs: 1–28 and 139–153. In still another aspect, the antibody comprises a light chain having an amino acid sequence selected from the group consisting of SEQ ID NOs: 29–69 and 154–181. In yet another aspect, the antibody comprises a heavy chain having an amino acid sequence selected from the group consisting of SEQ ID NOs: 1–28 and 139–153 and a light chain having an amino acid sequence selected from the group consisting of SEQ ID NOs: 29–69 and 154–181.

In another embodiment of the isolated binding protein, the binding protein is an antibody fusion protein.

In another embodiment of the isolated protein, the protein is substantially purified.

The invention also includes an isolated DNA encoding the isolated protein of the invention. In one embodiment, the isolated DNA has a nucleotide sequence selected from the group consisting of SEQ ID NOs: 70–138 and 182–224. In another embodiment, the DNA is substantially purified.

The invention also includes an isolated DNA encoding a protein obtained by generating a synthetic DNA library in a virus vector expressing said protein; adding a magnetic label to cells expressing said antigen-bearing moiety; incubating virus expressing said protein with said magnetically labeled cells in the presence of an excess of non-labeled cells which do not express said antigen-bearing moiety to form a mixture, wherein said virus binds to said magnetically labeled cells; isolating virus bound cells from said mixture and obtaining DNA encoding said protein therefrom. In one embodiment, the DNA has a nucleotide sequence selected from the group consisting of SEQ ID NOs: 70–138 and 182–224.

The invention further includes a substantially pure protein obtained by generating a synthetic DNA library in a virus vector expressing said protein; adding a magnetic label to cells expressing said antigen-bearing moiety; incubating virus expressing said protein with said magnetically labeled cells in the presence of an excess of non-labeled cells which do not express said antigen-bearing moiety to form a mixture, wherein said virus binds to said magnetically labeled cells; isolating virus bound cells from said mixture and isolating said protein therefrom. In one embodiment, the protein has an amino acid sequence selected from the group consisting of SEQ ID NOs: 1–69 and 139–181.

The invention also includes a substantially pure preparation of a protein obtained by expressing said protein from DNA encoding said protein, wherein said DNA is obtained by generating a synthetic DNA library in a virus vector expressing said protein; adding a magnetic label to cells expressing said antigen-bearing moiety; incubating virus expressing said protein with said magnetically labeled cells in the presence of an excess of non-labeled cells which do not express said antigen-bearing moiety to form a mixture, wherein said virus binds to said magnetically labeled cells; isolating virus bound cells from said mixture and obtaining DNA encoding said protein therefrom. In one embodiment, the protein has an amino acid sequence selected from the group consisting of SEQ ID NOs: 1–69 and 139–181.

The invention further relates to a method of isolating a DNA encoding a multi-subunit protein which binds to an antigen-bearing moiety. This method comprises (a) generating a phage display library comprising a plurality of virus vectors. A first of the virus vectors comprises a first heterologous DNA encoding a subunit of the protein and expresses the subunit on the surface thereof. A second of the virus vectors comprises a second heterologous DNA encoding a different subunit of the protein and expresses the different subunit on the surface thereof.

(b) adding a magnetic label to cells bearing the antigen-bearing moiety on their surface.

(c) incubating the phage display library with the magnetically labeled cells in the presence of an excess of non-labeled cells which do not express the antigen-bearing moiety to form a mixture. The first and second virus vectors thereby bind to the magnetically labeled cells.

(d) isolating magnetically labeled cells from the mixture. The first and second virus vectors are thereby isolated from the mixture.

(e) obtaining the first heterologous DNA from the first virus vector.

(f) ligating at least the portion of the first heterologous DNA encoding the subunit and at least the portion of the second heterologous DNA encoding the different subunit to form a hybrid heterologous DNA.

(g) generating a hybrid virus vector comprising the hybrid heterologous DNA and expressing the subunit and the different subunit of the protein on the surface thereof.

(h) adding a magnetic label to cells bearing the antigen-bearing moiety on their surface.

(i) incubating the hybrid virus vector with the magnetically labeled cells in the presence of an excess of non-labeled cells which do not express the antigen-bearing moiety to form a mixture. The hybrid virus vector thereby binds to the magnetically labeled cells.

(j) isolating magnetically labeled cells from the mixture. The hybrid virus vector is thereby isolated from the mixture.

(k) obtaining DNA encoding the protein from the isolated virus vector. The DNA is thereby isolated.

The invention also relates to a method of isolating a multi-subunit protein which binds to an antigen-bearing moiety. This method comprises (a) generating a phage display library comprising a plurality of virus vectors. A first of the virus vectors comprises a first heterologous DNA encoding a subunit of the protein and expresses the subunit on the surface thereof. A second of the virus vectors comprises a second heterologous DNA encoding a different subunit of the protein and expresses the different subunit on the surface thereof.

(b) adding a magnetic label to cells bearing the antigen-bearing moiety on their surface.

(c) incubating the phage display library with the magnetically labeled cells in the presence of an excess of non-labeled cells which do not express the antigen-bearing moiety to form a mixture. The first and second virus vectors thereby bind to the magnetically labeled cells.

(d) isolating magnetically labeled cells from the mixture. The first and second virus vectors are thereby isolated from the mixture.

(e) obtaining the first heterologous DNA from the first virus vector.

(f) ligating at least the portion of the first heterologous DNA encoding the subunit and at least the portion of the second heterologous DNA encoding the different subunit to form a hybrid heterologous DNA.

(g) generating a hybrid virus vector comprising the hybrid heterologous DNA and expressing the subunit and the different subunit of the protein on the surface thereof.

(h) adding a magnetic label to cells bearing the antigen-bearing moiety on their surface.

(i) incubating the hybrid virus vector with the magnetically labeled cells in the presence of an excess of non-labeled cells which do not express the antigen-bearing moiety to form a mixture. The hybrid virus vector thereby binds to the magnetically labeled cells.

(j) isolating magnetically labeled cells from the mixture. The hybrid virus vector is thereby isolated from the mixture.

(k) isolating the protein from the isolated virus vector. The protein is isolated.

BRIEF DESCRIPTION OF THE DRAWINGS

FIG. 1 is a diagram of a strategy for cell-surface Fab-phage panning using magnetically-activated cell sorting.

FIG. 7 comprises FIGS. 7A and 7B. FIG. 7B is an alignment of the CDR3 regions of the anti-Rh(D) heavy chains.

FIG. 8 comprises FIGS. 8A, 8B, and 8C. FIG. 8A, comprising FIGS. 8A and 8A-1 through 8A-4, is an alignment of anti-Rh(D) heavy chains to their nearest germline V, D, and J genes. Also illustrated are the putative intermediate heavy chain sequences (Ca, Cb, Da, Db, Dc). The number of nucleotide differences from a germline $V_H$ is tabulated to the right of each sequence. In general, D segments showed poor homology with known D genes so mutations were not scored in these regions. Replacement mutations are indicated with letters, silent mutations are indicated as "*", identities are indicated as ".", and insertions are indicated as "-". Sequences derived from the 5'$V_H$ primers used in library construction are indicated as ">". FIG. 8A is a map demonstrating how FIGS. 8A-1 to 8A-4 are arranged. FIG. 8B, comprising FIGS. 8B, 8B-1, and 8B-2 is an alignment of the four VH3 genes utilized by anti-Rh(D) heavy chains. FIG. 8B is a map depicting the arrangement of FIGS. 8B-1 and 8B-2.

FIG. 10 comprises FIGS 10A and 10B. FIG. 10A, comprising FIGS. 10A and 10A-1 through 10A-4, is an alignment of anti-Rh(D)κ light chains to their nearest germline V and J genes, and indicates predominance of DPK-9 usage from the $V_κI$ family. Nomenclature for clones is similar to that for heavy chains but uses the letters "F" through "I".

FIG. 10A is a map depicting the arangement of FIGS. 10A-1 through 10a-4. FIG. 10B, comprising FIGS. 10B, 10B-1, and 10B-2 is an alignment of the four $V_κ$ genes utilized by anti-Rh(D) light chains. FIG. 10B is a map showing the arrangement of FIGS. 10B-1 and 10B-2. Symbols are the same as those used in FIG. 8A.

FIG. 11 comprises FIG. 11A and 11B. FIG. 11A comprising FIGS. 11A and 11A-1 through 11A-4, is an alignment of anti-Rh(D)λ light chains to their nearest germline V and J genes. FIG. 11A is a map depicting the arrangement of FIGS. 11A-1 through 11A-4. FIGS. 11B, 11B-1, and 11B-2, is an alignment of the $10V_λ$ germline genes utilized, and illustrates the use of a diverse set of variable region genes derived from multiple families. However, all of the clones use the identical $J_λ$ gene segment. FIG. 11B is a map representing the arrangement of FIGS. 11B-1 and 11B-2. Nomenclature for the clones is similar to that for heavy chains but uses the letters "J" through "S". Symbols are the same as those used in FIG. 8A.

FIG. 12, comprising

FIG. 13 depicts the results of determinations of the Rh(D) binding epitope of anti-Rh(D) Fab/phage clones. The five different agglutination patterns obtained from screening all of the 53 Fab/phage clones are illustrated. The particular clones shown in FIG. 13 are identified by their unique heavy chain/light chain pairings using the nomenclature defined in FIGS. 7, 10, and 11. For E1/M3, reactivity with additional Rh(D) variant cells is required to distinguish its specificity for epD3 from that for epD9. Inclusion of the category IVb cell permits the identification of a new epitope designated "epDX".

FIG. 14, comprising

FIG. 15, comprising In FIG. 15A, Rh(D)-positive RBCs were incubated with soluble Fabs only, phage-displayed Fabs only, or combinations of the two, as indicated. In FIG. 15B, Rh(D)-positive RBCs that were blood group B were used. After washing, RBCs were resuspended in anti-M13 antibody and assessed for agglutination induced by phage-displayed Fabs. Soluble Fabs were used "full-strength" while Fab/phage preparations were present in limiting amounts to increase the sensitivity of the inhibition assay, as described herein. In FIG. 15C, mutual inhibition of epD3 and epD6/7 anti-Rh(D) antibodies was demonstrated with Rh(D)-positive RBCs, $\gamma_1\kappa$ and $\gamma_1\lambda$ soluble Fabs, and light chain isotype-specific antisera (see text for details). In these examples, the anti-epD3 and anti-epD6/7 antibodies were clones E1/M3 and D5/I3, respectively. The anti-blood group B antibody was isolated from an IgG phage display library made from the splenic B cells of a blood group O donor.

FIG. 16, comprising

DETAILED DESCRIPTION

Figure 2:
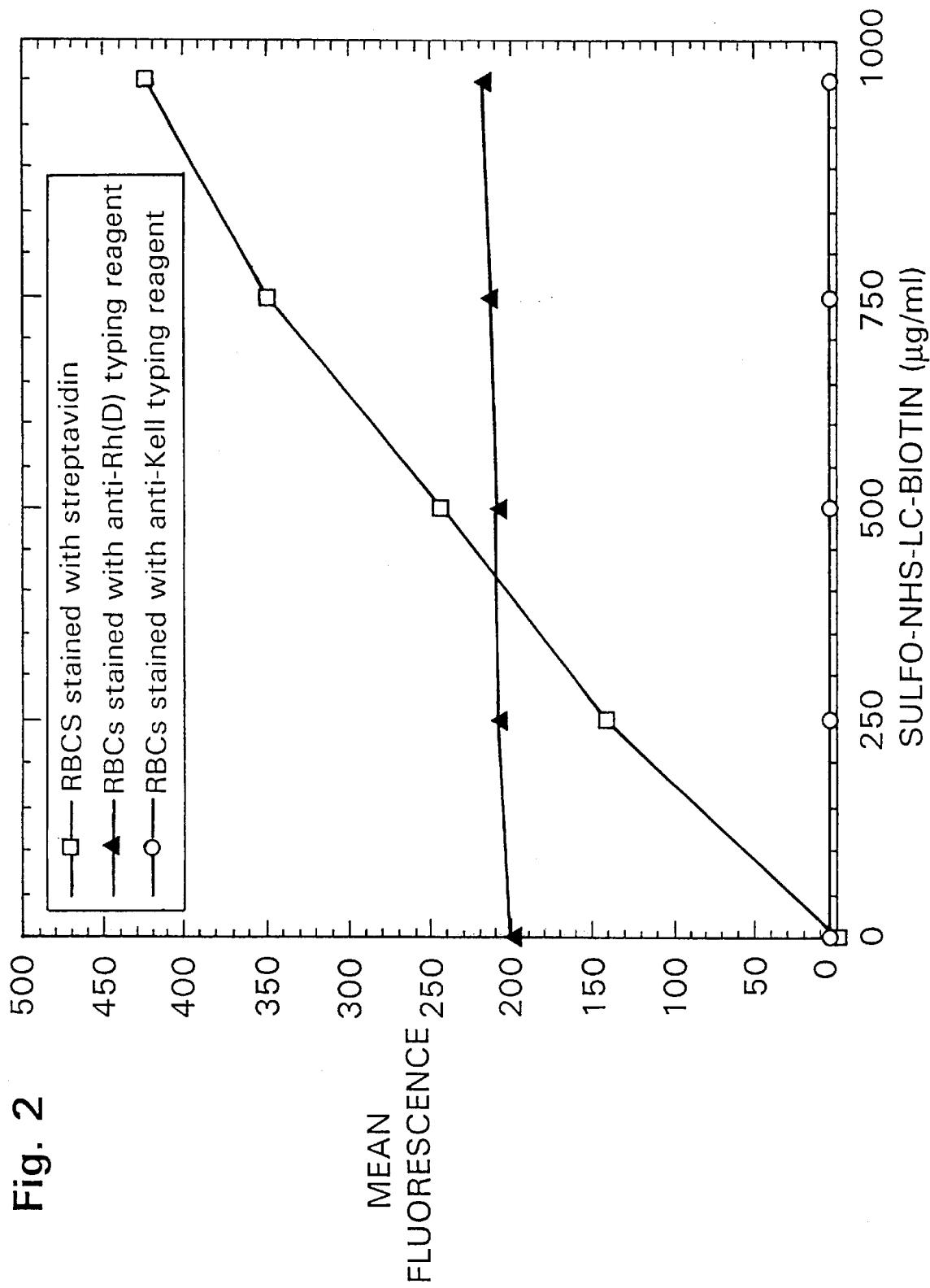
FIG. 2 is a graph depicting cell-surface biotinylation of human RBCs.

According to the present invention, there is provided a novel method of isolating DNA encoding a protein and the protein encoded thereby, wherein the protein is preferably an antibody, which protein is capable of specifically binding to an antigen-bearing moiety.

As exemplified herein but not limited thereto, the method comprises generating bacteriophage which encode human antibodies. Specifically in the present invention, anti-Rh(D) RBC Fab/phage antibodies encoded by an M13 filamentous phage library are obtained. The library is generated from antibody-producing cells obtained from a hyperimmunized donor by first obtaining cDNA derived from mRNA expressed in the antibody-producing cells. Ig encoding fragments of the cDNA are obtained using the polymerase chain reaction (PCR) and primers specific for such fragments of DNA. Ig-specific DNA so obtained is cloned into a bacteriophage. Bacteriophage encoding the Ig fragments are panned against a mixture of antigen-positive, biotinylated RBC-target cells pre-coated with streptavidin-conjugated magnetic microbeads and excess non-labeled RBCs. Bacteriophage which express antibodies on the phage surface, which antibodies are specific for the target cell antigen, bind to the labeled cells. These phage are separated from phage which are bound to non-labeled cells and from phage which are not bound to the cells using a magnetic column. Phage so separated encode and display antibody specific for antigens on the target cells.

To generate a phage antibody library, a cDNA library is first obtained from mRNA which is isolated from cells which express the desired protein to be expressed on the phage surface, e.g., the desired antibody. cDNA copies of the mRNA are produced using reverse transcriptase. cDNA which specifies Ig fragments are obtained by PCR and the resulting DNA is cloned into a suitable bacteriophage vector to generate a bacteriophage DNA library comprising DNA specifying Ig genes. The procedures for making a bacteriophage library comprising heterologous DNA are well known in the art and are described, for example, in Sambrook et al. (1989, *Molecular Cloning: A Laboratory Manual*, Cold Spring Harbor, N.Y.).

A bacteriophage library may also be obtained using cDNA rather than PCR-amplified Ig encoding fragments of cDNA. Generation of a cDNA library is useful for the isolation of proteins which are not antibodies, such as ligands and the like.

Bacteriophage which encode the desired protein, e.g., an antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell.

For panning of bacteriophage, i.e., selection of phage which express the desired antibody, cells which express the corresponding antigen are labeled with a detectable label such as biotin. Streptavidin-conjugated magnetic beads are then added to the cells. The cells are mixed with an excess of non-labeled cells which do not express the antigen. This cell mixture is then incubated with the phage library, wherein phage which express the antibody bind to cells expressing the antigen. The presence of the excess non-labeled cells in the mixture serves as a means of removing bacteriophage which do not express the antibody but which might otherwise bind to antigen-expressing cells non-specifically. The details of the experimental procedures for practicing the present invention are provided herein in the experimental detail section.

Antigen-expressing cells having antibody-expressing phage bound thereto are magnetically removed from the mixture. One example of magnetic removal involves pouring the mixture of magnetic and non-magnetic cells into a column in the selective presence or absence of a magnetic field surrounding the column. Alternatively, magnetic cells may be separated from non-magnetic cells in solution by simply holding a magnet against the side of a test tube and attracting the cells to the inner wall and then carefully removing the non-magnetic cells from the solution.

Thus, the method of the invention involves a procedure for enriching a population of recombinant phage for those expressing specific phage-displayed ligands derived from natural or synthetic phage DNA libraries by simultaneously performing negative and positive selection against a mixture of magnetically-labeled receptor-positive particles (i.e., cells) and non-labeled receptor-negative particles.

The terms "bacteriophage" and "phage" are used interchangeably herein and refer to viruses which infect bacteria. By the use of the terms "bacteriophage library" or "phage library" as used herein, is meant a population of bacterial viruses comprising heterologous DNA, i.e., DNA which is not naturally encoded by the bacterial virus.

The term "virus vector" includes a virus into which heterologous DNA has been inserted. The virus vector may be a bacteriophage or may be a eukaryotic virus.

By the term "target cell" as used herein, is meant a cell which expresses an antigen against which the desired antibody is sought.

By the term "panning" or "panned" as used herein, is meant the process of selecting phage which encode the desired antibody.

By the term "Fab/phage" as used herein, is meant a phage particle which expresses the Fab portion of an antibody.

By the term "scFv/phage" are used herein, is meant a phage particle which expresses the Fv portion of an antibody as a single chain.

By "excess non-labeled cells" is meant an amount of non-labeled cells which exceeds the number of labeled cells. Preferably, the ratio of labeled cells to non-labeled cells is about 1:2. More preferably, the ratio of labeled cells to non-labeled cells is greater than about 1:4. Even more preferably, the ratio of labeled cells to non-labeled cells is greater than about 1:10.

While the method of the invention as exemplified herein describes the generation of phage which encode the Fab portion of an antibody molecule, the method should not be construed to be limited solely to the generation of phage encoding Fab antibodies. Rather, phage which encode single chain antibodies (scFV/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFV DNA may be generated following the procedures described in Marks et al., 1991, *J. Mol. Biol.* 222:581–597. Panning of phage so generated for the isolation of a desired antibody is conducted as described herein for phage libraries comprising Fab DNA.

The invention should also be construed to include synthetic phage display libraries in which the heavy and light chain variable regions may be synthesized such that they include nearly all possible specificities. Therefore, antibody-displaying libraries can be "natural" or "synthetic" (Barbas, 1995, *Nature Medicine* 1:837–839; de Kruif et al. 1995, *J. Mol. Biol.* 248:97–105). Antibody-displaying libraries comprising "natural" antibodies are generated as described in the experimental example section. Antibody-displaying libraries comprising "synthetic" antibodies are generated following the procedure described in Barbas (1995, supra) and the references cited therein.

The method of the invention should be further construed to include generation of phage display libraries comprising phage other than M13 as exemplified herein. Other bacteriophage, such as lambda phage, may also be useful in the method of the invention. Lambda phage display libraries have been generated which display peptides encoded by heterologous DNA on their surface (Sternberg et al., 1995, *Proc. Natl. Acad. Sci. USA* 92:1609–1613). Moreover, it is contemplated that the method of the invention may be extended to include viruses other than bacteriophage, such as eukaryotic viruses. In fact, eukaryotic viruses may be generated which encode genes suitable for delivery to a mammal and which encode and display an antibody capable of targeting a specific cell type or tissue into which the gene is to be delivered. For example, retroviral vectors have been generated which display functional antibody fragments (Russell et al., 1993, *Nucl. Acids Res.* 21:1081–1085).

The red blood cell antibodies to which antibodies may be generated include, but are not limited to, Rh antigens, including Rh(D), Rh(C), Rh(c), Rh(E), Rh(e), and other non-Rh antigens, including red blood cell antigens in the Kell, Duffy, Lutheran and Kidd blood groups.

Thus, the method of the invention is not limited solely to the isolation of DNA encoding anti-Rh(D) antibodies, but rather may be used for the isolation of DNA encoding antibodies directed against any RBC antigen or other cell antigen, such as, but not limited to, tumor-specific antigen, bacterial antigens, and the like. The method of the invention is also useful for typing platelets by generating phage antibodies specific for a number of clinically important platelet antigens, notably, $P1^{A1}/P1^{A2}$, $Bak^a/Bak^b$, $Pen^A/Pen^B$, and the like.

The invention is further useful for typing donor white blood cells for HLA antigens for the purposes of matching donors and recipients for potential transplant matching in the case of both solid (for example, kidney, heart, liver, lung) and non-solid (for example, bone marrow) organ or tissue transplanting.

To detect binding of phage expressing antibody directed against one of these non-red blood cell antigens, the non-red blood cells may be agglutinated or trapped following the procedures described herein for agglutination or trapping of red blood cells. Prior to agglutination or trapping, the cells may be rendered "visible" by staining or other labeling technique in order that agglutination or trapping is apparent to the naked eye or scanner.

The method of the invention is most useful for the generation of a protein which binds to an antigen-bearing moiety, where the antigen-bearing moiety is not easily purified in soluble form. Thus, the antigen-bearing moiety includes antigens which are associated with other structures, usually membranes in the cell such as cell membranes or cell organelle membranes.

In accordance with the present invention, the antigen-bearing moiety may be a protein, a lipid, a carbohydrate or a nucleic acid, or it may be a complex of at least two of a protein, a lipid, a carbohydrate and a nucleic acid, it being appreciated that many antigen-bearing moieties in cells are not comprised of one of these components alone. Preferably, the antigen-bearing moiety is a membrane bound protein, such as an antigen or a receptor protein. However, when the antigen-bearing moiety is a carbohydrate, it may be a carbohydrate expressed on a glycolipid, for example, a P blood group antigen or other antigen.

By the term "antigen-bearing moiety" as used herein, is meant a molecule to which an antibody binds.

By the term "antigen-binding protein" as used herein, is meant a polypeptide molecule, such a an antibody, a fragment thereof or an antibody fusion protein, which is capable of specifically binding to another molecule.

By the term "antibody fusion protein" as used herein, is meant a polypeptide molecule having an amino acid sequence which comprises the amino acid sequence of a portion of an antigen-binding protein. The portion of the antigen-binding protein may, for example, be an entire antibody or a fragment thereof.

The method of the invention is also useful for the generation of autoimmune antibodies such as those involved in autoimmune hemolytic anemia (AIHA) (Siegel et al., 1994, *Structural analysis of red cell autoantibodies*, Garratty (ed.) *Immunobiology of Transfusion Medicine*, Dekker, New York, N.Y.). Autoimmune antibodies that are directed against cell antigens which are cell surface membrane associated or cell organelle membrane associated may be isolated using the technology described herein. Autoimmune diseases and their associated antigens to which antibodies may be isolated include, but are not limited to the following: Myasthenia gravis (acetylcholine receptor; neurons), chronic inflammatory demyelinating polyneuropathy (myelin; neurons), autoimmune thyroid disease (thyroid stimulating hormone receptor; thyroid cells), primary biliary cirrhosis (mitochondrial autoantigens; liver mitochondria), idiopathic thrombocytopenic purpura (platelet membrane integrins; platelets), pemphigus vulgaris (epidermal antigens; epidermis), and Goodpasture's syndrome (basement membrane antigens; kidney or lung cells).

In fact, the method of the invention is useful for the isolation of DNA clones encoding any antibody directed against an antigen expressed on a cell, which cell can be labeled with a magnetic label and which cell can be obtained in sufficient quantities in an non-labeled form so as to provide an excess of non-labeled cells as required in the assay.

Further, the method of the invention is not limited to the isolation of DNA encoding antibodies but rather may also be used for the isolation of DNA encoding other peptides or proteins having specificity for cell proteins, such as, for example, but not limited to, ligands which bind cell receptor proteins, peptide hormones, and the like.

The invention should also not be construed as being limited to the use of biotin as the cell-labeling agent. Other labels may be used provided their addition to a cell does not disturb the structural integrity of any surface proteins expressed thereon and provided such labels permit the addition of a paramagnetic microbead or other magnetic substance thereto. Other such labels include, but are not limited to, cell surface proteins or carbohydrates which can be directly derivitized with magnetic beads that possess activated amine, carboxyl, or thiol groups. In addition, dyes such as fluorescein or rhodamine may also be covalently attached to cells in a manner similar to biotin and magnetic beads coated with anti-dye antibodies may be attached thereto.

The invention also includes a screening method which may be used to isolate a DNA encoding a multi-subunit protein which binds to an antigen-bearing moiety or, alternately, to isolate the multi-subunit protein itself. The multi-subunit protein may, for example, be an antibody or another immunoglobulin. It is well known that antibodies and other immunoglobulins comprise multiple subunits, often designated heavy and light chains.

According to this screening method, a phage display library is generated, either as described herein or using other generally known or hereafter-developed methods. The library comprises a plurality of virus vectors, including a first virus vector which comprises a first heterologous DNA encoding a subunit of the protein. The first virus vector expresses the subunit on its surface, either by itself or in association with one or more other subunits of the protein. The library also comprises a second virus vector which comprises a second heterologous DNA encoding a different subunit of the protein. The second virus vector expresses the different subunit on its surface, either by itself or in association with one or more other subunits of the protein. A magnetic label is added to cells bearing the antigen-bearing moiety on their surface, and the labeled cells are incubated with the phage display library in the presence of an excess of non-labeled cells which do not express the antigen-bearing moiety. The first and second virus vectors bind to the magnetically labeled cells, owing to interaction(s) between the antigen and the subunits of the protein expressed on the surface of the vectors.

After incubating the phage display library with the mixture of cells, magnetically labeled cells are isolated from the mixture. First and second virus vectors bound to the magnetically labeled cells are thereby also isolated from the mixture. The virus vectors are separated from the magnetically labeled cells (e.g. by culturing the cells in a manner in which the virus vectors are produced in the culture supernatant), and heterologous DNA is obtained from virus vectors that adhered to the magnetically labeled cells. The DNA may optionally be purified at this stage. DNA isolated from the virus vectors that adhered to the magnetically labeled cells includes the first heterologous DNA and the second heterologous DNA.

At least the portion of the first heterologous DNA encoding the subunit is ligated to at least the portion of the second heterologous DNA encoding the different subunit to form a hybrid heterologous DNA. For this purpose, it is advantageous that the virus vector be constructed in such a way that the portion of the first heterologous DNA encoding the subunit, the portion of the second heterologous DNA encoding the different subunit, or both, are flanked or surrounded by defined restriction endonuclease cleavage sites. In such constructs, the portion of the first heterologous DNA encoding the subunit may be removed, for example, by treating the first heterologous DNA with restriction endonucleases which specifically cleave the specific sites. This portion may then be ligated, for example either directly or after ligating a linker DNA thereto, to all or a portion of the second heterologous DNA to generate the hybrid heterologous DNA.

The hybrid heterologous DNA is then used to generate a hybrid virus vector comprising the hybrid heterologous DNA. The hybrid virus vector expresses the subunit and the different subunit of the protein on its surface. For example, if the first heterologous DNA encodes an antibody light chain and the second heterologous DNA encodes an antibody heavy chain, then the hybrid virus vector may express an antibody comprising equal numbers of heavy and light chains on its surface.

The hybrid virus vector is then incubated with the mixture of magnetically labeled cells having the antigen-bearing moiety on their surface and non-magnetically labeled cells which do not have the antigen-bearing moiety on their surface. Owing to interactions between the antigen and the subunits of the protein expressed on the surface of the hybrid virus vector, the hybrid virus vector binds with the magnetically labeled cells, and may therefore be isolated from the mixture of cells by isolating magnetically labeled cells from the mixture.

As described herein, hybrid virus vector particles are isolated from the magnetically labeled cells. The isolated hybrid virus vectors may be used as a source for obtaining either the multi-subunit protein or the hybrid heterologous DNA (which encodes the subunits of the protein), using standard methods.

The invention includes proteins and DNA encoding the same which are generated using the methods described herein. To isolate DNA encoding an antibody, for example, DNA is extracted from antibody expressing phage obtained according to the methods of the invention. Such extraction techniques are well known in the art and are described, for example, in Sambrook et al. (supra).

The invention includes a number of isolated or substantially purified DNAs encoding antigen-binding proteins, such as Rh(D)-binding proteins. For example, a DNA having a nucleotide sequence comprising at least one of SEQ ID NOs: 70–138 and 182–224, as described herein, is included. The isolated or substantially purified nucleic acid may have a nucleotide sequence selected from the group consisting of SEQ ID NOs: 70–138 and 182–224.

An "isolated DNA", as used herein, refers to a DNA sequence, segment, or fragment which has been purified from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to DNA which has been substantially purified from other components which naturally accompany the DNA, e.g., RNA or DNA or proteins which naturally accompany it in the cell.

The invention also includes a number of isolated or substantially purified proteins, such as Rh(D)-binding proteins. For example, a protein having an amino acid sequence comprising at least one of SEQ ID NOs: 1–69 and 139–181, as described herein, is included. The isolated or substantially purified protein may have an amino acid sequence selected from the group consisting of SEQ ID NOs: 1–69 and 139–181. The protein may be an antigen-binding protein, such as an antibody which comprises a heavy chain having an amino acid sequence selected from the group consisting of SEQ ID NOs: 1–28 and 139–153, a light chain having an amino acid sequence selected from the group consisting of SEQ ID NOs 29–69 and 154–181, or both. The protein may also be, for example, an antibody fusion protein.

An "isolated protein" as used herein, means a protein or polypeptide which has been separated from components which naturally accompany it in a cell. Typically, a protein or polypeptide is isolated when at least 10%, more preferably at least 20%, more preferably at least 50% of the total material (by volume, by wet or dry weight, or by mole percent or mole fraction) in a sample is the protein or polypeptide of interest.

The invention should also be construed to include DNAs which are substantially homologous to the DNA isolated according to the method of the invention. Preferably, DNA which is substantially homologous is about 50% homologous, more preferably about 70% homologous, even more preferably about 80% homologous and most preferably about 90% homologous to DNA obtained using the method of the invention.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g, 9 of 10, are matched or homologous, the two sequences share 90% homology. By way of example, the DNA sequences 3'ATTGCC 5' and 3'TATGCG 5' share 50% homology.

To obtain a substantially pure preparation of a protein comprising, for example, an antibody, generated using the methods of the invention, the protein may be extracted from the surface of the phage on which it is expressed. The procedures for such extraction are well known to those in the art of protein purification. Alternatively, a substantially pure preparation of a protein comprising, for example, an antibody, may be obtained by cloning an isolated DNA encoding the antibody into an expression vector and expressing the protein therefrom. Protein so expressed may be obtained using ordinary protein purification procedures well known in the art.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The present invention also provides for analogs of proteins or peptides obtained according to the methods of the invention. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included in the invention are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, the present invention provides for active fragments of the polypeptides. A specific polypeptide is considered to be active if it binds to an antigen-bearing moiety, for example, if a fragment of an antibody binds to its corresponding antigen in the same manner as the full length protein.

As used herein, the term "fragment," as applied to a polypeptide, will ordinarily be at least about fifty contiguous amino acids, typically at least about one hundred contiguous amino acids, more typically at least about two hundred continuous amino acids and usually at least about three hundred contiguous amino acids in length.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Isolation of Cell Surface-Specific Human Monoclonal Antibodies Using Phage Display and Magnetically-Activated Cell Sorting The experiments described in this Example provide procedures and results for the isolation and production of anti-Rh(D) red blood cell antibodies using Fab/phage display.

A method is described in FIG. 1 for the isolation of filamentous phage-displayed human monoclonal antibodies specific for non-purifiable cell surface expressed molecules. To optimize the capture of antigen-specific phage and minimize the binding of irrelevant phage antibodies, a simultaneous positive and negative selection strategy was employed. Cells bearing the antigen of interest are pre-coated with magnetic beads and are diluted into an excess of unmodified antigen-negative cells. Following incubation of the cell admixture with a Fab/phage library, the antigen positive cell population is retrieved using magnetically-activated cell sorting, and antigen-specific Fab/phage are eluted and propagated in bacterial culture. When this protocol was used with magnetically-labeled (Rh(D)-positive and excess non-labeled Rh(D)-negative human red blood cells and a Fab/phage library constructed from human peripheral blood lymphocytes, dozens of unique, clinically useful $_{\gamma 1}\kappa$ and $_{\gamma 1}\lambda$ anti-Rh(D) antibodies were isolated from a single alloimmunized individual.

The cell-surface selection method of the present invention is readily adaptable for use in other systems, such as for the identification of putative tumor-specific antigens, and provides a rapid (less than one month), high yield approach for isolating self-replicative antibody reagents directed at novel or conformationally-dependent cell-surface epitopes.

Creation of Fab/phage Display Libraries

Separate $_{\gamma 1}\kappa$ and $_{\gamma 1}\lambda$ phage libraries were constructed from $2\times10^7$ mononuclear cells derived from the peripheral blood from an Rh(D)-negative individual previously hyperimmunized with Rh(D)-positive red blood cells (RBCs). The phagemid vector pComb3 (Barbas, 1991, Proc. Natl. Acad. Sci. USA 88:7978–7982) was used to create the libraries utilizing previously published methods (Barbas et al., 1991, Combinatorial immunoglobulin libraries on the surface of phage (Phabs): Rapid selection of antigen-specific Fabs. Methods: A Companion to Methods in Enzymology 2:119–124; Siegel et al., 1994, Blood 83:2334–2344).

Briefly, cDNA was prepared from the mRNA of the donor cells and heavy chain and light chain immunoglobulin (Ig) cDNA segments were amplified using the polymerase chain reaction (PCR) and the battery of human Ig primers described by Kang et al. (1991, "Combinatorial Immunoglobulin Libraries on the Surface of Phage (Phabs): Rapid Selection of Antigen-Specific Fabs. Methods: A Companion to Methods" in Enzymology 2:111–118) supplemented by those of Silverman et al. (1995, J. Clin. Invest. 96:417–426). The heavy and light chain PCR products were cloned into pComb3 and electroporated into E. coli. Upon co-infection with VCSM13 helper phage (Stratagene, La Jolla, Calif.), Ig DNA was packaged into filamentous phage particles which express human Fab molecules fused to the gene III bacteriophage coat protein.

Panning Fab Phage Display Libraries for Anti-Rh(D) Clones

Rh(D)-positive RBCs were cell-surfaced biotinylated by incubating cells at a hematocrit of 10% with 500 $\mu$g/ml sulfo-NHS-LC-biotin (Pierce Chemical, Rockford, Ill.) for 40 minutes at room temperature (RT). Following 5 washes with phosphate-buffered saline (PBS), $8\times10^6$ biotinylated Rh(D)-positive RBCs were incubated with 10 $\mu$l of streptavidin-coated paramagnetic microbeads (MACS Streptavidin Microbeads, Mitenyi Biotec, Sunnyvale, Calif.) for 1 hour at RT in a total volume of 100 $\mu$l PBS. Non-reacted beads were removed by washing and then the magnetic bead-coated, Rh(D)-positive RBCs were mixed with a 10-fold excess ($8\times10^7$) of the Rh(D)-negative (unmodified) RBCs and $\sim 3\times10^{11}$ colony-forming units (cfu) of either the $_{\gamma 1}\kappa$ and $_{\gamma 1}\lambda$ Fab/phage libraries (prepared as described above) in a final volume of 40 $\mu$l PBS containing 2% non-fat dry milk (MPBS, Carnation, Nestle Food Products, Glendale, Calif.).

Following a 2 hour incubation at 37° C., the RBC/phage suspension was loaded at a flow rate of 10 $\mu$l/minute onto a MiniMACS magnetic type MS column (Mitenyi Biotec, Sunnyvale, Calif.) that was pre-equilibrated with 2% MPBS. This loading step was performed without a magnetic field around the column so as to prevent magnetic bead-coated RBCs from instantly adhering to the very top of the column, clogging it, and causing the trapping of Rh(D)negative non-biotinylated RBCs. Loading the RBC/phage incubation mixture in the absence of a magnetic field causes the antigen-negative and antigen-positive RBCs to distribute evenly throughout the column without running off since the excluded volume of the column is slightly greater than 40 $\mu$l. Once loaded, the column was placed in a magnetic field (MiniMACS magnetic separation unit, Mitenyi Biotec, Sunnyvale, Calif.) for 2 minutes to allow the Rh(D)-positive RBCs to adhere, and a series of 500 $\mu$l washes were performed with ice-cold MPBS followed by a final wash with PBS. A total of 3 washes were performed for the first 2 rounds of panning and a total of 6 washes were performed for all subsequent pannings. For each panning, the first wash was carried out at a flow rate of 10 μl/minute during which time the bulk of Rh(D)-negative RBCs washed off the column. All subsequent washes were performed at 200 μl/minute. Following the last wash, the column was removed from the magnetic field and the bead-coated/phage-coated Rh(D)-positive RBCs were flushed off the column with 500 μl PBS using the plunger from a 5 cc syringe (Becton-Dickinson, Franklin Lakes, N.J.).

The RBCs were immediately centrifuged for 5 seconds at 13,000×g and were then resuspended in 200 μl of 76 mM citrate, pH 2.4, to denature the Rh(D) antigen and elute bound phage. Following a 10 minute incubation period at RT with intermittent vortexing, the phage eluate and cellular debris were neutralized with 18 μl 2 M Tris base and were added to 10 ml of O.D.=1.0 XL1-Blue strain of *E. coli* (Stratagene, La Jolla, Calif.) grown in super broth (SB) (Barbas et al., 1991, supra) supplemented with 10 μg/ml tetracycline. After incubation for 15 minutes at RT, during which time the phage library enriched for Rh(D) binders was allowed to infect the bacterial culture, 10 ml of pre-warmed, 37° C. SB containing 40 μg/ml carbenicillin/10 μg/ml tetracycline was added to give final antibiotic concentrations of 20 μg/ml and 10 μg/ml, respectively. A small aliquot of culture (~100 μl) was immediately removed and titered on Luria broth/carbenicillin plates to determine the number of phage contained in the total eluate. The balance of the culture was shaken at 37° C. for 1 hour at 300 RPM. Additional antibiotics, additional SB, and VCSM13 helper phage were subsequently added and the culture was grown overnight at 30° C. as described (Siegel et al., 1994, supra).

Phagemid particles were purified from the culture supernatant by polyethylene glycol 8000 (PEG) precipitation (Barbas et al., 1991, supra), resuspended in 1% bovine serum albumin (BSA)/PBS, and dialyzed overnight to remove residual PEG that may lyse RBCs during subsequent rounds of panning. Thus, the resultant phage preparation serves as the input for the next round of panning. The $_{\gamma 1}\kappa$ and $_{\gamma 1}\lambda$ phage libraries were panned separately to prevent any bias in light chain isotype replication possibly introduced by bacterial amplification.

Screening Polyclonal Fab/Phage Libraries and Individual Phage Colonies for Anti-Rh(D) Reactivity The specificity of Fab/phage for the Rh(D) antigen was assessed using anti-M13 antibody as a bridging antibody to induce agglutination between RBCs that have bound anti-Rh(D) Fab/phage. One hundred μl aliquots of polyclonal Fab/phage from rounds of panning, or monoclonal Fab/phage derived from individual Fab/phage eluate clones, were incubated with 50 μl of a 3% suspension of RBCs of defined phenotype (i.e., Rh(D)-negative or -positive).

Following 1 hour incubation at 37° C., the RBCS were washed 3 times with 2 ml cold PBS to remove unbound Fab/phage. The resultant RBC pellets were resuspended in 100 μl of a 10 μg/ml solution of sheep anti-M13 antibody (5-Prime 3-Prime, Boulder, Col.) and transferred to the round-bottomed wells of a 96-well microtiter plate. Plates were left undisturbed (~2 hours) and were then read. Wells having a negative reaction exhibit sharp ~2 millimeter diameter RBC spots whereas in wells having positive reactions, i.e., agglutination, the RBCs in agglutinated wells form a thin carpet coating the entire floor of the well.

For hemagglutination assays utilizing mini-column gel cards (ID-Micro-Typing System, Ortho Diagnostics, Raritan, N.J.) (Lapierre et al., 1990, Transfusion 30:109–113), 25 μl of Fab/phage clones were mixed with 50 μl aliquots of RBCs (0.8% suspensions in Micro Typing System buffer, Ortho Diagnostics). The mixtures were placed in the reservoirs above the mini-columns which contain dextran-acrylamide beads previously suspended in 100 μl/ml anti-M13 antibody. After incubation at 37° C., the gel cards were centrifuged at 70×g for 10 minutes and were read.

Miscellaneous Methods

Preparation of fluorescently-labeled RBCs for flow cytometry was performed as described herein and samples were analyzed using a FACScan microfluorimeter equipped with Lysis II (Ver 1.1) software (Becton-Dickinson, Mountain View, Calif.). Plasmid DNA was prepared from bacterial clones (Qiawell Plus, Qiagen, Chatsworth, Calif.). Double-stranded DNA was sequenced using light chain or heavy chain Ig constant region reverse primers or unique pComb3 vector primers that anneal 5-prime to the respective Ig chain (Barbas et al., 1991, supra; Roben et al., 1995, J. Immunol. 154:6437–6445) and automated fluorescence sequencing (Applied Biosystems, Foster City, Calif.). Sequences were analyzed using MacVector Version 5.0 sequencing software (Oxford Molecular Group, Oxford, UK) and the Tomlinson database of Ig germline genes (Tomlinson et al., 1996, V Base Sequence Directory. MRC Center for Protein Engineering, Cambridge, UK).

Experimental Design for Cell Incubation and Separation Protocols

The experimental conditions described above for panning Fab/phage libraries for anti-RBC-reactive phage were determined after performing a series of initial studies aimed at optimizing the cell separation process and ultimate yield of antigen-specific Fab/phage. The main parameters investigated included:

Biotinylation Conditions were sought that would biotinylate the RBC surface in a manner such that a sufficient number of streptavidin-coated magnetic beads would bind to the cells causing the RBCs to be retained by a magnetic column. In this case, over-biotinylation that might destroy the antigenicity of the Rh(D) antigen or might make the cells non-specifically absorb antibody is to be avoided. To address this issue, Rh(D)-positive/Kell-negative RBCs (Kell being a RBC antigen; (Walker, ed. 1993, In: *Technical Manual*, 11th Ed., Bethesda, Md., American Association of Blood Banks) were incubated with a range of sulfo-NHS-LC-biotin concentrations and the degree of biotinylation was assessed by flow cytometry utilizing fluorescein-conjugated streptavidin.

To assess the degree of cell-surface biotinylation, 5 μl aliquots of 3% suspensions of Rh(D)-positive/Kell-negative RBCs biotinylated at varying biotin reagent concentrations were incubated with 200 μl of a 1/100 dilution of FITC-streptavidin (Jackson ImmunoResearch, Bar Harbor, Maine) for 30 min at 4° C. (FIG. 2). The mixture was washed with phosphate buffered saline (PBS) and analyzed by flow microfluorimetry (-□-). Aliquots of cells were also analyzed for retention of Rh(D)-antigenicity (-Δ-) (i.e., specific staining) or for lack of non-specific staining (-○-) by incubating the cells with 100 μl of either anti-Rh(D) or anti-Kell typing sera, respectively, washing the cells and then staining them with a 1/100 dilution of FITC-goat anti-human IgG (Jackson ImmunoResearch).

A linear, non-saturating response was observed (FIG. 2). Retention of Rh(D) antigenicity was assessed using anti-Rh (D) typing serum and was found to be unaffected by the derivatization of cell-surface proteins with biotin at all biotin concentrations tested (FIG. 2). Furthermore, the Kell-negative RBCs did not non-specifically adsorb anti-Kell antibodies.

Each biotinylated RBC sample was then incubated with an excess of streptavidin-coated magnetic microbeads and applied to a magnetic separation column. It was determined that as many as $10^8$ RBCs could be retained by the column for RBC samples biotinylated with greater than or equal to 500 μg/ml biotin reagent. Since the actual RBC/phage panning experiments were designed to use only ~$10^7$ Rh(D)-positive cells (see below), RBC biotinylation at 500 μg/ml was determined to be sufficient.

Concentration of Rh(D)-Positive and Rh(D)-Negative RBCs in Incubation Mixture

Figure 3A:
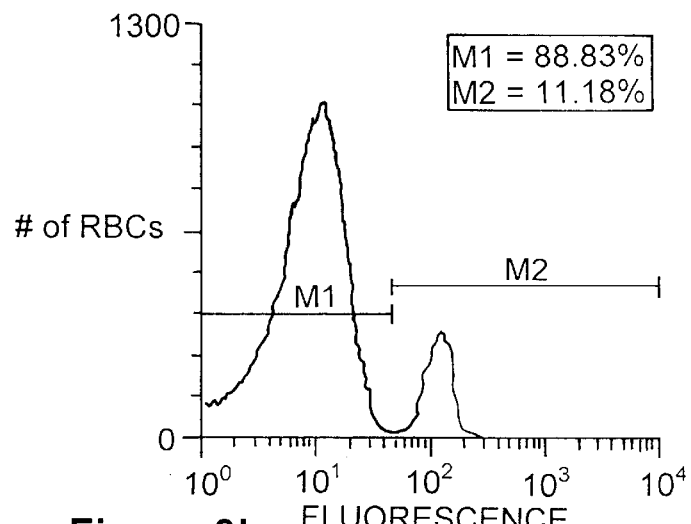
FIG. 3 is a series of graphs which validate the antigen-positive, antigen-negative cell separation procedure of the invention.
Figure 3B:
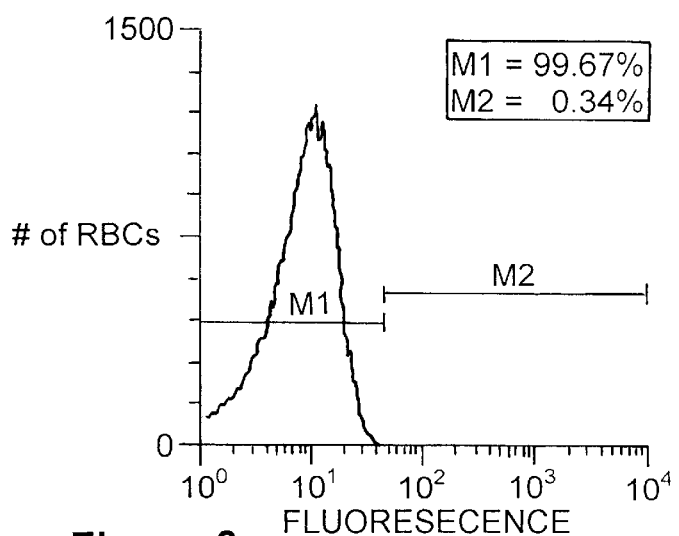
Figure 3C:
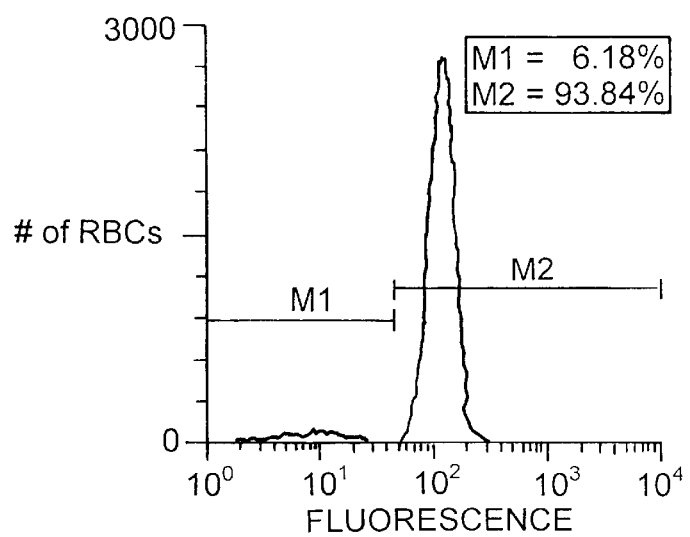
Figures 1, 3, 8A:
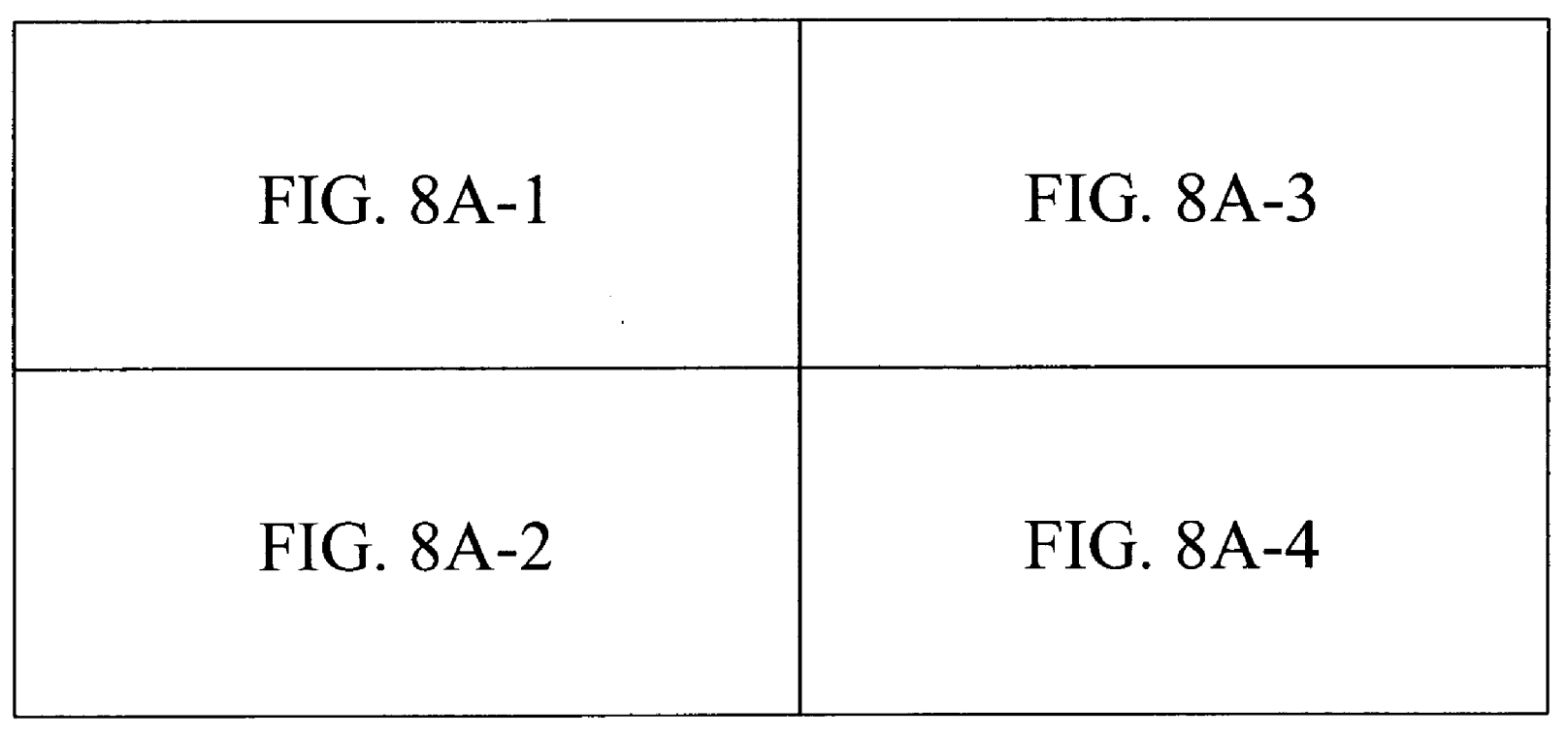

Prior to performing Fab/phage panning experiments, the ability of the magnetically-activated cell separation technique to separate Rh(D)-positive and Rh(D)-negative cells was assessed using anti-Rh(D) typing serum and flow cytometry (FIG. 3). Streptavidin-microbead coated, biotinylated Rh(D)-positive RBCs (8×$10^6$ cells) were mixed with a 10-fold excess of Rh(D)-negative non-coated RBCs (8×$10^7$ cells) in a 40 μl volume of PBS containing 2% non-fat dry milk (MPBS) and the mixture was applied to a MiniMACS column. The column was washed and the bound cells were eluted as described herein. Aliquots of RBCs contained in the original admixture (panel a), the column wash (panel b), and the column eluate (panel c) were stained with anti-Rh (D) typing serum and FITC-goat anti-human IgG as described in FIG. 2. The flow cytograms show that although ~90% of the cells in the column load were Rh(D)-negative (panel a), nearly all of them washed off of the column (panel b), yielding a column eluate that was almost entirely Rh(D)-positive cells (panel c). Since only ~6% of the final eluate comprise Rh(D)-negative cells (panel c), and Rh(D)-negative cells were initially present in a 10-fold excess to Rh(D)-positive cells, only ~0.6% of the initial antigen-negative immunosorbent cells contaminated the final antigen-positive preparation. This efficiency of the cell separation was deemed adequate for subsequent panning experiments with Fab/phage.

In the above-described experiment, to avoid clogging the magnetic separation column, it was necessary to load the column in the absence of a magnetic field. This necessitated a reaction volume of less than or equal to 40 μl so that none of the material would run off the column. On theoretical grounds (Kretzschmar et al., 1995, Anal. Biochem. 224:413–419), one can calculate the appropriate concentration of cells required in a 40 μl volume to capture greater than 50% of Fab/phage specific for a given cell surface antigen. Such a calculation is a function of the number of antigen sites per cell and the dissociation constant ($K_D$) of the bound Fab/phage. Using a value of ~100,000 Rh(D) antigen sites per RBC (phenotype "—D—/—D—") (Mollison et al., 1993, In: *Blood Transfusion in Clinical Medicine*, Oxford, Blackwell Scientific Publications) and the desired Fab/phage affinity in the $K_D = 10^{-8}$ to $10^{-9}$ M range, then 8×$10^6$ Rh(D)-positive RBCs in a 40 μl reaction volume would be required. Given this number of Rh(D)-positive cells, a 10-fold excess of Rh(D)-negative RBCs was found to be the maximum amount of antigen-negative cells that could be effectively separated from antigen-positive RBCs by the magnetic column (FIG. 3).

Construction and Panning of Fab/phage Libraries $_{\gamma1}\kappa$ and $_{\gamma1}\lambda$ phage libraries were prepared as described herein and were found to contain 7×$10^7$ and 3×$10^8$ independent transformants, respectively. Table 1 tabulates the panning results for the libraries.

Figure 4:
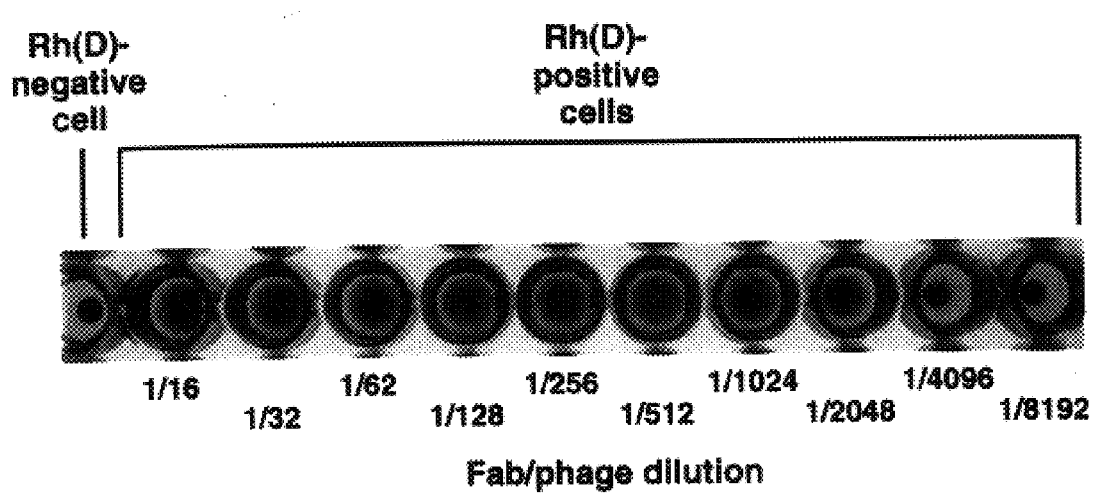
FIG. 4 is an image of a microplate agglutination assay wherein anti-Rh(D) Fab/phage agglutination titer was measured.

An RBC agglutination assay utilizing anti-M13 secondary antibody as bridging antibody was used to detect anti-Rh(D) Fab/phage activity in the panned polyclonal libraries and the individual randomly-picked Fab/phage clones (FIG. 4). The results shown are a representative example of the assay depicting negative reactivity to Rh(D)-negative RBCs and strongly positive reactivity to Rh(D)-positive RBCs for the $_{\gamma1}\kappa$ library (panning #2) out to a dilution of 1/2048.

In the case of the $_{\gamma1}\kappa$ library, significant enrichment for binding phage appears to occur after only one round of panning, whereas significant enrichment for the $_{\gamma1}\lambda$ library occurs during the second round. This is reflected by both the sharp increase in the percent of phage bound during a given round of panning as well as the ability of the polyclonal $_{\gamma1}\kappa$ and $_{\gamma1}\lambda$ Fab/phage libraries to agglutinate Rh(D)-positive RBCs after 1 and 2 rounds of panning, respectively (Table 1, FIG. 4).

Monoclonal Fab/phage were prepared from randomly-picked individual bacterial colonies obtained during each round of panning. It was apparent that by the third round of panning, all clones have anti-Rh(D) specificity (Table 1). To confirm that these Fab/phage have anti-Rh(D) specificity and are not binding to other unrelated antigens that may coincidentally be present on the particular Rh(D)-positive RBC and absent on the particular Rh(D)-negative RBC used in the agglutination assays, clones were screened against a panel of 11 Rh(D)-negative and-positive RBCs of varying blood group specificities to verify their anti-Rh(D) specificity (Walker, 1993, supra).

Clonal Analysis at the Genetic Level

To investigate the genetic diversity among the randomly picked anti-Rh(D) clones, plasmid DNA was prepared from each of the clones and the corresponding heavy and light chain Ig nucleotide sequences were identified. In Table 2 there is listed a number of attributes for each clone including the name of the most closely-related germline heavy or light chain Ig gene. More detailed analysis at the nucleotide level revealed that among all of the anti-Rh(D) binding clones, there were a large number of unique heavy and light chain DNA sequences (Table 3). Because of the random shuffling of heavy and light chain gene segments which occurs during the creation of a Fab/phage display library (Barbas et al., 1991, supra), it is evident that these heavy chains and light chains combined to form nearly 50 different anti-Rh(D) antibodies.

A detailed multiple alignment analysis of the predicted amino acid sequences revealed a total of twenty-five unique heavy chain, eighteen unique kappa light chain and twenty-three unique lambda light chain proteins. Due to the combinatorial effect during library construction, these heavy and light chain gene segments paired to produce fifty unique Fab antibodies ($20_{\gamma1\kappa}$ and $30_{\gamma1\lambda}$). Of interest, all twenty five unique heavy chains and nearly all of the eighteen unique kappa light chains were derived from only $5V_H$III or four VκI germline genes, respectively, while the lambda light chains were derived from a more diverse set of germline genes. Analysis of heavy and light chain nucleotide sequences from over sixty negative clones from the non-panned libraries were performed to verify the heterogeneity in variable region family representation before selection. Clones representing $V_H$ families I (13%), III (36%), IV (31%), V(15%) and VI (5%); Vκ families I (43%), II (14%), III (29%) and IV (14%); and Vγ families I (48%), II (4%), III (9%), IV (4%), V (9%), VI (17%) and VII (9%) were present.

Clonal Analysis at the Protein Level

Figure 5:
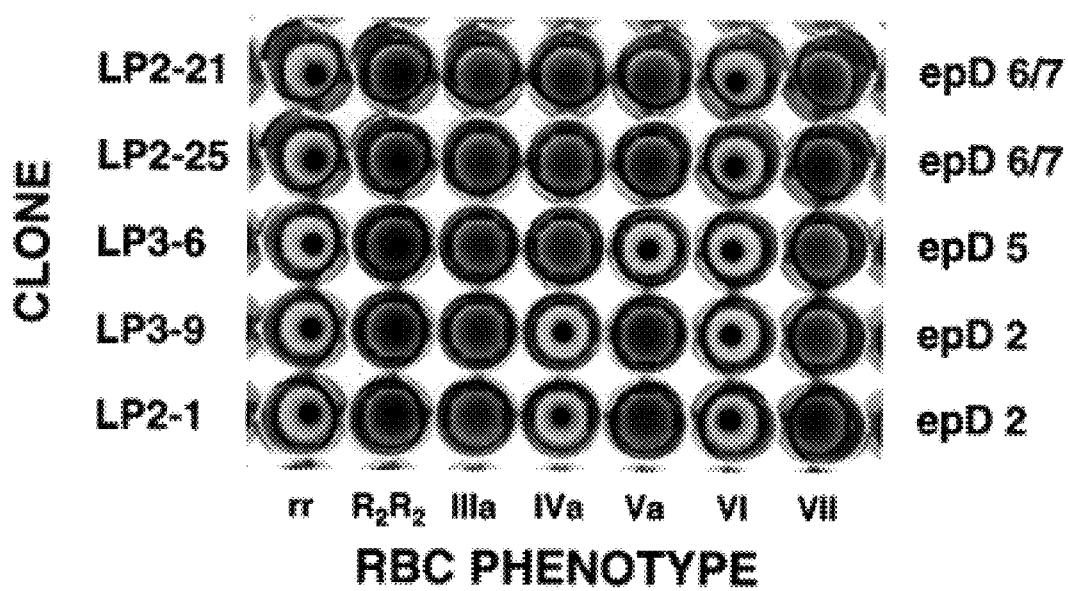
FIG. 5 is an image of a microplate agglutination assay showing determination of Rh(D) binding epitope for selected anti-Rh(D) Fab/phage clones.

To investigate the diversity in fine specificity (Rh(D) antigen epitope specificity) among the anti-Rh(D) clones, agglutination experiments were performed with selected clones and with sets of rare Rh(D)-positive RBCs which were obtained from individuals whose RBCs produce Rh(D) antigen lacking certain epitopes. Examining the pattern of agglutination of a particular anti-Rh(D) antibody with such sets of mutant RBCs enables the identification of the specific epitope on Rh(D) to which the antibody is directed (Mollison et al., 1993, supra). A representative example of such an experiment is shown in FIG. 5 and the Rh(D) epitopes for selected anti-Rh(D) Fab/phage clones are tabulated in Table 2.

Agglutination experiments were performed with anti-Rh(D)-negative RBCs (rr), Rh(D)-positive RBCs ($R_2R_2$), and "partial" Rh(D)-positive RBCs (mosaics IIIa, IVa, Va, VI, VII). The results shown are a representative example of the assay for 5 randomly-picked anti-Rh(D) Fab/phage clones (FIG. 5).

TABLE 1a $_{\gamma 1}\kappa$FAB/PHAGE LIBRARY PANNING RESULTS

| PANNING[1] | φINPUT (CFUs)[2] | φOUTPUT (CFUs)[3] | % BOUND[4] (× 10⁻⁴) | ENRICHMENT[5] | AGGLUT TITER[6] | BINDERS/ TOTAL (%)[7] |
|---|---|---|---|---|---|---|
| 0 | | | | | 0 | 0/16 (0) |
| 1 | 2.94 × 10¹¹ | 6.04 × 10⁵ | 2.1 | | 1/16 | 0/16 (0) |
| 2 | 2.15 × 10¹¹ | 1.68 × 10⁷ | 78.3 | 38.0 x | 1/2048 | 15/15 (100) |
| 3 | 1.72 × 10¹¹ | 1.44 × 10⁸ | 840.0 | 10.7 x | 1/2048 | 12/12 (100) |

TABLE 1b $_{\gamma 1}\lambda$FAB/PHAGE LIBRARY PANNING RESULTS

| PANNING[1] | φINPUT (CFUs)[2] | φOUTPUT (CFUs)[3] | % BOUND[4] (× 10⁻⁴) | ENRICHMENT[5] | AGGLUT TITER[6] | BINDERS/ TOTAL (%)[7] |
|---|---|---|---|---|---|---|
| 0 | | | | | 0 | 0/16 (0) |
| 1 | 2.28 × 10¹¹ | 3.48 × 10⁵ | 1.5 | | 0 | |
| 2 | 5.51 × 10¹¹ | 1.34 × 10⁶ | 2.4 | 1.6 x | 1/128 | 32/36 (89) |
| 3 | 3.93 × 10¹¹ | 3.86 × 10⁸ | 980.0 | 404.0 x | 1/512 | 24/24 (100) |
| 4 | 2.87 × 10¹¹ | 3.08 × 10⁸ | 1100.0 | 1.1 x | 1/1024 | |

[1]panning round, where "0" represents the initial, non-panned Fab/phage library
[2]number of colony-forming units (CFUs) of phage (φ) incubated with Rh(D)-positive/negative RBC admixture
[3]total number of CFUs of φ contained in eluate
[4](φoutput/φinput) × 100
[5]fold increase in % bound from compared to previous round of panning
[6]agglutination titer; see text and FIG. 4number of Rh(D)-binding Fab/phage clones per total number of clones screened from panning round; see Table 2 for details TABLE 2a ANALYSIS OF $_{\gamma 1}\kappa$FAB/PHAGE CLONES

| CLONE[1] | AGGLU[2] | VH FAM[3] | VH GENE[4] | $V_\kappa$ FAM[5] | $V_\rho$ GENE[6] | D EPITOPE[7] |
|---|---|---|---|---|---|---|
| KPO-1 | neg | 3 | DP-47/V3-23 | 4 | DPK24/VklVKlobeck | |
| KPO-2 | neg | 3 | DP-31/V3-9P | 3 | DPK22/A27 | |
| KPO-3 | neg | 3 | DP-58/hv3d1EG | 4 | DPK24/VklVKlobeck | |
| KPO-4 | neg | 4 | 3d279d+ | — | no light chain | |
| KPO-5 | neg | 3 | DP-29/12-2 | 1 | LFVK431 | |
| KPO-6 | neg | 4 | DP-79/4d154 | 1 | DPK9/012 | |
| KPO-7 | neg | 3 | V3-48/hv3d1 | 4 | DPK24/VklVKlobeck | |
| KPO-8 | neg | 4 | DP-70/4d68 | 2 | DPK18/A17 | |
| KPO-9 | neg | 1 | DP-14/V1-18 | 1 | DPK9/012 | |
| KPO-10 | neg | 4 | DP-70/4d68 | 1 | DPK9/012 | |
| KPO-11 | neg | 5 | DP-73/V5-51 | 1 | DPK9/012 | |
| KPO-12 | neg | 3 | DP-54/V3-7 | 2 | DPK18/A17 | |
| KPO-13 | neg | 3 | V3-48/hv3d1 | 1 | Vb' | |
| KPO-14 | neg | 6 | DP-74/VH-VI | 1 | DPK6/Vb" | |
| KPO-15 | neg | 3 | DP-46/3d216 | 3 | Vg/38K | |
| KPO-16 | neg | 6 | DP-74/VH-VI | 1 | DPK9/012 | |
| KP1-1 | neg | 4 | V71-4+ | 3 | DPK22/A27 | |
| KP1-2 | neg | 4 | 3d279d+ | 1 | DPK8/Vd+ | |
| KP1-3 | neg | 1 | 4M28 | 1 | DPK9/012 | |
| KP1-4 | neg | 4 | DP-79/4d154 | 3 | Vg/38K | |
| KP1-5 | neg | 3 | DP-38/9-1 | 3 | DPK22/A27 | |

TABLE 2a-continued

ANALYSIS OF γ1κFAB/PHAGE CLONES

| CLONE[1] | AGGLU[2] | VH FAM[3] | VH GENE[4] | Vκ FAM[5] | Vρ GENE[6] | D EPITOPE[7] |
|---|---|---|---|---|---|---|
| KP1-6 | neg | 4 | DP-70/4d68 | 1 | L12a/PCRdil6-5 | |
| KP1-7 | neg | 5 | DP-73/V5-51 | 2 | DPK15/A19 | |
| KP1-8 | neg | 4 | DP-70/4d68 | 3 | DPK22/A27 | |
| KP1-9 | neg | — | no heavy chain | — | no light chain | |
| KP1-10 | neg | — | no heavy chain | 3 | DPK22/A27 | |
| KP1-11 | neg | 1 | DP-15/V1-8+ | 1 | DPK9/O12 | |
| KP1-12 | neg | 3 | b28e | — | no light chain | |
| KP1-13 | neg | 3 | DP-47/V3-23 | 4 | DPK24/VklVKlobeck | |
| KP1-14 | neg | 3 | DP-31/V3-9P | 3 | DPK21/humkv328h5 | |
| KP1-15 | neg | 1 | DP-7/21-2 | 4 | DPK24/VklVKlobeck | |
| KP1-16 | neg | 5 | DP-73/V51 | 3 | DPK22/A27 | |
| KP2-1 | pos | 3 | DP-50/hv3019b9 | 1 | DPK9/O12 | epD6/7 |
| KP2-2 | pos | 3 | DP-50/hv3019b9 | 1 | DPK9/O12 | epD6/7 |
| KP2-3 | pos | 3 | DP-50/hv3019b9 | 1 | DPK9/O12 | epD6/7 |
| KP2-4 | pos | 3 | b28m | 1 | DPK9/O12 | epD2 |
| KP2-5 | pos | 3 | b28m | 1 | DPK9/O12 | epD1 |
| KP2-6 | pos | 3 | DP-50/hv3019b9 | 1 | DPK9/O12 | epD6/7 |
| KP2-7 | pos | 3 | DP-50/hv3019b9 | 1 | DPK9/O12 | epD5 |
| KP2-8 | pos | 3 | DP-50/hv3019b9 | 1 | DPK9/O12 | |
| KP2-9 | pos | 3 | DP-50/hv3019b9 | 1 | DPK9/O12 | epD2 |
| KP2-10 | pos | 3 | DP-50/hv3019b9 | 1 | DPK9/O12 | epD2 |
| KP2-11 | pos | 3 | DP-50/hv3019b9 | 1 | DPK9/O12 | epD2 |
| KP2-12 | pos | 3 | DP-50/hv3019b9 | 1 | DPK9/O12 | epD1 |
| KP2-13 | pos | 3 | DP-50/hv3019b9 | 1 | DPK9/O12 | epD6/7 |
| KP2-14 | pos | 3 | DP-50/hv3019b9 | 2 | DPK15/A19 | epD2 |
| KP2-15 | pos | 3 | DP-50/hv3019b9 | 1 | DPK9/O12 | epD6/7 |
| KP3-1 | pos | 3 | DP-50/hv3019b9 | 1 | DPK9/O12 | |
| KP3-2 | pos | 3 | DP-50/hv3019b9 | 1 | DPK9/O12 | epD6/7 |
| KP3-3 | pos | 3 | DP-50/hv3019b9 | 1 | DPK9/O12 | |
| KP3-4 | pos | 3 | DP-49/1.9111 | 1 | DPK9/O12 | epD5 |
| KP3-5 | pos | 3 | DP-50/hv3019b9 | 1 | DPK9/O12 | |
| KP3-6 | pos | 3 | DP-50/hv3019b9 | 1 | A30/SG3+ | epD6/7 |
| KP3-7 | pos | 3 | DP-50/hv3019b9 | 1 | DPK8/Vd+ | epD6/7 |
| KP3-8 | pos | 3 | DP-50/hv3019b9 | 1 | DPK9/O12 | epD6/7 |
| KP3-9 | pos | 3 | DP-50/hv3019b9 | 1 | DPK9/O12 | |
| KP3-10 | pos | 3 | DP-50/hv3019b9 | 1 | DPK9/O12 | |
| KP3-11 | pos | 3 | DP-50/hv3019b9 | 1 | DPK9/O12 | |
| KP3-12 | pos | 3 | DP-46/3d216 | 1 | DPK9/O12 | |

[1]nomenclature: prefix "KPO" denotes "γ1κFab/phage library, panning 0", "KP1" denotes "γ1κFab/phage library, panning 1", etc.
[2]agglutination negative or positive against Rh(D)-positive RBC
[3]Ig heavy chain variable region gene family per Tomlinson et al., supra
[4]closest related Ig heavy chain variable region gene per Tomlinson et al. supra
[5]Ig light chain variable region gene family per Tomlinson et al., supra
[6]closest related Ig light chain variable region gene per Tomlinson et al., supra
[7]Rh(D) epitope as defined by rare RBC agglutination pattern (see FIG. 5 and text)

TABLE 2b

ANALYSIS OF γ1ρFAB/PHAGE CLONES

| CLONE[1] | U[2] | VH FAM[3] | VH GENE[4] | Vρ FAM[5] | Vκ GENE[6] | D EPITOPE[7] |
|---|---|---|---|---|---|---|
| LPO-1 | neg | 4 | DP-65/3d75d | 1 | DPL7/IGLV1S2 | |
| LPO-4 | neg | 4 | DP-70/4d68 | 6 | IGLV8A1 | |
| LPO-3 | neg | 6 | DP-74/VH-VI | 7 | DPL18/VL7.1 | |
| LPO-4 | neg | 3 | DP-29/12-2 | 1 | DPL3/Iv122 | |
| LPO-5 | neg | 3 | DP-38/9-1 | 6 | IGLV6S1/LV6SW-G | |
| LPO-6 | neg | 1 | 4M28 | 1 | DPL3/Iv122 | |
| LPO-7 | neg | 1 | 8M27 | 1 | DPL2/Iv1L1 | |
| LPO-8 | neg | 5 | DP-58/V5-51 | 6 | IGLV6S1/LV6SW-G | |
| LPO-9 | neg | 5 | DP-73/V5-51 | 1 | DPL7/1GLV1S2 | |
| LPO-10 | neg | 3 | DP-38/9-1 | 1 | DPL2/Iv1L1 | |
| LPO-11 | neg | 3 | DP-31/V3-9P | 3 | DPL23/VLIII.1 | |
| LPO-12 | neg | — | no heavy chain | 1 | DPL7/1GLV1S2 | |
| LPO-13 | neg | 3 | DP-47/V3-23 | — | no light chain | |
| LPO-14 | neg | 4 | DP-71/3d197d | 6 | IGLV6S1/LV6SW-G | |

TABLE 2b-continued

ANALYSIS OF ᵧ₁ρFAB/PHAGE CLONES

| CLONE[1] | U[2] | VH FAM[3] | VH GENE[4] | $V_\rho$ FAM[5] | $V_\kappa$ GENE[6] | D EPITOPE[7] |
|---|---|---|---|---|---|---|
| LPO-15 | neg | 4 | DP-70/4d68 | 4 | IGLV8A1 | |
| LPO-16 | neg | 3 | DP-54/V3-7 | 7 | DPL19 | |
| LP2-1 | pos | 3 | DP-50/hv3019b9 | 1 | DPL2/Iv1L1 | epD2 |
| LP2-2 | pos | 3 | DP-77/WHG16 | 1 | DPL3/Iv122 | |
| LP2-3 | pos | 3 | DP-49/1.9111 | 1 | DPL3/Iv122 | epD1 |
| LP2-4 | neg | 4 | 3d279d+ | 1 | DPL2/Iv1L1 | |
| LP2-5 | pos | 3 | DP-49/1.9111 | 3 | DPL16/IGLV3S1 | epD5 |
| LP2-6 | pos | 3 | DP-50/hv3019b9 | 1 | DPL7/IGLV1S2 | epd2 |
| LP2-7 | pos | 3 | b28m | 1 | DPL7/IGLV1S2 | epD2 |
| LP2-8 | pos | 3 | DP-49/1.9111 | 3 | IGLV3S2=Iv318 | epD1 |
| LP2-9 | pos | 3 | DP-50/hv3019b9 | 3 | DPL16/IGLV3S1 | epD2 |
| LP2-10 | pos | 3 | DP-77/WHG16 | 1 | DPL3/LV122 | |
| LP2-11 | neg | 1 | DP-75-VI-2 | 1 | DPL5/LV117d | |
| LP2-12 | pos | 3 | DP-77/WHG16 | 1 | DPL2/LV1L1 | epD2 |
| LP2-13 | pos | 3 | COS-8/hv3005f3 | 4 | IGLV8A1 | |
| LP2-14 | pos | 3 | DP-49/1.9111 | 1 | DPL7/IGLV1S2 | epD5 |
| LP2-15 | pos | 3 | DP-50/hv3019b9 | 3 | DPL16/IGLV3S1 | |
| LP2-16 | pos | 3 | DP-49/1.9111 | 2 | Iv2046 | epd1 |
| LP2-17 | pos | 3 | DP-77/WHG16=V3-21+ | 1 | DPL3/Iv122 | epD3/9 |
| LP2-18 | pos | 3 | DP-49/1.9111 | 2 | VL2.1~DPL10/Iv2066 | epD1 |
| LP2-19 | pos | 3 | DP-50/hv3019b9 | 3 | DPL16/1GLV3S1 | epD2 |
| LP2-20 | neg | 3 | V3-49+ | 3 | DPL16/1GLV3S1 | |
| LP2-21 | pos | 3 | DP-50/hv3019b9 | 7 | DPLIS/VL7.1 | epD6/7 |
| LP2-22 | pos | 3 | DP-49/1.9111 | 2 | Iv2046 | |
| LP2-23 | pos | 3 | DP-49/1.9111 | 3 | DPL16/IGLV3S1 | epD5 |
| LP2-24 | pos | 3 | DP-77/WHG16 | 1 | DPL3/Iv122 | |
| LP2-25 | pos | 3 | DP-50/v3019b9 | 7 | DPL18/VL7.1 | epD6/7 |
| LP2-26 | pos | 3 | DP-49/1.9111 | 3 | DPL16/IGLV3S1 | |
| LP2-27 | neg | 3 | COS-6/DA-8 | 2 | VL2.1 | |
| LP2-28 | pos | 3 | COS-8/hv3005f3 | 4 | IGLV8A1 | |
| LP2-29 | pos | 3 | DP-49/1.9111 | | DPL13 | |
| LP2-30 | pos | 3 | DP-50/hv3019b9 | 3 | DPL16/IGLV3S1 | |
| LP2-31 | pos | 3 | DP-50/hv3019b9 | 7 | DPL18/VL7.1 | |
| LP2-32 | pos | 3 | DP-49/1.9111 | 1 | DPL2/Iv1L1 | |
| LP2-33 | pos | 3 | DP-50/hv3019b9 | 7 | DPL18/VL7.1 | |
| LP2-34 | pos | 3 | DP-50/hv3019b9 | 7 | DPL18/VL7.1 | |
| LP2-35 | pos | 3 | DP-50/hv3019b9 | 3 | DPL16/1GLV3S1 | |
| LP2-36 | pos | 3 | DP-50/hv3019b9 | 3 | DPL16/IGLV3S1 | |
| LP3-1 | pos | 3 | DP-50/hv3019b9 | 3 | DPL16/IGLV3S1 | epD2 |
| LP3-2 | pos | 3 | DP-49/1.9111 | 3 | DPL16/IGLV3S1 | epD1 |
| LP3-3 | pos | 3 | DP-49/1.9111 | 3 | DPL16/IGLV3S1 | |
| LP3-4 | pos | 3 | DP-50/hv3019b9 | 7 | DPL18/VL7.1 | epD6/7 |
| LP3-5 | pos | 3 | DP-49/1.9111 | 1 | DPL5/LV117d | epD5 |
| LP3-6 | pos | 3 | DP-49/1.9111 | 1 | DPL5/LV117d | epD1 |
| LP3-7 | pos | 3 | DP-77/WHG16 | 1 | DPL2/Iv1L1 | epD5 |
| LP3-8 | pos | 3 | b28m | 1 | DPL7/IGLVIS2 | epD2 |
| LP3-9 | pos | 3 | DP-50/hv3019b9 | 3 | DPL16/IGLV3S1 | epD2 |
| LP3-10 | pos | 3 | DP-50/hv3019b9 | 3 | DPL16/IGLV3S1 | |
| LP3-11 | pos | 3 | DP-50/hv3019b9 | 3 | DPLI6/IGLV3S1 | epD2 |
| LP3-12 | pos | 3 | COS-8/hv3005f3 | 4 | IGLV8A1 | epD6/7 |
| LP3-13 | pos | 3 | DP-50/hv3019b9 | 1 | DPL2/Iv1L1 | epD2 |
| LP3-14 | pos | 3 | DP-49/1.9111 | 3 | DPL16/IGLV3S1 | |
| LP3-15 | pos | 3 | DP-77/WHG16 | 1 | DPL3/Iv122 | epD1 |
| LP3-16 | pos | 3 | DP-49/1.9111 | 1 | DPL2/Iv1L1 | epD5 |
| LP3-17 | pos | 3 | DP-50/hv3019b9 | 3 | DPL16/IGLV3S1 | |
| LP3-18 | pos | 3 | DP-50/hv3019b9 | 3 | DPL16/IGLV3S1 | |
| LP3-19 | pos | 3 | DP-50/hv3019b9 | 3 | DPL16/IGLV3S1 | epD5 |
| LP3-20 | pos | 3 | DP-50/hv3019b9 | 1 | DPL2/Iv1L1 | |
| LP3-21 | pos | 3 | DP-49/1.911 | 1 | DPL3/Iv122 | |
| LP3-22 | pos | 3 | COS-8/hv3005f3 | 1 | DPL2/Iv1L1 | |
| LP3-23 | pos | 3 | DP-49/1.9111 | 3 | DPL16/IGLV3S1 | |
| LP3-24 | pos | 3 | DP-50/hv3019b9 | 3 | DPL16/IGLV3S1 | |

[1] nomenclature: prefix "LPO" denotes "ᵧ₁λFab/phage library, panning 0", "LP1" denotes "ᵧ₁λFab/phage library, panning 1", etc.
[2] agglutination negative or positive against Rh(D)-positive RBC
[3] Ig heavy chain variable region gene family per Tomlinson et al., supra
[4] closest related Ig heavy chain variable region gene per Tomlinson et al. supra
[5] Ig light chain variable region gene family per Tomlinson et al., supra
[6] closest related Ig light chain variable region gene per Tomlinson et al., supra
[7] Rh(D) epitope as defined by rare RBC agglutination pattern (see FIG. 5 and text)

TABLE 3

SUMMARY OF FAB/PHAGE CLONAL ANALYSIS

| | |
|---|---|
| Number of unique heavy chains | 25 |
| Number of unique κ light chains | 18 |
| Number of unique λ light chains | 23 |
| Number of $_{\gamma 1}\kappa$ antibodies | 20 |
| Number of $_{\gamma 1}\lambda$ antibodies | 30 |
| Number Rh(D) epitope specificities represented | 5 |

Use of Fab/Phage Antibodies as Blood Bank Typing Reagents

The ability of the anti-Rh(D) Fab/phage preparations to accurately distinguish Rh(D)-negative from Rh(D)-positive RBCs in microplate hemagglutination assays (FIGS. 4 and 5) provided evidence that a gel test (Lapierre et al., 1990, Transfusion 30:109–1130) used by blood banks to phenotype RBCs using conventional antisera could be adapted for use with Fab/phage.

Figure 6:
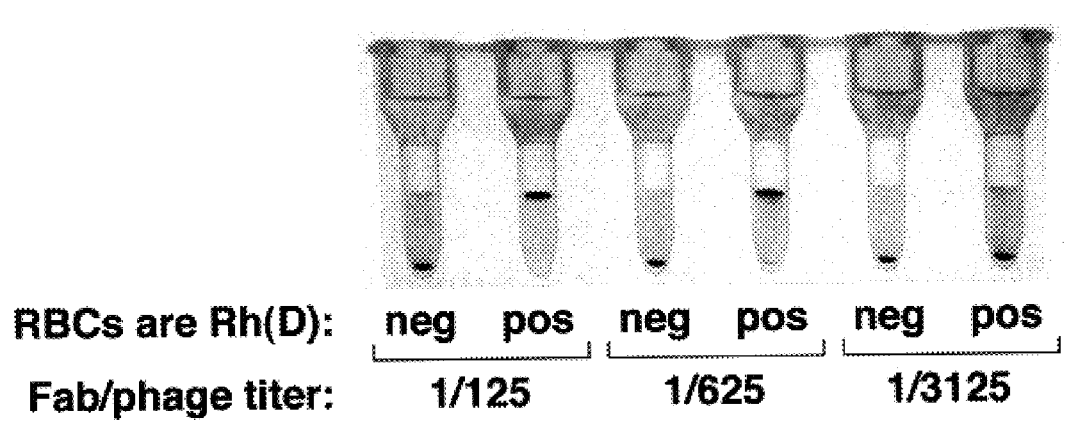
FIG. 6 is an image depicting the use of Fab/phage antibodies in a gel card assay.

The gel test comprises a plastic card of approximately 5×7 cm, containing 6 mini-columns each filed with about 20 µl of dextran-acrylamide beads suspended in anti-human globulin (Coombs reagent). Red cells to be typed are incubated with the desired human anti-sera and are centrifuged through the gel. RBCs which are positive for antigens to which the antisera is directed agglutinate as they encounter the anti-human globulin and become trapped in or above the gel matrix. Unreactive RBCs sediment through the gel particles and form a pellet at the bottom of the microtube. Because the gel test offers a number of advantages over traditional blood banking methods for RBC phenotyping including decreased reagent volumes, the elimination of a cell washing step and a more objective interpretation of results, many blood bank facilities have adapted this new technology. As shown in FIG. 6, anti-Rh-(D) Fab/phage can be used with gel cards that are modified to contain anti-M13 antibody.

To perform the assay, Rh(D)-negative or -positive red blood cells were incubated with dilutions of anti-Rh(D) Fab/phage ($_{\gamma 1}\kappa$ library, panning #2) and were centrifuged into micro-columns containing beads suspended in anti-M13 antibody. Undiluted Fab/phage stock had a titer of 5×10$^{12}$ cfu/ml similar to that in the microplate settling assay (FIG. 4). Because the volume of Fab/phage used in this assay is one-fourth of that in the microplate assay, the amount of Fab/phage present in the 1/625 dilution is approximately equal to that present in the 1/2048 dilution in FIG. 4. Therefore, the number of Fab/phage required to yield a positive result is essentially equivalent in both assays.

In other assays which were performed as just described, when anti-M13 antibody was eliminated from the assay, no agglutination of red blood cells was observed. In addition, anti-IgG antibody does not react with recombinant Fabs expressed on the surface of the bacteriophage. Only Rh-positive cells which were reacted with anti-Rh phage were agglutinated when anti-M13 antibody was present in the assay. It should be noted that when high concentrations of anti-M13 antibody were used, even Rh-negative cells appeared to be agglutinated. This is an artifact resulting from the cross-linking of unbound (i.e., non-reacted) phage which becomes crosslinked in the presence of high amounts of anti-M13 antibody and forms a semi-impenetrable mat through which not all the Rh-negative cells can traverse. In the experiments described herein, an anti-M13 concentration of about 100 µg/ml was considered to be optimal for agglutination and for the prevention of false positive results. Depending on the precise concentrations of reagents and cells used in the assay, the concentration of anti-M13 may deviate from this number.

To assess the relative sensitivity of an anti-M13 modified Micro Typing System, the columns of the Micro Typing System cards had added to them 100 µg/ml of anti-M13 antibody. Rh-negative or Rh-positive red blood cells were incubated with undiluted or with five-fold serial dilutions (1/5, 1/25, 1/125, 1/625 and 1/3125) of anti-Rh phage antibodies. The cards were centrifuged and samples were assessed for agglutination. The modified Micro Typing System card assay was capable of detecting anti-Rh agglutination at a dilution of between 1/625 and 1/3125.

Procedures for Isolation of Tumor-Specific Antibodies

Fab/phage specific for tumor cells are useful for in vitro diagnosis (lab assays of biopsy, fluid, or blood samples), in vivo labeling of tumor/metastasis (coupling of antibody to imaging probe), or for treatment of malignancy (coupling of antibodies to chemical or radioactive toxins). Tumor-specific antibodies are also useful for the identification of novel antigens or markers on tumor cells which may form the basis for anti-tumor vaccines. Further, tumor-specific antibodies useful for the generation of anti-idiotypic antibodies may also form the basis for anti-tumor vaccines.

Anti-tumor antibodies are generated essentially as described herein for the generation of anti-Rh antibodies. Tumor cells, for example, but not limited to, malignant melanoma cells, are cell-surface biotinylated, labeled with streptavidin-magnetic microbeads, and are then mixed with excess normal melanocytes. Fab/phage libraries are generated from peripheral blood lymphocytes of melanoma patients who possess therapeutically useful anti-tumor antibodies. A number of melanoma patients who have "cured" themselves apparently have done so by mounting a humoral (ie., antibody) immune response. These Fab/phage libraries are incubated with the admixture of cells. Fab/phage which are directed against epitopes specific for malignant cells will bind to the malignant cells and may then be isolated utilizing the magnetic column panning approach.

Isolation of Fab/Phage that Identify Bacterial Virulence Factors

The approach described herein may be used to isolate Fab/phage capable of detecting differences between the virulent bacteria and their nonpathogenic counterparts. In this case, the virulent strain of bacteria is magnetically labeled, diluted with the non-pathogenic counterpart, and an Fab/phage library which is generated from lymphocytes obtained from individuals infected with the virulent strain is added. Fab/phage which are isolated in this manner may be useful for the identification of novel bacterial antigens against which antibacterial compounds and/or vaccines may be developed.

EXAMPLE 2

Genetic and Immunological Properties of Phage-Displayed Human Anti-Rh(D) Antibodies Clinically, the human Rh(D) antigen is the most important red blood cell (RBC) membrane protein in transfusion medicine. The alloimmune response against Rh(D) produces high affinity IgG antibodies which cause hemolytic transfusion reactions and hemolytic disease of the newborn (HDN). The prophylactic use of Rh(D)-immune globulin in pregnant Rh(D)-negative women has been a major advance in the prevention of HDN, yet the mechanism by which the drug exerts its immune modulatory effect is not well understood.

Monoclonal antibodies derived from the B cells of Rh(D)-immune globulin donors have defined several dozen Rh(D)

epitopes (Scott, 1996, Transfus. Clin. Biol. 3:333). Paradoxically, the Rh(D) antigen, a circa 30 kD transmembrane protein, has minimal extracellular mass and presents a very limited surface area for epitope expression. Because molecular cloning of a large repertoire of anti-Rh(D) antibodies has not previously been performed, these observations remain non-reconciled.

Rational development of recombinant formulations of Rh(D)-immune globulin would be facilitated by molecular cloning of a large number of anti-Rh(D) antibodies. Such cloning would also aid in the design of therapeutic agents that block antibody binding. Furthermore, comprehensive genetic analysis of anti-Rh(D) antibodies within a given alloimmunized individual would serve as a paradigm for human immune repertoire development, an area of which limited information is currently available. Previously, no more than 8 IgG anti-Rh(D) human monoclonal antibodies have been derived from a single individual (Boucher et al., 1997, Blood 89:3277).

In Example 1, a technique useful for isolating Fab/phage antibodies directed against antigens expressed on cell surfaces was described. Using this technique and intact human red blood cells (RBCs), highly diverse $\gamma_1\kappa$ and $\gamma_1\lambda$. Fab/phage libraries against the Rh(D) antigen from the B cells of a single Rh(D)-immune globulin donor were generated.

In this Example, a detailed genetic and serological analysis of 53 unique anti-Rh(D) antibodies derived from 83 randomly chosen clones is presented. These data demonstrate extensive genetic homology between antibodies directed against different Rh(D) epitopes. Evidence is provided herein that antibodies directed against different epitopes can be clonally related. Finally, a model is described which reconciles the serological diversity of anti-Rh(D) antibodies with the topological constraints imposed by the Rh(D) antigen.

The materials and methods used in the experiments presented in this Example are now described.

Production of Monoclonal Anti-Rh(D) Phage-Displayed and Soluble Fab Molecules

Methods for the isolation of human anti-Rh(D)-specific antibodies from $\gamma_1\kappa$ and $\gamma_1\lambda$ Fab/phage display libraries using the pComb3H phagemid vector and a cell-surface panning protocol have been described (Siegel et al., 1997, J. Immunol. Meth. 206:73). Soluble anti-Rh(D) Fab preparations for inhibition studies were produced from bacterial cultures transfected with plasmid DNA from which the M13 gene III coat protein sequence had been excised as described (Siegel et al., 1994, Blood 83:2334; Barbas et al., 1991, Methods: A Companion to Meth. Enzymol. 2:119). Cultures were grown by shaking at 300 RPM at 37° C. in superbroth (30 g/L tryptone, 20 g/L yeast, 10 g/L MOPS, pH 7.00) containing 20 mM $MgCl_2$ and 50 mg/ml carbenicillin to an $OD_{600}$ of 0.5. Isopropyl-β-D-thiogalactopyranoside (IPTG) was added to 1 mM and cultures were shaken overnight at 30° C. Bacterial pellets were harvested and resuspended in 1/50th of the initial culture volume with osmotic shock buffer (500 mM sucrose, 1 mM EDTA, 100 mM Tris, pH 8.00), incubated for 30' at 4° C., and centrifuged at 16,000×g for 15' at 4° C. Fab-containing supernatants were dialyzed against PBS and used in agglutination experiments without further purification.

Anti-Rh(D) Antibody Binding Assays

The binding of anti-Rh(D) Fab/phage or soluble Fab molecules to normal or partial Rh(D) antigens was assessed by indirect agglutination assays as described (Siegel et al., 1994, Blood 83:2334; Siegel et al., 1997, J. Immunol. Meth. 206:73). Briefly, 100 μl aliquots of phage-displayed Fabs or soluble Fabs were incubated with 50 μl of a 3% suspension of RBCs. Following a one-hour incubation at 37° C., the RBCs were washed 3 times with 2 ml of cold PBS to remove unbound antibody. The resulting RBC pellets were resuspended in 100 μl of a 10 μg/ml solution of sheep anti-M 13 antibody (5 Prime-3 Prime, Boulder, Col.) for Fab/phage experiments or goat anti-human κ or λ light chain antibody (Tago, Burlingame, Calif.) for $\gamma_1\kappa$ or $\gamma_1\lambda$ soluble Fab experiments, respectively. The RBC suspensions were transferred to the round-bottomed wells of a 96-well microplate and left undisturbed for 2 hours. Negative reactions show sharp ~2 millimeter diameter RBC spots whereas the RBCs in agglutinated wells form a thin carpet coating the entire floor of the well (Siegel et al., 1997, J. Immunol. Meth. 206:73). Agglutination titers for recombinant antibodies were determined by performing serial 2-fold dilutions in 1% BSA/PBS. Typically, Fab/phage had agglutination titers of 1/1024 to 1/2048 (where "neat" is defined as $5\times10^{12}$ cfu/ml; Siegel et al., 1997, J. Immunol. Meth. 206:73) and soluble Fabs had agglutination titers of 1/64 to 1/128 when prepared as described above.

For determining Rh(D) epitope specificity for anti-Rh(D) Fab/phage antibodies, the following reference Rh(D) variant cells were used: O/$D^{IIIa}$Cce, G positive; B/$D^{IIIc}$Cce; A/$D^{IVa}$ce; A/$D^{IVa}$ce; O/$D^{IVa}$ce; O/$D^{IVb}$Cce; B/$D^{IVb}$Cce, $Go^a$ negative, Rh32 negative; O/$D^{Va}$Cce; O/$D^{Va}$cEe, $D^w$ positive; O/$D^{VI}$Cce; B/$D^{VI}$Cce; AB/$D^{VI}$Cce; A/$D^{VI}$cEe; O/$D^{VII}$Cce; and O/$D^{VII}$Cce. Each Fab/phage antibody was tested on at least 3 separate occasions against at least 2 different examples of each variant cell type and identical epitope assignments were obtained each time. For antibodies that demonstrated not-previously-described patterns of reactivity or repeatedly weak reactivity against one type of cell, monoclonal Fab/phage were prepared on a least 4 separate occasions to verify the patterns of reactivity.

For inhibition studies, the ability of antibodies with different Rh(D) epitope specificities to compete with each other for binding was assessed by preparing stocks of each clone in both a soluble Fab form and a phage-displayed form. Pair-wise combinations of soluble Fabs and Fab/phage were prepared and added to Rh(D)-positive RBCs. The resulting incubation mixes comprised 50 μl of a 3% suspension of RBCs, 100 μl of undiluted soluble Fab, and 100 μl of Fab/phage diluted to its highest agglutinating titer. Following a 1-hour incubation at 37° C., RBCs were washed, resuspended in anti-M13 antibody, and placed in microplate wells as described above. That the amount of soluble Fab present in an incubation mixture was sufficient to compete away a Fab/phage that shared the same binding site was determined by verifying that each soluble Fab preparation could block its own Fab/phage.

Inhibition experiments were also performed using pair-wise combinations of soluble Fabs instead of soluble Fab and Fab/phage combinations. In this type of experiment, pairs of soluble Fabs specific for different epitopes were chosen such that one Fab contained a λ light chain and the other a κ light chain. Incubations with RBCs were performed with one Fab in excess and the other in limiting amounts. Blocking of the latter antibody was assessed using a secondary antibody (anti-λ or anti-κ) specific for its light chain isotype.

Nucleotide Sequencing and Analysis

Plasmid DNA for sequencing was prepared using the Qiawell™ system (Qiagen, Chatsworth Calif.). Double-stranded DNA was sequenced using light chain or heavy chain immunoglobulin constant region reverse primers or a set of unique pComb3H vector primers that anneal 5' to the respective immunoglobulin chain (Barbas et al., 1991, Methods: A Companion to Meth. Enzymol. 2:119; Roben et al., 1995, J. Immunol. 154:6437) and automated fluorescence sequencing (Applied Biosystems, Foster City, Calif.). Sequence analysis and variable region germline assignments were performed using DNAplot (Althaus et al., 1996, DNAPLOT, http://www.mrc_cpe.cam.ac.uk/imt_doc/DNAsearch.html) and the V Base Directory of Human V Gene Sequences (March 97 update; Tomlinson et al., 1996, V Base Directory of Human V Gene Sequences, http://www.mrc_cpe.cam.ac.uk/imt_doc/vbase_home_page.html). Germline assignments were corroborated with the MacVector (v. 6.0) software package (Oxford Molecular Group, Oxford, UK) against the same database. Multiple sequence alignments and predictions of isoelectric point were calculated using the Pileup and Isoelectric programs of the GCG software package (v. 8.0.1; GCG, Madison Wis.). Statistical analysis was performed with Statview (Abacus Concepts, Berkeley Calif.).

The results of the experiments presented in this Example are now described.

Sequence Analysis of Anti-Rh(D) Heavy and Light Chains

Example 1 describes the use of Fab/phage display and cell-surface panning to isolate a large array of anti-Rh(D) antibodies from the peripheral blood lymphocytes of a single hyperimmunized donor. Separate $\gamma_1\kappa$ and $\gamma_1\lambda$ Fab/phage display libraries were constructed and contained $7 \times 10^7$ and $3 \times 10^8$ independent transformants, respectively, based on electroporation efficiency. Each library was panned independently using a simultaneous positive/negative selection strategy with magnetically-labeled Rh(D)-positive RBCs and unmodified Rh(D)-negative RBCs as described. Following two rounds of panning, 32 of 36 $\gamma_1\lambda$ and 15 of 15 $\gamma_1\kappa$ clones were positive for anti-Rh(D) activity. After the third round of panning, 24 out of 24 $\gamma_1\lambda$ and 12 out of 12 $\gamma_1\kappa$ clones were positive. Nucleotide sequencing of the 83 positive clones revealed a total of 28 unique heavy and 41 unique light chains. Due to combinatorial effects during phage display library construction, heavy and light chain gene segments paired to produce 53 unique Fab antibodies.

Anti-Rh(D) Heavy Chains

Figure 7A:
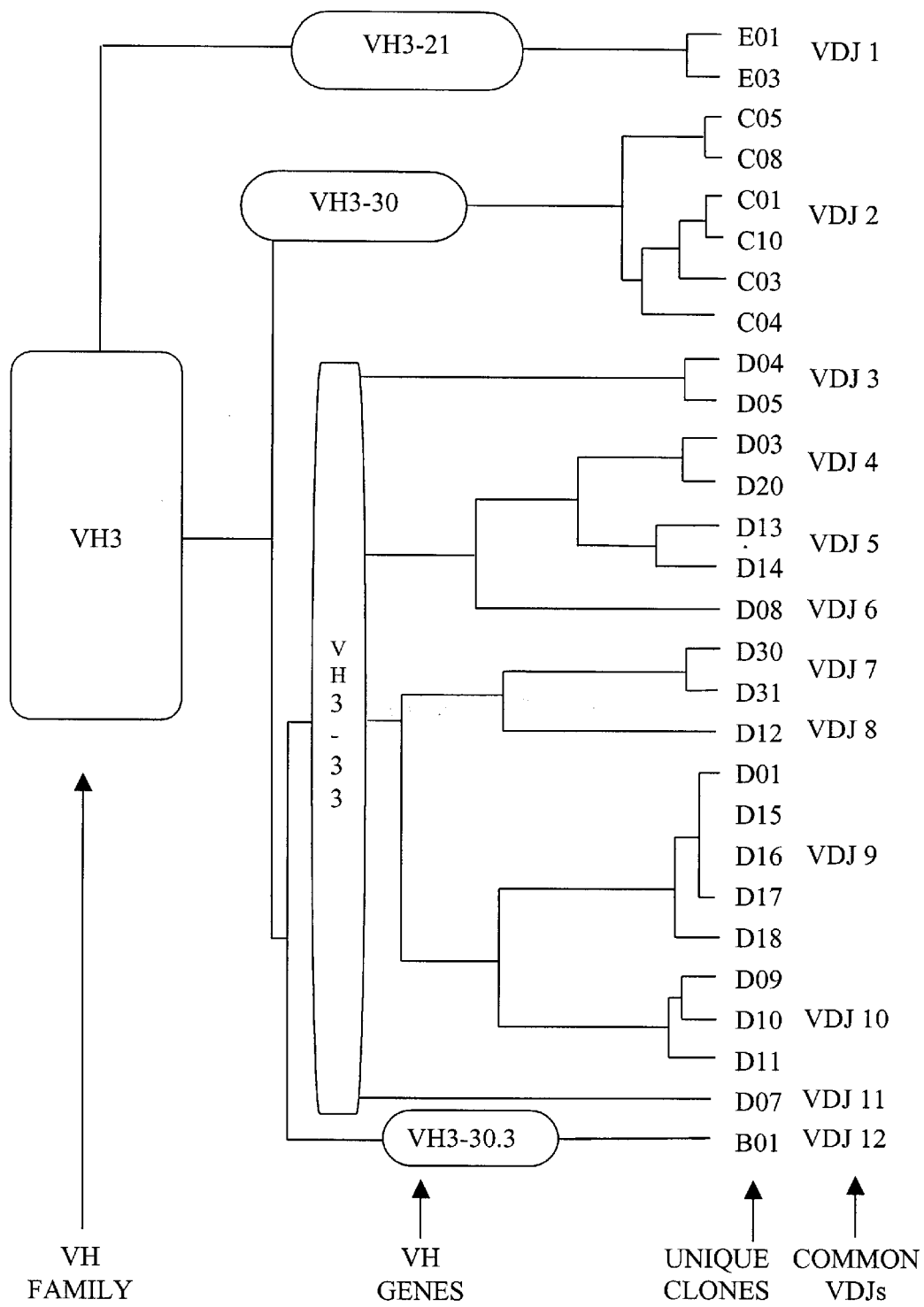
FIG. 7A is a dendrogram which depicts the relationship among the anti-Rh (D) heavy chains described herein in Example 2. The 28 unique heavy chain clones are organized by $V_H$ family, $V_H$ germline gene, and VDJ rearrangement. Each heavy chain clone is identified by a numeral preceded by a letter ("B" through "E") which denotes its gerinline gene. The 28 heavy chains comprised 12 distinct VDJ regions, designated VDJ1–VDJ12. Clones with identical VDJ joins putatively result from intra-clonal diversity of 12 original B lymphocytes.
Figures 1, 8B:
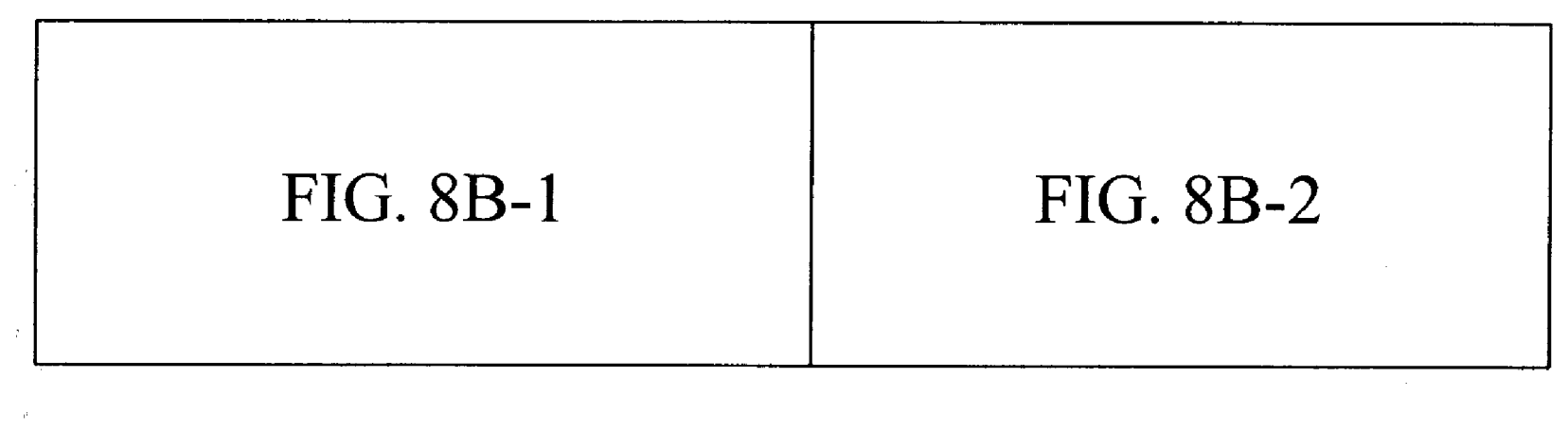
Figure 8C:
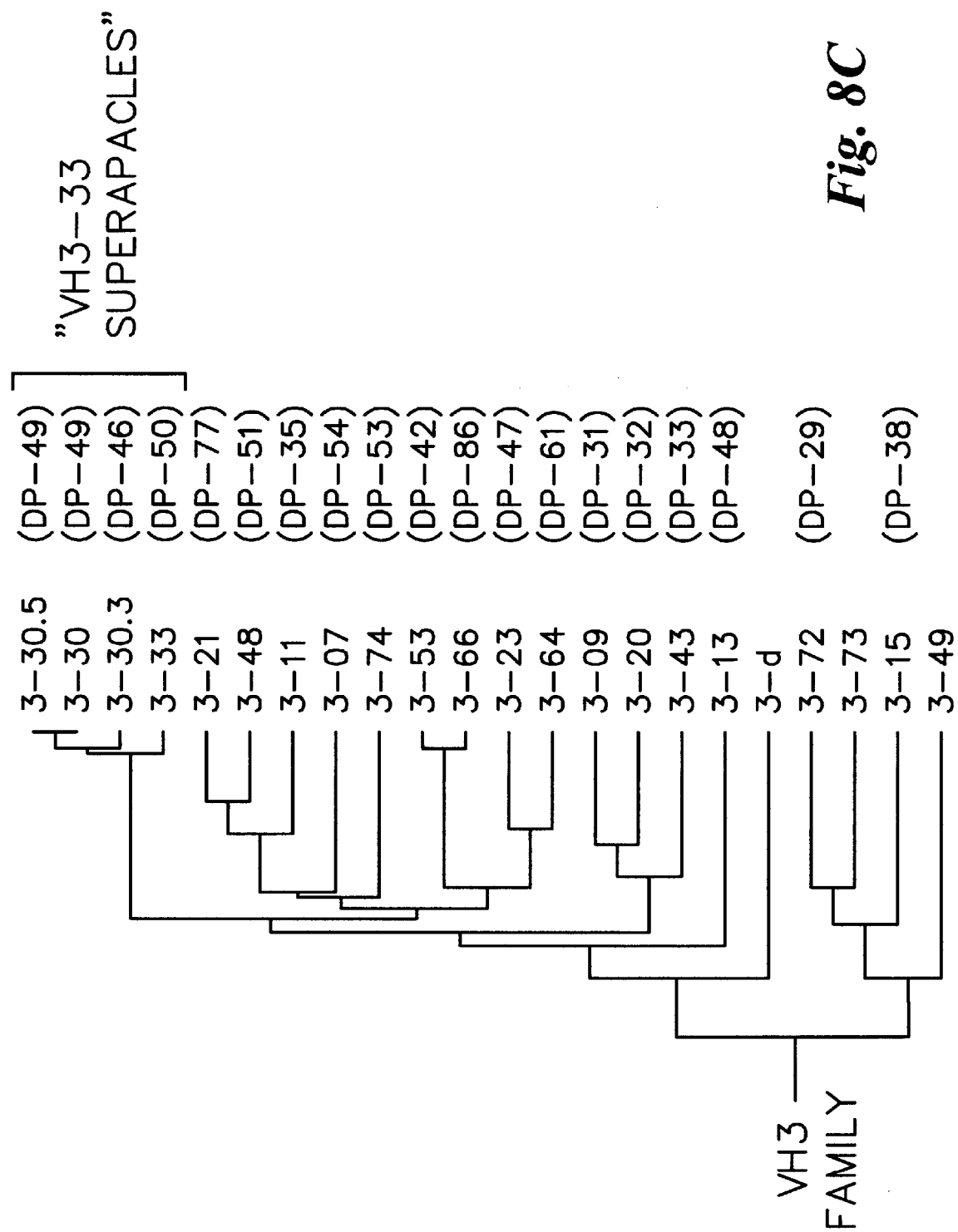
FIG. 8C is a dendrogram which depicts the relationship among human VH3 family germline genes, and illustrate relatedness of VH3-21, VH3-30. VH3-33, and VH3-30.3 and the surprising restriction in $V_H$ gene usage. The VH3-30.5 gene is present in only certain haplotypes and is identical to VH3-30.

All of the heavy chain sequences used $V_H III$ family-encoded gene products, as indicated in FIGS. 7 and 8. Several heavy chain sequences shared identical VDJ joining regions, and 12 unique VDJ rearrangements were identified. These rearrangements were designated VDJ1 through VDJ12. Alignment of these sequences against the V Base Directory of Human V Gene Sequences revealed that only four $V_H III$ genes were used by these antibodies: VH3-21, VH3-30, VH3-33, and VH 3-30.3. VH3-21 was used by 1 of the 12 VDJs and 2 of the 28 clones; VH3-30 was used by 1 VDJ and 6 clones; VH3-33 was used by 9 VDJs and 19 clones; and VH3-30.3 was used by 1 VDJ and 1 clone. Interestingly, VH3-30, VH3-33, and VH3-30.3 comprise a set of closely related genes (>98% homology; FIG. 8B) and their next nearest neighbor, VH3-07, is only 90% homologous (FIG. 8C). Hereafter, these three genes are referred to as the "VH3-33 superspecies". Heavy chain E1 differed from VH3-21 by six mutations and differed from VH3-48 by ten mutations; hence, it was assigned to the former germline gene. Because there were no common mutations among the VH3-33 clones, it is highly probable that the donor possessed the VH3-33 germline gene. However, we could not formally rule out gene duplication with allelic variants of VH3-33 or the existence of variant alleles of the other germline genes in the donor. The isolation of clones sharing multiple VDJ joining regions strongly suggests that cloning artifacts cannot account for the $V_H$ restrictions observed.

Neither $J_H$ nor D segments showed restriction. At least 9 different D segments were used and $J_H$ gene utilization comprised $J_H 6$ (5 VDJs and 9 clones), $J_H 4$ (4 VDJs and 10 clones), $J_H 3$ (2 VDJs and 8 clones) and $J_H 5$ (1 VDJ and 1 clone). All four $V_H$ genes were Chothia class 1-3 (Chothia et al., 1992, J. Mol. Biol. 227:799), and the CDR3s showed a narrow range of length from 15 to 19 residues.

Figure 9:
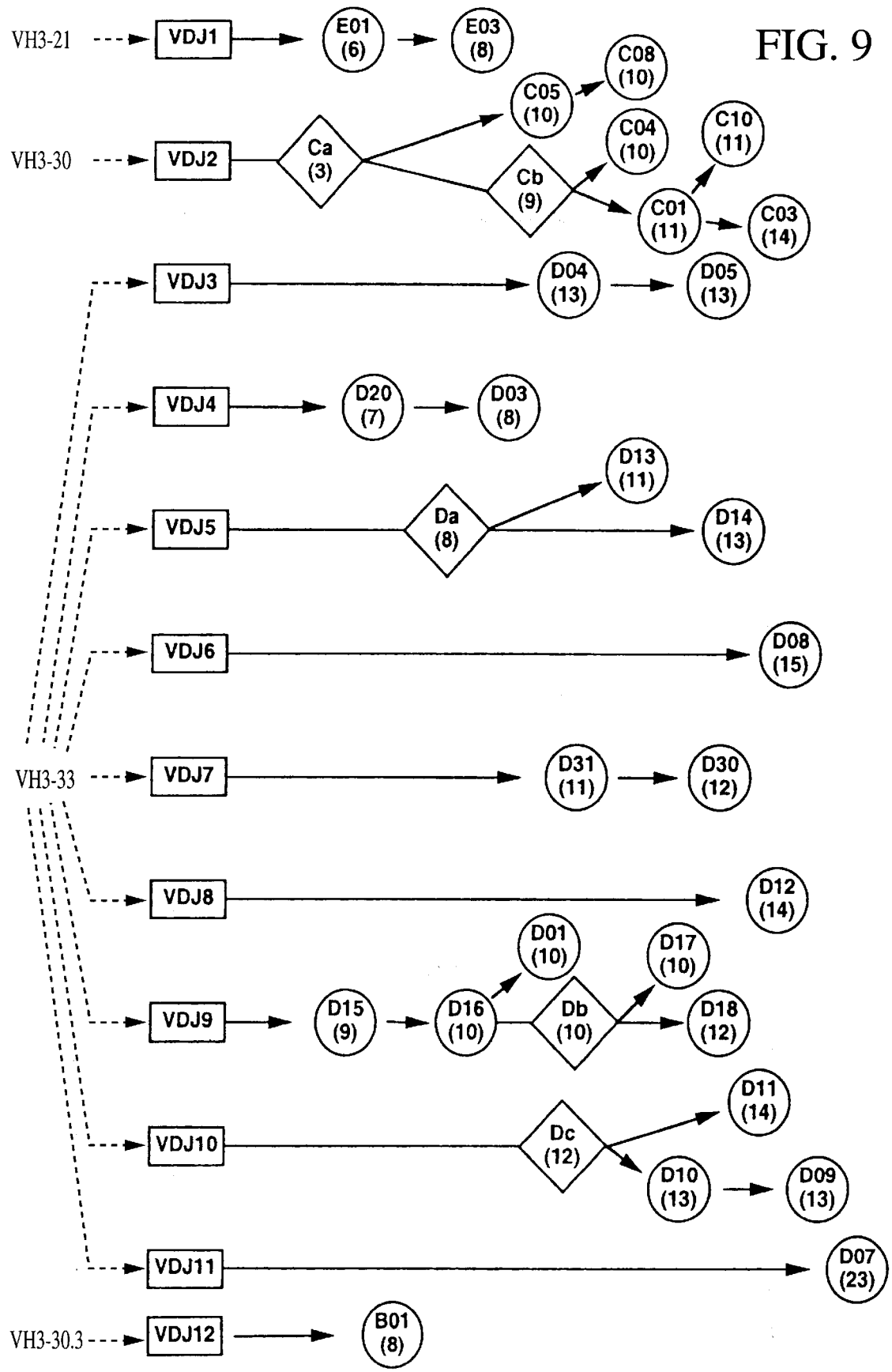
FIG. 9 is an ontogenic tree of anti-Rh(D) heavy chains constructed using nucleotide alignment data. Circles represent isolated and sequenced clones, and diamonds represent putative intermediates. The number of nucleotide mutations from its germline $V_H$ gene is indicated in parentheses below the clone name. The distance along the horizontal axis represents the degree of mutation (including J segments) within the constraints of the diagram.

Because rearranged heavy chain genes demonstrate extensive diversity, clones sharing identical VDJ rearrangements are generally considered to have arisen from the same clone. Based upon nucleotide alignment with the germline genes, the ontogeny tree in FIG. 9 was constructed for the 12 VDJs and 28 clones. By using the most parsimonious mutation scheme (i.e. postulating the minimum number of mutations), putative intermediate antibodies were derived for several of the VDJs and were designated Ca, Cb, Da, Db, and Dc (FIGS. 8A and 9). Compared with the isolated heavy chain clones, which had between 6 and 23 nucleotide differences from their germline counterparts, these putative intermediates had between 3 and 12 mutations from germline. Based upon the ontogeny tree, the number of independent mutations could be tabulated among the clones. The most commonly mutated residues were 52a and 58 (7 independent mutations), followed by residues 30, 31 and 50 (6 mutations), and residue 55 (5 mutations). In the VH3-33 superspecies, residues 52a and 58 in CDR2 are tyrosine residues and residue 52a was mutated to phenylalanine in 6 of the 11 VDJs derived from VH3-33 superspecies $V_H$ genes. Mutations at residue 58 comprised glutamate (3), aspartate (2), histidine (1) and asparagine (1). The AGY serines at residues 30, 31 and 55 were mutated to a number of different amino acids, although the AGY serine at 82b was conserved in all clones. The valine at residue 50 in the VH3-33 superspecies also had a diverse set of mutations. This distribution of "hot spots" is similar to that seen with non-productive rearrangements as previously reported by Dörner et al (1997, J. Immunol. 158:2779).

Anti-Rh(D) Light Chains

Figures 1, 3, 10A:
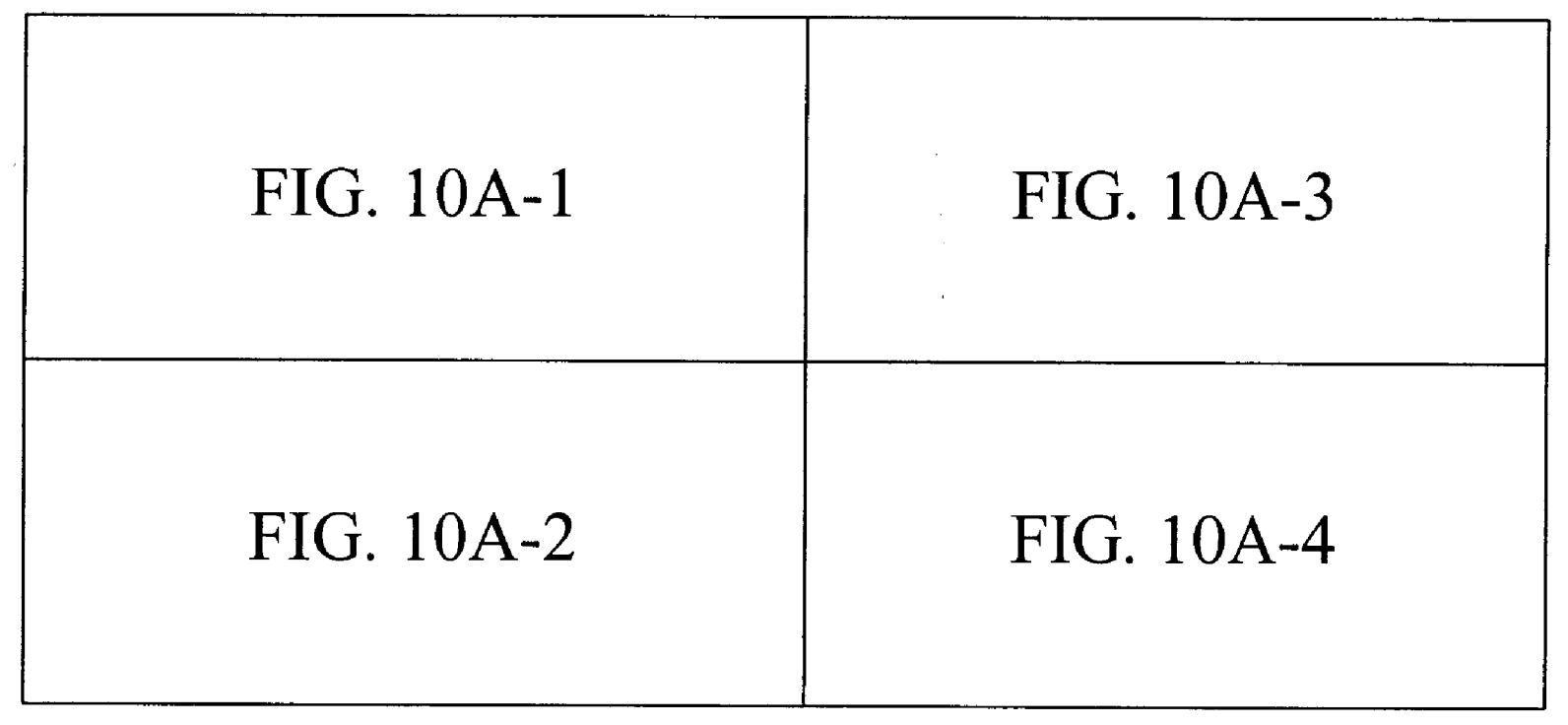
Figures 1, 10B:
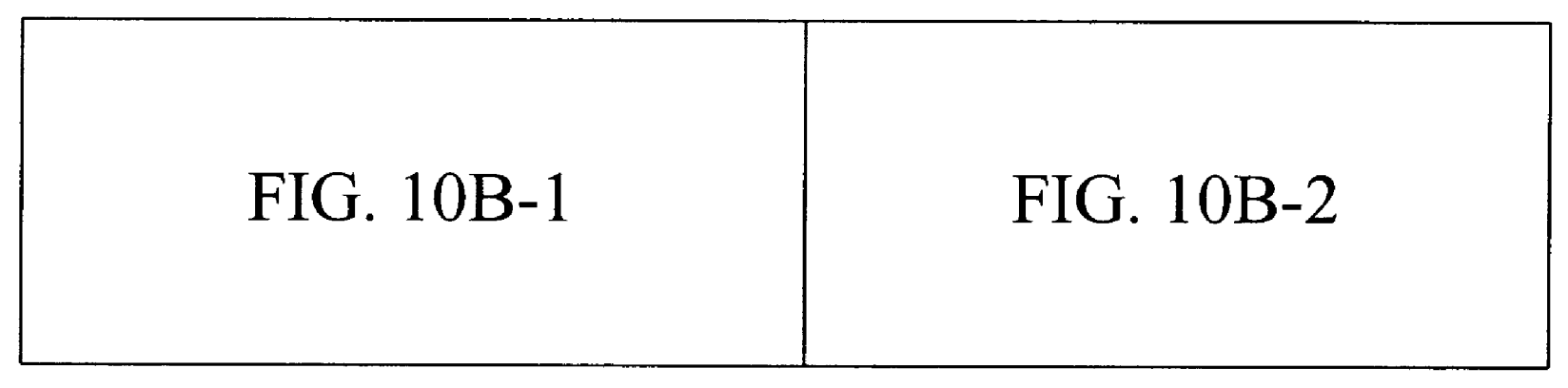

Seventeen of the 18 $\kappa$ light chains were from the $V_\kappa I$ family and the remaining light chain originated from a $V_\kappa II$ family member germline gene (FIG. 10). Only four $V_\kappa$ germline genes were used (15 clones were derived from DPK9 alone), and the $\kappa$ light chain clones had between 1 and 49 mutations from their corresponding $V_\kappa$ germline genes. All five of the known $J_\kappa$ genes were used and were each joined to the DPK9 gene in one or more clones. Because the light chains showed considerably less diversity in their joining regions than the heavy chains, it was difficult to assign common clonal origins. However, an ontogeny tree was constructed by grouping common V and J gene segments along with common mutations. Based upon this analysis, the 18$\kappa$ chains comprised at least 10 different recombination events.

Figures 1, 3, 11A:
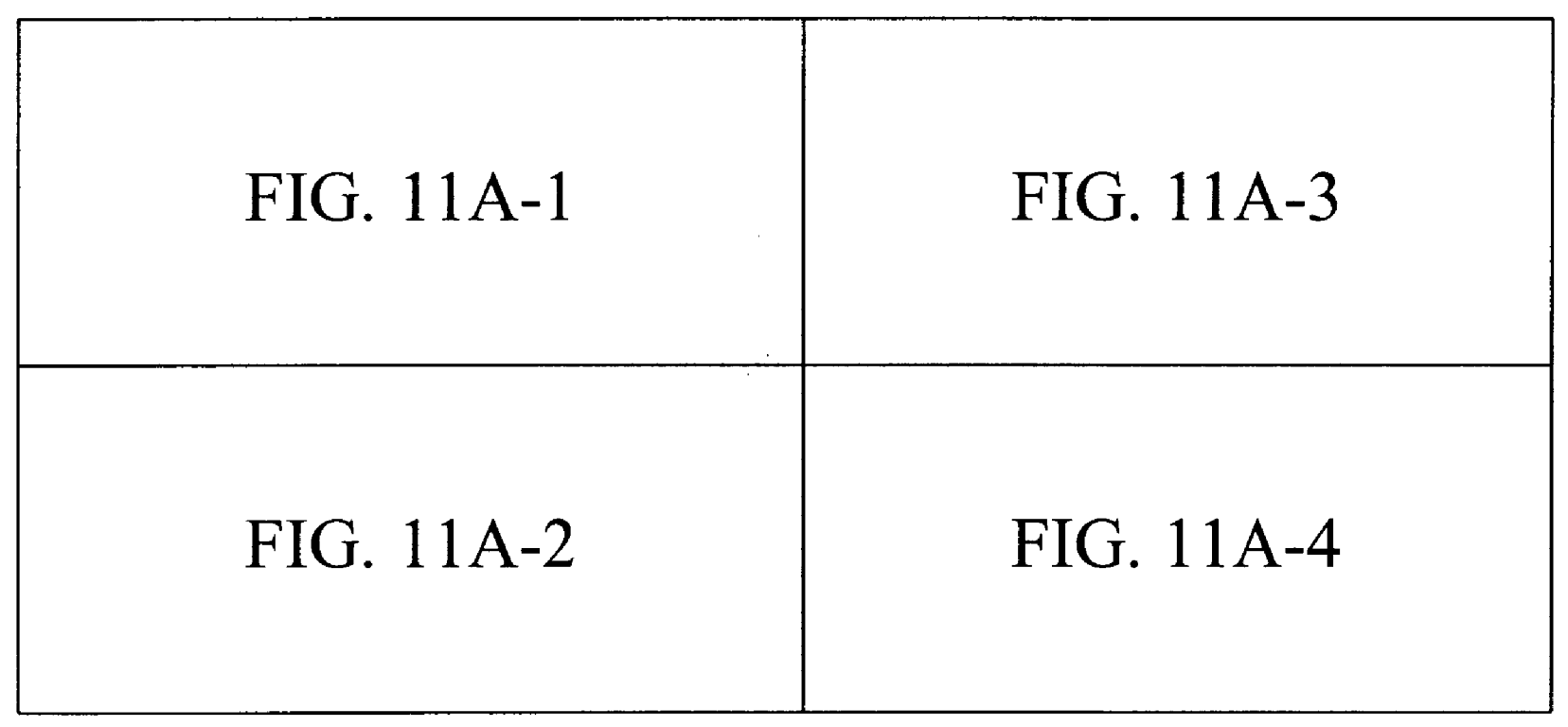
Figure 11B:
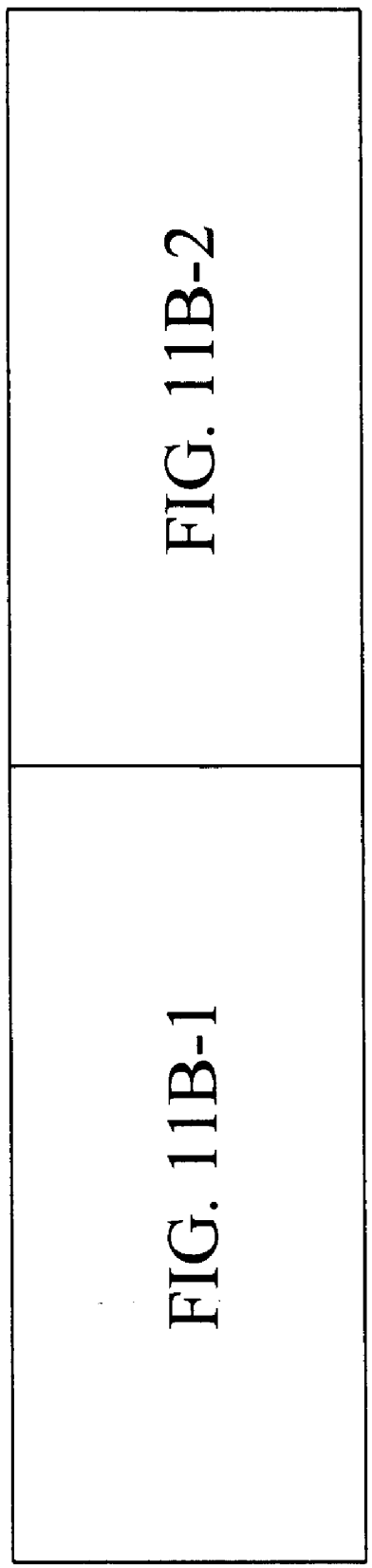
FIG. 11B, comprising

$\lambda$ light chains were restricted by their $J_\lambda$ gene usage but showed no restriction in their use of $V_\lambda$ genes (FIG. 11). The 23$\lambda$ light chains all used the $J_\lambda 2$Vasicek gene but were derived from $V_\lambda I$ (12 clones), $V_\lambda III$ (5), $V_\lambda VII$ (3), $V_\lambda II$ (2) and $V_\lambda IV$ (1) family genes. The number of mutations ranged from 2 to 41 from the nearest germline $V_\lambda$ gene. Based upon common joining regions and mutations, these 23 1 light chains were derived from at least 13 different B cells.

Assessment of the Diversity of the Non-Panned Libraries

Figure 12A:
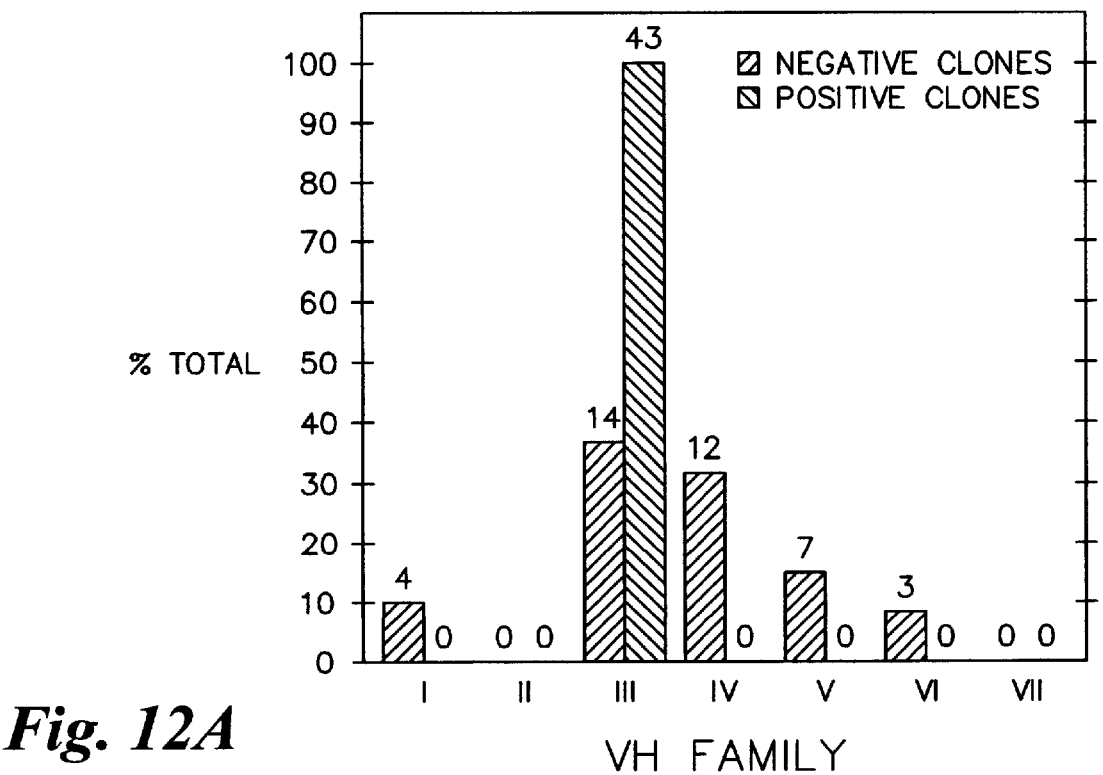
FIGS. 12A, 12B, and 12C, is a trio of graphs which depict comparisons of variable region gene family usage for anti-Rh(D)-specific clones and randomly-picked, non-Rh(D)-binding clones from original $γ_1κ$ and $γ_1λ$ non-selected libraries. Upwardly-angled hatched bars reveal heterogeneity in $V_H$ (FIG. 12A), $V_κ$ (FIG. 12B), and $V_λ$ (FIG. 12C) family representation before selection for anti-Rh(D) specificity. Numbers above bars represent absolute number of clones in that group.
Figure 12B:
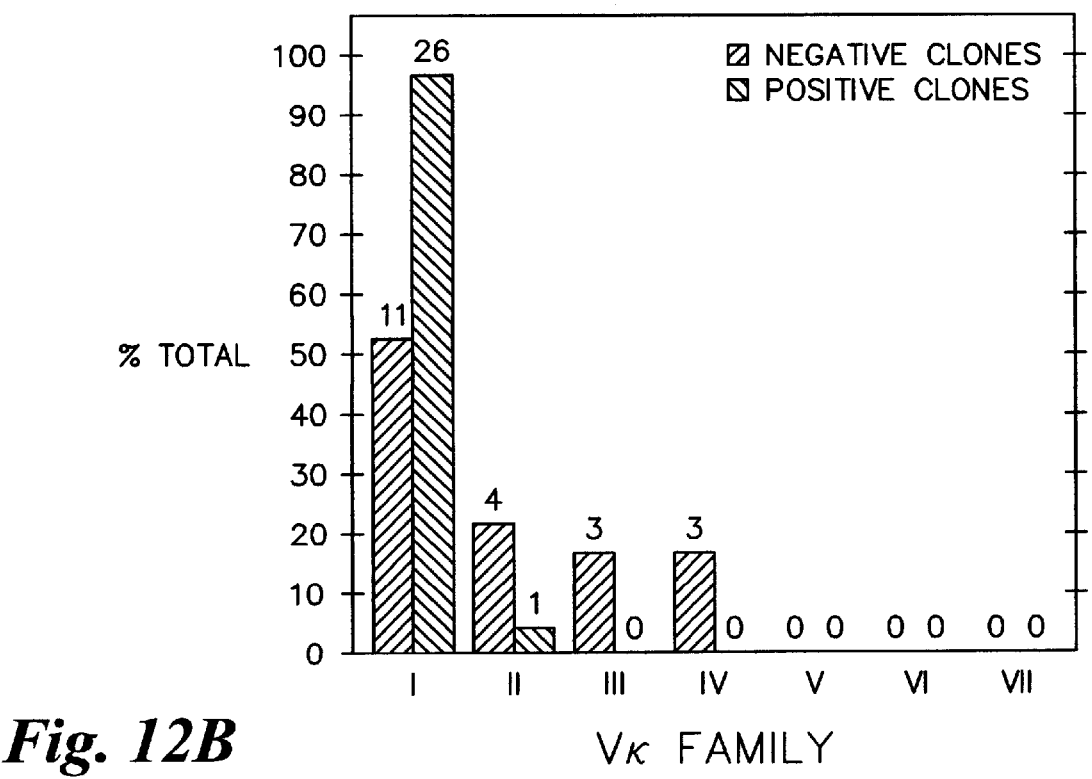
Figure 12C:
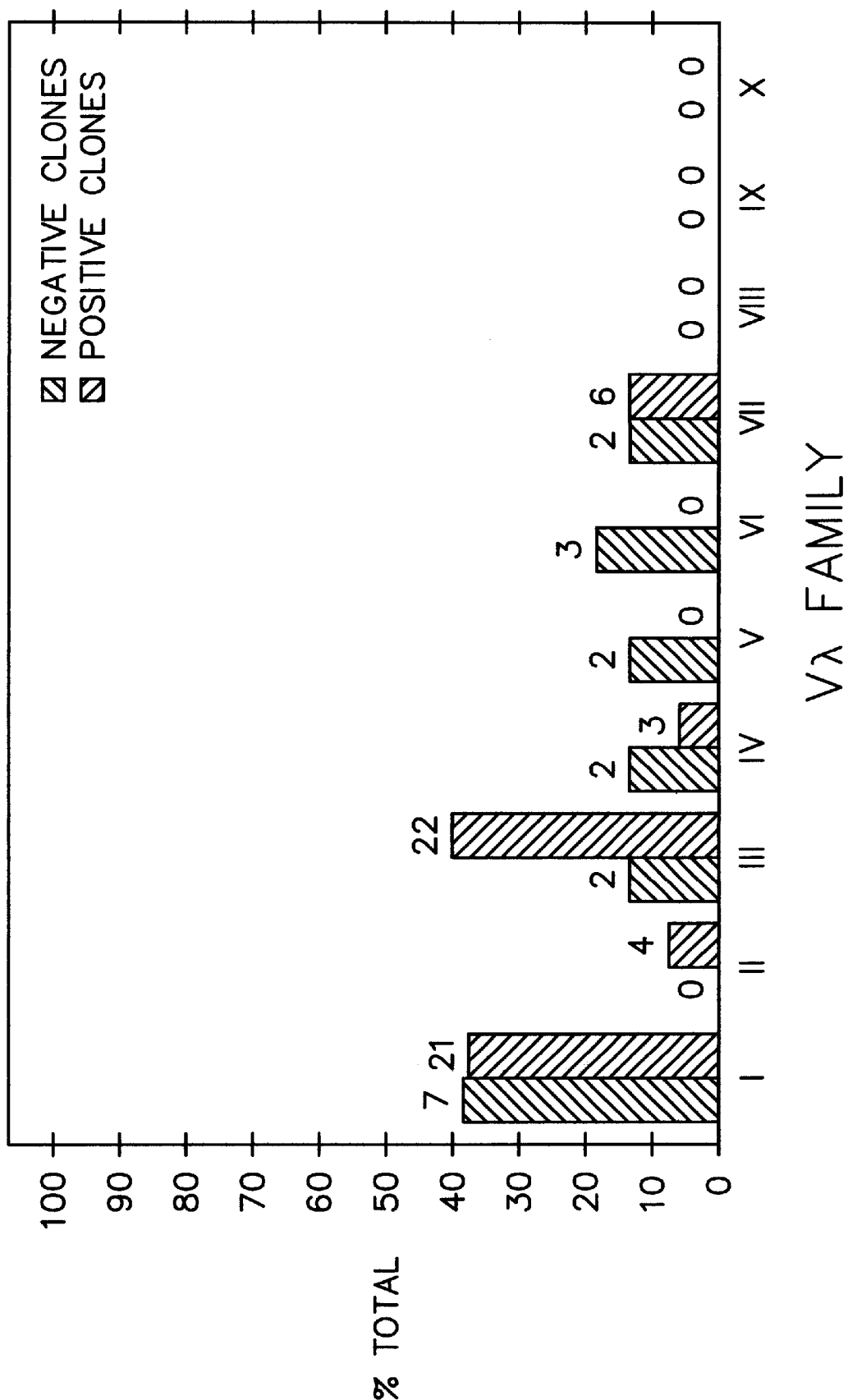

In order to determine whether the apparent restriction in gene usage of the anti-Rh(D) antibodies could have been due to pre-selection factors (i.e. cloning artifacts), the diversity of the non-panned $\gamma_1\kappa$ and $\gamma_1\lambda$ Fab/phage libraries was assessed. By sequencing 39 randomly-picked clones, we determined that there were no duplicate heavy or light chain sequences, and that there was significant heterogeneity in V gene family representation before selection (FIG. 12). In fact, the variable region gene family distribution was not unlike that found by other investigators for IgG-secreting lymphocytes in adult peripheral blood (Stollar, 1995, Ann. NY Acad. Sci. 764:547). Furthermore, of the 14 $V_H$III-encoded negative clones, only one used a VH3-33 super-species germline gene (VH3-30.3); the other 13 were encoded by VH3-07 (3), 3-09 (2), 3-15 (2), 3-48 (2), 3-72 (2), 3-23 (1), and DP-58 (1). Therefore, the restriction of the 83 anti-Rh(D) clones to the VH3-33, 3-30, 3-30.3 and 3-21 genes is significant and not a result of skewed representation of certain germline genes within the originally constructed $\gamma_1\kappa$ and $\gamma_1\lambda$ Fab/phage libraries.

Heavy and Light Chain Contribution to Rh(D) Epitope Specificity

Because of the conformational dependency of Rh(D) antigenicity, Rh(D) "epitopes" have been classically defined through the use of RBCs obtained from rare individuals whose cells appear to produce Rh(D) antigens "lacking" certain epitopes. Examining the pattern of agglutination of a particular anti-Rh(D) monoclonal antibody with such sets of partial Rh(D) RBCs enables one to categorize that antibody's fine specificity.

Monoclonal Fab/phage preparations were prepared in triplicate for each of the 53 anti-Rh(D) clones and tested against a panel of Rh(D) category cells IIIa/c, IVa, IVb, Va, VI, and VII. This panel of cells can differentiate between the Rh(D) epitope specificities as described by Lomas et al. (1989, Vox Sang 57:261; designated epitopes epD1, epD2, epD3, epD4, epD5, and epD6/7). Agglutination experiments using the Fab/phage clones demonstrated five different patterns of reactivity, including a new pattern which had not been described in the original study by Lomas et al. or in the more recently-described (Scott, 1996, Transfus. Clin. Biol. 3:333; Stollar, 1995, Ann. N.Y. Acad. Sci. 764:547) 9-, 30-, or 37-epitope systems (as indicated by the data depicted in FIGS. 13 and 14). Although nearly all Fab/phage gave unequivocal agglutination reactions, a few antibodies gave repeatedly weak patterns of reactivity against one of the panel cells. For these reactions, monoclonal Fab/phage were prepared on at least 4 separate occasions to verify the patterns of reactivity.

The most commonly-recognized epitope was epD6/7, against which 13 of the clones described herein were directed. Interestingly, monoclonal anti-Rh(D) clones isolated using conventional tissue culture methods are most often specific for epD6/7 (Mollison et al., 1993, In: *Blood Transfusions in Clinical Medicine*, 9th ed., Blackwell Scientific, Oxford, U.K.). EpD2, epD1, and epD3 were recognized by 10, 7, and 2 clones, respectively. Six clones agglutinated cells of categories IIIa/c, IVa, and VII, but not of categories IVb, Va, and VI, and were designated anti-"epDX". This pattern is identical to epD1, except that the IVa cell is agglutinated. Three clones gave intermediate reactions with cell IVa, but otherwise showed patterns consistent with epDX or epD1. These clones were designated epDX[1] or epD1[X] depending on whether this reactivity against cell IVa was stronger or weaker, respectively (see FIG. 14). Similarly, reaction patterns for epD1 and epD2 differ by a positive reaction with the category Va cell; therefore, one clone was given epD2[1] specificity because it gave only moderate reactivity against that cell. Such variable reactions against one or more partial Rh(D) cells have been observed for anti-Rh(D) monoclonal antibodies produced through conventional tissue culture methods (Tippett et al., 1996, Vox Sang. 70:123).

Figure 14A:
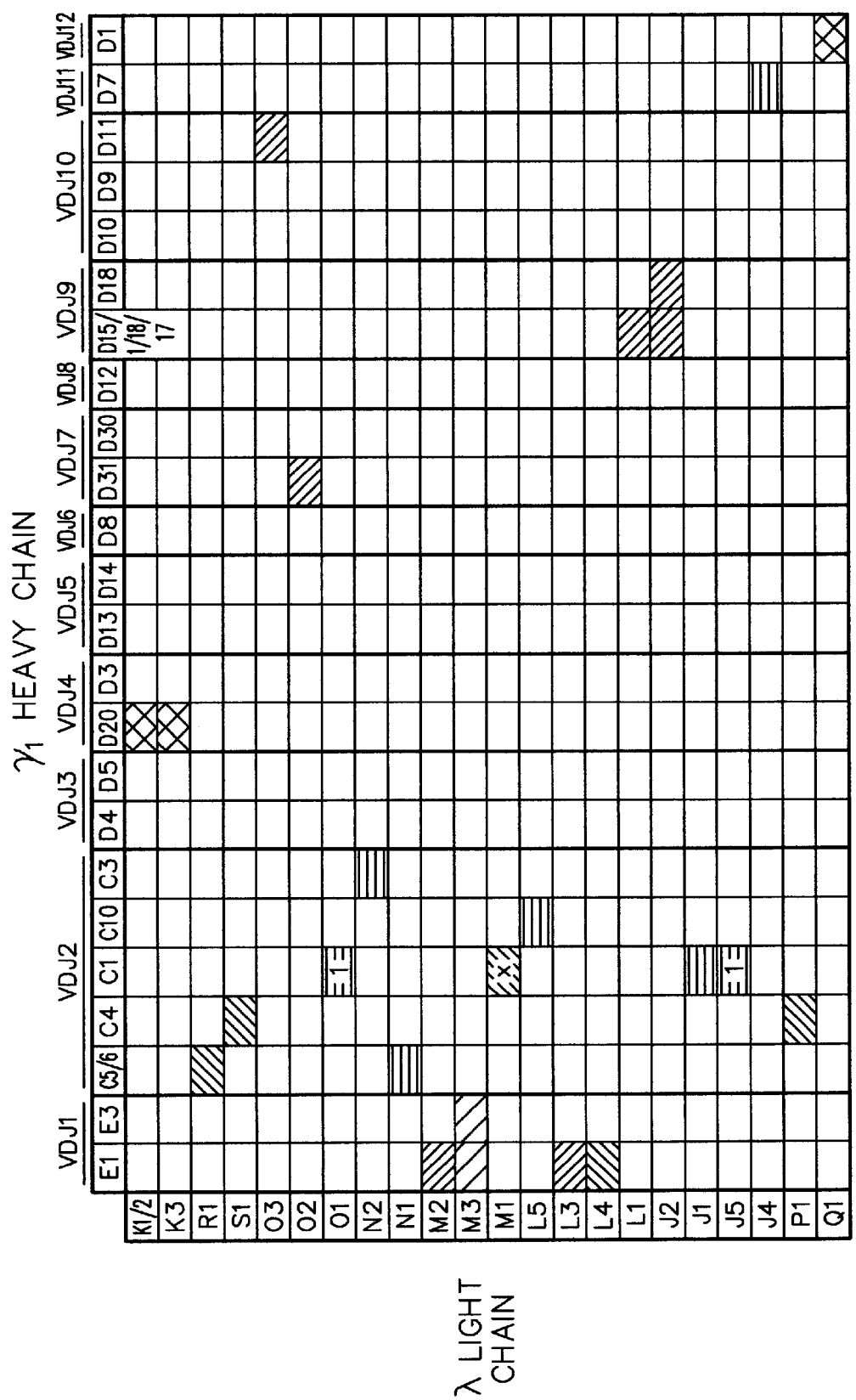
FIGS. 14A and 14B, is matrix illustrating the genetic composition and epitope specificity of anti-Rh(D) antibodies. The horizontal axis represents the unique $γ_1$ heavy chains and the vertical axis represents the unique (FIG. 14A) and (FIG. 14B) λ and κ light chains (based on amino acid sequence). A shaded pattern at the intersection of a heavy chain/light chain pair indicates the Rh(D) epitope specificity observed for that Fab/phage antibody. A few clones gave mixed patterns of reactivity as described herein. Although heavy chains D1, D15, D16, and D17 differ in nucleotide sequence, these chains have an identical amino acid sequence and thus comprise a single column. Similarly, heavy chains C5 and C8 and λ light chains K1 and K2 encode the same proteins. The pairings of these 28 heavy and 41 light chain nucleotide gene segments, which produced 53 unique Fab transcripts, encoded 43 different Fab proteins, as indicated in the matrix.
Figure 14B:
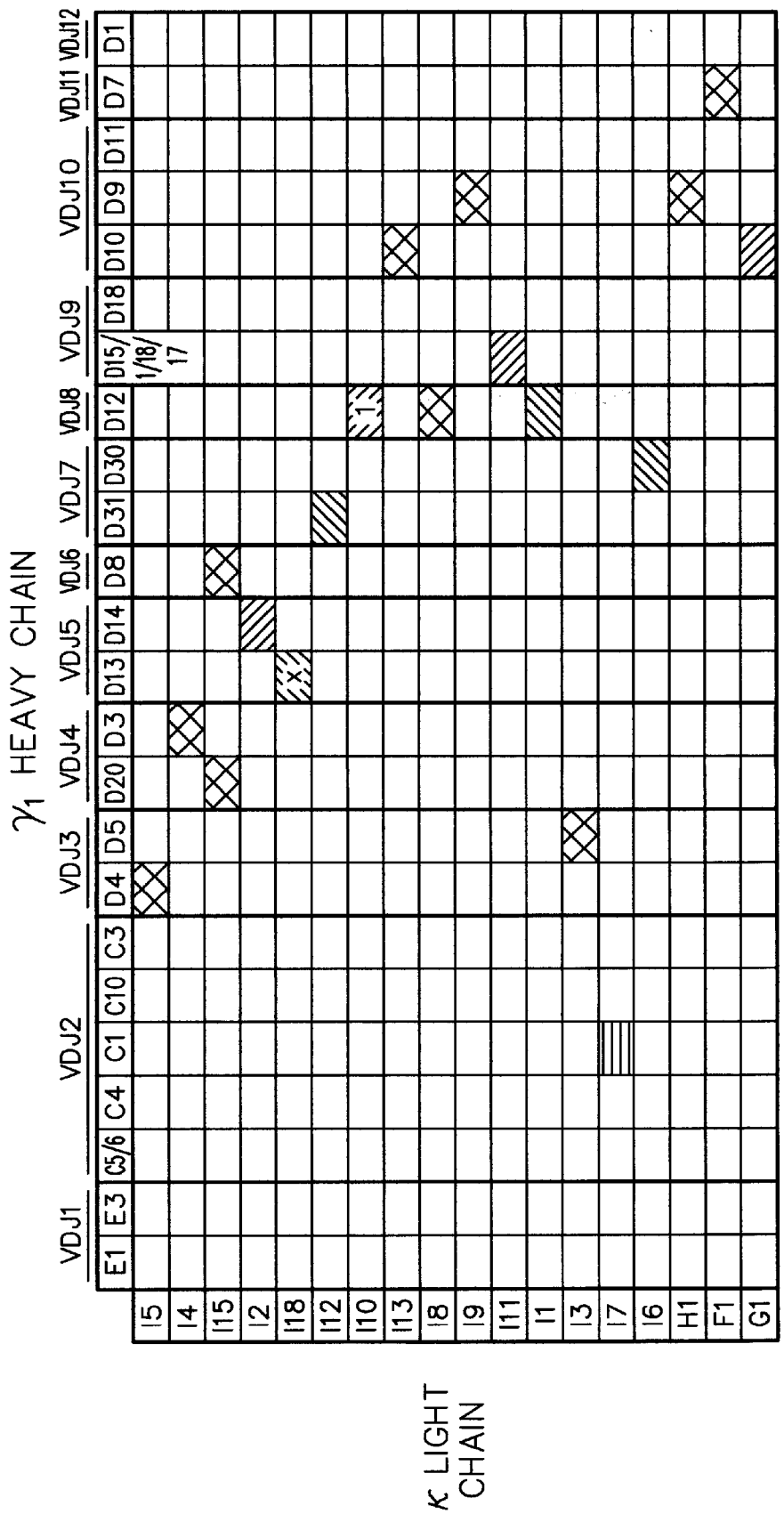

Because of the reassortment of heavy and light chain gene segments that occurs during the construction of a phage display library, a number of clones were isolated that shared either a heavy (e.g. E1) or light (e.g. M3) chain sequence (FIG. 14). Some heavy chains were found to have paired with both κ and λ light chains (e.g. C1, D20) and each demonstrated anti-Rh(D) specificity. Interestingly, some heavy chains (e.g. E1, D12) mapped to different epitopes depending upon the light chains with which they were paired. In particular, the light chains of two such clones, E1/M2 and E1/M3, differed by only three amino acid residues (FIG. 11) and these differences appear to confer specificity for epD2 vs. epD3.

Inhibition Studies

Figure 15A:
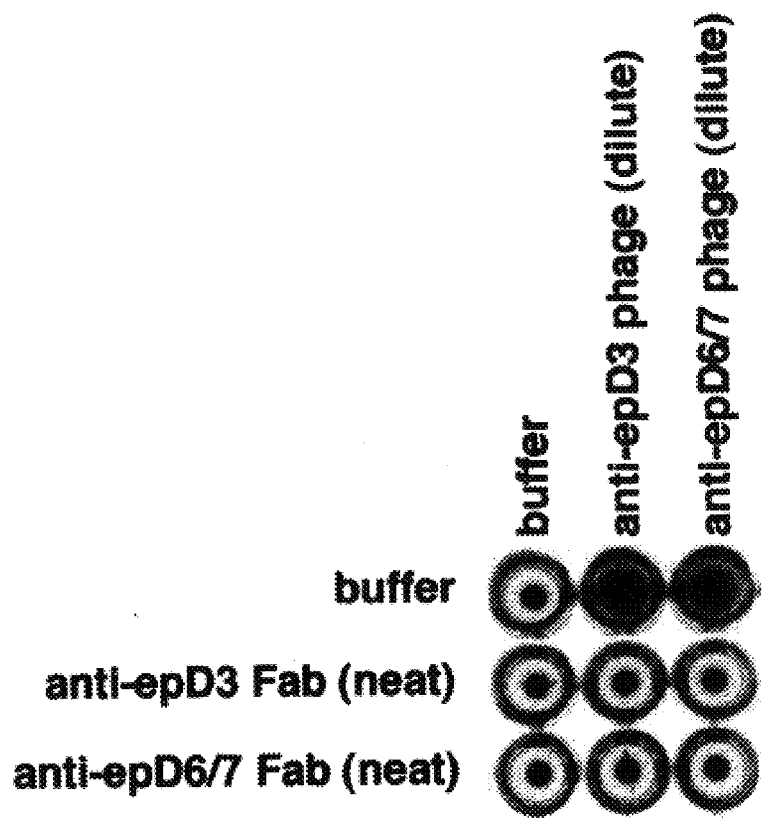
FIGS. 15A, 15B, and 15C, depicts the results of inhibition studies performed using recombinant anti-Rh(D) antibodies. The figures show results of representative experiments demonstrating the mutual inhibition of antibodies directed at two different Rh(D) epitopes (in this example, epD3 and epD6/7, FIGS. 15A and 15C), but not between an Rh(D) antibody and an unrelated recombinant anti-RBC antibody (an anti-blood group B antibody, FIG. 15B).
Figure 15B:
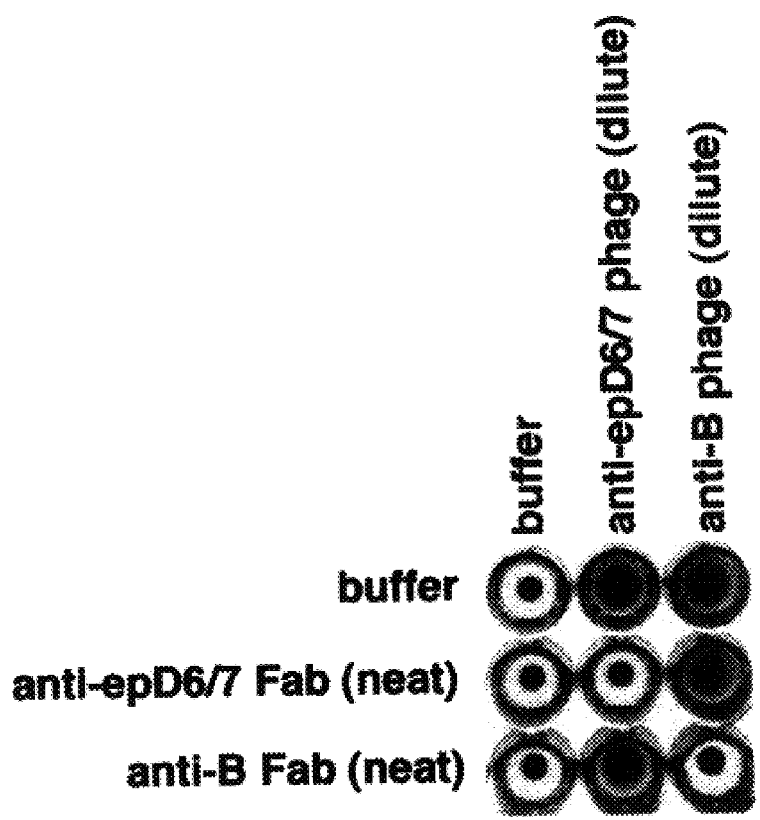
Figure 15C:
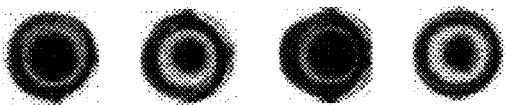

To investigate the topological relationships among the Rh(D) epitopes, inhibition studies were performed. Gorick et al. (1988, Vox Sang. 55:165) used pairs of non-labeled and $^{125}$I-labeled anti-Rh(D) monoclonal antibodies to demonstrate that antibodies to at least three different Rh(D) epitopes (subsequently identified as epD1, D6 and D7; Lomas et al., 1989, Vox Sang. 57:261) could inhibit one another. Recombinant antibodies to five Rh(D) epitopes were used to confirm and extend those findings (FIG. 15). In one series of experiments, the ability to express each antibody in both a soluble Fab as well as phage-displayed form was exploited to determine whether a soluble Fab directed against one epitope would inhibit the agglutination induced by an Fab/phage directed against a different epitope. Reciprocal pairs of soluble Fab and Fab/phage specific for epD1, epD2, epD3, epD6/7, and epDX were tested. All ten combinations showed mutual inhibition patterns (illustrated in FIG. 15A for an anti-epD3/anti-epD6/7 combination). To show that this inhibition was not due to non-specific factors, a control with an irrelevant RBC-binding recombinant antibody (an anti-blood group B antibody) was performed (FIG. 15B). That sufficient inhibitory amounts of soluble Fab was present were first verified by demonstrating that each soluble Fab could inhibit its own Fab/phage (FIGS. 15A and 15B; samples on diagonal). Similar results were obtained using pairs of soluble Fabs which differed in their light chain isotype composition (FIG. 15C).

Isoelectric Point Analysis of Anti-Rh(D) Antibodies

The restriction in $V_H$ germline gene usage to only four $V_H$III family members was intriguing in light of their ability to confer specificity to a number of Rh(D) epitopes. $V_H$ germline gene segments used to encode anti-Rh(D) antibodies are among the most cationic segments available in the human $V_H$ repertoire which may be used to account for the relatively high pI of polyclonal anti-Rh(D)-containing antisera (Boucher et al., 1997, Blood 89:3277; Abelson et al., 1959, J. Immunol. 83:49; Frame et al., 1969, Immunology 16:277). Although the cationic nature of the antibodies may be important for binding to Rh(D), a constitutive net positive charge may be necessary to permeate the highly negative RBC ζ potential, thus permitting antibody to contact antigen (Mollison et al., 1993, In: *Blood Transfusion in Clinical Medicine*, 9th ed., Blackwell Scientific, Oxford, U.K.). In either case, analysis of the predicted pI for the 28 heavy chains and 41 light chains isolated here showed an interesting phenomenon for the heavy chains, as compared with the light chains. Using the pI interval scale of Boucher et al. (1997, Blood 89:3277), the average pI of the four germline $V_H$ segments used to encode the 28 heavy chains is high (9.87±0.15), significantly higher than that of 39 randomly-picked, non-Rh(D) binding clones from the original non-panned libraries (9.24±0.80, $P<10^{-5}$). Similar to the results of Boucher et al., the addition of D and $J_H$ segments and the introduction of somatic mutation did not significantly change the pI of the average anti-Rh(D) heavy chain (9.81±0.33, P<0.37). However, for the light chains, the average pI of their germline counterparts was not cationic, but the light chains became so through the addition of $J_L$ segments and somatic mutation. Overall, for all 18κ and 23λ light chains, paired t-test analyses before and after somatic mutation showed a significant increase in net positive charge when comparing germline $V_L$ (6.63±1.47) with expressed $V_L$ (7.28±1.51, P<$10^{-3}$) or germline $V_L J_L$ (7.43±1.47) with antibodies, although one heterohybridoma was an outlier, having a CDR3 length of 28 residues. κ light chains were biased towards $V_\kappa 1$ family members and λ light chains demonstrated the preferential use of the $J_\lambda 2$Vasicek gene. The only qualitative discrepancy was in $V_\lambda$ family usage where Fab/phage clones demonstrated a slight preference for $V_\lambda I$ vs. $V_\lambda III$ family members for conventional monoclonal antibodies. However, in both cohorts, DPL16 was used more often than any other λ light chain gene.

TABLE 3

Comparison of IgG Fab/phage library-derived anti-Rh(D) monoclonal antibodies prepared as described herein with those previously produced by conventional tissue culture methods

| Attribute | Previously Published* | Current Study | |
|---|---|---|---|
| Heavy Chains | | (by clone)† | (by VDJ) |
| VH3 family derived | 12/21 (57%) | 28/28 (100%) | 12/12 (100%) |
| VH3-33 superspecies‡/VH3 | 10/12 (83%) | 26/28 (93%) | 11/12 (92%) |
| VH3-33/VH3 | 9/12 (75%) | 19/28 (68%) | 9/12 (75%) |
| VH3-21/VH3 | 1/12 (8%) | 2/28 (7%) | 1/12 (8%) |
| VH4-34 derived | 2/21 (10%) | 0/28 (0%) | 0/12 (0%) |
| JH6 usage | 15/21 (71%) | 9/28 (32%) | 5/12 (42%) |
| CDR3 length | 16–20 (28§) | 15–19 | |
| κ Light Chains | | | |
| Vκ1 family derived/total ρ | 8/12 (67%) | 17/18 (94%) | |
| Jκ1 usage/total ρ | 4/12 (33%) | 6/18 (33%) | |
| Jκ2 usage/total ρ | 4/12 (33%) | 6/18 (33%) | |
| λ Light Chains | | | |
| Vλ1 family derived/total λ | 2/8 (25%) | 12/23 (52%) | |
| Vλ3 family derived/total λ | 5/8 (63%) | 5/23 (22%) | |
| DPL16 derived/V13 family | 3/5 (60%) | 4/5 (80%) | |
| Jλ2Vasicek usage/total λ | 6/8 (75%) | 23/23 (100%) | |

Notes for Table 3
*Compiled from a total of 21 sequences of IgG anti-Rh(D) antibodies isolated from multiple subjects originally published by Bye et., Hughes-Jones et al., Chouchane et al., and Boucher et al. and available from Genbank. One light chain (Oak-3) was not available in Genbank and was not included in the assessment.
†For heavy chains, left column tabulates each clone separately; right column tabulates clones on the basis of shared V-D-J joining regions
‡VH3-33 superspecies defined as the group of VH3 family germline genes comprising VH3-33, VH3-30, and VH30.3.
§CDR3 length outlier expressed $V_L J_L$ (8.55±1.35, P<$10^{-7}$). There was no significant increase in a similar analysis of 16 non-Rh(D) binding clones (P<0.59 and P<0.19, respectively). Examination of the light chain sequences listed in FIGS. 10 and 11 revealed that this increase in pI resulted from mutations that not only introduced positively-charged residues, but also eliminated some negatively-charged residues. There were 31 such events, 29 (91%) of which occurred in the light chain CDR regions.

Conventional and Phage-Displayed Anti-Rh(D) Monoclonal Antibodies

The phage-display derived anti-Rh(D) clones were compared with those produced by conventional tissue culture techniques (EBV-transformation and cell fusion). Despite the relatively small number of previously-published sequences for IgG anti-Rh(D) antibodies (N=21) and the fact that they were derived from over 10 different donors, there was surprisingly good correlation between the two groups, as indicated in Table 3. Both cohorts demonstrated a predominance of $V_H$III-family encoded germline genes, particularly those of the VH3-33 superspecies. CDR3 regions had similar lengths ranging from 15–19 residues for Fab/phage antibodies and 16–20 for conventional monoclonal It has been suggested in the literature that the VH4-34 (VH4.21) germline gene, a gene used by many autoantibodies and cold agglutinins, may play an important role in the immune response to Rh(D) (Silberstein et al., 1991, Blood 78:2377; Pascuel et al., 1991, J. Immunol. 146:4385; Silverman et al., 1988, J. Exp. Med. 168:2361; Thompson et al., 1991, Scand. J. Immunol. 34:509). However, these conclusions arose from the analysis of IgM monoclonal antibodies and only 2 of the 21 published anti-Rh(D) IgG sequences used VH4-34 (Bye et al., 1992, J. Clin. Invest. 90:2481). In a related series of experiments, aliquots of the $\gamma_1 \kappa$ and $\gamma 1\lambda$ libraries obtained after the second and third rounds of selection were pooled and then panned against the VH4-34 specific rat anti-idiotypic monoclonal antibody (9G4; Stevenson et al., 1989, Br. J. Haematol. 72:9). Although VH4-34 encoded antibodies were successfully enriched, the Fab/phage were not specific for Rh(D) and displayed serological characteristics similar to those of cold agglutinins.

Rh(D) Epitopes and Significance of Antibody Sequences

Since the initial report by Argall et al. in 1953 (J. Lab. Clin. Med. 41:895), it has been recognized that rare individuals who type as Rh(D)-positive can produce allo-anti-Rh(D) antibodies in response to Rh(D) immunization by transfusion or pregnancy. This phenomenon was explained by hypothesizing that the Rh(D) antigen is a "mosaic structure" and that these individuals were producing alloantibodies to parts of the mosaic they lack. By systematically examining patterns of reactivity between their cells and sera, RBCs expressing partial Rh(D) antigens were divided into categories, each presumed to have a different abnormality in their Rh(D) antigen. Through the subsequent use of index panels of monoclonal anti-Rh(D) antibodies, a series of epitopes were defined of which the number and combination varied from one Rh(D) category to another. As new monoclonal antibodies were produced, their reactivity profiles against these partial Rh(D) RBCs became the standard method for determining Rh(D) antibody epitope specificity. Molecular analyses of partial Rh(D) phenotypes have shown that the Rh(D) genes in these individuals have either undergone intergenic recombination with the highly homologous Rh(CE) gene, or, less commonly, have sustained point mutation(s) (Cartron et al., 1996, Transfus. Clin. Biol. 3:497).

Figure 16A:
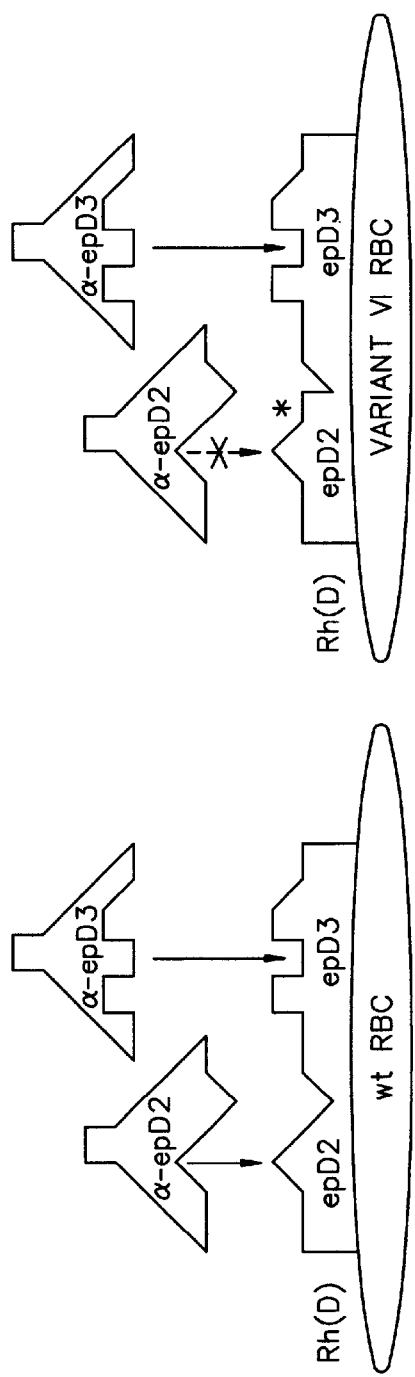
FIGS. 16A, 16B, and 16C, depict models for Rh(D) antigen/antibody binding. A conventional model (depicted in FIG. 16A) and a model described herein (depicted in FIG. 16B) for Rh(D) antigen/antibody binding predict different combining sites and genetic relationships between antibodies. As depicted in FIG. 16C, if antibodies directed at different Rh(D) epitopes are clonally related, then the expressed repertoire will differ between Rh(D)-negative and partial Rh(D) individuals.

As noted earlier, to investigate the topological relationships among Rh(D) epitopes, Gorick et al. performed competition experiments with Rh(D) monoclonal antibodies and observed varying degrees of inhibition (Gorick et al., 1988, Vox Sang. 55:165). These results, when combined with those of Lomas et al. (1989, Vox Sang. 57:261), suggested a model for Rh(D) in which epitopes are spatially distinct yet demonstrate a certain degree of overlap as illustrated in FIG. 16A. This model explained how antibodies to two different Rh(D) epitopes (in this case epD2 and epD3) could inhibit each other's binding to wild type Rh(D), and how a change in the structure of Rh(D) in category VI RBCs (asterisk in FIG. 16A) would cause the loss of epD2. However, based upon this concept of Rh(D) epitopes as distinct domains, one would expect that antibodies against different epitopes of Rh(D) would be structurally and genetically distinct as well. Thus, it was surprising that the anti-Rh(D) clones described herein demonstrated such marked restriction in gene usage. For example, only two superspecies of $V_H$ genes were used despite specificities for 4 of the original 6 Rh(D) epitopes described by Lomas et al. (1989, Vox Sang. 57:261). Furthermore, multiple specificities could arise from a single heavy chain depending upon the light chain with which it was paired (e.g. E1 with M2, M3, L3, or L4). In addition, other clones repeatedly demonstrated variable weak reactivity against certain Rh(D) category RBCs that would affect the epitope specificities to which they were assigned (e.g. C1 with O1, M1, or J5).

Several hypotheses could account for these findings. The most simplistic interpretation is that the heavy chain does not directly interact with the antigen, but rather is responsible for bringing the antibody in close proximity with the antigen. The specific interactions between the light chain and the antigen would then determine the epitope specificity for that antibody. In this regard, the data presented herein are consistent with the observations of Boucher et al. (1997, Blood 89:3277) on the relative cationic nature of anti-Rh(D) heavy chains. However, because it was determined during the studies described herein that light chains become cationic during somatic mutation, the charge of the entire antibody may play a role in its ability to bind, resulting in the selection and expansion of particular B-cell clones.

Figure 16B:
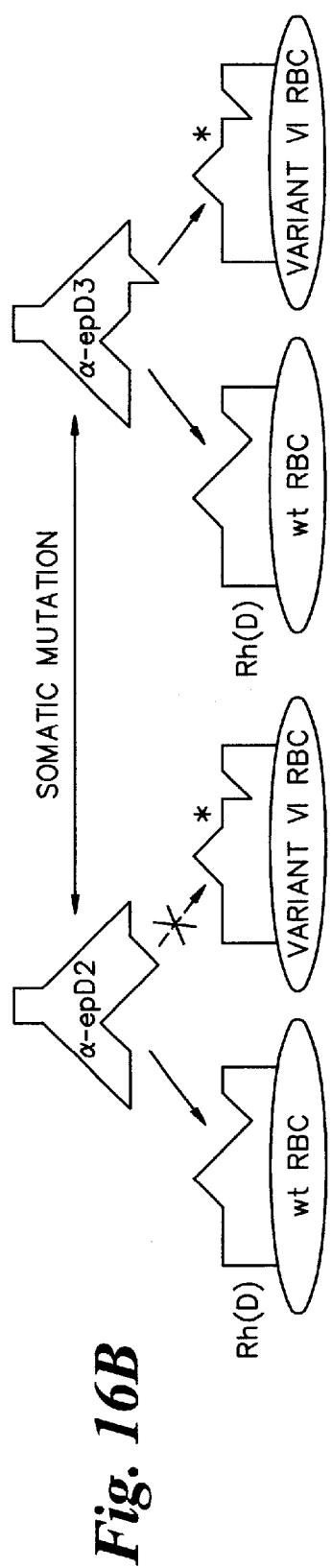

A more compelling hypothesis is that Rh(D) epitopes do not differ spatially but differ only in the number and arrangement of contact residues presented, as illustrated in FIG. 16B. In other words, the "footprints" of most, if not all, anti-Rh(D) antibodies are essentially identical to one another. The genetic events which produce partial Rh(D) molecules result in the loss of certain critical key points of contact necessary for some antibodies to bind; alternatively, they result in the formation of new structures that interfere with the binding of other anti-Rh(D) immunoglobulins. For example, the introduction of a "ledge" in Rh(D) category VI cells (asterisk in FIG. 16B) does not interfere with the binding of an anti-epD3 antibody, but does prevent the binding of anti-epD2. Therefore, category VI RBCs are said to have epD3 but "lack" epD2.

This model is consistent with the inhibition experiments described herein (e.g. FIG. 15) and with those of Gorick et al. (1988, Vox Sang. 55:165) and offers an explanation for the marked restriction in heavy chain gene usage. This model also reconciles a mechanism by which one heavy chain (e.g. E1) can confer binding to multiple epitopes and why some of the recombinant anti-Rh(D) antibodies described herein, as well as some conventionally-produced monoclonal antibodies (e.g. Tippett et al., 1996, Vox Sang. 70:123), display variable reactivity against certain categories of partial Rh(D) RBCs. From the antigen's perspective, this model explains how a single point mutation in Rh(D) can result in the loss of multiple Rh(D) epitopes (such as T283I in category HMi RBCs) and how the residues associated with the expression of some epitopes appear to be distributed among nearly all the extracellular loops of Rh(D). It also provides an understanding as to how $\geq 37$ "epitopes" can fit on the relatively small extracellularly-exposed surface of the Rh(D) molecule.

This concept of "coincident" epitopes is best exemplified by comparing the E1/M2 and E1/M3 clones described herein. The only difference between the reactivity of E1/M2 and E1/M3 is the ability of the latter antibody to agglutinate Rh(D) category VI cells, as depicted in FIG. 13. Hence, E1/M2 is classified as an anti-epD2 and E1/M3 as an anti-epD3 antibody. Light chains M2 and M3 differ by only 3 residues: D82A, G95aA, and W96V, as indicated in FIG. 11. Therefore, some combination of these three residues confers reactivity against category VI cells. In other words, epD2 and epD3, as seen by the E1/M2 and E1/M3 antibodies, differ by the binding constraints imposed by at most three mutations. If the model depicted in FIG. 16A were correct and the epitopes were independent, these mutations would have to cause enough structural alteration in the antibody combining site so that a completely separate epitope on the same antigen would be recognized. It would seem unlikely that these 3 mutations could cause such a change, especially given the lack of internal homology domains in Rh(D). Therefore, it is concluded that it is far more plausible that the footprints of these 2 antibodies are essentially identical, and that one or more of these mutations (e.g. the tryptophan in CDR3 of M2) prevent(s) the interaction of E1/M2 with category VI RBCs. Since other clones demonstrate that the light chain can confer specificity against epD1, epD2, or epD3 (with the E1 heavy chain); epD1 or epDX (with C5); and epD1, epD2, and epD6/7 (with D12), we suggest that all 5 of these epitopes have similar antibody combining sites.

Immunologic and Clinical Implications of Proposed Model

The model depicted in FIG. 16B leads to additional predictions concerning the Rh(D) immune response beyond simply clarifying what is meant by an Rh(D) epitope. It is commonly stated in the transfusion medicine literature that individuals whose RBCs express partial Rh(D) antigens are free to make antibodies to the Rh(D) epitopes they lack (Mollison et al., 1993, In: *Blood Transfusion in Clinical Medicine*, 9th ed. Blackwell Scientific, Oxford, U.K.).

Therefore, an individual who produces category VI RBCs should be able to make anti-epD2 but not anti-epD3. If these epitopes were truly independent, then the immune repertoire of the anti-epD2 antibodies made by a category VI individual would be similar to those produced by an Rh(D)-negative person. However, to the immune system, epD2 and epD3 are not independent.

Figure 16C:
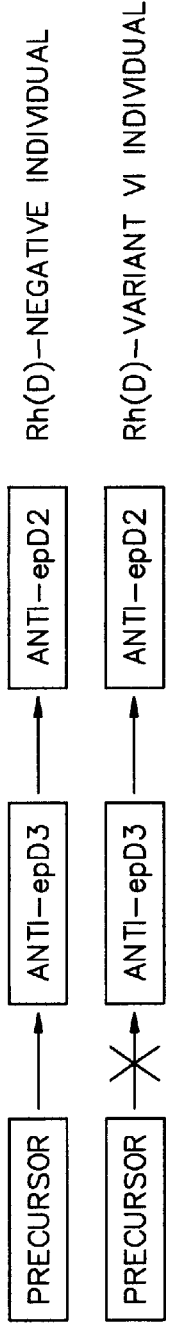

It is herein postulated that somatic mutation of an anti-epD3 antibody can change its fine specificity to that of epD2 (or vice-versa, see FIG. 16C). Suppose that the preferred way of making an anti-epD2 antibody is through an anti-epD3 intermediate. To an Rh(D)-negative individual, this process can take place unimpeded. However, in a category VI individual, this route would be unfavorable because an anti-epD3 antibody would be self-reactive. As a result, such an individual would have to make anti-epD2 antibodies by alternative routes or by tolerating some degree of auto-reactivity in the process. With respect to the latter point, it is of interest to note that a transient production of auto-anti-Rh(D) frequently precedes or accompanies the early production of allo-anti-Rh(D) in individuals who express partial Rh(D) antigens (Chown et al., 1963, Vox Sang. 8:420; Macpherson et al., 1966, J. Clin. Pathol. 45:748; Beard et al., 1971, Med. Genet. 8:317; Cook 1971, Br. J. Haematol. 20:369; Holland et al., Transfusion 13:363 (Abstract); Issit, 1985, In: *Applied Blood Group Serology*, 3rd ed., Montgomery Scientific, Miami Fla.). It is predicted, therefore, that the anti-epD2 antibodies from a category VI individual would be different in composition (i.e. gene usage) and quite possibly quantitatively depressed as compared to an Rh(D)-negative individual. This may be analogous to the antibodies of the ABO blood group system in which it has been observed that anti-A and anti-B titers in blood group O individuals are significantly higher than in blood group B or A individuals, respectively (Ichikawa, 1959, Jap. J. Med. Sci. Biol. 12:1). Blood group O individuals are unconstrained in creating their anti-A and anti-B immune repertoires while individuals who produce A or B antigens (2 nearly identical structures) must do so in a manner that avoids self-reactivity.

In the case of antibodies E1/M2 and E1/M3, they appear to have arisen from a common precursor B cell rather than directly from each other (FIG. 11). To test the framework of the hypothesis presented herein, i.e. somatic mutation resulting in "epitope migration" of an antibody, one may construct the precursors and potential intermediates between the M2 and M3 light chains and then determine what Rh(D) epitope specificities (if any) they express. This concept of epitope migration has been previously reported for murine anti-cryptococcal and anti-type II collagen antibodies (Mukherjee etal., 1995, J. Exp. Med. 181:405; Mo et al., 1996, J. Immunol. 157:2440).

If the model proposed herein for Rh(D) epitopes is correct, then the question of the number of epitopes may be obsolete. There may be as many epitopes as can be differentiated by the number of cell categories, i.e. $2^n$ epitopes where n is the number of distinct partial Rh(D) RBCs.

A more important question is the interrelationships between the various epitopes. For example, are some epitopes "further away" than others—not in the topological sense, but in terms of the number of mutational hits an antibody needs to receive in order to change its serologic reactivity. Furthermore, does the humoral immune response in a partial Rh(D) individual differ from that in an Rh(D)-negative individual in the manner predicted by this model? One may find that allo-anti-Rh(D) antibodies made by partial Rh(D) individuals are not as clinically significant, i.e. capable of inducing hemolysis. This may explain why hemolytic disease of the newborn due to anti-Rh(D) produced by pregnant individuals with partial Rh(D) phenotypes is so rare even when taking into account the low prevalence of the partial Rh(D) phenotypes (Mollison et al., 1993, In: *Blood Transfusion in Clinical Medicine*, 9th ed. Blackwell Scientific, Oxford, U.K.). A better understanding of the immune response to Rh(D) in these patients may alleviate concerns regarding the need to identify such individuals to ensure that they only receive Rh(D)-negative blood products for transfusion and Rh(D)-immune globulin during pregnancy (Jones et al., 1995, Trans. Med. 5:171). Furthermore, with respect to the design of recombinant Rh(D)-immune globulin for use in Rh(D)-negative patients, it may not be necessary to formulate cocktails of monoclonal antibodies containing multiple Rh(D) epitope specificities.

Sequence Data

Genbank accession numbers for anti-Rh(D) heavy chains are as follows:

B01, AF044419; C01, AF044420; C03, AF044421; C04, AF044422; C05, AF044423; C08, AF044424; C10, AF044425; D01, AF044426; D03, AF044427; D04, AF044428; D05, AF044429; D07, AF044430; D08, AF044431; D09, AF044432; D10, AF044433; D11, AF044434; D12, AF044435; D13, AF044436; D14, AF044437; D15, AF044438; D16, AF044439; D17, AF044440; D18, AF044441; D20, AF044442; D30, AF044443; D31, AF044444; E01, AF044445; E03, AF044446.

Genbank accession numbers for anti-Rh(D) κ light chains are as follows: F01, AF044447; G01, AF044448; H01, AF044449; I01, AF044450; I02, AF044451; I03, AF044452; I04, AF044453; I05, AF044454; I06, AF044455; I07, AF044456; I08, AF044457; I09, AF044458; I10, AF044459; I11, AF044460; I12, AF044461; I13, AF044462; I15, AF044463; I16, AF044464.

Genbank accession numbers for anti-Rh(D) λ light chains are as follows: J01, AF044465; J02, AF044466; J04, AF044467; J05, AF044468; K01, AF044469; K02, AF044470; K03, AF044471; L01, AF044472; L03, AF044473; L04, AF044474; L05, AF044475; M01, AF044476; M02, AF044477; M03, AF044478; N01, AF044479; N02, AF044480; O01, AF044481; O02, AF044482; O03, AF044483; P01, AF044484; Q01, AF044485; R01, AF044486; S01, AF044487.

Amino Acid Sequences of Anti-Rh(D) Heavy and Light Chains

The amino acid sequences of various anti-Rh(D) chains are represented using single letter amino acid codes, as described herein.

The amino acid sequence of the anti-Rh(D) chain B01 is EVQLLESGGGVVQPGRSLRLSCAASGFT-FRSYAMHWVRQAPGKGLEWVAAT AYDGKNKYY-ADSVKGRFTISRDNSKNTLFLQMNSL-RAEDTAVFYCARGGFYY DSSGYYGLRHYFDSWGQGTLVTVSS (SEQ ID NO: 1).

The amino acid sequence of the anti-Rh(D) chain C01 is EVQLLESGGGVVQPGRSLRLSCAASGFS-FSSYGMHWVRQAPGKGLEWVSVIS YDGHHKNY-ADSVKGRFTISRDNSKKTLYLQMNSL-RPEDTAVYYCANLRGEVT RRASVPFDIWGPGTMVTVSS (SEQ ID NO: 2).

The amino acid sequence of the anti-Rh(D) chain C03 is EVQLLESGGGVVQHGRSLRLSCAASGFS-FSSYGMHWVRQAPGKGLEWVSVIS YDGHHKNY-ADSVKGRFTISRDNSKKTLYLQMNSL-

RPEDTAVYYCANLRGEVT
RRASVPFDIWGPGTMVTVSS (SEQ ID NO: 3).

The amino acid sequence of the anti-Rh(D) chain C04 is
EVQLLESGGGVVQPGRSLRLSCAASGFS-
FSTYGMHWVRQAPGKGLEWVSVIS YDGHNKNY-
ADSVKGRFTISRDNSKKTLYLQMNSL-
RPEDTAVYYCANLRGEVT
RRASIPFDIWGQGTMVTVSS (SEQ ID NO: 4).

The amino acid sequence of the anti-Rh(D) chain C05 is
EVQLLESGGGVVQPGRSLRLSCAASGFS-
FSSYGMHWVRQAPGKGLEWVAVIS YDGTNKY-
FADSVKGRFTISRDNSKKTLYLQMTSL-
RPEDTAVYFCANLRGEVTR
RASVPLDIWGQGTMVTVSS (SEQ ID NO: 5).

The amino acid sequence of the anti-Rh(D) chain C08 is
EVQLLESGGGVVQPGRSLRLSCAASGFS-
FSSYGMHWVRQAPGKGLEWVAVIS YDGTNKY-
FADSVKGRFTISRDNSKKTLYLQMTSL-
RPEDTAVYFCANLRGEVTR
RASVPLDIWGQGTMVTVSS (SEQ ID NO: 6).

The amino acid sequence of the anti-Rh(D) chain C10 is
EVQLLESGGGVVQPGRSLRLSCAASGFS-
FSSYGMHWVRQAPGKGLEWVSVIS YDGHHKNY-
ADSVKGRFTISRDNSKKTLYLQMNSL-
RPEDTAVYYCANLRGEVT
RRASVPFDIWGPGTLVTVSS (SEQ ID NO: 7).

The amino acid sequence of the anti-Rh(D) chain D01 is
EVQLLESGGGVVQPGRSLRLSCVVSGFT-
FNNYGMHWVRQAPGKGLEWVAVI WFDGSNKYY-
ADSVKGRFTISRDNSKNTLYLQMNSL-
RAEDTAVYYCARENQIK
LWSRYLYYFDYWGQGTLVTVSS (SEQ ID NO: 8).

The amino acid sequence of the anti-Rh(D) chain D03 is
EVQLLESGGGVVQPGRSLRLSCAASG-
FTFSTYGMHWVRQAPGKGLEWVAVI WFDGSNKEY-
ADSVKGRFTVSRDNSKNTLYLQMNSL-
RAEDTAVYYCAREEVV
RGVILWSRKFDYWGQGTLVTVSS (SEQ ID NO: 9).

The amino acid sequence of the anti-Rh(D) chain D04 is
EVQLLESGGGVAQPGRSLRLSCVASGFS-
LRSYGMHWVRQAPGKGLEWVADI WFDGSNKDY-
ADSVKGRFTISRDNSKNTLYLQMNSL-
RAEDTAVYYCARDWRV
RAFSSGWLSAFDIWGQGTMVTVSS (SEQ ID NO: 10).

The amino acid sequence of the anti-Rh(D) chain D05 is
EVQLLEESGGGVAQPGRSLRLSCVASGF-
SLRSYGMHWVRQAPGKGLEWVADI WFDGSNKDY-
ADSVKGRFTISRDNSKNTLYLQMNSL-
RAEDTAVYYCARDWRV
RAFSSGWLSAFDIWGQGTTVSVSS (SEQ ID NO: 11).

The amino acid sequence of the anti-Rh(D) chain D07 is
EVQLLESGGGVVQPGRSLRLSCAVSG-
FTLTNYGMHWVRQAPGKGLEWVAHV WYDGSK-
TEYADSVKGRFAVSRDK-
SKNTLFLQMNSLTAEDTAIYYCARERREK
VYILFYSWLDRWGQGTLVTVSS (SEQ ID NO: 12).

The amino acid sequence of the anti-Rh(D) chain D08 is
EVQLLEESGGGVVQPGRSLRLSCAASG-
FTFSSYGMHWVRQAPGRGLEWVALI WYDGGNKEY-
ADSVKGRFSISRDNSKNTLYLQVNSL-
RADDTAVYYCARDQRA
AAGIFYYSRMDVWGQGTTVTVSS (SEQ ID NO: 13).

The amino acid sequence of the anti-Rh(D) chain D09 is
EVQLLESGGGVVQPGRSLRLSCEASKFT-
LYNYGMHWVRQAPGKGLEWVAFI WFDG-
SNKYYEDSVKGRFTVSRDNSKNT-
LYLQMNSLRAEDTAVYYCAREGSK
KVALSRYYYYMDVWGQGTTVTVSS(SEQ ID NO: 14).

The amino acid sequence of the anti-Rh(D) chain D10 is

EVQLLESGGGVVQPGRSLRLSCEASKFT-
LYNYGMHWVRQAPGKGLEWVAFI WFDG-
SNKYYEDSVKGRFTVSRDNSKNT-
LYLQMNSLRAEDTAVYYCAREVSK
KVALSRYYYYMDVWGQGTTVTVSS (SEQ ID NO: 15).

The amino acid sequence of the anti-Rh(D) chain D11 is

EVQLLESGGGVVQPGRSLRLSCEASKFT-
LYNYGMHWVRQAPGEGLEWVAFIW FDGSNKYY-
ADSVKGRFTVSRDNSKNTLYLQMNSL-
RAEDTAVYYCAREVSKKL
ALSRYYYYMDVWGQGTTVTVSS (SEQ ID NO: 16).

The amino acid sequence of the anti-Rh(D) chain D12 is

EVQLLESGGGVVQPGRSLRLACAASGFS-
FRSYGMHWVRQAPGRGLEWVAFT WFDG-
SNKYYVDSVKGRFTISRDNSKNT-
LYLEMNSLRVDDTAVYYCAREASML
RGISRYYYAMDVWGPGTTVTVSS (SEQ ID NO: 17).

The amino acid sequence of the anti-Rh(D) chain D13 is

EVQLLESGGGVVQPGRSLRLSCAASG-
FTFSTYGMHWVRQAPGKGLEWVAVI WFDGSN-
RDYAESVKGRFTISRDKSKNT-
LYLQMNSLRAEDSAVYYCARENVAR
GGGGVRYKYYFDYWGQGTLVTVSS (SEQ ID NO: 18).

The amino acid sequence of the anti-Rh(D) chain D14 is

EVQLLESGGGLVQPGGSLRLSCAASG-
FTFSTYGMHWVRQAPGKGLEWVAVIW FDG-
SKRDYAESVKGRFTISRDNSKNT-
LYLQMNSLRAEDSAVYYCARENVARG
GGGIRYKYYFDYWGQGTLVTVSS (SEQ ID NO: 19).

The amino acid sequence of the anti-Rh(D) chain D15 is

EVQLLESGGGVVQPGRSLRLSCVVSGFT-
FNNYGMHWVRQAPGKGLEWVAVI WFDGSNKYY-
ADSVKGRFTISRDNSKNTLYLQMNSL-
RAEDTAVYYCARENQIK
LWSRYLYYFDYWGQGTLVTVSS (SEQ ID NO: 20).

The amino acid sequence of the anti-Rh(D) chain D16 is

EVQLLESGGGVVQPGRSLRLSCVVSGFT-
FNNYGMHWVRQAPGKGLEWVAVI WFDGSNKYY-
ADSVKGRFTISRDNSKNTLYLQMNSL-
RAEDTAVYYCARENQIK
LWSRYLYYFDYWGQGTLVTVSS (SEQ ID NO: 21).

The amino acid sequence of the anti-Rh(D) chain D17 is

EVQLLESGGGVVQPGRSLRLSCVVSGFT-
FNNYGMHWVRQAPGKGLEWVAVI WFDGSNKYY-
ADSVKGRFTISRDNSKNTLYLQMNSL-
RAEDTAVYYCARENQIK
LWSRYLYYFDYWGQGTLVTVSS (SEQ ID NO: 22).

The amino acid sequence of the anti-Rh(D) chain D18 is

EVQLLESGGGVVQPGRSLRLSCVVSGFT-
FNNYGMHWVRQASGKGLEWVAVI WFDGSNKYY-

ADSVKGRFTISRDNSKNTLYLQMNSLRAEDTAVYYCARENQIK LWSRYLYYFDYWGQGTLVTVSS (SEQ ID NO: 23).

The amino acid sequence of the anti-Rh(D) chain D20 is EVQLLESGGGVVQPGRSLRLSCAASGFTFSTYGMHWVRQAPGKGLEWVAVI WFDGSNKEYADSVKGRFTISRDNSKNTLYLQMNSLRAEDTAVYYCAREEVVR GVILWSRKFDYWGQGTLVTVSS (SEQ ID NO: 24).

The amino acid sequence of the anti-Rh(D) chain D30 is EVQLLESGGGVVQPGRSLRLSCAASGFTFSSYGMRWVRQAPGKGLEWVAVV YYDGSNKHYSDSVKGRFTISRDNSKNTLYLQMDSLRAEDTAVYYCARERNFR SGYSRYYYGMDVWGPGTTVTVSS (SEQ ID NO: 25).

The amino acid sequence of the anti-Rh(D) chain D31 is EVQLLESGGGVVQPGRSLRLSCAASGFTFSSYGMHWVRQAPGKGLEWVAVV YYDGSNKHYSDSVKGRFTISRDNSKNTLYLQMDSLRAEDTAVYYCARERNFR SGYSRYYYGMDVWGPGTTVTVSS (SEQ ID NO: 26).

The amino acid sequence of the anti-Rh(D) chain E01 is EVQLLESGGGLVKPGGSLRLSCAASGFTFSSYSMHWVRQAPGKGLEWVSSISN SNTYIYYADAVKGRFTISRDNAKNSLYLQMNSLRAEDTAVYYCARDSRYSNFL RWVRSDGMDVWGQGTTVIVSS (SEQ ID NO: 27).

The amino acid sequence of the anti-Rh(D) chain E03 is EVQLLESGVESGGGLVKPGGSLRLSCAASGFTFSSYSMHWVRQGPGKGLEWV SSISNSNTYIYYADAVKGRFTISRDNAKNSLYLQMNSLRAEHTAVYYCARDSR YSNFLRWVRSDGMDVWGQGTTVIVSS (SEQ ID NO: 28).

The amino acid sequence of the anti-Rh(D) chain F01 is AELTQSPSSLSASVGDRVTITCRASQGFRNDLGWYQQKPGKAPKRLIYATSSLQ SGVPSRFSGSGSGTEFTLTINSLQPEDSATYYCLQHNSFPWTFGQGTKVEIKR (SEQ ID NO: 29).

The amino acid sequence of the anti-Rh(D) chain G01 is AELTQSPLSLPVTPGEPASISCRSSQSLLHSSGFNFLDWYLQKPGQSPQLLIYMG SNRASGVPDRFSGSGSGTDFTLKINRVEAEDVGVYYCMQALQFPLTFGGGTKV EIKR (SEQ ID NO: 30).

The amino acid sequence of the anti-Rh(D) chain H01 is AELTQSPSFLSASVGDRVTITCRASQGITSYLAWYQQKPGKAPKLLIYAASTLQ SGVPSRFSGSGSGTEFTLTIASLQPDDFATYYCQQLNNYPPFTFGPGTKVDIKR (SEQ ID NO: 31).

The amino acid sequence of the anti-Rh(D) chain I01 is AELTQSPSSLSASVGDRVTITCRASQSISSYLNWYQQKPGKAPKLLIYAASSLQS GVPSRFSGSGSGTDFTLTISSLQPEDFATYYCQQSYSTPPYTFGQGTKLEIKR (SEQ ID NO: 32).

The amino acid sequence of the anti-Rh(D) chain I02 is AELTQSPSSLSASVGDRVTITCRASQSISSYLNWYQQKPGKAPKLLIYAASSLQS GVPSRFSGSGSGTDFTLTISSLQPEDFATYYCQQSYSTLWTFGQGTKVEIKR (SEQ ID NO: 33).

The amino acid sequence of the anti-Rh(D) chain I03 is AELTQSPSSLSASVADRVTITCRTSRNINRYLNWYQQKPGKAPKLLIYAASSLQ SGVPSRFSGSGSGTDFTLTITSLQPEDFATYYCQQSYSTPFTFGPGTKVDLKR (SEQ ID NO: 34).

The amino acid sequence of the anti-Rh(D) chain I04 is AELTQSPSSLSASVGDRVTITCRASQNIRRSLNWYQQKPGKAPKLLIYAASSLQ SGVPSRFSGSGSGTDFTLTISSLQPEDFATYYCQQSSNTPWTFGQGTKVEIKR (SEQ ID NO: 35).

The amino acid sequence of the anti-Rh(D) chain I05 is AELTQSPSSLSASVGDRVTITCRASQSIRRYLNWYQHKPGKAPKLLIFAASSLQS GVPSRFTGSGSGTDFTLTISSLQPEDFATYYCQQSYSTPQTFGQGTKVEIKR (SEQ ID NO: 36).

The amino acid sequence of the anti-Rh(D) chain I06 is AELTQSPSSLSASVGDRVTITCRASQSISSYLNWYQQKPGKAPKLLIYAASSLQS GVPSRFSGSGSGTDFTLTISSLQPEDFATYYCQQSYSTPITFGQGTRLEIKR (SEQ ID NO: 37).

The amino acid sequence of the anti-Rh(D) chain I07 is AELTQSPSSLSASVGDRVTITCRASQSISSYLNWYQQKPGKAPKLLIYAASSLQS GVPSRFSGSGSGTDFTLTISSLQPEDFATYYCQQSYSTPRTFGGGTKVEIKR (SEQ ID NO: 38).

The amino acid sequence of the anti-Rh(D) chain I08 is AELTQSPFSLSASVGDRVTITCRASQTISRSLNWYQHKPGEAPKLLIYAASSLQR GVPPRFSGSGSGTDFTLTISSLQPEDFATYFCQQSVRIPYSFGQGTKLEIKR (SEQ ID NO: 39).

The amino acid sequence of the anti-Rh(D) chain I09 is AELTQSPSSLSASVGDRVTITCRASQSISSYLNWYQQKPGKAPKLLIYAASSLQS GVPSRFSGSGSGTDSTLTIS SLQPEDFATYYCQQLNSYPYTFGQGTKLEIKR (SEQ ID NO: 40).

The amino acid sequence of the anti-Rh(D) chain I10 is AELTQSPSSLSASVGDRVTITCRASQNISSYLNWYQQKPGKAPKLLIYAASSLQ SGVLSRFSGSGSGTDFTLTIS SLQPEDFATYYCQQSYSTPPYSFGQGTKLEIKR (SEQ ID NO: 41).

The amino acid sequence of the anti-Rh(D) chain I11 is AELTQSPSSLSASVGDRVTITCRASQSISSYLNWYQQKPGKAPTLLINAASSLQS GVPSRFSGSGSGTDFTLTISSLQPEDFAIYYCQQRETFGQGTKLEIKR (SEQ ID NO: 42).

The amino acid sequence of the anti-Rh(D) chain I12 is AELTQSPSSLSASVGDRVTITCRASQSISSYLNWYQQKPGKAPKLLIYAASSLQS GVPSRFSGSGSGTDFTLTISSLQPEDFATYYCQQSYSTPPYTFGQGTKLEIKR (SEQ ID NO: 43).

The amino acid sequence of the anti-Rh(D) chain I13 is AELTQSPSSLSASVGDRVTITCRASQSISRYLNWYQQKPGKAPKLLIYAASSLQ SGVPSRFSGSGSGTDFTLTISSLQPEDFATYYCQQSYGTPHSFGRGTKLEIKR (SEQ ID NO: 44).

The amino acid sequence of the anti-Rh(D) chain I15 is AELTQSPSSLSASVGDRVTITCRANQNIRRSLNWYQQKPGKAPNLLIYAASTLQ GGVPSRFSGSGSGTDFTLTISSLQLADFATYYCQQTSATPWTFGQGTKVEIKR (SEQ ID NO: 45).

The amino acid sequence of the anti-Rh(D) chain I16 is AELTQSPSSLSPASVGDRVTITCRASQTIGFNLNWYQQTSGKPPKLLIYGVSKLQ NGVPSRFSGSGSGTEFTLTISSLQPEDFATYYCQQTNDALWTFGQGTKVEVRR (SEQ ID NO: 46).

The amino acid sequence of the anti-Rh(D) chain J01 is AELQDPVVSVALGQTVRITCQGDGLRSYYASWYQQKPGQAPKLVMYGRNNR PSGIPGRFSGSSSGQTAALTITGTQAEDEADYYCQSRATSGNPVVFGGGTKLTV L (SEQ ID NO: 47).

The amino acid sequence of the anti-Rh(D) chain J02 is
AELQDPVVSVALGQTVRITCQGDGLRSY-
YASWYQQKPGQAPKLVMYGRNNR PSGIPDRF-
SGSSSGQTAALTITGTQAEDEADYYCQS-
RATSGNPVVFGGGTKLTV L (SEQ ID NO: 48).

The amino acid sequence of the anti-Rh(D) chain J04 is
AELQDPVVSVALGQTVRITCQGDSLRSY-
YASWYQQKPGQAPVLVIYGKNSRPS GIPDRFSGSSS-
GNTASLTITGAQAEDEADYYCSSRGSPH-
VAFGGGTKLTVL (SEQ ID NO: 49).

The amino acid sequence of the anti-Rh(D) chain J05 is
AELQDPVVSVALGQTVKITCQGDSLRKY-
YASWYQQKPGQAPVLVFYARNSRP SGIPDRFSGSNS-
GTTASLTIAGARAEDEADYYCHSRDSNG-
HHRVFGGGTKLTV L (SEQ ID NO: 50).

The amino acid sequence of the anti-Rh(D) chain K01 is
AELTQEPSLTVSPGGTVTLTCASST-
GAVTSRYFPNWFQQKPGQAPRPLIYSASN KHSWT-
PARFSGSLLGGKAALTLSGVQPEDE-
AEYYCLLYYSGAWVFGGGTKLT VL(SEQ ID NO: 51).

The amino acid sequence of the anti-Rh(D) chain K02 is
AELTQEPSLTVSPGGTVTLTCASST-
GAVTSRYFPNWFQQKPGQAPRPLIYSASN KHSWT-
PARFSGSLLGGKAALTLSGVQPEDE-
AEYYCLLYYSGAWVFGGGTKLT VL (SEQ ID NO: 52).

The amino acid sequence of the anti-Rh(D) chain K03 is
AELTQPPSLTVSPGGTVTLTCASST-
GAVTSRYFPNWFQQKPGQAPRALIYGSNN KHSWT-
PARFSGSLLGGKAALTLSGVQPEDE-
AEYYCLLFYAGAWAFGGWTKLT VL (SEQ ID NO: 53).

The amino acid sequence of the anti-Rh(D) chain L01 is
AELTQPPSASGTPGQRVTISCSGGSS-
NIASNTVNWYQQLPGTAPKLLIYSNNQR PSGVPDRF-
SGSKSGTSATLVITGLQTGDEADYY-
CGTWDHSRSGAVFGGGTKLT VL (SEQ ID NO: 54).

The amino acid sequence of the anti-Rh(D) chain L03 is
AELTQPPSASGTPGQRVTISCSGSSS-
NIGNNHVSWYQQLPGMAPKLLIYSNGQR PSGVP-
DRFSGSKSGTSASLAISGLQSEDEADYY-
CAAWHDSLYGPVFGGGTKLT VL (SEQ ID NO: 55).

The amino acid sequence of the anti-Rh(D) chain L04 is
AELTQPPSASGTPGQRVSISCSGSSS-
NIGSNTVNWYQQLPGTAPKLLISTNNQGP SGVPDRF-
SGSKSGTSSSLAISGLRSEAEDDYY-
CAAWDDTLNGVVFGGGTKLTV L (SEQ ID NO: 56).

The amino acid sequence of the anti-Rh(D) chain L05 is
AELTQPPSASGTPGLRVTISCSGSSS-
NIGSNIVNWYQQLPGTAPKLLIFSNNKRPS GVPDRF-
SGSKSGTSASLAISGLQSEDEADYY-
CATWDDSLNGRVFGGGTKLTVL (SEQ ID NO: 57).

The amino acid sequence of the anti-Rh(D) chain M01 is
AELTQPPSASGTPGQRVTISCSGSN-
FNIGSNYVFWYQHVPGTAPKLLIYNNNQR PSGVP-
DRLSGSKSGASASLAINGLRSD-
DEADYYCTGWDDRLSGLIFGGGPKVT VL (SEQ ID NO: 58).

The amino acid sequence of the anti-Rh(D) chain M02 is
AELTQPPSASGTPGQRVTISCSGSSS-
NIGSNYVYWYQQLPGTAPKLLIYRNNQR PSGVP-
DRFSGSKSGTSASLAISGLRSEDEADYY-
CAAWDDSLSGWVFGGGTKLT VL (SEQ ID NO: 59).

The amino acid sequence of the anti-Rh(D) chain M03 is
AELTQPPSASGTPGQRVTISCSGSSS-
NIGSNYVYWYQQLPGTAPKLLIYRNNQR PSGVP-
DRFSGSKSGTSASLAISGLRSEAEADYY-
CAAWDDSLSAVVFGGGTKLT VLL (SEQ ID NO: 60).

The amino acid sequence of the anti-Rh(D) chain N01 is
AELTQPPSVSAAPGQKVTISCSGSSS-
NIDSNYVSWYQQLPGTAPKLLIFDNYRRP SGIPDRF-
SGSKSGTSATLGITGLQTGDEADYY-
CATWDDSLNGRVFGGGTKLTV L (SEQ ID NO: 61).

The amino acid sequence of the anti-Rh(D) chain N02 is
AELTQPPSVSAAPGQKVTISCSGSSS-
NIGNNYVSWYQQLPGTAPKLLIYDNNKR PSGIPDRF-
SGSKSGTSATLGITGLQTGDEADYY-
CGTWDSSLSAGRVRRMFGGG TKLTVLG (SEQ ID NO: 62).

The amino acid sequence of the anti-Rh(D) chain O01 is
AELTQPPSVSGAPGQRVTISCTGSSSNI-
GAPYGVHWYQQFPGTAPKLVIYNDNN RPSGVPDRF-
SGSKSGTSASLAITGLQAEDEADYYC-
QSYDSSLSGRVFGGGTKLT VL (SEQ ID NO: 63).

The amino acid sequence of the anti-Rh(D) chain O02 is
AELTQPPSVSGAPGQTVTISCTGSSSSI-
GARYDVHWYQHLPGTAPKLLIYGNHN RPSGVPDRF-
SGSKSGTSASLAITGLQAEDEAEYYC-
QSYDNSLSGSSVFFGGGTK LTVL (SEQ ID NO: 64).

The amino acid sequence of the anti-Rh(D) chain O03 is
AELTQPPSGAPGQTVTISCTGSSSNI-
GAGYDVHWYQQLPGTAPKLLIYGNSNRP SGVPDRF-
SGSKSGTSASLAITGLQAEDEADYYC-
QSYDSSLSGPYVVFGGGTKLT VL (SEQ ID NO: 65).

The amino acid sequence of the anti-Rh(D) chain P01 is
AELTQPPSVSVAPRQTARITCGGDKIG-
SNTVHWYRQMSGQAPVLVIYEDKKRP PGIPERF-
SGSTSGTTATLSISGAQVEDEADYYCYS-
RDNSGDQRRVFGAGTKLTV L (SEQ ID NO: 66).

The amino acid sequence of the anti-Rh(D) chain Q01 is
AELTQPPSATASLGGSVKLTCILQSGH-
RNYAVAWHHQEAGKGPRFLMTVTND GRHIKGDGIP-
DRFSGSASGAERYLSISGLQSEDEGDYY-
CQTWGTGMHVFGGGT KLTVL (SEQ ID NO: 67).

The amino acid sequence of the anti-Rh(D) chain R01 is
AELTQPPSASGSPGQSVTISCTGASSDV-
GAYKHVSWYQQHPGKAPKLLTHEGT KRPSGVPDRF-
SGSKSGNTASLTVSGLQAEDEADYYCSS-
FAGNSVIFGGGTKLT VL (SEQ ID NO: 68).

The amino acid sequence of the anti-Rh(D) chain S01 is
AELTQPPSVSGSPGQSITISCSDVGNYN-
LVSWYQQYPGKAPKLIIYEGSKRPSGV SSRFSGSRS-
GNTASLTISGLQAEDEADYHCCSYAISS-
RIFGGGTKLTVL (SEQ ID NO: 69).

Nucleotide Sequences of Anti-Rh(D) Heavy and Light Chains

The nucleotide sequence of the portion of the clone encoding the anti-Rh(D) chain B01 is
GAGGTGCAGCTGCTCGAGTCTGGGGGAG-
GCGTGGTCCAGCCTGGGAGGTC CCTGAGACTCTC-
CTGTGCAGCCTCTGGATTCACCTTCAG-
GAGCTATGCTATG
CACTGGGTCCGCCAGGCTCCAG-
GCAAGGGGCTGGAGTGGGTGGCAGCTAC
AGCATATGATGGAAAAAATAAATAC-
TACGCAGACTCCGTGAAGGGCCGAT TCAC-
CATCTCCAGAGACAATTCCAAGAA-
CACGCTGTTTCTGCAAATGAACA
GCCTGAGAGCTGAGGACACGGCTGT-
GTTTTACTGTGCGAGAGGCGGATTTT ACTATGAT-
AGTAGTGGTTATTACGGCTTGAGGCAC-
TACTTTGACTCCTGGG
GCCAGGGAACCCTGGTCACCGTCTCCTCA (SEQ ID NO: 70).

The nucleotide sequence of the portion of the clone encoding the anti-Rh(D) chain C01 is
GAGGTGCAGCTGCTCGAGTCTGGGGGAG-
GCGTGGTCCAGCCTGGGAGGTC CCTGAGACTCTC- CTGTGCAGCCTCTGGATTCTCCTTCAG-
TAGCTATGGCATG
CACTGGGTCCGCCAGGCTCCAG-
GCAAGGGGCTGGAGTGGGTGTCAGTTATA TCATAT-
GATGGACATCATAAAAACTATGCA-
GACTCCGTGAAGGGCCGATTC
ACCATCTCCAGAGACAATTCCAA-
GAAAACGCTGTACCTGCAAATGAACAGC
CTGAGACCTGAGGACACGGCTGTATAT-
TACTGTGCGAACCTAAGGGGGGA
AGTAACTCGTCGTGCGTCTGTTC-
CCTTTGATATCTGGGGCCCAGGGACAAT GGTCAC-
CGTCTCTTCA (SEQ ID NO: 71).

The nucleotide sequence of the portion of the clone encoding the anti-Rh(D) chain C03 is
GAGGTGCAGCTGCTCGAGTCGGGGGGAG-
GTGTGGTCCAGCATGGGAGGTC CCTGAGACTGTC-
CTGTGCAGCCTCTGGATTCTCCTTCAG-
TAGCTATGGCATG
CACTGGGTCCGCCAGGCTCCAG-
GCAAGGGGCTGGAGTGGGTGTCAGTTATA TCATAT-
GATGGACATCATAAAAACTATGCA-
GACTCCGTGAAGGGCCGATTC
ACCATCTCCAGAGACAATTCCAA-
GAAAACGCTGTACCTGCAAATGAACAGC
CTGAGACCTGAGGACACGGCTGTATAT-
TACTGTGCGAACCTAAGGGGGA
AGTAACTCGTCGTGCGTCTGTTC-
CCTTTGATATATGGGGCCCAGGGACAAT GGTCAC-
CGTGTCTTCA (SEQ ID NO: 72).

The nucleotide sequence of the portion of the clone encoding the anti-Rh(D) chain C04 is
GAGGTGCAGCTGCTCGAGTCTGGGGGAG-
GCGTGGTCCAGCCTGGGAGGTC CCTGAGACTCTC-
CTGTGCAGCCTCTGGATTCTCCTTCAG-
TACCTATGGCATG
CACTGGGTCCGCCAGGCTCCAG-
GCAAGGGGCTGGAGTGGGTGTCAGTTATA TCATAT-
GATGGACATAATAAAAACTATGCA-
GACTCCGTGAAGGGCCGATTC
ACCATCTCCAGAGACAATTCCAA-
GAAAACGCTGTACCTGCAAATGAACAGC
CTGAGACCTGAGGACACGGCTGTGTAT-
TACTGTGCGAACCTAAGGGGGA
AGTAACTCGTCGTGCGTCTATTC-
CTTTTGATATCTGGGGCCAAGGGACAAT GGTCAC-
CGTCTCTTCA (SEQ ID NO: 73).

The nucleotide sequence of the portion of the clone encoding the anti-Rh(D) chain C05 is
GAGGTGCAGCTGCTCGAGTCGGGGGGAG-
GCGTGGTCCAGCCTGGGAGGTC CCTGAGACTCTC-
CTGTGCAGCCTCTGGATTCAGCTTCAG-
TAGTTATGGCATG
CACTGGGTCCGCCAGGCTCCAG-
GCAAGGGGCTGGAGTGGGTGGCAGTTAT ATCGTAT-
GATGGAACTAATAAATACTTTGCA-
GACTCCGTGAAGGGCCGATT
CACCATCTCCAGAGACAATTCCAA-
GAAAACGCTGTATCTGCAAATGACCAG CCT-
GAGACCTGAGGACACGGCTGTG-
TATTTCTGTGCGAACCTAAGGGGGA
AGTAACTCGTCGTGCGTCCGTACCTCT-
TGATATCTGGGGCCAAGGGACAAT GGTCAC-
CGTCTCTTCA (SEQ ID NO: 74).

The nucleotide sequence of the portion of the clone encoding the anti-Rh(D) chain C08 is
GAGGTGCAGCTGCTCGAGTCGGGGGGAG-
GCGTGGTCCAGCCTGGGAGGTC CCTGAGACTCTC-
CTGTGCAGCCTCTGGATTCAGCTTCAG-
TAGTTATGGCATG
CACTGGGTCCGCCAGGCTCCAG-
GCAAGGGGCTGGAGTGGGTGGCAGTTAT ATCGTAT-
GATGGAACTAATAAATACTTTGCA-
GACTCCGTGAAGGGCCGATT
CACCATCTCCAGAGACAATTCCAA-
GAAAACGCTGTATCTGCAAATGACCAG CCT-
GAGACCTGAGGACACGGCTGTG-
TATTTCTGTGCGAACCTAAGGGGGA
AGTAACTCGTCGTGCGTCTGTACCTCT-
TGATATCTGGGGCCAAGGGACAAT GGTCAC-
CGTCTCTTCA (SEQ ID NO: 75).

The nucleotide sequence of the portion of the clone encoding the anti-Rh(D) chain C10 is
GAGGTGCAGCTGCTCGAGTCTGGGGGAG-
GCGTGGTCCAGCCTGGGAGGTC CCTGAGACTCTC-
CTGTGCAGCCTCTGGATTCTCCTTCAG-
TAGCTATGGCATG
CACTGGGTCCGCCAGGCTCCAG-
GCAAGGGGCTGGAGTGGGTGTCAGTTATA TCATAT-
GATGGACATCATAAAAACTATGCA-
GACTCCGTGAAGGGCCGATTC
ACCATCTCCAGAGACAATTCCAA-
GAAAACGCTGTACCTGCAAATGAACAGC
CTGAGACCTGAGGACACGGCTGTATAT-
TACTGTGCGAACCTAAGGGGGA
AGTAACTCGTCGTGCGTCTGTTC-
CCTTTGATATCTGGGGCCCAGGGACATTG GTCAC-
CGTCTCTTCA (SEQ ID NO: 76).

The nucleotide sequence of the portion of the clone encoding the anti-Rh(D) chain D01 is
GAGGTGCAGCTGCTCGAGTCTGGGGGAG-
GCGTGGTCCAGCCTGGGAGGTC CCTGAGACTCTC-
CTGTGTAGTGTCTGGTTTCACCT-
TCAATAACTATGGCATG
CACTGGGTCCGCCAGGCTCCAG-
GCAAGGGGCTGGAGTGGGTGGCAGTTATT
TGGTTTGATGGAAGTAATAAATACTATG-
CAGACTCCGTGAAGGGCCGATTC ACCATCTCCA-
GAGACAATTCCAAGAACACACTGTACCT-
GCAAATGAACAGC
CTGAGAGCCGAGGACACGGCTGTATAT-
TACTGTGCGAGAGAGAACCAGAT AAAGCTATG-
GTCCCGATACCTTTACTACTTTGAT-
TACTGGGGCCAGGGAAC
CCTGGTCACCGTCTCCTCA (SEQ ID NO: 77).

The nucleotide sequence of the portion of the clone encoding the anti-Rh(D) chain D03 is
GAGGTGCAGCTGCTCGAGTCTGGGGGAG-
GCGTGGTCCAGCCTGGGAGGTC CCTGAGACTCTC-
CTGTGCAGCGTCTGGATTCACCTTCAG-
TACCTATGGCATG
CACTGGGTCCGCCAGGCTCCAGGCAAGG-
GACTGGAGTGGGTGGCAGTTAT ATGGTTTGATG-
GAAGTAATAAGGAATATGCAGACTCCGT-
GAAGGGCCGATT
CACCGTCTCCAGAGACAATTCCAAGAA-
CACGCTGTATCTACAAATGAACAG CCTGAGAGC-
CGAGGACACGGCTGTGTATTACTGTGC-
GAGAGAAGAAGTGG
TTCGGGGAGTTATCTTATGGTCTCG-
GAAGTTTGACTACTGGGGCCAGGGAA CCCTGGT-
CACCGTCTCCTCA (SEQ ID NO: 78).

The nucleotide sequence of the portion of the clone encoding the anti-Rh(D) chain D04 is
GAGGTGCAGCTGCTCGAGTCGGGGGGAG-
GCGTGGCCCAGCCTGGGAGGTC CCTGAGACTCTC- CTGTGTAGCGTCTGGATTCAGCCTCAGGAGCTATGGCAT GCACTGGGTCCGCCAGGCTCCTGGCAAGGGGCTGGAGTGGGTGGCAGATA TATGGTTTGATGGAAGTAATAAAGATTATGCAGACTCCGTGAAGGGCCGAT TCACCATCTCCAGAGACAATTCCAAGAACACGTTGTATCTTCAAATGAACA GCCTGAGAGCCGAGGATACGGCTGTGTATTATTGTGCGAGAGATTGGAGGG TGCGGGCCTTTAGTAGTGGCTGGTTAAGTGCTTTTGATATCTGGGGCCAAG GGACAATGGTCACCGTCTCCTCA (SEQ ID NO: 79).

The nucleotide sequence of the portion of the clone encoding the anti-Rh(D) chain D05 is GAGGTGCAGCTGCTCGAGGAGTCTGGGGGAGGCGTGGCCCAGCCTGGGAG GTCCCTGAGACTCTCCTGTGTAGCGTCTGGATTCAGCCTCAGGGAGCTATGG CATGCACTGGGTCCGCCAGGCTCCTGGCAAGGGGCTGGAGTGGGTGGCAG ATATATGGTTTGATGGAAGTAATAAAGATTATGCAGACTCCGTGAAGGGCC GATTCACCATCTCCAGAGACAATTCCAAGAACACGTTGTATCTTCAAATGA ACAGCCTGAGAGCCGAGGACACGGCTGTGTATTATTGTGCGAGAGATTGGA GGGTGCGGGCCTTTAGTAGTGGCTGGTTAAGTGCTTTTGATATCTGGGGCC AAGGGACCACGGTCAGCGTCTCCTCA (SEQ ID NO: 80).

The nucleotide sequence of the portion of the clone encoding the anti-Rh(D) chain D07 is GAGGTGCAGCTGCTCGAGTCTGGGGGAGGCGTGGTCCAGCCTGGGAGGTC CTGAGACTCTCCTGTGCAGTGTCTGGATTCACCCTAACTAATTATGGCATG CACTGGGTCCGCCAGGCTCCAGGCAAGGGGCTGGAGTGGGTGGCACATGT CTGGTATGATGGAAGTAAAACAGAATATGCAGACTCCGTCAAGGGCCGATT CGCCGTCTCCAGAGACAAATCCAAGAACACACTGTTTCTGCAAATGAACAG CCTGACAGCCGAGGACACGGCTATTTATTACTGTGCGAGAGAGGAGAGAGA AAGTCTATATATTGTTCTACTCGTGGCTCGACCGCTGGGGCCAGGGAA CCCTGGTCACCGTCTCCTCA (SEQ ID NO: 81).

The nucleotide sequence of the portion of the clone encoding the anti-Rh(D) chain D08 is GAGGTGCAGCTGCTCGAGGAGTCTGGGGGAGGCGTGGTCCAGCCTGGGAG GTCCCTGAGACTCTCCTGTGCAGCGTCTGGGTTCACCTTCAGTAGCTATGGC ATGCACTGGGTCCGCCAGGCTCCAGGCAGGGGGCTGGAGTGGGTGGCTCTT ATATGGTACGATGGAGGTAACAAAGAGTATGCAGACTCCGTGAAGGGCCG CTTCAGCATCTCCAGAGACAATTCCAAGAACACTCTGTATCTGCAAGTGAA CAGCCTGAGAGCCGACGACACGGCTGTCTATTACTGTGCGAGAGACCAGA GAGCAGCAGCGGGTATCTTTTATTATTCCCGTATGGACGTCTGGGGCCAAG GGACCACGGTCACCGTCTCCTCA (SEQ ID NO: 82).

The nucleotide sequence of the portion of the clone encoding the anti-Rh(D) chain D09 is GAGGTGCAGCTGCTCGAGTCTGGGGGAGGCGTGGTCCAGCCTGGGAGGTC CTGAGACTCTC CTGTGAAGCGTCTAAATTCACCCTCTACAATTATGGCATG CACTGGGTCCGCCAGGCTCCAGGCAAGGGGCTGGAGTGGGTGGCATTTATA TGGTTTGATGGAAGTAATAAATACTATGAAGACTCCGTGAAGGGCCGATTC ACCGTCTCCAGAGACAATTCCAAGAACACGCTGTATCTGCAAATGAACAGC CTGAGAGCCGAGGACACGGCTGTGTATTACTGTGCGAGAGAAGGATCTAA GAAGGTGGCACTTTCTAGGTATTACTATTATATGGACGTCTGGGGCCAGGG GACCACGGTCACTGTCTCGTCA (SEQ ID NO: 83).

The nucleotide sequence of the portion of the clone encoding the anti-Rh(D) chain D10 is GAGGTGCAGCTGCTCGAGTCTGGGGGAGGCGTGGTCCAGCCTGGGAGGTC CTGAGACTCTCCTGTGAAGCGTCTAAATTCACCCTCTACAATTATGGCATG CACTGGGTCCGCCAGGCTCCAGGCAAGGGGCTGGAGTGGGTGGCATTTATA TGGTTTGATGGAAGTAATAAATACTATGAAGACTCCGTGAAGGGCCGATTC ACCGTCTCCAGAGACAATTCCAAGAACACGCTGTATCTGCAAATGAACAGC CTGAGAGCCGAGGACACGGCTGTGTATTACTGTGCGAGAGAAGTATCTAAG AAGGTGGCACTTTCTAGGTATTACTATATGGACGTCTGGGGCCAGGGACCA CGGTCACTGTCTCCTCA (SEQ ID NO: 84).

The nucleotide sequence of the portion of the clone encoding the anti-Rh(D) chain D11 is GAGGTGCAGCTGCTCGAGTCTGGGGGAGGCGTGGTCCAGCCTGGGAGGTC CTGAGACTCTCCTGTGAAGCGTCTAAATTCACCCTCTACAATTATGGCATG CACTGGGTCCGCCAGGCTCCAGGCGAAGGGCTGGAGTGGGTGGCATTTATA TGGTTTGATGGAAGTAATAAATACTATGCAGACTCCGTGAAGGGCCGATTC ACCGTCTCCAGAGACAATTCCAAGAACACGCTGTATCTGCAAATGAACAGC CTGAGAGCCGAGGACACGGCTGTGTATTACTGTGCGAGAGAAGTATCTAAG AAGCTGGCACTTTCTAGGTACTACTATATGGACGTCTGGGGCCAGGGACCA CGGTCACTGTCTCCTCA (SEQ ID NO: 85).

The nucleotide sequence of the portion of the clone encoding the anti-Rh(D) chain D12 is GAGGTGCAGCTGCTCGAGTCGGGGGGAGGCGTGGTCCAGCCTGGGAGGTC CTGAGACTCGCCTGTGCAGCGTCTGGATTCAGCTTCAGGAGCTATGGCAT GCACTGGGTCCGCCAGGCTCCAGGCAGGGGGCTGGAGTGGGTGGCATTTAC ATGGTTTGATGGAAGCAATAAATATTGTAGACTCCGTGAAGGGCCGATT CACCATCTCCAGAGACAATTCCAAGAACACGCTGTATCTGGAAATGAACAG CCTGAGAGTCGATGACACGGCTGTATATTACTGTGCGAGAGAGGCGTCTAT GCTTCGCGGAATTAGCAGATACTACTACGCGATGGACGTCTGGGGCCCAGG GACCACGGTCACCGTCTCCTCA (SEQ ID NO: 86).

The nucleotide sequence of the portion of the clone encoding the anti-Rh(D) chain D13 is GAGGTGCAGCTGCTCGAGTCTGGGGGAGGCGTGGTCCAGCCTGGGAGGTC CTGAGACTCTC CTGTGCAGCGTCTGGATTCACCTTCAG-
TACTTATGGCATG
CACTGGGTCCGCCAGGCTCCAG-
GCAAGGGGCTGGAGTGGGTGGCAGTTAT ATG-
GTTTGATGGAAGTAACAGAGACTATGCA-
GAGTCCGTGAAGGGCCGATT
CACCATCTCCAGAGACAAGTCCAAGAA-
CACACTGTATCTGCAAATGAACAG CCTGAGAGC-
CGAGGACTCGGCTGTGTATTATTGTGC-
GAGAGAAAATGTGGC
TCGTGGGGGGGGGGGCGTTCGATACAAG-
TACTACTTTGACTACTGGGGCCA GGGAACCCTGGT-
CACCGTCTCCTCA (SEQ ID NO: 87).

The nucleotide sequence of the portion of the clone encoding the anti-Rh(D) chain D14 is
GAGGTGCAGCTGCTCGAGTCGGGGGGAG-
GCTTGGTACAGCCTGGGGGGTC CCTGAGACTCTC-
CTGTGCAGCGTCTGGATTCACCTTCAG-
TACTTATGGCATG
CACTGGGTCCGCCAGGCTCCAG-
GCAAGGGGCTGGAGTGGGTGGCAGTTAT ATG-
GTTTGATGGAAGTAAGAGAGACTATGCA-
GAGTCCGTGAAGGGCCGATT
CACCATCTCCAGAGACAACTCCAAGAA-
CACACTGTATCTGCAAATGAACAG CCTGAGAGC-
CGAGGACTCGGCTGTGTATTACTGTGC-
GAGAGAAAATGTGGC
TCGTGGGGGGGGGGGCATTCGATACAAG-
TACTACTTTGACTACTGGGGCCA GGGAACCCTGGT-
CACCGTCTCCTCA (SEQ ID NO: 88).

The nucleotide sequence of the portion of the clone encoding the anti-Rh(D) chain D15 is
GAGGTGCAGCTGCTCGAGTCTGGGGGAG-
GCGTGGTCCAGCCTGGGAGGTC CCTGAGACTCTC-
CTGTGTAGTGTCTGGATTCACCT-
TCAATAACTATGGCATG
CACTGGGTCCGCCAGGCTCCAG-
GCAAGGGGCTGGAGTGGGTGGCAGTTATT
TGGTTTGATGGAAGTAATAAATACTATG-
CAGACTCCGTGAAGGGCCGATTC ACCATCTCCA-
GAGACAATTCCAAGAACACACTGTACCT-
GCAAATGAACAGC
CTGAGAGCCGAGGACACGGCTGTATAT-
TACTGTGCGAGAGAGAACCAGAT AAAGCTATG-
GTCCCGATACCTTTACTACTTTGAC-
TACTGGGGCCAGGGAAC
CCTGGTCACCGTCTCCTCA (SEQ ID NO: 89).

The nucleotide sequence of the portion of the clone encoding the anti-Rh(D) chain D16 is
GAGGTGCAGCTGCTCGAGTCTGGGGGAG-
GCGTGGTCCAGCCTGGGAGGTC CCTGAGACTCTC-
CTGTGTAGTGTCTGGTTTCACCT-
TCAATAACTATGGCATG
CACTGGGTCCGCCAGGCTCCAG-
GCAAGGGGCTGGAGTGGGTGGCAGTTATT
TGGTTTGATGGAAGTAATAAATACTATG-
CAGACTCCGTGAAGGGCCGATTC ACCATCTCCA-
GAGACAATTCCAAGAACACACTGTACCT-
GCAAATGAACAGC
CTGAGAGCCGAGGACACGGCTGTATAT-
TACTGTGCGAGAGAGAACCAGAT AAAGCTATG-
GTCCCGATACCTTTACTACTTTGAC-
TACTGGGGCCAGGGAAC
CCTGGTCACCGTCTCCTCA (SEQ ID NO: 90).

The nucleotide sequence of the portion of the clone encoding the anti-Rh(D) chain D17 is
GAGGTGCAGCTGCTCGAGTCTGGGGGAG-
GCGTGGTCCAGCCTGGGAGGTC CCTGAGACTCTC-
CTGTGTAGTGTCTGGTTTCACCT-
TCAATAACTATGGCATG
CACTGGGTCCGCCAGGCTCCAG-
GCAAGGGGCTGGAGTGGGTGGCAGTTATT
TGGTTTGATGGAAGTAATAAATACTATG-
CAGACTCCGTGAAGGGCCGATTC ACCATCTCCA-
GAGACAATTCCAAGAACACACTGTACCT-
GCAAATGAACAGC
CTGAGAGCCGAGGACACGGCTGTATAT-
TACTGTGCGAGAGAGAACCAGAT AAAGCTATG-
GTCCCGATACCTTTACTACTTTGAC-
TACTGGGGCCAGGGAAC
CCTGGTCACCGTCTCCTCC (SEQ ID NO: 91).

The nucleotide sequence of the portion of the clone encoding the anti-Rh(D) chain D18 is
GAGGTGCAGCTGCTCGAGTCTGGGGGAG-
GCGTGGTCCAGCCTGGGAGGTC CCTGAGACTCTC-
CTGTGTAGTGTCTGGTTTCACCT-
TCAATAACTATGGCATG
CACTGGGTCCGCCAGGCTTCAG-
GCAAGGGGTTGGAGTGGGTGGCAGTTATT
TGGTTTGATGGAAGTAATAAATACTATG-
CAGACTCCGTGAAGGGCCGATTC ACCATCTCCA-
GAGACAATTCCAAGAACACACTGTACCT-
GCAAATGAACAGC
CTGAGAGCCGAGGACACGGCTGTATAT-
TACTGTGCGAGAGAGAACCAGAT AAAGCTATG-
GTCCCGATACCTTTACTACTTTGAC-
TACTGGGGCCAGGGAAC
CCTGGTCACCGTGTCCTCA (SEQ ID NO: 92).

The nucleotide sequence of the portion of the clone encoding the anti-Rh(D) chain D20 is
GAGGTGCAGCTGCTCGAGTCGGGGGGAG-
GCGTGGTCCAGCCTGGGAGGTC CCTGAGACTCTC-
CTGTGCAGCGTCTGGATTCACCTTCAG-
TACCTATGGCATG
CACTGGGTCCGCCAGGCTCCAGGCAAGG-
GACTGGAGTGGGTGGCAGTTAT ATGGTTTGATG-
GAAGTAATAAGGAATATGCAGACTCCGT-
GAAGGGCCGATT
CACCATCTCCAGAGACAATTCCAAGAA-
CACGCTGTATCTACAAATGAACAG CCTGAGAGC-
CGAGGACACGGCTGTGTATTACTGTGC-
GAGAGAAGAAGTGG
TTCGGGGAGTTATCTTATGGTCTCG-
GAAGTTTGACTACTGGGGCCAGGGAA CCCTGGT-
CACCGTCTCCTCA (SEQ ID NO: 93).

The nucleotide sequence of the portion of the clone encoding the anti-Rh(D) chain D30 is
GAGGTGCAGCTGCTCGAGTCGGGGGGAG-
GCGTGGTCCAGCCTGGGAGGTC CCTGAGACTCTC-
CTGTGCAGCGTCTGGATTCACCTTCAG-
TAGCTATGGCATG
CGCTGGGTCCGGCAGGCTCCAG-
GCAAGGGGCTGGAGTGGGTGGCAGTTGT CTAC-
TATGATGGAAGTAACAAACACTATTCA-
GACTCCGTGAAGGGCCGATT
CACCATCTCCAGAGACAACTCCAAGAA-
CACGCTGTATCTACAAATGGACAG CCTGAGAGC-
CGAGGACACGGCTGTGTATTACTGTGC-
GAGAGAAAGAAATTT
TCGGAGTGGTTATTCCCGCTACTAC-
TACGGTATGGACGTCTGGGGCCCAGG GACCACG-
GTCACCGTCTCCTCA (SEQ ID NO: 94).

The nucleotide sequence of the portion of the clone encoding the anti-Rh(D) chain D31 is
GAGGTGCAGCTGCTCGAGTCGGGGGGAG-
GCGTGGTCCAGCCTGGGAGGTC CCTGAGACTCTC- The nucleotide sequence of the portion of the clone encoding the anti-Rh(D) chain E01 is
GAGGTGCAGCTGCTCGAGTCTGGGGGAG-
GCCTGGTCAAGCCTGGGGGGTC CCTGAGACTCTC-
CTGTGCAGCCTCTGGATTCACCTTCAG-
TAGCTATAGCATG
CACTGGGTCCGCCAGGCTCCAGG-
GAAGGGGCTGGAGTGGGTCTCATCCATT AGTAAT-
AGTAATACTTACATATACTACGCAGACG-
CAGTGAAGGGCCGATTC
ACCATCTCCAGAGACAACGCCAAGAACT-
CACTGTATCTGCAAATGAACAGC CTGAGAGC-
CGAGGACACGGCTGTGTACTACTGTGC-
GAGAGATTCTAGATAC
AGTAATTTCCTCCGTTGGGTTCGGAGC-
GACGGTATGGACGTCTGGGGCCAA GGGACCACG-
GTCATCGTCTCCTCA (SEQ ID NO: 96).

The nucleotide sequence of the portion of the clone encoding the anti-Rh(D) chain E03 is
GAGGTGCAGCTGCTCGAGTCTGGGGTG-
GAGTCTGGGGGAGGCCTGGTCAA
GCCTGGGGGGTCCCTGAGACTCTCCTGT-
GCAGCCTCTGGATTCACCTTCAGT AGCTATAGCAT-
GCACTGGGTCCGCCAGGGTCCAGG-
GAAGGGGCTGGAGTG
GGTCTCATCCATTAGTAATAGTAATACT-
TACATATACTACGCAGACGCAGT GAAGGGCCGAT-
TCACCATCTCCAGAGACAACGCCAA-
GAACTCACTGTATCT
GCAAATGAACAGCCTGAGAGCCGAGCA-
CACGGCTGTGTACTACTGTGCGA GAGATTCTA-
GATACAGTAATTTCCTCCGTTGGGTTCG-
GAGCGACGGTATGG
ACGTCTGGGGCCAAGGGACCACGGT-
CATCGTCTCCTCA (SEQ ID NO: 97).

The nucleotide sequence of the portion of the clone encoding the anti-Rh(D) chain F01 is
GCCGAGCTCACCCAGTCTCCATCCTC-
CCTGTCTGCATCTGTAGGAGACAGA GTCACCAT-
CACTTGCCGGGCAAGTCAGGGCTTTA-
GAAATGATTAGGCTGG
TATCAGCAGAAACCAGGGAAAGC-
CCCTAAGCGCCTGATCTATGCTACATCC AGTTTG-
CAAAGTGGGGTCCCATCAAGGTTCAGCG-
GCAGTGGATCTGGGACA
GAATTCACTCTCACAATCAACAGCCTG-
CAGCCTGAAGATTCTGCAACTTAT TACTGTCTA-
CAGCATAATAGTTTCCCGTGGACGTTCG-
GCCAAGGGACCAAG GTGGAAATCAAACGA (SEQ ID NO: 98).

The nucleotide sequence of the portion of the clone encoding the anti-Rh(D) chain G01 is
GCCGAGCTCACTCAGTCTCCACTCTC-
CCTGCCCGTCACCCCTGGAGAGCCG GCCTC-
CATCTCCTGCAGGTCTAGTCAGAGCCTC-
CTGCATAGTAGTGGATTCA
ACTTTTTGGATTGGTACCTGCAGAAGC-
CAGGGCAGTCTCCACAGCTCCTGA TCTATATGGGT-
TCTAATCGGGCCTCCGGGGTCCCTGA-
CAGGTTCAGTGGCA
GTGGATCAGGCACAGATTTTACACT-
GAAAATCAACAGAGTGGAGGCTGAG GATGT-
TGGGGTTTATTACTGCATGCAAGCTCTA-
CAATTTCCTCTCACTTTCG
GCGGAGGGACCAAGGTGGAGATCAAACGA (SEQ ID NO: 99).

The nucleotide sequence of the portion of the clone encoding the anti-Rh(D) chain H01 is
GCCGAGCTCACCCAGTCTCCATCCTTC-
CTGTCTGCATCTGTAGGAGACAGA GTCACCAT-
CACTTGCCGGGCCAGTCAGGGCATTAC-
GAGTTATTTAGCCTGG
TATCAGCAAAAACCAGGGAAAGC-
CCCTAAGCTCCTAATCTATGCTGCATCC ACTTTG-
CAAAGTGGGGTCCCATCAAGGTTCAGCG-
GCAGTGGATCTGGGACA
GAATTCACTCTCACAATCGCCAGCCTG-
CAGCCTGATGATTTTGCAACTTATT ACTGTCAA-
CAGCTTAATAATTAC-
CCCCCTTTCACTTTCGGCCCTGGGACCAA
AGTGGATATCAAACGA (SEQ ID NO: 100).

The nucleotide sequence of the portion of the clone encoding the anti-Rh(D) chain I01 is
GCCGAGCTCACCCAGTCTCCATCCTC-
CCTATCTGCATCTGTAGGAGACAGA GTCACCAT-
CACTTGCCGGGCAAGTCAGAGCATTAG-
CAGCTATTTAAATTGG
TATCAGCAGAAACCAGGGAAAGC-
CCCTAAGCTCCTGATCTATGCTGCATCC AGTTTG-
CAAAGTGGGGTCCCATCAAGGTTCAGTG-
GCAGTGGATCTGGGACA
GATTTCACTCTCACCATCAGCAGTCTG-
CAACCTGAAGATTTTGCAACTTACT ACTGTCAACA-
GAGTTACAGTACCCCTCCGTA-
CACTTTTGGCCAGGGGACCA
AGCTGGAGATCAAACGA (SEQ ID NO: 101).

The nucleotide sequence of the portion of the clone encoding the anti-Rh(D) chain I02 is
GCCGAGCTCACCCAGTCTCCATCCTC-
CCTGTCTGCATCTGTAGGAGACAGA GTCACCAT-
CACTTGCCGGGCAAGTCAGAGCATTAG-
CAGCTATTTAAATTGG
TATCAGCAGAAACCAGGGAAAGC-
CCCTAAGCTCCTGATCTATGCTGCATCC AGTTTG-
CAAAGTGGGGTCCCATCAAGGTTCAGTG-
GCAGTGGATCTGGGACA
GATTTCACTCTCACCATCAGCAGTCTG-
CAACCTGAAGATTTTGCAACTTACT ACTGTCAACA-
GAGTTACAGTACCCTGTGGACGTTCGGC-
CAAGGGACCAAGG TGGAAATCAAACGA (SEQ ID NO: 102).

The nucleotide sequence of the portion of the clone encoding the anti-Rh(D) chain I03 is
GCCGAGCTCACCCAGTCTCCATCCTC-
CCTGTCTGCATCTGTAGCGGACAGA GTCACCAT-
CACTTGCCGGACAAGTCGGAACATTAA-
CAGATACTTAAATTGG
TATCAGCAGAAACCAGGGAAAGC-
CCCTAAGCTCCTGATTTATGCTGCATCC AGTTTG-
CAAAGTGGGGTCCCATCAAGGTTCAGTG-
GCAGTGGATCTGGGACA GATTTCACTCTCACCATCACCAGTCTG-
CAACCTGAAGATTTTGCCACTTACT ACTGTCAACA-
GAGTTACAGTACCCCTTTCACTTTCGGC-
CCTGGGACCAAAG TGGATCTCAAACGA (SEQ ID
NO: 103).

The nucleotide sequence of the portion of the clone encoding the anti-Rh(D) chain I04 is
GCCGAGCTCACTCAGTCTCCATCCTC-
CCTGTCTGCATCTGTAGGAGACAGA GTCACCAT-
CACTTGCCGGGCAAGTCAGAACATTAG-
GAGGTCTTTAAATTGG
TATCAACAGAAACCAGGGAAAGC-
CCCTAAGCTCCTGATCTATGCTGCATCC AGTTTG-
CAAAGTGGGGTCCCATCAAGGTTCAGTG-
GCAGTGGATCTGGGACA
GATTTCACTCTCACCATCAGCAGTCTG-
CAACCTGAAGATTTTGCAACTTACT ACTGTCAGCA-
GAGTTCCAATACCCCGTGGACGTTCGGC-
CAAGGGACCAAGG TGGAAATCAAACGA (SEQ ID
NO: 104).

The nucleotide sequence of the portion of the clone encoding the anti-Rh(D) chain I05 is
GCCGAGCTCACCCAGTCTCCATCCTC-
CCTGTCTGCATCTGTAGGAGACAGA GTCACCAT-
CACTTGCCGGGCAAGTCAGAGCATTAG-
GAGGTATTTAAATTGG
TATCAGCACAAACCAGGGAAAGC-
CCCTAAGCTCCTGATCTTTGCTGCATCC AGTTTG-
CAAAGTGGGGTCCCATCAAGGTTCACTG-
GCAGTGGATCTGGGACA
GATTTCACTCTCACCATCAGCAGTCTG-
CAACCTGAAGATTTTGCAACTTACT ACTGTCAACA-
GAGTTACAGTACCCCTCAAACGTTCGGC-
CAAGGGACCAAGG TGGAAATCAAACGA (SEQ ID
NO: 105).

The nucleotide sequence of the portion of the clone encoding the anti-Rh(D) chain I06 is
GCCGAGCTCACCCAGTCTCCATCCTC-
CCTGTCTGCATCTGTAGGAGACAGA GTCACCAT-
CACTTGCCGGGCAAGTCAGAGCATTAG-
CAGCTATTTAAATTGG
TATCAGCAGAAACCAGGGAAAGC-
CCCTAAGCTCCTGATCTATGCCGCATCC AGTTTG-
CAAAGTGGGGTCCCATCAAGGTTCAGTG-
GCAGTGGATCTGGGACA
GATTTCACTCTCACCATCAGCAGTCTG-
CAACCTGAAGATTTTGCAACTTACT ACTGTCAACA-
GAGTTACAGTACCCCGATCACCTTCGGC-
CAAGGGACACGAC TGGAGATTAAACGA (SEQ ID
NO: 106).

The nucleotide sequence of the portion of the clone encoding the anti-Rh(D) chain I07 is
GCCGAGCTCACCCAGTCTCCATCCTC-
CCTGTCTGCATCTGTAGGAGACAGA GTCACCAT-
CACTTGCCGGGCAAGTCAGAGCATTAG-
CAGCTATTTAAATTGG
TATCAGCAGAAACCAGGGAAAGC-
CCCTAAGCTCCTGATCTATGCTGCATCC AGTTTG-
CAAAGTGGGGTCCCATCAAGGTTCAGTG-
GCAGTGGATCTGGGACA
GATTTCACTCTCACCATCAGCAGTCTG-
CAACCTGAAGATTTTGCAACTTACT ACTGTCAACA-
GAGTTACAGTACCCCTCGAACTTTCG-
GCGGAGGGACCAAGG TGGAGATCAAACGA (SEQ
ID NO: 107).

The nucleotide sequence of the portion of the clone encoding the anti-Rh(D) chain I08 is
GCCGAGCTCACCCAGTCTCCATTCTC-
CCTGTCTGCATCTGTCGGAGACAGA GTCACCAT-
AACTTGCCGGGCAAGTCAGACCATTAG-
CAGGTCTTTAAATTGG
TATCAGCATAAACCAGGGGAAGC-
CCCTAAGCTCCTGATCTATGCTGCATCC AGTCTG-
CAGCGTGGGGTCCCACCCAGGTTCAGTG-
GCAGTGGATCTGGGACA
GATTTCACTCTCACCATCAGCAGTCTG-
CAACCTGAAGACTTTGCGACTTACT TCTGTCAA-
CAGAGTGTCAGAATCCCGTACAGTTTTG-
GCCAGGGGACCAAGC TGGAGATCAAACGA (SEQ
ID NO: 108).

The nucleotide sequence of the portion of the clone encoding the anti-Rh(D) chain I09 is
GCCGAGCTCACCCAGTCTCCATCCTC-
CCTGTCTGCATCTGTAGGAGACAGA GTCACCAT-
CACTTGCCGGGCAAGTCAGAGCATTAG-
CAGCTATTTAAATTGG
TATCAGCAGAAACCAGGGAAAGC-
CCCTAAGCTCCTGATCTATGCTGCATCC AGTTTG-
CAAAGTGGGGTCCCATCAAGGTTCAGTG-
GCAGTGGATCTGGGACA
GATTCCACTCTCACCATCAGCAGTCTG-
CAACCTGAAGATTTTGCAACTTATT ACTGTCAA-
CAGCTTAATAGTTACCCGTACACTTTTG-
GCCAGGGGACCAAGC TGGAGATCAAACGA (SEQ
ID NO: 109).

The nucleotide sequence of the portion of the clone encoding the anti-Rh(D) chain I10 is
GCCGAGCTCACCCAGTCTCCATCCTC-
CCTGTCTGCATCTGTAGGAGACAGA GTCACCAT-
CACTTGCCGGGCAAGTCAGAACATTAG-
CAGCTATTTAAATTGG
TATCAGCAGAAACCAGGGAAAGC-
CCCTAAGCTCCTGATCTATGCTGCATCC AGTTTG-
CAAAGTGGGGTCCTATCAAGGTTCAGTG-
GCAGTGGATCTGGGACA
GATTTCACTCTCACCATCAGCAGTCTG-
CAACCTGAAGATTTTGCAACTTACT ACTGTCAACA-
GAGTTACAGTACCCCTCCGTAT-
AGTTTTGGCCAGGGGACCA
AGCTGGAGATCAAACGA (SEQ ID NO: 110).

The nucleotide sequence of the portion of the clone encoding the anti-Rh(D) chain I11 is
GCCGAGCTCACCCAGTCTCCATCCTC-
CCTGTCTGCATCTGTAGGAGACAGA GTCACCAT-
CACTTGCCGGGCAAGTCAGAGCATTAG-
CAGCTATTTAAATTGG
TATCAGCAGAAACCAGGGAAAGC-
CCCTACGCTCCTGATCAATGCTGCATCC AGTTTG-
CAAAGTGGGGTCCCATCAAGGTTCAGTG-
GCAGTGGATCTGGGACA
GATTTCACTCTCACCATTAGCAGTCTG-
CAACCTGAAGATTTCGCAATTACT ACTGTCAACA-
GAGAGAAACTTTTGGCCAGGGGAC-
CAAGCTGGAGATCAAA CGA (SEQ ID NO: 111).

The nucleotide sequence of the portion of the clone encoding the anti-Rh(D) chain I12 is
GCCGAGCTCACCCAGTCTCCATCCTC-
CCTATCTGCATCTGTAGGAGACAGA GTCACCAT-
CACTTGCCGGGCAAGTCAGAGCATTAG-
CAGCTATTTAAATTGG
TATCAGCAGAAACCAGGGAAAGC-
CCCTAAGCTCCTGATCTATGCTGCATCC AGTTTG-
CAAAGTGGGGTCCCATCAAGGTTCAGTG-
GCAGTGGATCTGGGACA GATTTCACTCTCACCATCAGCAGTCTG-
CAACCTGAAGATTTTGCAACTTACT ACTGTCAACA-
GAGTTACAGTACCCCTCCGTA-
CACTTTTGGCCAGGGGACCA
AGCTGGAGATCAAACGA (SEQ ID NO: 112).

The nucleotide sequence of the portion of the clone encoding the anti-Rh(D) chain I13 is
GCCGAGCTCACCCAGTCTCCATCCTC-
CCTGTCTGCCTCTGTAGGAGACAGA GTCACCAT-
CACTTGCCGGGCAAGTCAGAGCATTAG-
CAGGTATTTAAATTGG
TATCAGCAGAAACCAGGGAAAGC-
CCCTAAGCTCCTGATCTATGCTGCATCC AGTTTG-
CAAAGTGGGGTCCCATCAAGGTTCAGTG-
GCAGTGGATCTGGGACA
GATTTCACTCTCACCATCAGCAGTCTG-
CAACCTGAAGATTTTGCAACTTACT ACTGTCAACA-
GAGTTACGGTACCCCTCACAGTTTTGGC-
CGGGGGACCAAGC TGGAGATCAAACGA (SEQ ID NO: 113).

The nucleotide sequence of the portion of the clone encoding the anti-Rh(D) chain I15 is
GCCGAGCTCACCCAGTCTCCTTCCTC-
CCTGTCTGCATCTGTAGGAGACAGA GTCACCAT-
CACTTGCCGGGCAAATCAGAACATTCG-
TAGATCTTTAAATTGG
TATCAGCAGAAACCAGGGAAAGC-
CCCTAACCTCCTGATCTATGCTGCATCC ACATTG-
CAAGGTGGGGTCCCATCAAGGTTCAGTG-
GCAGTGGATCTGGGACA
GATTTCACTCTCACCATCAGCAGTCTG-
CAACTTGCGGATTTTGCAACTTACT ACTGTCAACA-
GACTTCCGCTACCCCGTGGACGTTCGGC-
CAAGGGACCAAGG TGGAAATCAAACGA (SEQ ID NO: 114).

The nucleotide sequence of the portion of the clone encoding the anti-Rh(D) chain I16 is
GCCGAGCTCACCCAGTCTCCATCGTC-
CCTGCCTGCATCTGTGGGAGACAGA GTCACCAT-
CACTTGCCGGGCAAGTCAGACTATTG-
GTTTTAATTTAAATTGGT
ATCAGCAAACATCTGGGAAGC-
CCCCTAAACTCCTAATCTATGGTGTTTCCA AGTTG-
CAAAATGGGGTCCCTTCACGGTTCAGTG-
GCAGTGGGTCCGGGACGG
AATTCACCCTCACAATCAGCAGTCTG-
CAGCCTGAGGATTTTGCGACTTATTA TTGTCAACA-
GACTAACGATGCGTTGTGGACGTTCGGC-
CAAGGGACCAAAGT GGAAGTCAGACGA (SEQ ID NO: 115).

The nucleotide sequence of the portion of the clone encoding the anti-Rh(D) chain J01 is
GCCGAGCTCCAGGACCCTGTTGTGTCT-
GTGGCCTTGGGACAGACAGTCAGG ATCACTTGC-
CAAGGAGACGGCCTCAGAAGTTATTATG-
CAAGCTGGTACCAG
CAGAAGCCGGGACAGGCCCCGAAACT-
TGTCATGTACGGTAGAAACAACCG GCCCTCAGG-
GATCCCAGACCGATTCTCTGGCTC-
CAGCTCAGGGCAGACAGC
TGCCTTGACCATCACGGGGACTCAGGCG-
GAGGATGAGGCTGACTATTACTG TCAGTCCCGTGC-
CACCAGCGGTAACCCTGTGGTGTTCG-
GCGGAGGGACTAA GCTGACCGTCCTG (SEQ ID NO: 116).

The nucleotide sequence of the portion of the clone encoding the anti-Rh(D) chain J02 is
GCCGAGCTCCAGGACCCTGTTGTGTCT-
GTGGCCTTGGGACAGACAGTCAGG ATCACTTGC-
CAAGGAGACGGCCTCAGAAGTTATTATG-
CAAGCTGGTACCAG
CAGAAGCCGGGACAGGCCCCGAAACT-
TGTCATGTACGGTAGAAACAACCG GCCCTCAGG-
GATCCCAGACCGATTCTCTGGCTC-
CAGCTCAGGGCAGACAGC
TGCCTTGACCATCACGGGGACTCAGGCG-
GAGGATGAGGCTGACTATTACTG TCAGTCCCGTGC-
CACCAGCGGTAACCCTGTGGTGTTCG-
GCGGAGGGACTAA GCTGACCGTCCTG (SEQ ID NO: 117).

The nucleotide sequence of the portion of the clone encoding the anti-Rh(D) chain J04 is
GCCGAGCTCCAGGACCCTGTTGTGTCT-
GTGGCCTTGGGACAGACAGTCAGG ATCACATGC-
CAAGGAGACAGCCTCAGAAGCTATTATG-
CAAGCTGGTACCAG
CAGAAGCCAGGACAGGCCCCTGTACT-
TGTCATCTATGGTAAAAACAGCCGG CCCTCAGG-
GATCCCAGACCGATTCTCTGGCTC-
CAGCTCAGGAAACACAGCT
TCGTTGACCATCACTGGGGCTCAGGCG-
GAAGATGAGGCGGACTATTATTGT AGT-
TCGCGGGCAGCCCCACGTGGCATTCG-
GCGGAGGGACCAAACTGAC CGTCCTG (SEQ ID NO: 118).

The nucleotide sequence of the portion of the clone encoding the anti-Rh(D) chain J05 is
GCCGAGCTCCAGGACCCTGTTGTGTCT-
GTGGCCTTGGGACAGACAGTCAAG ATCACATGC-
CAGGGAGACAGCCTCAGAAAGTATTATG-
CAAGCTGGTACCA
GCAGAAGCCAGGACAGGCCCCTGTGCT-
TGTCTTCTATGCTAGAAATAGCCG GCCCTCAGG-
GATCCCAGACCGATTCTCTGGCTC-
CAACTCAGGAACCACAGC
TTCCTTGACCATCGCTGGGGCTCGGGCG-
GAAGATGAGGCTGACTATTACTG TCACTCCCGG-
GACAGCAATGGTCACCATCGGGTGTTCG-
GCGGAGGGACCAA GCTGACCGTCCTA (SEQ ID NO: 119).

The nucleotide sequence of the portion of the clone encoding the anti-Rh(D) chain K01 is
GCCGAGCTCACTCAGGAGCCCTCACT-
GACTGTGTCCCCAGGAGGGACAGTC ACTCTCAC-
CTGTGCTTCCAGCACTGGAGCAGTCAC-
CAGTCGTTACTTTCCAA
ACTGGTTCCAGCAGAAACCTGGACAAG-
CACCCAGGCCACTGATTTATAGTG CAAGCAA-
CAAACACTCCTGGACCCCTGCCCGGT-
TCTCAGGCTCCCTCCTTG
GGGGCAAAGCTGCCCTGACACTGTCAG-
GTGTGCAGCCTGAGGACGAGGCT GAGTATTACT-
GCCTGCTCTACTATAGTGGTGCTTGGGT-
GTTCGGCGGAGGG ACCAAGTTGACCGTCCTT (SEQ ID NO: 120).

The nucleotide sequence of the portion of the clone encoding the anti-Rh(D) chain K02 is
GCCGAGCTCACTCAGGAGCCCTCACT-
GACTGTGTCCCCAGGAGGGACAGTC ACTCTCAC-
CTGTGCTTCCAGCACTGGAGCAGTCAC-
CAGTCGTTACTTTCCAA
ACTGGTTCCAGCAGAAACCTGGACAAG-
CACCCAGGCCACTGATTTATAGTG CAAGCAA-
CAAACACTCCTGGACCCCTGCCCGGT- TCTCAGGCTCCCTCCTTG GGGGCAAAGCTGCCCTGACACTGTCAG- GTGTGCAGCCTGAGGACGAGGCT GAGTATTACT- GCCTGCTCTACTATAGTGGTGCTTGGGT- GTTCGGCGGAGGG ACCAAGCTGACCGTCCTA (SEQ ID NO: 121).

The nucleotide sequence of the portion of the clone encoding the anti-Rh(D) chain K03 is GCCGAGCTCACTCAGCCACCCTCACT- GACTGTGTCCCCAGGAGGGACAGTC ACTCTCAC- CTGTGCTTCCAGCACTGGAGCAGTCAC- CAGTCGTTACTTTCCAA ACTGGTTCCAGCAGAAACCTGGCCAG- GCACCCAGGGCACTGATTTATGGTT CAAACAA- CAAACACTCCTGGACCCCTGCCCGGT- TCTCAGGCTCCCTCCTTG GGGGCAAAGCTGCCCTGACACTGTCAG- GTGTGCAGCCTGAGGACGAGGCG GAGTATTACT- GCCTGCTCTTCTATGCTGGTGCT- TGGGCGTTCGGCGGATGGA CCAAGCTGACCGTCCTA (SEQ ID NO: 122).

The nucleotide sequence of the portion of the clone encoding the anti-Rh(D) chain L01 is GCCGAGCTCACGCAGCCGCCCT- CAGCGTCTGGGACCCCCGGGCAGAGGGT CAC- CATCTCTTGTTCTGGAGGCAGCTCCAA- CATCGCAAGTAATACTGTAAA CTGGTACCAGCAACTCCCAGGAACGGC- CCCCAAACTCCTCATCTATAGTAA TAATCAGCGGC- CCTCAGGGGTCCCTGACCGATTCTCTG- GCTCCAAGTCTGG CACCTCAGCCACCCTGGTCATCAC- CGGGCTCCAGACTGGGGACGAGGCCGA TTAT- TACTGCGGAACATGGGATCACAGCCG- GAGTGGTGCGGTGTTCGGCGG AGGGACCAAACTGACCGTCTTA (SEQ ID NO: 123).

The nucleotide sequence of the portion of the clone encoding the anti-Rh(D) chain L03 is GCCGAGCTCACTCAGCCACCCT- CAGCGTCTGGGACCCCCGGGCAGAGGGTC ACCATCTCTTGTTCTGGCAGTAGCTC- CAACATCGGAAATAATCATGTAAGC TGGTACCAG- CAACTCCCAGGAATGGCCCCCAAACTC- CTCATCTATTCTAAT GGTCAGCGGCCCTCAGGGGTCCCTGAC- CGATTCTCTGGCTCCAAGTCTGGC ACCTCAGCCTC- CCTGGCCATCAGCGGCCTCCAGTCTGAG- GATGAGGCTGAT TATTATTGTGCAGCATGGCATGACAGC- CTCTATGGTCCGGTGTTCGGCGGA GGGAC- CAAGCTGACCGTCCTC (SEQ ID NO: 124).

The nucleotide sequence of the portion of the clone encoding the anti-Rh(D) chain L04 is GCCGAGCTCACTCAGCCACCCT- CAGCGTCTGGGACCCCGGGCAGAGGGTC AGCATCTCTTGTTCTGGAAGCAGCTC- CAACATCGGAAGTAATACTGTAAAC TGGTACCAG- CAGCTCCCAGGAACAGCCCCCAAACTC- CTCATCTCTACTAAT AATCAGGGGCCCTCAGGAGTCCCTGAC- CGATTCTCTGGCTCCAAGTCTGGC ACCTCATCCTC- CCTGGCCATCAGTGGGCTCCGGTCAGAG- GCTGAGGATGAT TATTACTGTGCAGCATGGGATGACAC- CCTGAATGGTGTGGTATTCGGCGGA GGGAC- CAAACTGACCGTCCTA (SEQ ID NO: 125).

The nucleotide sequence of the portion of the clone encoding the anti-Rh(D) chain L05 is GCCGAGCTCACTCAGCCACCCT- CAGCGTCTGGGACTCCCGGGCTGAGGGTC ACCATCTCTTGTTCTGGAAGCAGCTC- CAACATCGGAAGTAATATTGTAAAC TGGTACCAG- CAGCTCCCAGGAACGGCCCCCAAACTC- CTCATCTTTAGTAAT AATAAGCGGCCCTCAGGGGTCCCTGAC- CGATTCTCTGGCTCCAAGTCTGGC ACCTCAGCCTC- CCTGGCCATCAGTGGGCTCCAGTCTGAG- GATGAGGCTGAT TATTACTGTGCTACATGGGATGACAGC- CTGAATGGTCGGGTGTTCGGCGGA GGGAC- CAAGCTGACCGTCCTA (SEQ ID NO: 126).

The nucleotide sequence of the portion of the clone encoding the anti-Rh(D) chain M01 is GCCGAGCTCACTCAGCCACCCT- CAGCGTCTGGGACCCCCGGGCAGCGGGTC ACCATCTCTTGTTCTGGGAGCAACT- TCAACATCGGAAGTAATTATGTATTCT GGTACCAG- CATGTTCCAGGAACGGCCCCAAAACTC- CTCATCTATAATAATA ATCAACGCCCTCTGGGGTCCCTGAC- CGACTCTCTGGCTCCAAGTCTGGCG CCTCAGC- CTCCCTGGCCATCAATGGGCTCCGGTC- CGATGATGAGGCTGATT ATTACTGTACAGGATGGGATGACCGCCT- GAGTGGCCTGATTTTCGGCGGAG GGCCAAAAGT- GACCGTCCTA (SEQ ID NO: 127).

The nucleotide sequence of the portion of the clone encoding the anti-Rh(D) chain M02 is GCCGAGCTCACGCAGCCGCCCT- CAGCGTCTGGGACCCCCGGGCAGAGGGT CAC- CATCTCTTGTTCTGGAAGCAGCTCCAA- CATCGGAAGTAATTATGTATAT TGGTACCAGCAGCTCCCAGGAACGGC- CCCCAAACTCCTCATCTATAGGAAT AATCAGCGGC- CCTCAGGGGTCCCTGACCGATTCTCTG- GCTCCAAGTCTGGC ACCTCAGCCTCCCTGGCCAT- CAGTGGGCTCCGGTCCGAGGATGAGGCTGAT TAT- TACTGTGCAGCATGGGATGACAGCCT- GAGTGGTTGGGTGTTCGGCGGA GGGACCAAGCTGACCGTCCTA (SEQ ID NO: 128).

The nucleotide sequence of the portion of the clone encoding the anti-Rh(D) chain M03 is GCCGAGCTCACTCAGCCACCCT- CAGCGTCTGGGACCCCCGGGCAGAGGGTC ACCATCTCTTGTTCTGGAAGCAGCTC- CAACATCGGAAGTAATTATGTATACT GGTACCAG- CAGCTCCCAGGAACGGCCCCCAAACTC- CTCATCTATAGGAATA ATCAGCGGCCCTCAGGGGTCCCTGAC- CGATTCTCTGGCTCCAAGTCTGGCA CCTCAGCCTC- CCTGGCCATCAGTGGGCTCCGGTCCGAG- GCTGAGGCTGATT ATTACTGTGCGGCATGGGATGACAGCCT- GAGTGCCGTGGTATTCGGCGGAG GGACCAAACT- GACCGTCCTA (SEQ ID NO: 129).

The nucleotide sequence of the portion of the clone encoding the anti-Rh(D) chain N01 is GCCGAGCTCACGCAGCCGCCCTCAGT- GTCTGCGGCCCCAGGACAGAAGGTC ACCATCTC- CTGCTCTGGAAGCAGCTCCAACATTGA- CAGTAACTATGTATCCT GGTACCAGCAGCTCCCAGGAACAGC- CCCCAAACTCCTCATTTTTGACAATT ATAGGCGAC- CCTCAGGGATTCCTGACCGATTCTCAG- GCTCCAAGTCTGGCA CGTCAGCCACCCTGGGCATCACCG-GACTCCAGACTGGGGACGAGGCCGATT ATTACT-GTGCAACATGGGATGACAGCCTGAATG-GTCGGGTGTTCGGCGGAG GGACCAAGCTGACCGTCCTA (SEQ ID NO: 130).

The nucleotide sequence of the portion of the clone encoding the anti-Rh(D) chain N02 is GCCGAGCTCACGCAGCCGCCCTCAGT-GTCTGCGGCCCCAGGACAGAAGGTC ACCATCTC-CTGCTCTGGAAGCAGCTCCAACATTGG-GAATAATTATGTGTCCT GGTACCAGCAACTCCCAGGAACAGC-CCCCAAACTCCTCATTTATGACAATA ATAAGCGAC-CCTCAGGGATTCCTGACCGATTCTCTG-GCTCCAAGTCTGGCA CGTCAGCCACCCTGGGCATCACCG-GACTCCAGACTGGGGACGAGGCCGATT ATTACT-GCGGAACATGGGATAGCAGCCTGAGT-GCTGGCCGCGTTCGGCGGA TGTTCGGCGGAGGGACCAAGTTGACCGTCCTGGGT (SEQ ID NO: 131).

The nucleotide sequence of the portion of the clone encoding the anti-Rh(D) chain O01 is GCCGAGCTCACGCAGCCGCCCTCAGT-GTCTGGGGCCCCAGGGCAGAGGGT CACCATCTC-CTGCACTGGGAGCAGCTCCAA-CATCGGGGCACCTTATGGTGT ACACTGGTACCAGCAGTTTCAGGAA-CAGCCCCCAAACTCGTCATCTACAA TGACAA-CAATCGGCCCTCAGGGGTCCCTGAC-CGATTCTCTGGCTCCAAGTC TGGCACCTCAGCCTCCCTGGCCAT-CACTGGGCTCCAGGCTGAGGATGAGGC TGATTAT-TACTGCCAGTCCTATGACAGCAGCCT-GAGTGGAAGGGTGTTCGG CGGAGGGACCAAGCTGACCGTCCTA (SEQ ID NO: 132).

The nucleotide sequence of the portion of the clone encoding the anti-Rh(D) chain O02 is GCCGAGCTCACGCAGCCGCCCTCAGT-GTCTGGGGCCCCAGGGCAGACGGTC ACCATCTC-CTGCACTGGGAGCAGCTCCAG-CATCGGGGCACGTTATGATGTA CACTGGTACCAACACCTTCCAGGAA-CAGCCCCCAAACTCCTCATCTATGGT AACCA-CAATCGGCCCTCAGGGGTCCCTGAC-CGATTCTCTGGCTCCAAGTCT GGCACCTCAGCCTCCCTGGCCAT-CACTGGGCTCCAGGCTGAGGATGAGGCT GAATAT-TATTGCCAGTCCTATGACAACAGCCT-GAGTGGTTCGTCTGTCTTTT TCGGCGGAGGGACCAAGCTGACCGTCCTA (SEQ ID NO: 133).

The nucleotide sequence of the portion of the clone encoding the anti-Rh(D) chain O03 is GCCGAGCTCACGCAGCCGC-CCTCTGGGGCCCCAGGCCAGACGGTCACCATC TCCTGCACTGGGAGCAGCTCCAA-CATCGGGGCAGGTTATGATGTACACTGG TACCAG-CAGCTTCCAGGAACAGCCCCCAAACTC-CTCATCTATGGTAACAGC AATCGGCCCTCAGGGGTCCCTGACCGAT-TCTCTGGCTCCAAGTCTGGCACC TCAGCCTCCCTG-GCCATCACTGGGCTCCAGGCTGAGGAT-GAGGCTGATTAT TACTGCCAGTCCTATGACAGCAGCCT-GAGTGGTCCCTATGTGGTATTCGGC GGAGGGAC-CAAGCTGACCGTCCTA (SEQ ID NO: 134).

The nucleotide sequence of the portion of the clone encoding the anti-Rh(D) chain P01 is GCCGAGCTCACTCAGCCACCCTCGGTGT-CAGTGGCCCCAAGACAGACGGCC AGGATTACCT-GTGGGGGGGACAAAATCGGAAGTAA-CACTGTGCATTGGTA CCGGCAGATGTCAGGCCAGGCCCCTGT-TCTGGTCATCTATGAAGACAAAAA ACGAC-CCCCCGGGATCCCTGAGAGATTCTCTG-GTTCCACCTCAGGGACAAC GGCCACCTTGAGTATCAGTGGGGCCCAG-GTTGAGGATGAAGCTGACTACTA CTGTTATTCAA-GAGACAACAGTGGTGATCAGAGAAGGGT-GTTCGGCGCAG GGACCAAGCTGACCGTCCTA (SEQ ID NO: 135).

The nucleotide sequence of the portion of the clone encoding the anti-Rh(D) chain Q01 is GCCGAGCTCACTCAGCCACCCTCCGC-CACTGCCTCCCTGGGAGGCTCGGTC AAACTCAC-CTGCATTCTGCAGAGTGGCCACAGAAAT-TACGCCGTCGCTTGG CATCACCAAGAAGCAGGGAAGGGCCCGC-GATTTTTGATGACGGTTACCAAT GATGGCAGGCA-CATCAAGGGGGACGGGATCCCT-GATCGCTTCTCAGGCTCC GCCTCTGGGGCTGAACGCTACCTCTC-CATCTCCGGCCTCCAGTCTGAGGAT GAGGGTGAC-TACTACTGTCAGACCTGGGGCACTG-GCATGCATGTGTTCGGC GGAGGGACCAAACTGACCGTCCTA (SEQ ID NO: 136).

The nucleotide sequence of the portion of the clone encoding the anti-Rh(D) chain R01 is GCCGAGCTCACTCAGCCTCCCTC-CGCGTCCGGGTCTCCTGGACAGTCAGTC ACCATCTCCTGCACTGGAGCCAGCAGT-GACGTTGGTGCTTATAAGCACGTC TCCTGGTAC-CAACAACACCCAGGCAAAGC-CCCCAAACTCCTGACTCATGAG GGCACTAAGCGGCCCTCAGGGGTCCCT-GATCGCTTCTCTGGCTCCAAGTCT GGCAACACG-GCCTCCCTGACCGTCTCTGGGCTCCAG-GCTGAGGATGAGGCT GATTATTACTGCAGCTCATTTGCAGG-TAATTCCGTGATATTCGGCGGAGGG ACCAAGCT-GACCGTCCTA (SEQ ID NO: 137).

The nucleotide sequence of the portion of the clone encoding the anti-Rh(D) chain S01 is GCCGAGCTCACTCAGCCTCCCTCCGT-GTCTGGGTCTCCTGGACAGTCGATC ACCATCTCCT-GCAGTGATGTTGGGAATTATAACCT-TGTCTCCTGGTACCAAC AGTACCCAGGCAAGGCCCCCAAACTCAT-AATTTATGAGGGCAGTAAGCGG CCCT-CAGGGGTTTCTAGTCGCTTCTCTGGCTC-CAGGTCTGGCAACACGGCCT CCCTGACAATCTCTGGGCTCCAGGCT-GAGGACGAGGCTGATTATCACTGCT GCTCATATG-CAATTAGTAGCAGGATTTTCGGCGGAGG-GACCAAGCTGACCG TCCTA (SEQ ID NO: 138).

EXAMPLE 3

Isolation of Anti-Rh(D) Monoclonal Antibodies to Conventional and Novel Epitopes Using a Heavy Chain/Light Chain Shuffling Approach In view of the results obtained in Examples 1 and 2 herein, heavy and light chains of antibodies of various Rh(D)

epitope specificities were randomly recombined in order to generate anti-Rh(D) antibodies having additional patterns of reactivity with Rh(D) variant cells. Using this approach, plasmid DNA obtained from the Fab/phage display libraries described in panning rounds 2 and 3 of Example 1 was randomly recombined to generate a "shuffled" Fab/phage display library. When the Rh(D) specificity of antibodies of this "shuffled" library was determine, it was found that many of these antibodies exhibited novel epitope specificity. Significantly, antibody clones having novel Rh(D) epitope specificity were identified, including clones which bind to wild type and certain partial D type red blood cells but which do not bind to D category III red blood cells. The experiments described in this Example therefore demonstrate that the methods described in this specification may be used to generate antibody clones useful for diagnostic and therapeutic applications in humans.

The materials and methods used in the experiments described in this Example are now described.

Creation of Shuffled Fab/Phage Display Library

Two microgram aliquots of DNA obtained from libraries LP2, LP3, KP2, and KP3 (described herein in Example 1) were digested using the restriction endonucleases SpeI and XhoI (15 and 60 units, respectively) in order to dissociate DNA segments encoding individual (full length) heavy chains from library plasmids encoding individual (full length) light chains. Endonuclease/DNA mixtures were incubated overnight at 37° C. After the restriction endonucleases were removed using standard phenol/chloroform and chloroform extraction techniques, the DNA was precipitated using ethanol.

Equivalent amounts of DNA from each of the four libraries (500 nanograms total) were mixed, and then the heavy chain-encoding DNA fragments were re-ligated into the library plasmids encoding individual light chains. This ligation was performed overnight at 20° C. in the presence of 3.5 units of T4 DNA ligase in a total reaction volume of 70 microliters. This treatment generated re-ligated library plasmids encoding a light chain and a heavy chain, wherein the light chain and the heavy chain were not necessarily encoded by a single plasmid in the original library DNA. For this reason, the library of re-ligated plasmids was designated a "shuffled" library.

Three microliters of shuffled library suspension were mixed with an aliquot of XL1-Blue electrocompetent cells (obtained from Stratagene, La Jolla, Calif.), and the cells were electroporated according to standard methods. Electroporated cells were cultured on plates containing Luria broth comprising 100 micrograms per milliliter carbenicillin.

Anti-Rh(D) Specificity of "Shuffled" Library Antibodies

Fifty-six randomly chosen colonies were selected, and monoclonal Fab/phage preparations were separately produced from each of these individual colonies, using the methods described herein in Example 1. Rh(D) specificity was determined by indirect agglutination using anti-M13 antibody, as described herein in Examples 1 and 2. Plasmid DNA was separately prepared from each of the Fab/phage preparations which exhibited Rh(D) specificity, and the DNA sequences encoding the heavy and light chains expressed by each preparation were determined as described herein.

The results of the experiments presented in this Example are now described.

Anti-Rh(D) Specificity of "Shuffled" Library Antibodies

Of the 56 randomly-chosen "shuffled" library clones, 34 (61%) demonstrated specificity for Rh(D). The Rh(D) epitope specificity, the agglutination pattern, and the heavy and light chain sequences of these 34 clones are listed in Table 4. Of these 34 clones, 19 exhibited specificity for previously-described Rh(D) epitopes (e.g. epD 1, epD 2, epD 6/7, and epD X), and one bound too weakly to wild-type Rh(D)-positive red blood cells to characterize is epitope specificity (i.e. clone SH44). However, 14 of the clones identified in Table 4 exhibited novel Rh(D) epitope specificity. Some of these 14 antibody clones comprised a heavy chain, a light chain, or both, that were identified herein in Examples 1 or 2. However, half (17/34) of the heavy chain sequences and about 80% (28/34) of the light chain sequences had not been identified in Examples 1 or 2.

The Rh(D)-specific antibody clones isolated from the "shuffled" library are useful for characterizing and classifying patient red blood cells that express variant forms of the Rh(D) antigen. Of particular interest are clones SH18, SH20, and SH46. These three clones agglutinate wild type red blood cells and certain partial D-type red blood cells, but do not agglutinate D category III red blood cells (a.k.a. partial Rh(D)III cells). It is believed that all previously-characterized human monoclonal anti-Rh(D) antibodies agglutinate D category III red blood cells. Therefore these three clones are particularly useful for differentiating D category III red blood cells from other types of red blood cells.

From a clinical perspective, it has heretofore only been possible to retrospectively identify D category III red blood cells in a patient after they have been erroneously presumed to have wild-type Rh(D)-positive cells. For example, transfusion of an individual having D category III red blood cells with wild-type Rh(D) cells induces production of anti-Rh(D) alloantibodies in the individual. Previously, the presence of D category III red blood cells in patients could only be determined by the production of such anti-Rh(D) alloantibodies in a transfusion recipient who does not naturally harbor D category III red blood cells. Although providing transfused blood comprising D category III red blood cells to a patient who does not naturally harbor such cells will not necessarily cause immediate harm to the patient, the patient thereby becomes alloimmunized against D category III red blood cells. Such alloimmunized individuals may develop complications including hemolytic transfusion reactions or hemolytic disease of the newborn.

TABLE 4

Analysis of Anti-RH(D) Clones Obtained by Chain Shuffling.

| CLONE | HEAVY CHAIN SEQUENCE† | LIGHT CHAIN SEQUENCE† | AGGLUTINATION PATTERN‡ wt | III | IVa | IVb | V | V1 | VII | Rh(D) SPECIFICITY |
|---|---|---|---|---|---|---|---|---|---|---|
| SH04 | SEQ ID NOs: 24/93 | SEQ ID NOs: 35/104 | + | + | + | + | + | 0 | + | epD 6/7 |
| SH08 | SEQ ID NOs: 12/81 | SBQ ID NOs: 154/197 | + | + | + | + | + | 0 | + | epD 6/7 |

TABLE 4-continued Analysis of Anti-RH(D) Clones Obtained by Chain Shuffling.

| CLONE | HEAVY CHAIN SEQUENCE† | LIGHT CHAIN SEQUENCE† | AGGLUTINATION PATTERN‡ | | | | | | | Rh(D) SPECIFICITY |
|---|---|---|---|---|---|---|---|---|---|---|
| | | | wt | III | IVa | IVb | V | V1 | VII | |
| SH10 | SEQ ID NOs: 139/182 | SEQ ID NOs: 47/116 | + | 0 | 0 | 0 | 0 | 0 | 0 | novel |
| SH12 | SEQ ID NOs: 9/78 | SEQ ID NOs: 155/198 | + | + | + | + | + | 0 | + | epD 6/7 |
| SH13 | SEQ ID NOs: 26/95 | SEQ ID NOs: 156/199 | + | 0 | 0 | 0 | 0 | 0 | 0 | novel |
| SH14 | SEQ ID NOs: 24/93 | SEQ ID NOs: 157/200 | + | + | + | + | + | 0 | + | epD 6/7 |
| SH16 | SEQ ID NOs: 140/183 | SEQ ID NOs: 158/201 | + | 0 | + | + | 0 | 0 | 0 | novel |
| SH17 | SEQ ID NOs: 141/184 | SEQ ID NOs: 47/116 | + | + | 0 | 0 | 0 | 0 | + | epD 1 |
| SH18 | SEQ ID NOs: 142/185 | SEQ ID NOs: 159/202 | + | 0 | + | + | 0 | 0 | 0 | novel |
| SH20 | SEQ ID NOs: 143/186 | SEQ ID NOs: 160/203 | + | 0 | + | + | + | 0 | 0 | novel |
| SH21 | SEQ ID NOs: 9/78 | SEQ ID NOs: 161/204 | + | + | + | 0 | + | 0 | 0 | novel |
| SH24 | SEQ ID NOs: 144/187 | SEQ ID NOs: 162/205 | + | 0 | 0 | 0 | 0 | 0 | 0 | novel |
| SH25 | SEQ ID NOs: 145/188 | SEQ ID NOs: 35/104 | + | + | 0 | 0 | + | 0 | + | epD 2 |
| SH26 | SEQ ID NOs: 21/90 | SEQ ID NOs: 163/206 | + | + | + | 0 | 0 | 0 | 0 | novel |
| SH28 | SEQ ID NOs: 146/189 | SEQ ID NOs: 164/207 | + | + | 0 | 0 | + | 0 | + | epD 2 |
| SH30 | SEQ ID NOs: 12/81 | SEQ ID NOs: 165/208 | + | + | + | + | + | 0 | + | epD 6/7 |
| SH32 | SEQ ID NOs: 147/190 | SEQ ID NOs: 166/209 | + | 0 | 0 | 0 | 0 | 0 | 0 | novel |
| SH34 | SEQ ID NOs: 5/74 | SEQ ID NOs: 167/210 | + | + | 0 | 0 | 0 | 0 | + | epD 1 |
| SH36 | SEQ ID NOs: 14/83 | SEQ ID NOs: 168/211 | + | 0 | 0 | 0 | 0 | 0 | 0 | novel |
| SH37 | SEQ ID NOs: 148/191 | SEQ ID NOs: 50/119 | + | + | + | 0 | 0 | 0 | + | epD X § |
| SH39 | SEQ ID NOs: 149/192 | SEQ ID NOs: 169/212 | + | 0 | 0 | 0 | 0 | 0 | 0 | novel |
| SH41 | SEQ ID NOs: 24/93 | SEQ ID NOs: 170/213 | + | + | + | + | + | 0 | + | epD6/7 |
| SH44 | SEQ ID NOs: 150/193 | SEQ ID NOs: 171/214 | + | | | | | | | not determined |
| SH46 | SEQ ID NOs: 13/82 | SEQ ID NOs: 172/215 | + | 0 | + | + | 0 | 0 | 0 | novel |
| SH47 | SEQ ID NOs: 151/194 | SEQ ID NOs: 173/216 | + | + | 0 | 0 | + | 0 | + | epD 2 |
| SH48 | SEQ ID NOs: 6/75 | SEQ ID NOs: 174/217 | + | + | 0 | 0 | 0 | 0 | + | epD 1 |
| SH49 | SEQ ID NOs: 17/86 | SEQ ID NOs: 175/218 | + | + | 0 | 0 | 0 | 0 | + | epD 1 |
| SH50 | SEQ ID NOs: 146/189 | SEQ ID NOs: 176/219 | + | + | 0 | 0 | 0 | 0 | + | epD 1 |
| SH51 | SEQ ID NOs: 17/86 | SEQ ID NOs: 177/220 | + | + | 0 | 0 | + | 0 | + | epD 2 |
| SH52 | SEQ ID NOs: 24/93 | SEQ ID NOs: 178/221 | + | + | 0 | 0 | 0 | 0 | + | epD 1 |
| SH53 | SEQ ID NOs: 146/189 | SEQ ID NOs: 47/116 | + | 0 | 0 | 0 | 0 | 0 | 0 | novel |
| SH54 | SEQ ID NOs: 152/195 | SEQ ID NOs: 179/222 | + | + | 0 | 0 | 0 | 0 | + | epD 1 |
| SH55 | SEQ ID NOs: 21/90 | SEQ ID NOs: 180/223 | + | + | 0 | 0 | + | 0 | + | epD 2 |
| SH56 | SEQ ID NOs: 153/196 | SEQ ID NOs: 181/224 | + | + | 0 | 0 | 0 | 0 | 0 | novel |

Notes for Table 4
†"SEQ ID NOs: A/B" means that the chain had amino acid sequence "A" and was encoded by nucleotide sequence "B".
‡ "+" means agglutination occurred; "0" means agglutination did not occur.
*weak
§ as discussed in Example 2.

Amino Acid Sequences of Anti-Rh(D) Heavy and Light Chains

The amino acid sequences of various anti-Rh(D) antibody chains were as follows, and are represented using single letter amino acid codes.

The amino acid sequence of the heavy chain of anti-Rh(D) antibody clone SH10 is
EVQLLEESGGGVVQPGRSLRLSCAASG-FTFSRNGMHWVRQAPGKGLEWVAFI WFDGSNKYY-ADSVKGRFTISRDNSKNTLYLQMNSL-RADDTAVYYCAREEALF RGLTRWSYGMDVWGQGTTVSVSS (SEQ ID NO: 139).

The amino acid sequence of the heavy chain of anti-Rh(D) antibody clone SH16 is
EVQLLESGGGVVQPGRSLRLSCAASG-FTFSSYGMHWVRQAPGRGLEWVALIW YDGGNKEY-ADSVKGRFSISRDNSKNTLYLQVNSL-RADDTAVYYCARDQRAA AGIFYYSRMDVWGQGTTVTVSS (SEQ ID NO: 140).

The amino acid sequence of the heavy chain of anti-Rh(D) antibody clone SH17 is
EVQLLESGGGVQPGGSLRLSCGAS-GIPFVSSWMAWVRQAPGKGLEWVANIK QDG-SKKNYVDSVEGRFTISRD-NAKNSLYLQMDSLRAEDTRIYYCARDSLTCFD YWGQGALVTVSS (SEQ ID NO: 141).

The amino acid sequence of the heavy chain of anti-Rh(D) antibody clone SH18 is
EVQLLESGGGVVQPGRSLRLSCAASGFT-FRSYAMHWVRQAPGKGLEWVAAT AYDGKNKYY-ADSVKGRFTISRDNSMNTLFLQMNSL-RAEDTAVFYCARGGFYY DSSGYYGLRHYFDSWGQGTLVTVSS (SEQ ID NO: 142).

The amino acid sequence of the heavy chain of anti-Rh(D) antibody clone SH20 is
EVQLLEESGGGVVQPGRSLRLSCAASG-FTFRSYAMHWVRQAPGKGLEWVAVI SYDGSTIYY-ADSVKGRFTISRANSKNTLFLQMNSLRT-EDTAVYYCTRGGFYYD SSGYYGLRHYFDYWGQGTLVTVSS (SEQ ID NO: 143).

The amino acid sequence of the heavy chain of anti-Rh(D) antibody clone SH24 is
EVQLLESGGGVAQPGRSLRLSCVASGFS-LRSYGMHWVRQAPGKGLEWVADI WFDGSNKDY-ADSVKGRFTISRDNSKNTLYLQMNSL-RAEDTAVYYCARDWRV RAFSSGWLSAFDIWGQGTMVTVSS (SEQ ID NO: 144).

The amino acid sequence of the heavy chain of anti-Rh(D) antibody clone SH25
EVQLLEESGGGVVQPGRSLRLACAASGF-SFRSYGMHWVRQAPGRGLEWVAFT WFDG-SNKYYVDSVKGRFTISRDNSKNT-LYLEMNSLRVDDTAVYYCAREAPML RGISRYYYAMDVWGPGTTVTVSS (SEQ ID NO: 145).

The amino acid sequence of the heavy chain of each of anti-Rh(D) antibody clones SH28, SH50, and SH53 is EVQLLESGGGGVQPGRSLRLSCAASGFTFNSYAMYWVRQPPGKGLEWVAAIW YDGSNKEYADFVKGRFTISRDNSKNTLSLQMNSLRDEDTAVYYCAREANLLR GWSRYYYGMDVWGQGTTVTVSS (SEQ ID NO: 146).

The amino acid sequence of the heavy chain of anti-Rh (D) antibody clone SH32 is EVQLLESGGGVVQPGRSLRLSCEASKFTLYNYGMHWVRQAPGKGLEWVAFI WFDGSNKYYEDSVKGRFTVSRDNSKNTLYLQMNSLRAEDTAVYYCARELSK KVALSRYYYYMDVWGQGTTVTVSS (SEQ ID NO: 147).

The amino acid sequence of the heavy chain of anti-Rh (D) antibody clone SH37 is EVQLLESGGGVVQPGRSLRLSCEASKFTLYNYGMHWVRQAPGKGLEWVAFI WFDGSNKYYEDSVKGRFTVSRDNSKNTLYLQMNSLRAEDTAVYYCARELSK KVALSRYYYYMDVWGQGTTVTVSS (SEQ ID NO: 148).

The amino acid sequence of the heavy chain of anti-Rh (D) antibody clone SH39 is EVQLLEQSGGGVVQPGRSLRLSCAASGFTFSSYGMHWVRQAPGKGLEWVAVI WFDGSNKEYADSVKGRFTISRDNSKNTLYLQMNSLRAEDTAVYYCAREEVVR GVILWSRKFDYWGQGTLVTVSS (SEQ ID NO: 149).

The amino acid sequence of the heavy chain of anti-Rh (D) antibody clone SH44 is EVQLLESGGGVAQPGRSLRLSCVASGFSLRSYGMHWVRQAPGKGLEWVADI WFDGSNKDYADSVKGRFTISRDNSKNTLYLQMNSLRAEDTAVYYCARDWRV RAFSSGWLSAFDIWGQGTMVTVSS (SEQ ID NO: 150).

The amino acid sequence of the heavy chain of anti-Rh (D) antibody clone SH47 is EVQLLESGGGVVQPGRSLRLSCAASGFSFSNYAMHWVRQAPGKGLEWVAVTS FDGSIKDYADSVKGRFTISRDNSKNTLYLQMNSLRDEDTAVYYCARERGMIVV VRRRNAFDIWGQGTMVTVSS (SEQ ID NO: 151).

The amino acid sequence of the heavy chain of anti-Rh (D) antibody clone SH54 is EVQLLESGGGVVQPGRSLRLSCAASGFTFSRNGMHWVRQAPGKGLEWVAFIW FDGSNKYYADSVKGRFTISRDNSKNTLYLQMNSLRADDTAVYYCAREEALFR GLTRWSYGMDVWGQGTTVSVSS (SEQ ID NO: 152).

The amino acid sequence of the heavy chain of anti-Rh (D) antibody clone SH56 is EVQLLESGGGVVQPGRSLRLSCAASGFTFSSYGMHWVRQAPGKGLEWVAVV YYDGSNKHYSDSVKGRFTIFRDNSKNTLYLQMDSLRAEDTAVYYCARERNFR SGYSRYYYGMDVWGPGTTVTVSS (SEQ ID NO: 153).

The amino acid sequence of the light chain of anti-Rh(D) antibody clone SH8 is AELTQSPSSLAASVGDRVTITCRANQTIRTSLNWYQQRPGKAPNLLIYGASRLH SGVPSRFSGGISGADFTLTISSLQPEDFATYYCQQTYGYSRTFGQGTKVDIKR (SEQ ID NO: 154).

The amino acid sequence of the light chain of anti-Rh(D) antibody clone SH12 is AELTQSPFSLSASVGDRVTITCRASHNIYRSLNWFQHKPGEAPKLLVYAASSLQ RGVPTRFSGSGSGTDFTLTISSLQPEDSATYFCQQSVTFPYTFGQGTKLEIRR (SEQ ID NO: 155).

The amino acid sequence of the light chain of anti-Rh(D) antibody clone SH13 is AELTQSPSSLSASVGDRVTITCRASQSISSYLNWYQQKPGKAPKLLIYAASSLRS GVPSRFSGSGSGTDFTLTISSLQPEDFATYYCQQSYSTPYTFGQGTKLEIKR (SEQ ID NO: 156).

The amino acid sequence of the light chain of anti-Rh(D) antibody clone SH14 is AELTQSPSSLSASVGDRVTITCRASQNIRRSLNWYQHKPGRAPRLLIYAASTLQ SGVPSRFRGSGSGTDFTLTINSLQPADFATYYCQQSSNTPWTFGHGTKVEIKR (SEQ ID NO: 157).

The amino acid sequence of the light chain of anti-Rh(D) antibody clone SH16 is AELTQSPSSLSASVGDRVTITCRASQSISSYLNWYQQKPGKAPKLLIYAASSLQS GVPSRFSGSGSGTDFTLTISSLQPEDFATYYCQQSYSTPPTFGGGTKVEIKR (SEQ ID NO: 158).

The amino acid sequence of the light chain of anti-Rh(D) antibody clone SH18 is AELTQSPSSLSASVGDRVTITCRASQSISIALNWYQQRPGKAPKLLMYATSTLQ SGVPSRFSGSGSGTDFTLTISSLQPEDFATYYCQQYYNKPTFGPGTKVDIKR (SEQ ID NO: 159).

The amino acid sequence of the light chain of anti-Rh(D) antibody clone SH20 is AELTQSPFSLSASVGDRVTITCRASQSISRSLNWYQHKPGEAPKLLIYAASSLQR GVPPRFSGSGSGTDFTLTISSLQPEDFATYFCQQSVRIPYSFGQGTKLEIKR (SEQ ID NO: 160).

The amino acid sequence of the light chain of anti-Rh(D) antibody clone SH21 is AELTQSPSFLSASVGDRVTITCRASQGIRSYLAWYQQKPGKAPKLLIYAASTLQ SGVPSRFSGSGSGTEFTLTIASLQPDDFATYYCQQLNNYPPFTFGPGTKVDIKR (SEQ ID NO: 161).

The amino acid sequence of the light chain of anti-Rh(D) antibody clone SH24 is AELTQSPSSLSASVGDRVTITCRASQSISTYLNWYQQRPGKAPNLLIYAASTLQ RGVPSRFTGSGSGTDFTLTISSLQPEDFATYYCQQSYTTLWTFGQGTKMEIRR (SEQ ID NO: 162).

The amino acid sequence of the light chain of anti-Rh(D) antibody clone SH26 is AELTQSPSSLSASVGDRVTITCRASQSISSYLNWYQQKPGKAPKLLIYAASSLQS GVPSRFSGSGSGTDFTLTISSLQPEDFATYYCQQSYSFRRYSFGQGTKLEIKR (SEQIDNO: 163).

The amino acid sequence of the light chain of anti-Rh(D) antibody clone SH28 is AELTQSPSSLSASVGDRVTITCRADQNIRRSLNWFQQKPGKAPKLLIYAASSLQ SGVPSRFSGSGSGTDFTLTISSLQPEDFATYYCQQSSSTPWTFGRGTKVEIKR (SEQ ID NO: 164).

The amino acid sequence of the light chain of anti-Rh(D) antibody clone SH30 is AELTQSPSSLSASVGDRVTITCRASQSIRRSLNWYQQSPGKTPKLLIYAASSLQS GVPSRFSGSGSGTDFTLTISSLQPEDFATYYCQQSYSTLTFGGGTKVEIKR (SEQ ID NO: 165).

The amino acid sequence of the light chain of anti-Rh(D) antibody clone SH32 is AELTQEPSLTVSPGGTVTLTCASSTGAVTSRYFPNWFQQKPGQAPRALIYGSNN KHSWT-

PARFSGSLLGGKAALTLSGVQPEDE-AEYYCLLFYAGAWAFGGGTKLT VL (SEQ ID NO: 166).

The amino acid sequence of the light chain of anti-Rh(D) antibody clone SH34 is AELTQSPSSLSASVGDRVTITCRASQ-SISSYLNWYQQKPGKAPKLLIYAASGLQ SGVPSRF-SGSGSGTDFTLTISSLQPEDFATYYCQQ-SYSTPPYTFGQGTKLEIKR (SEQ ID NO: 167).

The amino acid sequence of the light chain of anti-Rh(D) antibody clone SH36 is AELTQSPSSLSASVGDRVTITCRASQ-SISSYLNWYQQKPGKSPKLLIYAASSLQS GVPSRF-SGSGSGTDFTLTISSLQPEDFATYYCQQ-SYSTPPAFGPGTKVDIKR (SEQ ID NO: 168).

The amino acid sequence of the light chain of anti-Rh(D) antibody clone SH39 is AELTQSPSSLSASVGDRVTITCRASQTI-GRYLNWYQQRPGKAPKLLVYAVSSLQ SGAPSRF-SGSGSGTHFTLTITSLQPEDFATYFCQQ-SYSSPFTFGQGTKVEIKR (SEQ ID NO: 169).

The amino acid sequence of the light chain of anti-Rh(D) antibody clone SH41 is AELTQSPSSLSASVGDRVTIT-CRASQNIRRSLNWYQHKPGRAPRLLIYAASTLQ SGVPSRFRGSGSGTDFTLTINSLQPAD-FATYYCQQSSNTPWTFGHGTKVEIKR (SEQ ID NO: 170).

The amino acid sequence of the light chain of anti-Rh(D) antibody clone SH44 is AELTQSPSSLSASVGDRVIIT-CRASQTIPRFLNWYQQKPGKAPVLLIHSISSLQSG VPSRFSASGSGTEFTLTISSLQPEDFA-TYYCQQSYSNLSFGPGTTVDIRR (SEQ ID NO: 171).

The amino acid sequence of the light chain of anti-Rh(D) antibody clone SH46 is AELTQSPSSLSASVGDRVTIT-CRASQYISSYLNWYQQKPGKAPNLLIYAASSLQ SGVPSRFSGSGSGTDFTLTISSLQPED-FATYYCQQTYSSPSTFGPGTKVDIKR (SEQ ID NO: 172).

The amino acid sequence of the light chain of anti-Rh(D) antibody clone SH47 is AELTQSPSSLSASVGDRVTITCRASQ-SISNYLNWYQQKPGKAPNLLIYAASSLQ SGVPSRF-SGSGSGTDFTLTISSLQPEDFATYYCQQ-SYSYPRTFGQGTKVEIRR (SEQ ID NO: 173).

The amino acid sequence of the light chain of anti-Rh(D) antibody clone SH48 is AELTQSPSSLSASVGDRVTIT-CRASQYISSYLNWYQQKPGKAPNLLIYAASSLQ SGVPSRFSGSGSGTDFTLTISSLQPED-FATYYCQQTYSSPSTFGPGTKVDIKR (SEQ ID NO: 174).

The amino acid sequence of the light chain of anti-Rh(D) antibody clone SH49 is AELTQSPSSLSASVGDRVTVTCRASQ-SISSYLNWYQQKPGKAPKLLIYAASSLQ SGVPSRF-SGSGSGTDFTLTISSLQPEDFATYYCQQ-SYSTPWTFGQGTKVEIKR (SEQ ID NO: 175).

The amino acid sequence of the light chain of anti-Rh(D) antibody clone SH50 is AELTQSPSSLSASVGDRVTVTCRASQ-SISSYLNWYQQKPGKAPKLLIYAASSLQ SGVPSRF-SGSGSGTDFTLTISSLQPEDFATYYCQQ-SYSTPWTFGQGTKVEIKR (SEQ ID NO: 176).

The amino acid sequence of the light chain of anti-Rh(D) antibody clone SH51 is AELTQSPSFLSASVGDRVTITCRASQ-GIRSYLAWYQQKPGKAPKLLIYAASTLQ SGVPSRF-SGSGSGTEFTLTISSLQPEDFATYYC-QQLNNYPPFTFGPGTKVDIKR (SEQ ID NO: 177).

The amino acid sequence of the light chain of anti-Rh(D) antibody clone SH52 is AELTQSPGTLSLSPGERATLSCRASQ-SISSSYLAWYQQKPGQAPRLLIYGASSRA TGIPDRF-SGSGSGTDFTLTISRLEPEDFAVYYC-QQYGSSPWTFGQGTKVEIKR (SEQ ID NO: 178).

The amino acid sequence of the light chain of anti-Rh(D) antibody clone SH54 is AELTQSPSSMSASVGDRVTIT-CRASQSIGTYLNWYQQKPGKAPKLLIYAASSLQ SGVPSRFSGSGSGTDFTLTISSLQPED-FATYYCQQSYSTPWTFGQGTKVEIKR (SEQ ID NO: 179).

The amino acid sequence of the light chain of anti-Rh(D) antibody clone SH55 is AELTQPPSASGTPGQRVTISCSGSSS-NIGSKYVYWYQQLPGTAPKLLIYSNNQR PSGVP-DRFSAFKSGTSASLAITGLQAEDEANYY-CQSYDSGLSGWVFGGGTKLT VL (SEQ ID NO: 180).

The amino acid sequence of the light chain of anti-Rh(D) antibody clone SH56 is AELTQSPSSLSASVGDRVTITCRASQ-SISRYLNWYQQKPGKAPKLLIYAASSLQ SGVPSRF-SGSGSGTDFALTISSLLPEDFATYYC-QQGYSTPPYSFGQGTKLEIKR (SEQ ID NO: 181).

Nucleotide Sequences of Anti-Rh(D) Heavy and Light Chains

The nucleotide sequences encoding various anti-Rh(D) antibody clone chains were as follows.

The nucleotide sequence encoding the heavy chain of anti-Rh(D) antibody clone SH10 is
GAGGTGCAGCTGCTCGAGGAGTCTGGGG-GAGGCGTGGTCCAGCCTGGGAG GTCCCT-GAGACTCTCCTGTGCAGCGTCTGGGT-TCACCTTCAGTAGGAATGG
CATGCACTGGGTCCGCCAGGCTCCTG-GCAAGGGGCTGGAGTGGGTGGCATT TATATG-GTTTGATGGAAGTAATAAATACTATGCA-GACTCCGTGAAGGGCCG
ATTCACCATCTCCAGAGACAATTCCAA-GAACACGCTGTATCTGCAAATGAA CAGCCT-GAGAGCCGACGACACGGCTGTGTAT-TACTGTGCGAGAGAGGAGG
CTCTGTTTCGGGGACTTACTCGGTGGTC-CTACGGCATGGACGTCTGGGGCC AAGGGACCACG-GTCAGCGTCTCCTCA (SEQ ID NO: 182).

The nucleotide sequence encoding the heavy chain of anti-Rh(D) antibody clone SH16 is
GAGGTGCAGCTGCTCGAGTCTGGGGGAG-GCGTGGTCCAGCCTGGGAGGTC CCTGAGACTCTC-CTGTGCAGCGTCTGGGTTCACCTTCAG-TAGCTATGGCATG
CACTGGGTCCGCCAGGCTCCAG-GCAGGGGGCTGGAGTGGGTGGCTCTTATA TGG-TACGATGGAGGTAACAAAGAGTATGCA-GACTCCGTGAAGGGCCGCTT
CAGCATCTCCAGAGACAACTCCAAGAA-CACTCTGTATCTGCAAGTGAACAG CCTGAGAGC-CGACGACACGGCTGTCTATTACTGTGC-GAGAGACCAGAGAG
CAGCAGCGGGTATCTTTTATTATTCCCG-TATGGACGTCTGGGGCCAAGGGA CCACGGTCAC-CGTCTCCTCA (SEQ ID NO: 183).

The nucleotide sequence encoding the heavy chain of anti-Rh(D) antibody clone SH17 is
GAGGTGCAGCTGCTCGAGTCTGGGGGAGGCTTGGTCCAGCCGGGGGGGTC CCTGAGACTCTCCTGTGGTGCCTCTGGAATCCCCTTTGTTTCCTCTTGGATG GCCTGGGTCGCCAGGCCCAGGGAAGGGGCTGGAGTGGGTGGCCAACAT AAAACAAGATGGAAGTAAGAAAAACTATGTGGACTCTGTGGAGGGCCGAT TCACCATCTCCAGAGACAACGCGAAGAACTCACTTTATCTGCAAATGGACA GCCTGAGAGCCGAGGACACGCGGATATATTACTGTGCGCGAGATTCACTTA CTTGTTTTGACTACTGGGGCCAGGGAGCCCTGGTCACCGTCTCCTCA (SEQ ID NO: 184).

The nucleotide sequence encoding the heavy chain of anti-Rh(D) antibody clone SH18 is
GAGGTGCAGCTGCTCGAGTCTGGGGGAGGCGTGGTCCAGCCTGGGAGGTC CCTGAGACTCTCCTGTGCAGCCTCTGGATTCACCTTCAGGAGCTATGCTATG CACTGGGTCCGCCAGGCTCCAGGCAAGGGGCTGGAGTGGGTGGCAGCTAC AGCATATGATGGAAAAAATAAATACTACGCAGACTCCGTGAAGGGCCGAT TCACCATCTCCAGAGACAATTCCATGAACACGCTGTTTCTGCAAATGAACA GCCTGAGAGCTGAGGACACGGCTGTGTTTTACTGTGCGAGAGGCGGATTTT ACTATGATAGTAGTGGTTATTACGGCTTGAGGCACTACTTTGACTCCTGGG GCCAGGGAACCCTGGTCACCGTCTCCTCA (SEQ ID NO: 185).

The nucleotide sequence encoding the heavy chain of anti-Rh(D) antibody clone SH20 is
GAGGTGCAGCTGCTCGAGGAGTCTGGGGGAGGCGTGGTCCAGCCTGGGAG GTCCCTGAGACTCTCCTGCAGCCTCTGGATTCACCTTCAGAAGTTATGCT ATGCACTGGGTCCGCCAGGCTCCAGGCAAGGGGCTGGAGTGGGTGGCGGT TATATCATATGATGGAAGTACTATATACTACGCAGACTCCGTGAAGGGCCG ATTCACCATCTCCAGAGCCAATTCCAAGAACACGCTGTTTCTGCAAATGAA CAGCCTCAGAACTGAGGACACGGCTGTATATTACTGTACGAGAGGGGGGTT TTACTATGACAGTAGTGGTTATTACGGGTTGAGGCACTACTTTGACTACTGG GGCCAGGGAACCCTGGTCACCGTCTCTTCA (SEQ ID NO: 186).

The nucleotide sequence encoding the heavy chain of anti-Rh(D) antibody clone SH24 is
GAGGTGCAGCTGCTCGAGTCGGGGGGAGGCGTGGCCCAGCCTGGGAGGTC CCTGAGACTCTCCTGTGTAGCGTCTGGATTCAGCCTCAGGAGCTATGGCAT GCACTGGGTCCGCCAGGCTCCTGGCAAGGGGCTGGAGTGGGTGGCAGATA TATGGTTTGATGGAAGTAATAAAGATTATGCAGACTCCGTGAAGGGCCGAT TCACCATCTCCAGAGACAATTCCAAGAACACGTTGTATCTTCAAATGAACA GCCTGAGAGCCGAGGACACGGCTGTGTATTATTGTGCGAGAGATTGGAGG GTGCGGGCCTTTAGTAGTGGCTGGT-
TAAGTGCTTTTGATATCTGGGGCCAA GGGACAATGGTCACCGTCTCTTCA (SEQ ID NO: 187).

The nucleotide sequence encoding the heavy chain of anti-Rh(D) antibody clone SH25 is
GAGGTGCAGCTGCTCGAGGAGTCTGGGGGAGGCGTGGTCCAGCCTGGGAG GTCCCTGAGACTCGCCTGTGCAGCGTCTGGATTCAGCTTCAGGAGCTATGG CATGCACTGGGTCCGCCAGGCTCCAGGCAGGGGGCTGGAGTGGGTGGCATT TACATGGTTTGATGGAAGCAATAAATATTATGTAGACTCCGTGAAGGGCCG ATTCACCATCTCCAGAGACAATTCCAAGAACACGCTGTATCTGGAAATGAA CAGCCTGAGAGTCGATGACACGGCTGTATATTACTGTGCGAGAGAGGCGCC TATGCTTCGCCGGAATTAGCAGATACTACTACGCGATGGACGTCTGGGGCCC AGGGACCACGGTCACCGTCTCCTCA (SEQ ID NO: 188).

The nucleotide sequence encoding the heavy chain of each of anti-Rh(D) antibody clones SH28, SH50, and SH53 is
GAGGTGCAGCTGCTCGAGTCTGGGGGAGGCGGGGTCCAGCCTGGGAGGTC CCTGCGACTCTCCTGTGCGGCGTCTGGATTCACCTTCAATAGTTATGCCATG TACTGGGTCCGCCAGCCTCCAGGCAAGGGGCTGGAGTGGGTGGCAGCTATA TGGTATGATGGAAGTAATAAAGAATATGCAGATTTTGTGAAGGGCCGCTTC ACCATCTCCAGAGACAATTCCAAGAACACGCTGTCTCTGCAAATGAACAGC CTGAGAGACGAGGACACGGCTGTGTATTACTGTGCGAGAGAGGCGAATCT CCTCCGTGGCTGGTCTCGATACTACTACGGTATGGACGTCTGGGGCCAAGG GACCACGGTCACCGTCTCCTCA (SEQ ID NO: 189).

The nucleotide sequence encoding the heavy chain of anti-Rh(D) antibody clone SH32 is
GAGGTGCAGCTGCTCGAGTCGGGGGGAGGCGTGGTCCAGCCTGGGAGGTC CCTGAGACTCTCCTGTGAAGCGTCTAAATTCACCCTCTACAATTATGGCATG CACTGGGTCCGCCAGGCTCCAGGCAAGGGGCTGGAGTGGGTGGCATTTATA TGGTTTGATGGAAGTAATAAATACTATGAAGACTCCGTGAAGGGCCGATTC ACCGTCTCCAGAGACAATTCCAAGAACACGCTGTATCTGCAAATGAACAGC CTGAGAGCCGAGGACACGGCTGTGTATTACTGTGCGAGAGAACTATCTAAG AAGGTGGCACTTTCTAGGTATTACTACTATATGGACGTCTGGGGCCAGGGG ACCACGGTCACTGTCTCGTCA (SEQ ID NO: 190).

The nucleotide sequence encoding the heavy chain of anti-Rh(D) antibody clone SH37 is
GAGGTGCAGCTGCTCGAGGAGTCTGGGGGAGGCGTGGTCCAGCCTGGGAG GTCCCTGAGACTCTCCTGTGCAGTGTCTGGATTCACCCTAACTAATTATGGC ATGCACTGGGTCCGCCAGGCTCCAGGCAAGGGGCTGGAGTGGGTGGCACA TGTCTGGTATGATGGAAGTAAAACAGAATACGCAGACTCCGTCAAGGGCC GATTCGCCGTCTCCAGAGACAAATCCAAGAACACACTGTTTCTGCAAATGA ACAGCCTGACAGCCGAGGACACGGCTATTTATTACT- GTGCGAGAGAGAGG AGAGAGAAAGTCTATATATTGTTC- TACTCGTGGCTCGACCGCTGGGGCCAG GGAAC- CCTGGTCACCGTCTCCTCA (SEQ ID NO: 191).

The nucleotide sequence encoding the heavy chain of anti-Rh(D) antibody clone SH39 is GAGGTGCAGCTGCTCGAGCAGTCTGGGG- GAGGCGTGGTCCAGCCTGGGAG GTCCCT- GAGACTCTCCTGTGCAGCGTCTGGAT- TCACCTTCAGTAGCTATGGC ATGCACTGGGTCCGCCAGGCTCCAG- GCAAGGGACTGGAGTGGGTGGCAGT TATATG- GTTTGATGGAAGTAATAAGGAATATGCA- GACTCCGTGAAGGGCCG ATTCACCATCTCCAGAGACAATTCCAA- GAACACGCTGTATCTACAAATGAA CAGCCT- GAGAGCCGAGGACACGGCTGTGTAT- TACTGTGCGAGAGAAGAAG TGGTTCGGGGAGTTATCTTATGGTCTCG- AAGTTTGACTACTGGGGCCAGG GAACCCTGGT- CACCGTCTCCTCA (SEQ ID NO: 192).

The nucleotide sequence encoding the heavy chain of anti-Rh(D) antibody clone SH44 is GAGGTGCAGCTGCTCGAGTCGGGGGGAG- GCGTGGCCCAGCCTGGGAGGTC CCTGAGACTCTC- CTGTGTAGCGTCTGGATTCAGCCTCAG- GAGCTATGGCAT GCACTGGGTCCGCCAGGCTCCTG- GCAAGGGGCTGGAGTGGGTGGCAGATA TATG- GTTTGATGGAAGTAATAAAGATTATGCA- GACTCCGTGAAGGGCCGAT TCACCATCTCCAGAGACAATTCCAAGAA- CACGTTGTATCTTCAAATGAACA GCCTGAGAGC- CGAGGATACGGCTGTGTATTATTGTGC- GAGAGATTGGAGGG TGCGGGCCTTTAGTAGTGGCTGGT- TAAGTGCTTTTGATATCTGGGGCCAAG GGACAATG- GTCACCGTCTCTTCA (SEQ ID NO: 193).

The nucleotide sequence encoding the heavy chain of anti-Rh(D) antibody clone SH47 is GAGGTGCAGCTGCTCGAGTCTGGGGGAG- GCGTGGTCCAGCCTGGGAGGTC CCTGC- GACTCTCTTGTGCAGCCTCTGGAT- TCAGCTTCAGTAACTATGCTATG CACTGGGTCCGCCAGGCTCCAG- GCAAGGGGCTGGAGTGGGTGGCAGTTAC ATCATTTGATGGAAGCATTAAAGAC- TACGCAGACTCCGTGAAGGGCCGATT CAC- CATCTCCAGAGACAATTCCAAGAACA- CACTATATCTGCAAATGAACAG CCTGAGAGATGAGGACACGGCTGTATAT- TACTGTGCGAGAGAGCGGGGGA TGATAGTCGTG- GTCCGTCGCAGAAAT- GCTTTTGATATTTGGGGCCAAGGGA CAATGGTCACCGTCTCTTCA (SEQ ID NO: 194).

The nucleotide sequence encoding the heavy chain of anti-Rh(D) antibody clone SH54 is GAGGTGCAGCTGCTCGAGTCGGGGGGAG- GCGTGGTCCAGCCTGGGAGGTC CCTGAGACTCTC- CTGTGCAGCGTCTGGGTTCACCTTCAG- TAGGAATGGCAT GCACTGGGTCCGCCAGGCTCCTG- GCAAGGGGCTGGAGTGGGTGGCATTTAT ATG- GTTTGATGGAAGTAATAAATACTATGCA- GACTCCGTGAAGGGCCGATT CACCATCTCCAGAGACAATTCCAAGAA- CACGCTGTATCTGCAAATGAACAG CCTGAGAGC- CGACGACACGGCTGTGTATTACTGTGC- GAGAGAGGAGGCTCT GTTTCGGGGACTTACTCGGTGGTC- CTACGGTATGGACGTCTGGGGCCAAGG GACCACG- GTCAGCGTCTCCTCA (SEQ ID NO: 195).

The nucleotide sequence encoding the heavy chain of anti-Rh(D) antibody clone SH56 is GAGGTGCAGCTGCTCGAGTCGGGGGGAG- GCGTGGTCCAGCCTGGGAGGTC CCTGAGACTCTC- CTGTGCAGCGTCTGGATTCACCTTCAG- TAGCTATGGCATG CACTGGGTCCGGCAGGCTCCAG- GCAAGGGGCTGGAGTGGGTGGCAGTTGT CTAC- TATGATGGAAGTAACAAACACTATTCA- GACTCCGTGAAGGGCCGATT CACCATCTTCAGAGACAACTCCAAGAA- CACGCTGTATCTACAAATGGACAG CCTGAGAGC- CGAGGACACGGCTGTGTATTACTGTGC- GAGAGAAAGAAATTT TCGGAGTGGTTATTCCCGCTACTAC- TACGGTATGGACGTCTGGGGCCCAGG GACCACG- GTCACCGTCTCCTCA (SEQ ID NO: 196).

The nucleotide sequence encoding the light chain of anti-Rh(D) antibody clone SH8 is GCCGAGCTCACCCAGTCTCCATCCTC- CCTGGCTGCGTCTGTCGGAGACAGA GTCACCAT- CACTTGCCGGGCAAATCAGACCATCA- GAACCTCTTTAAATTGG TATCAACAAAGACCTGGGAAAGC- CCCTAACCTCCTGATCTATGGTGCATCC AGGTTG- CATAGTGGGGTCCCATCAAGGTTTAGTG- GCGGTATTTCTGGGGCA GACTTCACTCTCACCATCAGCAGTCTG- CAACCTGAAGATTTTGCAACTTACT ACTGTCAGCA- GACTTACGGTTATTCTCGAACGTTCGGC- CAAGGGACCAAGG TGGATATCAAACGA (SEQ ID NO: 197).

The nucleotide sequence encoding the light chain of anti-Rh(D) antibody clone SH12 is GCCGAGCTCACCCAGTCTCCATTCTC- CCTGTCTGCATCTGTAGGAGACAGA GTCACCAT- AACTTGCCGGGCAAGTCACAACATTTA- CAGGTCTTTAAATTGG TTTCAGCATAAACCAGGGGAAGC- CCCTAAGCTCCTGGTCTATGCTGCATCC AGTCTG- CAGCGTGGGGTCCCAACCAGGTTCAGTG- GCAGTGGATCTGGGACA GATTTCACTCTCACCATCAGCAGTCT- TCAACCTGAAGACTCTGCGACTTACT TCTGTCAA- CAGAGTGTCACATTCCCCTACACTTTTG- GCCAGGGGACCAAGC TGGAGATCAGACGA (SEQ ID NO: 198).

The nucleotide sequence encoding the light chain of anti-Rh(D) antibody clone SH13 is GCCGAGCTCACCCAGTCTCCATCCTC- CCTGTCTGCATCTGTAGGAGACAGA GTCACCAT- CACTTGCCGGGCAAGTCAGAGCATTAG- CAGCTATTTAAATTGG TATCAGCAGAAACCAGGGAAAGC- CCCTAAGCTCCTGATCTATGCTGCATCC AGTTTGC- GAAGTGGGGTCCCATCAAGGTTCAGTG- GCAGTGGATCTGGGACA GATTTCACTCTCACCATCAGCAGTCTG- CAACCTGAAGATTTTGCAACTTACT ACTGTCAACA- GAGTTACAGTACCCCCTACACTTTTGGC- CAGGGGACCAAGC TGGAGATCAAACGA (SEQ ID NO: 199).

The nucleotide sequence encoding the light chain of anti-Rh(D) antibody clone SH14 is
GCCGAGCTCACCCAGTCTCCATCCTCCCTGTCTGCATCTGTAGGAGACAGA GTCACCATCACTTGCCGGGCAAGTCAGAACATTAGGAGGTCTTTAAATTGG TATCAACACAAACCAGGGAGAGCCCCTAGACTCCTGATCTATGCTGCATCC ACTTTGCAAAGTGGGGTCCCATCAAGGTTCAGGGGCAGTGGATCTGGGACA GATTTCACTCTCACCATCAACAGTCTGCAACCTGCAGATTTTGCAACTTACT ACTGTCAGCAGAGTTCCAATACCCCGTGGACGTTCGGCCATGGGACCAAGG TGGAAATCAAACGA (SEQ ID NO: 200).

The nucleotide sequence encoding the light chain of anti-Rh(D) antibody clone SH16 is
GCCGAGCTCACCCAGTCTCCATCCTCCCTGTCTGCCTCTGTAGGAGACAGA GTCACCATCACTTGCCGGGCAAGTCAGAGCATTAGCAGCTATTTAAATTGG TATCAACAGAAACCAGGGAAAGCCCCTAAGCTCCTGATCTATGCTGCATCC AGTTTGCAAAGTGGGGTCCCATCAAGGTTCAGTGGCAGTGGATCTGGGACA GATTTCACTCTCACCATCAGCAGTCTGCAACCTGAAGATTTTGCAACTTACT ACTGTCAACAGAGTTACAGTACCCCTCCAACTTTCGGCGGAGGGACCAAGG TGGAGATCAAACGA (SEQ ID NO: 201).

The nucleotide sequence encoding the light chain of anti-Rh(D) antibody clone SH18 is
GCCGAGCTCACCCAGTCTCCATCCTCCCTCTCTGCATCTGTAGGAGACAGA GTCACCATCACTTGCCGGGCAAGTCAGAGTATTAGCATCGCTTTAAATTGG TATCAGCAGAGACCAGGGAAAGCCCCTAAGCTCCTGATGTATGCTACATCC ACTTTGCAAAGTGGGGTCCCATCAAGGTTCAGTGGCAGTGGATCTGGGACA GATTTCACTCTCACCATCAGCAGTCTGCAACCTGAAGATTTTGCAACTTACT ACTGTCAACAATATTACAATAAACCTACTTTCGGCCCTGGGACCAAGGTGG ATATCAAACGA (SEQ ID NO: 202).

The nucleotide sequence encoding the light chain of anti-Rh(D) antibody clone SH20 is
GCCGAGCTCACCCAGTCTCCATTCTCCCTGTCTGCATCTGTCGGAGACAGA GTCACCATAACTTGCCGGGCAAGTCAGAGCATTAGCAGGTCTTTAAATTGG TATCAACATAAACCAGGGGAAGCCCCTAAGCTCCTGATCTATGCTGCATCC AGTCTGCAGCGTGGGGTCCCACCCAGGTTCAGTGGCAGTGGATCTGGGACA GATTTCACTCTCACCATCAGCAGTCTGCAACCTGAAGACTTTGCGACTTACT CTGTCAACAGAGTGTCAGAATCCCGTACAGTTTTGGCCAGGGGACCAAGC TGGAGATCAAACGA (SEQ ID NO: 203).

The nucleotide sequence encoding the light chain of anti-Rh(D) antibody clone SH21 is
GCCGAGCTCACCCAGTCTCCATCCTTCCTGTCTGCATCTGTAGGAGACAGA GTCACCATCACTTGCCGGGCCAGTCAGGGCATTAGCGAGTTATTTAGCCTGG TATCAGCAAAAACCAGGGAAAGCCCCTAAGCTCCTAATCTATGCTGCATCC ACTTTGCAAAGTGGGGTCCCATCAAGGTTCAGCGGCAGTGGATCTGGGACA GAATTCACTCTCACAATCGCCAGCCTGCAGCCTGATGATTTTGCAACTTATT ACTGTCAACAGCTTAATAATTACCCCCCTTTCACTTTCGGCCCTGGGACCAA AGTGGATATCAAACGA (SEQ ID NO: 204).

The nucleotide sequence encoding the light chain of anti-Rh(D) antibody clone SH24 is
GCCGAGCTCACCCAGTCTCCATCCTCCCTGTCTGCATCTGTAGGAGACAGA GTCACCATCACTTGCCGGGCAAGTCAGAGCATTAGCACCTATTTAAATTGG TATCAGCAGAGACCAGGGAAAGCCCCTAACCTCCTGATCTATGCTGCATCC ACTTTGCAAAGGGGGGTCCCATCAAGGTTCACTGGCAGTGGATCTGGGACA GATTTCACTCTCACCATCAGCAGTCTGCAACCTGAAGATTTTGCAACTTACT ACTGTCAACAGAGTTACACTACCCTGTGGACGTTCGGCCAAGGGACCAAGA TGGAAATCAGACGA (SEQ ID NO: 205).

The nucleotide sequence encoding the light chain of anti-Rh(D) antibody clone SH26 is
GCCGAGCTCACCCAGTCTCCATCCTCCCTGTCTGCATCTGTAGGAGACAGA GTCACCATCACTTGCCGGGCAAGTCAGAGCATTAGCAGCTATTTAAATTGG TATCAGCAGAAACCAGGGAAAGCCCCTAAGCTCCTGATCTATGCTGCATCC AGTTTGCAAAGTGGGGTCCCATCAAGGTTCAGTGGCAGTGGATCTGGGACA GATTTCACTCTCACCATCAGCAGTCTGCAACCTGAAGATTTTGCAACTTACT ACTGTCAACAGAGTTACAGTTTCCGAAGGTACAGTTTTGGCCAGGGGACCA AGCTGGAGATCAAACGA (SEQ ID NO: 206).

The nucleotide sequence encoding the light chain of anti-Rh(D) antibody clone SH28 is
GCCGAGCTCACCCAGTCTCCATCCTCCCTGTCTGCATCTGTAGGAGACAGA GTCACCATCACTTGCCGGGCAGATCAGAACATTAGGAGGTCTTTAAATTGG TTTCAGCAGAAACCAGGGAAAGCCCCTAAGCTCCTGATCTATGCTGCATCC AGTTTGCAAAGTGGGGTCCCATCAAGGTTCAGTGGCAGTGGATCTGGGACA GATTTCACTCTCACCATCAGCAGTCTGCAACCTGAAGATTTTGCAACTTACT ACTGTCAACAGAGTTCCAGTACCCCGTGGACGTTCGGCCGAGGGACCAAGG TGGAAATCAAACGA (SEQ ID NO: 207).

The nucleotide sequence encoding the light chain of anti-Rh(D) antibody clone SH30 is
GCCGAGCTCACCCAGTCTCCATCCTCCCTGTCTGCATCTGTTGGAGACAGA GTCACCATCACTTGCCGGGCAAGTCAGAGCATTCGGAGGTCTTTAAATTGG TATCAGCAGAGTCCAGGGAAAACCCCTAAGCTCCTGATCTATGCTGCATCC AGTTTGCAAAGTGGGGTCCCATCAAGGTTCAGTGGCAGTGGATCTGGGACA GATTTCACTCTCACCATCAGCAGTCTGCAACCTGAAGATTTTGCAACTTACT ACTGTCAACAGAGTTACAGTACCCTCACTTTCGGCGGAGGGACCAAGGTGG AGATCAAACGA (SEQ ID NO: 208).

The nucleotide sequence encoding the light chain of anti-Rh(D) antibody clone SH32 is GCCGAGCTCACTCAGGAGCCCTCACT-GACTGTGTCCCCAGGAGGGACAGTC ACTCTCAC-CTGTGCTTCCAGCACTGGAGCAGTCAC-CAGTCGTTACTTTCCAA ACTGGTTCCAGCAGAAACCTGGCCAG-GCACCCAGGGCACTGATTTATGGTT CAAACAA-CAAACACTCCTGGACCCCTGCCCGGT-TCTCAGGCTCCCTCCTTG GGGGCAAAGCTGCCCTGACACTGTCAG-GTGTGCAGCCTGAGGACGAGGCG GAGTATTACT-GCCTGCTCTTCTATGCTGGTGCT-TGGGCGTTCGGCGGAGGG ACCAAGCTGACCGTCCTA (SEQ ID NO: 209).

The nucleotide sequence encoding the light chain of anti-Rh(D) antibody clone SH34 is GCCGAGCTCACCCAGTCTCCATCCTC-CCTGTCTGCATCTGTAGGAGACAGA GTCACCAT-CACTTGCCGGGCAAGTCAGAGCATTAG-CAGCTATTTAAATTGG TATCAGCAGAAACCAGGGAAAGC-CCCTAAGCTCCTGATCTATGCTGCATCC GGTTTG-CAAAGTGGGGTCCCATCAAGGTTCAGTG-GCAGTGGATCTGGGACA GATTTCACTCTCACCATCAGCAGTCTG-CAACCTGAAGATTTTGCAACTTACT ACTGTCAACA-GAGTTACAGTACCCCCCCGTA-CACTTTTGGCCAGGGGACCA AGCTGGAGATCAAACGA (SEQ ID NO: 210).

The nucleotide sequence encoding the light chain of anti-Rh(D) antibody clone SH36 is GCCGAGCTCACTCAGTCTCCATCCTC-CCTGTCTGCATCTGTAGGAGACAGA GTCACCAT-CACTTGCCGGGCAAGTCAGAGCATTAG-CAGCTATTTAAATTGG TATCAGCAGAAACCAGGGAAATC-CCCTAAGCTCCTGATCTATGCTGCATCC AGTTTG-CAAAGTGGGGTCCCATCAAGGTTCAGTG-GCAGTGGATCTGGGACA GATTTCACTCTCACCATCAGCAGTCTG-CAACCTGAAGATTTTGCAACTTACT ACTGTCAACA-GAGTTACAGTACCCCTCCGGCTTTCGGC-CCTGGGACCAAAG TGGATATCAAACGA (SEQ ID NO: 211).

The nucleotide sequence encoding the light chain of anti-Rh(D) antibody clone SH39 is GCCGAGCTCACCCAGTCTCCATCCTC-CCTGTCTGCATCTGTGGGAGACAGA GTCACCAT-CACTTGCCGGGCAAGTCAGACCATTGG-GAGGTATTTAAATTGG TATCAGCAGAGGCCAGGGAAAGC-CCCCAAACTCCTGGTATATGCTGTGTCC AGTTTG-CAAAGTGGGGCCCCATCAAGGTTCAGTG-GCAGTGGCTCTGGGACA CATTTCACTCTCACCATCACCAGTCTG-CAACCTGAAGATTTTGCAACTTACT TCTGCCAACA-GAGTTACAGTTCTCCTTTCACTTTTGGC-CAGGGGACCAAGGT TGAGATCAAACGA (SEQ ID NO: 212).

The nucleotide sequence encoding the light chain of anti-Rh(D) antibody clone SH41 is GCCGAGCTCACCCAGTCTCCATCCTC-CCTGTCTGCATCTGTAGGAGACAGA GTCACCAT-CACTTGCCGGGCAAGTCAGAACATTAG-GAGGTCTTTAAATTGG TATCAACACAAACCAGGGAGAGCCCCTA-GACTCCTGATCTATGCTGCATCC ACTTTG-CAAAGTGGGGTCCCATCAAGGT-TCAGGGGCAGTGGATCTGGGACA GATTTCACTCTCACCATCAACAGTCTG-CAACCTGCAGATTTTGCAACTTACT ACTGTCAGCA-GAGTTCCAATACCCCGTGGACGTTCGGC-CATGGGACCAAGG TGGAAATCAAACGA (SEQ ID NO: 213).

The nucleotide sequence encoding the light chain of anti-Rh(D) antibody clone SH44 is GCCGAGCTCACCCAGTCTCCATCGTC-CCTGTCTGCATCTGTAGGAGACAGA GTCATCAT-CACTTGCCGGGCAAGTCAGACCATTC-CCAGGTTCTTGAATTGGT ATCAACAGAAGCCTGGAAAAGCCCCTGT-TCTCCTGATTCATAGTATATCCA GTTTA-CAAAGTGGGGTCCCATCAAGGTTCAGT-GCCAGTGGATCTGGGACAG AGTTCACTCTCACCATCAGCAGTCTG-CAACCTGAAGATTTCGCAACTTACTA CTGCCAACA-GAGTTACAGTAATCTCTCTTTCGGC-CCTGGGACCACAGTGGA TATTAGACGA (SEQ ID NO: 214).

The nucleotide sequence encoding the light chain of anti-Rh(D) antibody clone SH46 is GCCGAGCTCACCCAGTCTCCATCCTC-CCTGTCTGCATCTGTAGGAGACAGA GTCACCAT-CACTTGCCGGGCAAGTCAGTACATTAG-CAGCTATTTAAATTGG TATCAGCAGAAACCAGGGAAAGC-CCCTAATCTCCTGATCTATGCTGCATCC AGTTTG-CAAAGTGGGGTCCCATCAAGGTTCAGTG-GCAGTGGATCTGGGACA GATTTCACTCTCACCATCAGCAGTCTG-CAACCTGAAGATTTTGCAACTTACT ACTGTCAACA-GACTTACAGTTCCCCTAGCACTTTCGGC-CCTGGGACCAAAG TGGATATCAAACGA (SEQ ID NO: 215).

The nucleotide sequence encoding the light chain of anti-Rh(D) antibody clone SH47 is GCCGAGCTCACCCAGTCTCCATCCTC-CCTGTCTGCATCTGTAGGAGACAGA GTCACCAT-CACTTGCCGGGCAAGTCAGAGCATTAG-CAACTATTTAAATTGG TATCAGCAGAAACCAGGAAAAGC-CCCTAACCTCCTGATCTATGCTGCATCC AGTTTG-CAAAGTGGGGTCCCATCAAGGTTCAGTG-GCAGTGGATCTGGGACA GATTTCACTCTCACCATCAGCAGTCTG-CAACCTGAAGATTTTGCAACTTACT ACTGTCAACA-GAGTTACAGTTATCCTCGCACGTTCGGC-CAAGGGACCAAGG TGGAGATCAGACGA (SEQ ID NO: 216).

The nucleotide sequence encoding the light chain of anti-Rh(D) antibody clone SH48 is GCCGAGCTCACCCAGTCTCCATCCTC-CCTGTCTGCATCTGTAGGAGACAGA GTCACCAT-CACTTGCCGGGCAAGTCAGTACATTAG-CAGCTATTTAAATTGG TATCAGCAGAAACCAGGGAAAGC-CCCTAATCTCCTGATCTATGCTGCATCC AGTTTG-CAAAGTGGGGTCCCATCAAGGTTCAGTG-GCAGTGGATCTGGGACA GATTTCACTCTCACCATCAGCAGTCTG-CAACCTGAAGATTTTGCAACTTACT ACTGTCAACA-GACTTACAGTTCCCCTAGCACTTTCGGC-CCTGGGACCAAAG TGGATATCAAACGA (SEQ ID NO: 217).

The nucleotide sequence encoding the light chain of anti-Rh(D) antibody clone SH49 is
GCCGAGCTCACCCAGTCTCCATCCTC-CCTGTCTGCATCTGTAGGAGACAGA GTCACCGT-CACTTGCCGGGCAAGTCAGAGCATTAG-CAGCTATTTAAATTGG TATCAGCAGAAACCAGGGAAAGC-CCCTAAGCTCCTGATCTATGCTGCATCC AGTTTG-CAAAGTGGGGTCCCATCAAGGTTCAGTG-GCAGTGGATCTGGGACA GATTTCACTCTCACCATCAGCAGTCTG-CAACCTGAAGATTTTGCAACTTACT ACTGTCAACA-GAGTTACAGTACCCCGTGGACGTTCGGC-CAAGGGACCAAG GTGGAAATCAAACGA (SEQ ID NO: 218).

The nucleotide sequence encoding the light chain of anti-Rh(D) antibody clone SH50 is
GCCGAGCTCACCCAGTCTCCATCGTC-CCTGTCTGCATCTGTAGGAGACAGA GTCACCAT-CACTTGCCGGACAAGTCAGAGCATTG-GCACCTATTTAAATTGG TATCAACAAAAACCAGGGAAAGC-CCCTAAACTCCTGATCTATGCTGCATCC AATGTG-CAAAGTGGGGTCCCATCAAGGTTCAGTG-GCGGTGGATCTGGGACA GGTTTCTCTCTCATCATCAGCAGTCTG-CAACCTGAAGATTTAGCAATTTACT ACTGCCAACA-GAGCTACAGTGTCCCTCCGTA-CAGCTTTGGCCCGGGGACCA AGCTGGAGATCAAACGA (SEQ ID NO: 219).

The nucleotide sequence encoding the light chain of anti-Rh(D) antibody clone SH51 is
GCCGAGCTCACACAGTCTCCATCCTTC-CTGTCTGCATCTGTAGGAGACAGA GTCACCAT-CACTTGCCGGGCCAGTCAGGGCATAAG-GAGTTATTTAGCCTGG TATCAGCAAAAACCAGGGAAAGC-CCCTAAGCTCCTAATCTATGCTGCATCC ACTTTG-CAAAGTGGGGTCCCATCAAGGTTCAGCG-GCAGTGGATCTGGGACA GAATTCACTCTCACAATCAGCAGCCTG-CAGCCTGAAGATTTTGCAACTTATT ACTGTCAA-CAGCTTAATAATTAC-CCCCCTTTCACTTTCGGCCCTGGGACCAA AGTGGATATCAAACGA (SEQ ID NO: 220).

The nucleotide sequence encoding the light chain of anti-Rh(D) antibody clone SH52 is
GCCGAGCTCACACAGTCTCCAGGCAC-CCTGTCTTTGTCTCCAGGGGAAAGA GCCAC-CCTCTCCTGCAGGGCCAGTCAGAGTATT-AGCAGCAGCTACTTAGCC TGGTACCAGCAGAAACCTGGCCAGGCTC-CCAGGCTCCTCATCTATGGTGCA TCCAGCAGGGC-CACTGGCATCCCAGACAGATTCAGTG-GCAGTGGGTCTGGG ACAGACTTCACTCTCACCATCAGCA-GACTGGAGCCTGAAGATTTTGCAGTG TATTACTGT-CAGCAGTATGGTAGCTCACCGTGGACGT-TCGGCCAAGGGACC AAGGTGGAAATCAAACGA (SEQ ID NO: 221).

The nucleotide sequence encoding the light chain of anti-Rh(D) antibody clone SH54 is
GCCGAGCTCACCCAGTCTCCATCCTC-CATGTCTGCATCTGTAGGAGACAGA GTCACCAT-CACTTGCCGGGCAAGTCAGAGCATTG-GCACTTATTTAAATTGG TATCAGCAGAAACCAGGGAAAGC-CCCTAAGCTCCTGATCTATGCTGCATCC AGTTTG-CAAAGTGGGGTCCCATCAAGGTTCAGTG-GCAGTGGATCTGGGACA GATTTCACTCTCACCATCAGCAGTCTG-CAACCTGAAGATTTTGCAACTTACT ACTGTCAACA-GAGTTACAGTACCCCGTGGACGTTCGGC-CAAGGGACCAAG GTGGAAATCAAACGA (SEQ ID NO: 222).

The nucleotide sequence encoding the light chain of anti-Rh(D) antibody clone SH55 is GCCGAGCTCACGCAGCCGCCCT-CAGCGTCTGGGACCCCCGGGCAGAGGGT CAC-CATCTCTTGTTCTGGAAGCAGCTCCAA-CATCGGAAGTAAATATGTATA CTGGTACCAGCAACTCCCAGGAACGGC-CCCCAAACTCCTCATTTATAGTAA TAATCAGCGGC-CCTCAGGGGTCCCTGACCGATTCTCTGC-CTTCAAGTCTGG CACCTCAGCCTCCCTGGCCAT-CACTGGGCTCCAGGCTGAGGATGAGGCTAA TTAT-TACTGCCAGTCCTATGACAGCGGCCT-GAGTGGCTGGGTGTTCGGCGG CGGGACCAAGCTGACCGTCCTA (SEQ ID NO: 223).

The nucleotide sequence encoding the light chain of anti-Rh(D) antibody clone SH56 is
GCCGAGCTCACCCAGTCTCCATCCTC-CCTGTCTGCATCTGTAGGAGACAGA GTCACCAT-CACTTGCCGGGCAAGTCAGAGCATTAG-CAGGTATTTAAATTGG TATCAGCAGAAACCAGGGAAAGC-CCCCAAGCTCCTGATCTATGCTGCATCC AGTTTG-CAAAGTGGGGTCCCATCAAGGTTCAGTG-GCAGTGGATCTGGGACA GATTTCGCTCTCACCATCAGCAGTCTGC-TACCTGAAGATTTTGCAACTTACT ACTGTCAA-CAGGGTTACAGTACCCCTCCGTA-CAGTTTTGGCCAGGGGACCA AGCTGGAGATCAAACGA (SEQ ID NO: 224).

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated protein having an amino acid sequence comprising a sequence selected from the group consisting of SEQ ID NOs: 1–69 and 139–181.

2. The isolated protein of claim 1, wherein the protein is an antigen-binding protein.

3. The isolated protein of claim 2, wherein the antigen is human Rh(D) protein.

4. The isolated protein of claim 1, wherein the protein has an amino acid sequence selected from the group consisting of SEQ ID NOs: 1–69 and 139–181.

5. The isolated protein of claim 1, wherein the protein is substantially purified.

6. The isolated protein of claim 1, wherein the protein has an amino acid sequence comprising a sequence selected from the group consisting of SEQ ID NOs: 1–27 and 139–153.

7. The isolated protein of claim 6, wherein the protein has an amino acid sequence comprising a sequence selected from the group consisting of SEQ ID NOs: 1–27.

8. The isolated protein of claim 6, wherein the protein has an amino acid sequence comprising a sequence selected from the group consisting of SEQ ID NOs: 139–153.

9. The isolated protein of claim 1, wherein the protein has an amino acid sequence comprising a sequence selected from the group consisting of SEQ ID NOs: 28–69 and 154–181.

10. The isolated protein of claim 9, wherein the protein has an amino acid sequence comprising a sequence selected from the group consisting of SEQ ID NOs: 28–44.

11. The isolated protein of claim 9, wherein the protein has an amino acid sequence comprising a sequence selected from the group consisting of SEQ ID NOs: 45–61.

12. The isolated protein of claim 9, wherein the protein has an amino acid sequence comprising a sequence selected from the group consisting of SEQ ID NOs: 62–69, and 154–163.

13. The isolated protein of claim 9, wherein the protein has an amino acid sequence comprising a sequence selected from the group consisting of SEQ ID NOs: 164–181.

14. The isolated protein of claim 4, wherein the protein has a sequence selected from the group consisting of SEQ ID NOs: 1–27 and 139–153.

15. The isolated protein of claim 14, wherein the protein has a sequence selected from the group consisting of SEQ ID NOs: 1–27.

16. The isolated protein of claim 14, wherein the protein has a sequence selected from the group consisting of SEQ ID NOs: 139–153.

17. The isolated protein of claim 4, wherein the protein has a sequence selected from the group consisting of SEQ ID NOs: 28–69 and 154–181.

18. The isolated protein of claim 17, wherein the protein has a sequence selected from the group consisting of SEQ ID NOs: 28–44.

19. The isolated protein of claim 17, wherein the protein has a sequence selected from the group consisting of SEQ ID NOs: 45–61.

20. The isolated protein of claim 17, wherein the protein has a sequence selected from the group consisting of SEQ ID NOs: 62–69, and 154–163.

21. The isolated protein of claim 17, wherein the protein has a sequence selected from the group consisting of SEQ ID NOs: 164–181.

* * * * *